(12) United States Patent
Mjalli et al.

(10) Patent No.: US 7,727,983 B2
(45) Date of Patent: Jun. 1, 2010

(54) OXADIAZOANTHRACENE COMPOUNDS FOR THE TREATMENT OF DIABETES

(75) Inventors: Adnan M. M. Mjalli, Oak Ridge, NC (US); Dharma Rao Polisetti, High Point, NC (US); Thomas Scott Yokum, Greensboro, NC (US); Kalpathy Santhosh, Jamestown, NC (US); Mustafa Guzel, Jamestown, NC (US); Christopher Behme, Jamestown, NC (US); Stephen Thomas Davis, Durham, NC (US)

(73) Assignee: TransTech Pharma, Inc., High Point, NC (US)

( * ) Notice: Subject to any disclaimer, the term of this patent is extended or adjusted under 35 U.S.C. 154(b) by 0 days.

(21) Appl. No.: 12/399,504

(22) Filed: Mar. 6, 2009
(Under 37 CFR 1.47)

(65) Prior Publication Data

US 2009/0306063 A1 Dec. 10, 2009

Related U.S. Application Data

(60) Provisional application No. 61/034,599, filed on Mar. 7, 2008.

(51) Int. Cl.
*C07D 498/02* (2006.01)
*A61K 31/5365* (2006.01)
(52) U.S. Cl. .................... 514/229.8; 544/101
(58) Field of Classification Search ............. 514/229.8; 544/101
See application file for complete search history.

(56) References Cited

U.S. PATENT DOCUMENTS

| 4,789,675 A | 12/1988 | Meguro et al. |
| 6,770,656 B2 | 8/2004 | Halazy et al. |
| 2004/0019072 A1 | 1/2004 | Canan-Koch et al. |
| 2005/0222036 A1 | 10/2005 | During et al. |

OTHER PUBLICATIONS

International Search Report, PCT App. No. PCT/US09/36333, mailed Jan. 12, 2010.

*Primary Examiner*—Kahsay T Habte
(74) *Attorney, Agent, or Firm*—Robert S. Dailey

(57) ABSTRACT

The present invention provides oxadiazoanthracene derivatives of the formula (I),

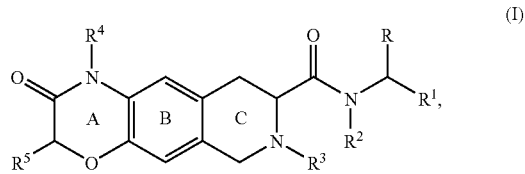

wherein A, B, C, R, $R^1$, $R^2$, $R^3$, $R^4$ and $R^5$ are as herein described, pharmaceutical compositions comprising oxadiazoanthracene derivatives, use of the oxadiazoanthracene derivatives for the preparation of pharmaceutical compositions, methods of use thereof for the treatment and/or prevention of disorders and diseases, such as diabetes, and intermediates useful for the preparation of oxadiazoanthracene derivatives of Formula (I).

46 Claims, No Drawings

OXADIAZOANTHRACENE COMPOUNDS FOR THE TREATMENT OF DIABETES

BACKGROUND OF THE INVENTION

The present invention provides oxadiazoanthracene derivatives, compositions comprising oxadiazoanthracene derivatives, use of the oxadiazoanthracene derivatives for the preparation of pharmaceutical compositions and methods of use thereof for the treatment and/or prevention of disorders and diseases wherein modulation of the human GLP-1 receptor is beneficial.

Type II diabetes mellitus is a metabolic disorder where disease progression may be characterized by peripheral tissue insulin resistance, hyperglycemia, islet b-cell compensation, hyperinsulinemia, dyslipidemia, increased liver gluconeogenesis and ultimate loss of b-cell mass and function. The pathophysiological consequences of aberrant glucose and lipid metabolism are toxicity to organs such as, but not limited to, the kidney, eye, peripheral neurons, vasculature and heart. Thus, there is a medical need for agents that may delay disease progression by improving glycemic control and b-cell mass and function.

Glucagon-like peptide-1 (GLP-1) is a member of the incretin family of neuroendocrine peptide hormones secreted from L-cells of the intestine in response to food ingestion. GLP-1 has multiple metabolic effects that are attractive for an antidiabetic agent. A key function of GLP-1 is to activate its receptor, GLP-1R, on the pancreatic b-cell to enhance glucose-dependent insulin secretion. Positive metabolic benefits of GLP-1 may include, but are not limited to, suppression of excessive glucagon production, decreased food intake, delayed gastric emptying, and improvement of b-cell mass and function. The positive effects of GLP-1 on b-cell mass and function offers the hope that GLP-1-based therapies may delay early stage disease progression. In addition, a GLP-1 agonist could be useful in combination therapies such as with insulin in patients with type I diabetes. Unfortunately, the rapid proteolysis of GLP-1 into an inactive metabolite limits its use as a therapeutic agent.

Validation of GLP-1R agonists as a therapeutic modality was achieved by Exendin-4 (Byetta® (Amylin Pharmaceuticals, Inc.)), a peptide GLP-1 receptor agonist recently approved for the treatment of Type II diabetes mellitus. Dosing of Exendin-4 by subcutaneous administration lowers blood glucose and decreases HbA1c levels, which are important biomarker measurements for disease control. Therefore, an oral GLP-1 receptor agonist should provide glycemic control while offering the convenience of oral dosing.

GLP-1R belongs to the class B receptor sub-class of the G protein-coupled receptor (GPCR) superfamily that regulates many important physiological and pathophysiological processes. In addition to the seven transmembrane domains characteristic of all GPCR family members, class B GPCRs contain a relatively large N-terminal domain. It is believed the binding and activation of these receptors by relatively large natural peptide ligands require both the N-terminal domain and the transmembrane domain of the receptor. In particular, class B GPCRs have proven difficult for the identification of low molecular weight non-peptide agonist molecules.

Because peptides, such as GLP-1, may lack sufficient oral bioavailability for consideration as oral drug agents, small molecule modulators of GLP-1R with oral bioavailability are highly desired. The present invention describes a class of compounds that modulate GLP-1R.

SUMMARY OF THE INVENTION

The present invention relates to compounds of formula (I), or a pharmaceutically acceptable salt thereof, methods comprising the use of compounds of formula (I), or a pharmaceutically acceptable salt thereof, for the preparation of pharmaceutical compositions, methods comprising the use of compounds of formula (I), or a pharmaceutically acceptable salt thereof, for the treatment and/or prevention of disorders and diseases, and pharmaceutical compositions comprising compounds of formula (I), or a pharmaceutically acceptable salt thereof,

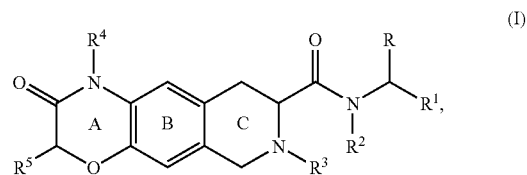

wherein A, B, C, R, $R^1$, $R^2$, $R^3$, $R^4$ and $R^5$ are as herein described.

The present invention further relates to intermediates useful, for example, in the synthesis of compounds of formula (I).

DETAILED DESCRIPTION OF THE INVENTION

Definitions

The following definitions are meant to clarify, but not limit, the terms defined. If a particular term used herein is not specifically defined, such term should not be considered indefinite. Rather, terms are used within their ordinary meanings.

As used herein the term "alkyl" refers to a straight or branched chain hydrocarbon having one to twelve carbon atoms, which may be optionally substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used throughout this specification, the number of atoms, such as carbon atoms in an alkyl group, for example, will be represented by the phrase "$C_x$-$C_y$ alkyl," or "$C_{x\text{-}y}$ alkyl," which refer to an alkyl group, as herein defined, containing from x to y, inclusive, carbon atoms. Similar terminology will apply for other terms and ranges as well. One embodiment of the present invention includes so-called 'lower' alkyl chains of one to six carbon atoms. Thus, $C_1$-$C_6$ alkyl represents a lower alkyl chain as hereabove described.

As used herein the term "alkenyl" refers to a straight or branched chain aliphatic hydrocarbon having two to twelve carbon atoms and containing one or more carbon-to-carbon double bonds, which may be optionally substituted as herein further described, with multiple degrees of substitution being allowed. Examples of "alkenyl" as used herein include, but are not limited to, vinyl, and allyl.

As used herein the term "alkynyl" refers to a straight or branched chain aliphatic hydrocarbon having two to twelve carbon atoms and containing one or more carbon-to-carbon triple bonds, which may be optionally substituted as herein further described, with multiple degrees of substitution being allowed. An example of "alkynyl" as used herein includes, but is not limited to, ethynyl.

As used herein, the term "alkylene" refers to a straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, and n-butylene.

As used herein, the term "alkenylene" refers to a straight or branched chain divalent hydrocarbon radical having from two to ten carbon atoms and containing one or more carbon-to-carbon double bonds, which may be optionally substituted as herein further described, with multiple degrees of substitution being allowed. Examples of "alkenylene" as used herein include, but are not limited to, vinylene, allylene, and 2-propenylene.

As used herein, the term "alkynylene" refers to a straight or branched chain divalent hydrocarbon radical having from two to ten carbon atoms and containing one or more carbon-to-carbon triple bonds, which may be optionally substituted as herein further described, with multiple degrees of substitution being allowed. An example of "alkynylene" as used herein includes, but is not limited to, ethynylene.

As used herein, the term "alkoxy" refers to the group $R^xO$—, where $R^x$ is alkyl.

As used herein, the term "alkenyloxy" refers to the group $R^xO$—, where $R^x$ is alkenyl.

As used herein, the term "alkynyloxy" refers to the group $R^xO$—, where $R^x$ is alkynyl.

As used herein, the term "alkylsulfanyl" refers to the group $R^xS$—, where $R^x$ is alkyl.

As used herein, the term "alkenylsulfanyl" refers to the group $R^xS$—, where $R^x$ is alkenyl.

As used herein, the term "alkynylsulfanyl" refers to the group $R^xS$—, where $R^x$ is alkynyl.

As used herein, the term "alkylsulfinyl" refers to the group $R^xS(O)$—, where $R^x$ is alkyl.

As used herein, the term "alkenylsulfinyl" refers to the group $R^xS(O)$—, where $R^x$ is alkenyl.

As used herein, the term "alkynylsulfinyl" refers to the group $R^xS(O)$—, where $R^x$ is alkynyl.

As used herein, the term "alkylsulfonyl" refers to the group $R^xSO_2$—, where $R^x$ is alkyl.

As used herein, the term "alkenylsulfonyl" refers to the group $R^xSO_2$—, where $R^x$ is alkenyl.

As used herein, the term "alkynylsulfonyl" refers to the group $R^xSO_2$—, where $R^x$ is alkynyl.

As used herein, the term "cycloalkyl" refers to an optionally substituted non-aromatic, three- to twelve-membered, cyclic hydrocarbon ring, optionally containing one or more degrees of unsaturation, which may be optionally substituted as herein further described, with multiple degrees of substitution being allowed. Exemplary "cycloalkyl" groups as used herein include, but are not limited to, cyclopropyl, cyclobutyl, cyclopentyl, cyclohexyl, and cycloheptyl, as well as rings containing one or more degrees of unsaturation but short of aromatic, such as cyclopropenyl, cyclobutenyl, cyclopentenyl, cyclohexenyl, and cycloheptenyl.

As used herein, the term "cycloalkylene" refers to a divalent, non-aromatic, three- to twelve membered, cyclic hydrocarbon ring, which may be optionally substituted as herein further described, with multiple degrees of substitution being allowed. Exemplary "cycloalkylene" groups include, but are not limited to, cyclopropylene, cyclobutylene, cyclopentylene, cyclohexylene, cycloheptylene, and substituted versions thereof. The term is intended to encompass divalent rings having different points of attachment as well as a common point of attachment, which connecting atom may also be referred to as "spiroatom."

As used herein, the terms "heterocyclic", "heterocycle", and "heterocyclyl" refers to an optionally substituted univalent non-aromatic mono- or polycyclic ring system, optionally containing one or more degrees of unsaturation and also containing one or more heteroatoms selected from the group consisting of nitrogen, oxygen, and sulfur, which may be optionally substituted, including oxidized, as herein further described, with multiple degrees of substitution being allowed. Typically, the ring is three to twelve-membered and is either fully saturated or has one or more degrees of unsaturation. Such rings may be optionally fused to one or more of another heterocyclic ring(s), cycloalkyl ring(s), aryl groups (as defined below) or heteroaryl groups (as defined below). Examples of "heterocyclic" groups as used herein include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "heterocyclylene" refers to an optionally substituted non-aromatic diradical ring system, optionally containing one or more degrees of unsaturation and also containing one or more heteroatoms, selected from the group consisting of nitrogen, oxygen, and sulfur, which may be optionally substituted, including oxidized, as herein further described, with multiple degrees of substitution being allowed. Typically, the ring is three to twelve-membered and is either fully saturated or has one or more degrees of unsaturation. Such rings may be optionally fused to one or more of another heterocyclic ring(s), cycloalkyl ring(s), aryl groups (as defined below) or heteroaryl groups (as defined below). Examples of "heterocyclylene" include, but are not limited to, tetrahydrofuran-2,5-diyl, morpholine-2,3-diyl, and pyran-2,4-diyl.

As used herein, the term "aryl" refers to a univalent aromatic carbon containing ring or polycyclic fused ring system (up to three rings) where each ring contains between 3 to 7 atoms, which may be optionally substituted as herein further described, with multiple degrees of substitution being allowed. Examples of "aryl" groups as used include, but are not limited to, phenyl, 2-naphthyl, 1-naphthyl, anthracene, phenanthrene, and indene.

As used herein, the term "arylene" refers to a divalent aromatic carbon containing ring or polycyclic fused ring system (up to three rings) where each ring contains between 3 to 7 atoms, which may be optionally substituted as herein further described, with multiple degrees of substitution being allowed. Examples of "arylene" include, but are not limited to, benzene-1,4-diyl, naphthalene-1,8-diyl.

As used herein, the term "heteroaryl" refers to a monocyclic five to seven membered aromatic ring, or to a fused bicyclic aromatic ring system comprising two of such aromatic rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzodioxolyl, benzothiophene, indole, indazole, benzimidizolyl, imidazopyridinyl, pyrazolopyridinyl, and pyrazolopyrimidinyl.

As used herein, the term "heteroarylene" refers to a monocyclic five- to seven-membered aromatic ring diradical, or to a fused bicyclic ring system comprising two such rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroarylene" used herein include, but are not limited to, furan-2,5-diyl, thiophene-2,4-diyl, and pyridine-2,4-diyl.

As used herein, the term "fused cycloalkylaryl" refers to one or two cycloalkyl groups fused to an aryl group, the aryl and cycloalkyl groups having two atoms in common, and wherein the aryl group is the point of substitution. Examples of "fused cycloalkylaryl" used herein include 5-indanyl, and 5,6,7,8-tetrahydro-2-naphthyl

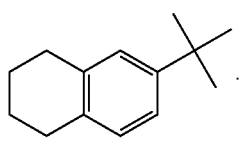

As used herein, the term "fused cycloalkylarylene" refers to a fused cycloalkylaryl, wherein the aryl group is divalent. Examples include

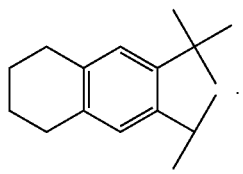

As used herein, the term "fused arylcycloalkyl" refers to one or two aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl) and

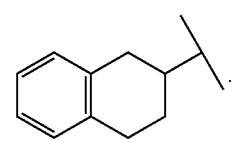

As used herein, the term "fused arylcycloalkylene" refers to a fused arylcycloalkyl, wherein the cycloalkyl group is divalent. Examples include 9,1-fluorenylene

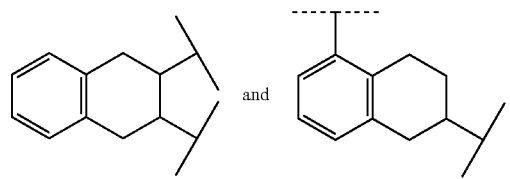

As used herein, the term "fused heterocyclylaryl" refers to one or two heterocyclyl groups fused to an aryl group, the aryl and heterocyclyl groups having two atoms in common, and wherein the aryl group is the point of substitution. Examples of "fused heterocyclylaryl" used herein include 3,4-methylenedioxy-1-phenyl and

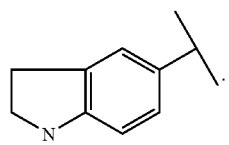

As used herein, the term "fused heterocyclylarylene" refers to a fused heterocyclylaryl, wherein the aryl group is divalent. Examples include

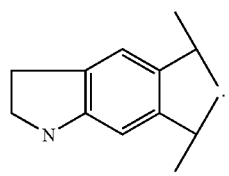

As used herein, the term "fused arylheterocyclyl" refers to one or two aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl) and

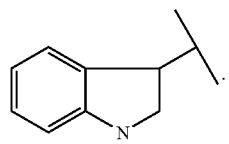

As used herein, the term "fused arylheterocyclylene" refers to a fused arylheterocyclyl, wherein the heterocyclyl group is divalent. Examples include

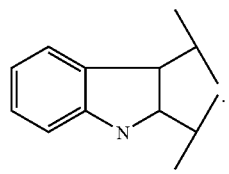

As used herein, the term "fused cycloalkylheteroaryl" refers to one or two cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl and

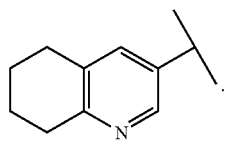

As used herein, the term "fused cycloalkylheteroarylene" refers to a fused cycloalkylheteroaryl, wherein the heteroaryl group is divalent. Examples include

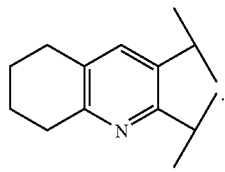

As used herein, the term "fused heteroarylcycloalkyl" refers to one or two heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl and

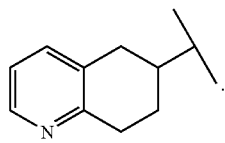

As used herein, the term "fused heteroarylcycloalkylene" refers to a fused heteroarylcycloalkyl, wherein the cycloalkyl group is divalent. Examples include

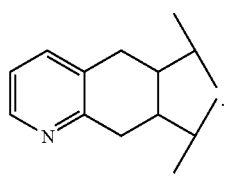

As used herein, the term "fused heterocyclylheteroaryl" refers to one or two heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl and

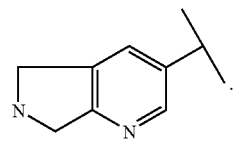

As used herein, the term "fused heterocyclylheteroarylene" refers to a fused heterocyclylheteroaryl, wherein the heteroaryl group is divalent. Examples include

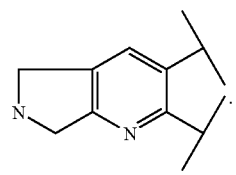

As used herein, the term "fused heteroarylheterocyclyl" refers to one or two heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include-5-aza-2,3-dihydrobenzofuran-2-yl and

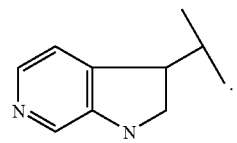

As used herein, the term "fused heteroarylheterocyclylene" refers to a fused heteroarylheterocyclyl, wherein the heterocyclyl group is divalent. Examples include

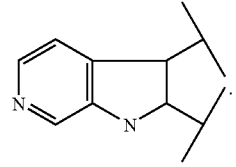

As used herein, the term "acyl" refers to the group $R^xC(O)$—, where $R^x$ is alkyl, alkenyl, alkynyl, cycloalkyl, cycloalkenyl, or heterocyclyl.

As used herein, the term "aroyl" refers to the group $R^xC(O)$—, where $R^x$ is aryl.

As used herein, the term "heteroaroyl" refers to the group $R^xC(O)$—, where $R^x$ is heteroaryl.

As used herein, the term "alkoxycarbonyl" refers to the group $R^xOC(O)$—, where $R^x$ is alkyl.

As used herein, the term "acyloxy" refers to the group $R^xC(O)O$—, where $R^x$ is alkyl, alkenyl, alkynyl, cycloalkyl, cycloalkenyl, or heterocyclyl.

As used herein, the term "aroyloxy" refers to the group $R^xC(O)O$—, where $R^x$ is aryl.

As used herein, the term "heteroaroyloxy" refers to the group $R^xC(O)O$—, where $R^x$ is heteroaryl.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

As used herein, the term "haloalkylene" refers to a straight or branched chain divalent hydrocarbon radical, substituted with at least one halogen. The term should be interpreted to include perfluoroalkylene groups such as —$CF_2$—.

As used herein, the term "haloalkoxy" refers to a group —$OR^x$, where $R^x$ is a haloalkyl group as herein defined. As non-limiting examples, haloalkoxy groups include —$O(CH_2)F$, —$O(CH)F_2$, and —$OCF_3$.

As used herein the term "nitro" refers to a group —$NO_2$.

As used herein the term "cyano" refers to a group —CN.

As used herein the term "azido" refers to a group —$N_3$.

As used herein the term "amide" refers to a group —C(O)$NR^xR^y$ or —$NR^xC(O)$—, where each $R^x$ and $R^y$ individually is hydrogen, alkyl, alkenyl, alkynyl, cycloalkyl, aryl, heterocylcyl, or heteroaryl.

As used herein "amino" refers to a group —$NR^xR^y$, where each of $R^x$ and $R^y$ individually is hydrogen, alkyl, alkenyl, alkynyl, cycloalkyl, aryl, heterocylcyl, or heteroaryl. As used herein, when either $R^x$ or $R^y$ is other than hydrogen, such a group may be referred to as a "substituted amino" or, for example if $R^x$ is H and $R^y$ is alkyl, as an "alkylamino."

As used herein, the term "oxo" shall refer to the substituent =O, and is available as a substituent on carbon atoms have at least two hydrogens available for substitution and on heteroatoms such as nitrogen and sulfur where the heteroatom may be oxidized to form a bond with the oxo substituent.

As used herein, the terms "hydroxy" and "hydroxyl" refer to a group —OH.

As used herein, the term "aminosulfonyl" refers to the substituent —$SO_2NH_2$.

As used herein, the term "mercapto" refers to the substituent —SH.

As used herein, the terms "carboxy" and "carboxyl" refer to the substituent —COOH.

As used herein, the term "carbamoyl" refers to the substituent —C(O)$NH_2$.

As used herein, the term "sulfanyl" refers to the substituent —S—.

As used herein, the term "sulfinyl" refers to the substituent —S(O)—.

As used herein, the term "sulfonyl" refers to the substituent —$S(O)_2$—.

As used herein, the term "optionally" means that the subsequently described event(s) may or may not occur.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

As used herein, the phrase "one or more substituents" refers to a number of substituents that equals from one to the maximum number of substituents possible based on the number of available bonding sites, provided that the above conditions of stability and chemical feasibility are met.

As used herein the terms "pharmaceutically acceptable carrier", "pharmaceutically acceptable diluent", and pharmaceutically acceptable excipient" means the carrier, diluent or excipient must be compatible with the other ingredients of the formulation and not deleterious to the recipient thereof.

As used herein the term "therapeutically effective amount" as used herein means that amount of active compound or pharmaceutical agent that elicits the biological or medicinal response in a tissue, system, animal, human, or subject that is being sought by a researcher, veterinarian, medical doctor, patient or other clinician, which includes reduction or alleviation of the symptoms of the disease being treated. When the active compound (i.e., active ingredient) is administered as the salt, references to the amount of active ingredient are to the free acid or free base form of the compound.

As used herein, "Subject(s)" include, for example, horses, cows, sheep, pigs, mice, dogs, cats, primates such as chimpanzees, gorillas, rhesus monkeys, and, humans. In one embodiment, a subject is a human. In another embodiment, a subject is a human in need of activation of GLP-1R.

Compounds

Embodiments of the present invention comprise substituted tetrahydroisoquinoline derivatives, compositions, and methods of use thereof. The present invention may be embodied in a variety of ways.

In a first aspect, the present invention provides tetrahydroisoquinoline derivatives which are modulators of GLP-1R which may be useful for the management and treatment of disease where modulation of the human GLP-1 receptor is beneficial.

In a first exemplary embodiment, the present invention provides a compound of Formula (I):

Formula (I)

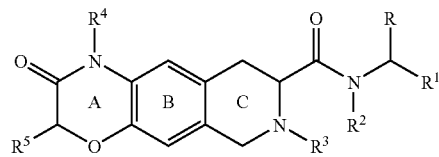

wherein

R is —$(CH_2)_p$-$G^1$-$L^1$-$G^2$, wherein $L^1$ is selected from the group consisting of: a direct bond, —$CH_2$—, —O—, —$N(R^{16})$—, —C(O)—, —CON($R^{16}$), —$N(R^{16})C(O)$—, —$N(R^{16})SO_2$—, —$SO_2N(R^{16})$—, —C(O)—O—, —O—C(O)—, —S—, —S(O)—, —$S(O)_2$—, and —C≡C—, wherein $R^{16}$ is selected from the group consisting of: —hydrogen, —alkyl, —aryl, —alkylene-aryl;

$G^1$ is selected from the group consisting of: alkynylene, arylene, heteroarylene, fused arylcycloalkylene, fused cycloalkylarylene, fused cycloalkylheteroarylene, fused heterocyclylarylene, and fused heterocyclylheteroarylene, wherein $G^1$ is optionally substituted 1-4 times with substituents independently selected from $R^{10}$, wherein
$R^{10}$ is $R^b$, $G^2$ is selected from the group consisting of: —aryl, —heteroaryl, —fused arylcycloalkyl, —fused cycloalkylaryl, —fused cycloalkylheteroaryl, —fused heterocyclylaryl, and —fused heterocyclylheteroaryl, wherein $G^2$ is optionally substituted 1-4 times with substituents independently selected from $R^{11}$, wherein
$R^{11}$ is $R^b$, $R^1$ is selected from the group consisting of: —CO$_2$H, —CO$_2$R$^{12}$, —C(O)NH$_2$, —C(O)NHR$^{12}$, —tetrazole, and acid isostere, wherein
$R^{12}$ is selected from the group consisting of: —C$_{1-10}$ alkyl, —cycloalkyl, and —aryl, wherein $R^{12}$ is optionally substituted 1-4 times with a group independently selected from $R^c$;

$R^2$ is selected from the group consisting of: —hydrogen, —alkyl, —phenyl, —cycloalkyl, —alkylene-cycloalkyl, and —alkylene-phenyl, wherein alkyl, phenyl, and cycloalkyl groups are optionally substituted 1-4 times with a group independently selected from $R^c$;

$R^3$ is selected from $R^a$;

$R^4$ is selected from $R^a$; and $R^5$ is -$G^3$-$L^2$-$Q^2$-$L^3$-$G^4$, wherein
$L^2$ and $L^3$ are independently selected from the group consisting of: a direct bond, —CH$_2$—, —O—, —N(R$^{26}$)—, —C(O)—, —CON(R$^{26}$)—, —N(R$^{26}$)C(O)—, —N(R$^{26}$)CON(R$^{27}$)—, —N(R$^{26}$)C(O)O—, —OC(O)N(R$^{26}$)—, —N(R$^{26}$)SO$_2$—, —SO$_2$N(R$^{26}$)—, —C(O)—O—, —O—C(O)—, —S—, —S(O)—, —S(O)$_2$—, and —N(R$^{26}$)SO$_2$N(R$^{27}$)—, wherein
R$^{26}$ and R$^{27}$ are independently selected from the group consisting of: hydrogen, —alkyl, —aryl, and —alkylene-aryl, wherein R$^{26}$ and R$^{27}$ are optionally substituted 1-4 times with R$^c$, or R$^{26}$ and R$^{27}$ are taken together with the atoms to which they are attached to form a heterocyclic ring of 5 to 7 members containing 0-2 additional heteroatoms independently selected from oxygen, nitrogen, and sulfur;

$Q^2$ is selected from the group consisting of: a direct bond, $C_{1-10}$ alkylene, $C_{2-10}$ alkenylene, and $C_{2-10}$ alkynylene, $G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
$G^3$ is optionally substituted 1-4 times with substituents independently selected from $R^8$, wherein $R^8$ is selected from $R^b$, $G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
$G^4$ is optionally substituted 1-4 times with substituents independently selected from $R^9$, wherein $R^9$ is selected from $R^b$, Rings B and C are optionally substituted 1-4 times with substituents independently selected from the group consisting of $R^b$;

$R^a$ is selected from the group consisting of:
a) —hydrogen,
b) —S(O)$_m$R$^d$,
c) —S(O)$_2$OR$^d$,
d) —S(O)$_m$NR$^d$R$^e$,
e) —C(O)R$^d$,
f) —CO$_2$R$^d$,
g) —C(O)NR$^d$R$^e$,
h) —haloalkyl,
i) —cycloalkyl,
j) —heterocyclyl,
k) —C$_{1-10}$ alkyl,
l) —C$_{2-10}$ alkenyl,
m) —C$_{2-10}$ alkynyl,
n) —aryl,
o) —heteroaryl,
p) —C$_{1-10}$ alkylene-aryl,
q) —C$_{2-10}$ alkynylene-aryl,
r) —C$_{1-10}$ alkylene-heteroaryl,
s) —C$_{2-10}$ alkynylene-heteroaryl, and
t) —C(R$^f$R$^g$)$_n$-aryl,
wherein alkyl, alkenyl, alkynyl, aryl, heterocyclyl, heteroaryl, and cycloalkyl groups are optionally substituted 1-4 times with a group independently selected from $R^c$;

$R^b$ is selected from the group consisting of:
a) —cycloalkyl,
b) —cyano,
c) —OR$^d$,
d) —NO$_2$,
e) —halogen,
f) —S(O)$_m$R$^d$,
g) —SR$^d$,
h) —S(O)$_2$OR$^d$,
i) —S(O)$_m$NR$^d$R$^e$,
j) —NR$^d$R$^e$,
k) —O(CR$^f$R$^g$)$_n$NR$^d$R$^e$,
l) —C(O)R$^d$,
m) —CO$_2$R$^d$,
n) —CO$_2$(CR$^f$R$^g$)$_n$CONR$^d$R$^e$,
o) —OC(O)R$^d$,
p) —C(O)NR$^d$R$^e$,
q) —NR$^d$C(O)R$^e$,
r) —OC(O)NR$^d$R$^e$,
s) —NR$^d$C(O)OR$^e$,
t) —NR$^d$C(O)NR$^d$R$^e$,
u) —CF$_3$,
v) —OCF$_3$,
w) —haloalkyl,
x) —haloalkoxy,
y) —C$_{1-10}$ alkyl,
z) —C$_{2-10}$ alkenyl,
aa) —C$_{2-10}$ alkynyl,
ab) —C$_{1-10}$ alkylene-aryl,
ac) —C$_{1-10}$ alkylene-heteroaryl, and
ad) —heteroaryl,
wherein alkyl, alkenyl, alkynyl, aryl, heteroaryl, and cycloalkyl groups are optionally substituted 1-4 times with a group independently selected from $R^c$;

$R^c$ is selected from the group consisting of:
a) —halogen,
b) —amino,
c) —carboxy,
d) —cyano,
e) —C$_{1-4}$ alkyl,
f) —O—C$_{1-4}$ alkyl,
g) —O—CF$_3$,
h) —cycloalkyl, i) —O-cycloalkyl,
j) —aryl,
k) —$C_{1-4}$ alkylene-aryl,
l) —hydroxy,
m) —$CF_3$,
n) —haloalkyl,
o) —haloalkoxy,
p) —O-aryl,
q) —heteroaryl,
r) —heteroarylene-$C_{1-10}$ alkyl,
s) —heterocyclyl,
t) —$CO_2$—$C_{1-10}$ alkyl,
u) —$CO_2$—$C_{1-10}$ alkyl-aryl,
v) —fused arylcycloalkyl,
w) —alkynylene-heteroaryl,
x) —alkylene-aryl,
y) —alkynylene-aryl,
z) —nitro,
aa) —N(H)—C(O)—$C_{1-6}$-alkyl, and
bb) —S—$C_{1-6}$-alkyl, $R^d$ and $R^e$ are independently selected from the group consisting of: hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$, $R^f$ and $R^g$ are independently selected from the group consisting of: hydrogen, $C_{1-10}$ alkyl, cycloalkyl, —$C_{1-10}$ alkylene-cycloalkyl, —carboxy, and aryl, wherein alkyl, cycloalkyl, and aryl groups are optionally substituted with one to four substituents independently selected from $R^c$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$;

m is an integer from 1 to 2;
n is an integer from 1 to 10; and
p is an integer from 0 to 2;

or a pharmaceutically acceptable salt thereof.

In a second exemplary embodiment, the present invention relates to compounds of the first exemplary embodiment, wherein Rings B and C of Formula (I) contain no further substitutions.

In a third exemplary embodiment, the present invention relates to compounds of the first or second exemplary embodiments, wherein, when a substituent is an aryl group, the aryl group is a phenyl group.

In a fourth exemplary embodiment, the present invention relates to compounds of the first through third exemplary embodiments, wherein, when a substituent is a heteroaryl group, each of the heteroaryl groups is independently selected from the group consisting of pyridinyl, pyridazinyl, pyrimidinyl, pyrazinyl, furanyl, pyrrolyl, pyranyl, thiophenyl, isoxazolyl, oxazolyl, thiazolyl, isothiazolyl, imidazolyl, pyrazolyl, indolyl, benzofuranyl, benzothiophenyl and quinolinyl.

In a fifth exemplary embodiment, the present invention relates to compounds of the first through fourth exemplary embodiments, wherein, when a substituent is a heterocyclyl group, each of the heterocyclyl groups is independently selected from the group consisting of piperidinyl, piperazinyl, morpholinyl, dioxanyl, pyrrolidinyl, tetrahydro furanyl, dioxolanyl, imidazolidinyl and pyrazolidinyl.

In a sixth exemplary embodiment, the present invention relates to compounds of the first through fifth exemplary embodiments, wherein $R^1$ is selected from the group consisting of —$CO_2H$ and —$CO_2R^{12}$.

In a seventh exemplary embodiment, the present invention relates to compounds of the first through fifth exemplary embodiments, wherein $R^1$ is —$CO_2H$.

In an eighth exemplary embodiment, the present invention relates to compounds of the first through seventh exemplary embodiments, wherein $R^2$ is selected from the group consisting of: hydrogen and —$C_{1-10}$ alkyl.

In a ninth exemplary embodiment, the present invention relates to compounds of the first through seventh exemplary embodiments, wherein $R^2$ is hydrogen.

In a tenth exemplary embodiment, the present invention relates to compounds of the first through ninth exemplary embodiments, wherein p is 1.

In an eleventh exemplary embodiment, the present invention relates to compounds of the first through tenth exemplary embodiments, wherein $L^1$ is a direct bond.

In a twelfth exemplary embodiment, the present invention relates to compounds of the first through ninth exemplary embodiments, wherein
p is 1,
$G^1$ is a substituted or unsubstituted phenyl,
$L^1$ is selected from the group consisting of a direct bond, —O—, and —N(H)C(O)—, and
$G^2$ is a phenyl group substituted 1-4 times with substituents independently selected from $R^{11}$, and $G^2$ is substituted with at least one substituent selected from the group consisting of:
a) —$C_{1-10}$ alkyl,
b) —haloalkyl,
c) —haloalkoxy,
d) —$CF_3$,
e) —$OCF_3$,
f) —halogen,
g) —O—$R^d$,
h) —cyano,
i) —C(O)$R^d$,
j) —$NR^dR^e$,
k) —cycloalkyl, and
l) —$CO_2R^d$,
wherein alkyl and cycloalkyl groups are optionally substituted 1-4 times with a group independently selected from $R^c$.

In a thirteenth exemplary embodiment, the present invention relates to compounds of the first through ninth exemplary embodiments, wherein
p is 1,
$G^1$ is a $C_{2-10}$ alkylene,
$L^1$ is a direct bond, and
$G^2$ is a substituted or unsubstituted phenyl group.

In a fourteenth exemplary embodiment, the present invention relates to compounds of the first through ninth exemplary embodiments, wherein
p is 1,
$G^1$ is —C≡C—,
$L^1$ is a direct bond, and
$G^2$ is a substituted or unsubstituted phenyl group substituted 1-4 times with substituents independently selected from $R^{11}$, and $G^2$ is substituted with at least one substituent selected from the group consisting of:
a) —$C_{1-10}$ alkyl,
b) —haloalkyl, c) —haloalkoxy,
d) —CF$_3$,
e) —OCF$_3$,
f) —halogen,
g) —O—R$^d$,
h) —cyano,
i) —C(O)R$^d$,
j) —NR$^d$R$^e$,
k) —cycloalkyl,
l) —CO$_2$R$^d$,
 wherein the alkyl and cycloalkyl groups are optionally substituted 1-4 times with a group independently selected from R$^c$.

In a fifteenth exemplary embodiment, the present invention relates to compounds of the first through ninth exemplary embodiments, wherein
 p is 1,
 G$^1$ is a substituted or unsubstituted phenyl,
 L$^1$ is a direct bond, and
 G$^2$ is selected from the group consisting of: indole, pyridine, pyrimidine, quinoline, isoxazole, wherein G$^2$ is optionally substituted or unsubstituted.

In a sixteenth exemplary embodiment, the present invention relates to compounds of the first through ninth exemplary embodiments, wherein
 p is 1,
 G$^1$ is an unsubstituted phenyl,
 L$^1$ is a direct bond, and
 G$^2$ is a phenyl, substituted with a cyano group.

In a seventeenth exemplary embodiment, the present invention relates to compounds of the first through sixteenth exemplary embodiments, wherein R$^3$ is selected from the group consisting of:
a) —C$_{1-10}$ alkyl,
b) —phenyl,
c) —thiophenyl,
d) —furanyl,
e) —pyridyl,
f) —C$_{1-10}$ alkylene-pyridyl,
g) —C$_{1-10}$ alkylene-aminothiazolyl,
h) —C$_{1-10}$ alkylene-imidazolyl,
i) —C$_{1-10}$ alkylene-oxazolyl,
j) —C$_{1-10}$ alkylene-thiophenyl,
k) —C$_{2-10}$ alkynylene-phenyl,
l) —C$_{2-10}$ alkynylene-thiophenyl,
m) —C$_{2-10}$ alkynylene-pyridyl,
n) —C$_{2-10}$ alkynylene-pyrimidinyl,
o) —SO$_2$-phenyl,
p) —CO$_2$—C$_{1-10}$ alkyl,
q) —CO$_2$-cycloalkyl,
r) —CO$_2$-tetrahydrofuranyl,
s) —CO$_2$-tetrahydropyranyl,
t) —CO$_2$—C$_{1-10}$ alkylene-cycloalkyl,
u) —CO$_2$—C$_{2-10}$-alkynyl,
v) —CO$_2$—CH$_2$—C≡C-phenyl,
w) —C(O)—C$_{1-10}$ alkyl,
x) —C(O)-phenyl,
y) —C(O)-naphthyl,
z) —C(O)-cycloalkyl,
aa) —C(O)-furanyl,
bb) —C(O)-thiophenyl,
cc) —C(O)-isoxazolyl,
dd) —C(O)—C$_{1-10}$ alkylene-cycloalkyl,
ee) —C(O)—NH—C$_{1-10}$ alkyl,
ff) —C(O)—NH-phenyl, and
gg) —C(O)—N(cycloalkyl)-C$_{1-10}$ phenyl,
 wherein the alkyl, alkynyl, cycloalkyl, tetrahydrofuranyl, tetrahydropyranyl, phenyl, naphthyl, thiophenyl, furanyl, pyridyl, pyrimidinyl, thiazolyl, imidazolyl, oxazolyl, and isoxazolyl groups are optionally substituted 1-4 times with a group independently selected from R$^c$.

In an eighteenth exemplary embodiment, the present invention relates to compounds of the first through sixteenth exemplary embodiments, wherein R$^3$ is —C$_{1-10}$ alkyl substituted with a phenyl group.

In a nineteenth exemplary embodiment, the present invention relates to compounds of the first through sixteenth exemplary embodiments, wherein R$^3$ is selected from the group consisting of:
a) —CO$_2$-tert-butyl,
b) —CO$_2$-n-hexyl,
c) —CO$_2$-isopropyl,
d) —CO$_2$— (tert-butylcyclohexyl)
e) —CO$_2$-tetrahydrofuran-2-yl,
f) —CO$_2$-tetrahydropyran-4-yl,
g) —CO$_2$—CH$_2$-cyclopropyl,
h) —C(O)NH-(tert-butylphenyl),
i) —C(O)-piperidin-2-yl,
j) —C(O)—NH-(trifluoromethoxyphenyl),
k) —C(O)—NH-(1,1-diphenylmethyl),
l) —C(O)-isopropyl,
m) —C(O)-phenyl,
n) —C(O)-(fluorophenyl),
o) —C(O)-(chlorophenyl),
p) —C(O)-(cyanophenyl),
q) —C(O)-pyridin-2-yl,
r) —C(O)-pyrimidin-4-yl,
s) —C(O)-furan-2-yl,
t) —C(O)-cyclobutyl,
u) —C(O)-cyclopentyl,
v) —C(O)-cyclohexyl,
w) —C(O)-thiophene-2-yl,
x) —C(O)-benzyl,
y) —C(O)-(fluorobenzyl),
z) —C(O)-(chlorobenzyl),
aa) —C(O)-(cyanobenzyl),
bb) —C(O)-(2,5-dimethyl-oxazol-4-yl),
cc) —CH$_2$-oxazol-2-yl,
dd) —CH$_2$-(1-methylimidazol-2-yl),
ee) —CH$_2$-pyridin-2-yl,
ff) —CH$_2$-furan-2-yl,
gg) —CH$_2$-thiazol-2-yl,
hh) —CH$_2$—C≡C-pyrimidin-2-yl,
ii) —CH$_2$—C≡C-phenyl,
jj) —CH$_2$-thiophene-2-yl,
kk) —(R)-1-(phenyl)-propyl, and
ll) —(S)-1-(phenyl)-propyl.

In an twentieth exemplary embodiment, the present invention relates to compounds of the first through nineteenth exemplary embodiments, wherein R$^4$ is selected from the group consisting of: hydrogen, C$_{1-10}$ alkyl, C$_{2-10}$ alkenyl, C$_{2-10}$ alkynyl, cycloalkyl, —C$_{1-10}$ alkylene-cycloalkyl, aryl, heteroaryl, and heterocyclyl, wherein the alkyl, alkenyl, alkynyl, cycloalkyl, aryl, heteroaryl, heterocyclyl groups are optionally substituted with one to four substituents independently selected from R$^c$.

In a twenty-first exemplary embodiment, the present invention relates to compounds of the first through nineteenth exemplary embodiments, wherein R$^4$ is selected from the group consisting of:
a) —hydrogen,
b) —C$_{1-6}$ alkyl, and
c) —C(O)—C$_{1-6}$ alkyl.

In a twenty-second exemplary embodiment, the present invention relates to compounds of the first through nineteenth exemplary embodiments, wherein $R^4$ is $-C_{1-3}$ alkyl.

In a twenty-third exemplary embodiment, the present invention relates to compounds of the first through nineteenth exemplary embodiments, wherein $R^4$ is hydrogen.

In a twenty-fourth exemplary embodiment, the present invention relates to compounds of the first through twenty-third exemplary embodiments, wherein $R^5$ is $-G^3-L^2-Q^2-L^3-G^4$, wherein
  $L^2$ is selected from the group consisting of: a direct bond, $-CH_2-$, $-O-$, $-N(R_{26})-$, $-C(O)-$, $-CON(R_{26})-$, $-N(R_{26})C(O)-$, $-N(R_{26})CON(R_{27})-$, $-N(R_{26})C(O)O-$, $-OC(O)N(R_{26})-$, $-N(R_{26})SO_2-$, $-SO_2N(R_{26})-$, $-C(O)-O-$, $-O-C(O)-$, $-S-$, $-S(O)-$, $-S(O)_2-$, and $-N(R_{26})SO_2N(R_{27})-$,
    wherein $R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$ or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
  $L^3$ is a direct bond;
  $Q^2$ is selected from the group consisting of: a direct bond, $C_{1-10}$ alkylene, $C_{2-10}$ alkenylene, and $C_{2-10}$ alkynylene;
  $G^3$ is a phenylene group,
    wherein $G^3$ is optionally substituted 1-4 times with substituents independently selected from $R^8$, wherein $R^8$ is selected from $R^b$; and
  $G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl,
    wherein $G^4$ is optionally substituted 1-4 times with substituents independently selected from $R^9$, wherein $R^9$ is selected from $R^b$.

In a twenty-fifth exemplary embodiment, the present invention relates to compounds of the first through twenty-third exemplary embodiments, wherein $R^5$ is $-G^3-L^2-Q^2-L^3-G^4$, wherein
  $L^2$ is selected from the group consisting of: $-CH_2-$, $-O-$, $-N(R^{26})-$, and $-C(O)-$,
    wherein $R^{26}$ is selected from the group consisting of: hydrogen, —alkyl, —aryl, and —alkylene-aryl;
  $L^3$ is a direct bond;
  $Q^2$ is a $C_{1-10}$ alkylene group;
  $G^3$ is a phenylene group,
    wherein $G^3$ is optionally substituted 1-4 times with substituents independently selected from $R^8$, wherein $R^8$ is selected from $R^b$; and
  $G^4$ is selected from the group consisting of: cycloalkyl, phenyl, pyridinyl, benzothiophenyl, benzothiazolyl, $G^4$ is optionally substituted 1-4 times with substituents independently selected from $R^9$, wherein $R^9$ is selected from $R^b$.

In a twenty-sixth exemplary embodiment, the present invention relates to compounds of the first through twenty-third exemplary embodiments, wherein $R^5$ is $-G^3-L^2-Q^2-L^3-G^4$, wherein
  $L^2$ is selected from the group consisting of: $-CH_2-$, $-O-$, $-N(R^{26})-$, and $-C(O)-$,
    wherein $R^{26}$ is selected from the group consisting of: hydrogen, —alkyl, —aryl, and —alkylene-aryl;
  $L^3$ is a direct bond;
  $Q^2$ is selected from the group consisting of: a direct bond and a $C_{1-10}$ alkylene group;
  $G^3$ is a phenylene group,
    wherein $G^3$ is optionally substituted 1-4 times with substituents independently selected from $R^8$, wherein $R^8$ is selected from $R^b$; and
  $G^4$ is a phenyl group, wherein $G^4$ is substituted 1-4 times with substituents independently selected from $R^9$, wherein $R^9$ is selected from $R^b$, and wherein $G^4$ is substituted with at least one substituent selected from the group consisting of:
    a) $-C_{1-6}$ alkyl,
    b) —haloalkyl,
    c) —halogen,
    d) —alkoxy,
    e) —haloalkoxy,
    f) $-CF_3$, and
    g) $-O-CF_3$.

In a twenty-seventh exemplary embodiment, the present invention relates to compounds of the first through twenty-third exemplary embodiments, wherein $R^5$ is $-G^3-L^2-Q^2-L^3-G^4$, wherein
  $L^2$ is $-O-$,
  $L^3$ is a direct bond;
  $Q^2$ is a $C_{1-10}$ alkylene group;
  $G^3$ is a phenylene group, and
  $G^4$ is a phenyl group, wherein $G^4$ is substituted 1-4 times with substituents independently selected from $R^9$, wherein $R^9$ is selected from $R^b$, and wherein $G^4$ is substituted with at least one substituent selected from the group consisting of:
    h) $-C_{1-6}$ alkyl,
    i) —haloalkyl,
    j) —halogen,
    k) —alkoxy,
    l) —haloalkoxy,
    m) $-CF_3$, and
    n) $-O-CF_3$.

In another embodiment of the present invention, the configuration of the compound of Formula (I) of the first exemplary embodiment is represented by Formula (I-A):

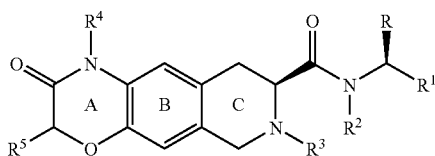

Formula (I-A)

wherein the variables are as defined above, or a pharmaceutically acceptable salt thereof.

In another embodiment of the present invention, the compound of Formula (I) of the first exemplary embodiment is represented by Formula (I-B):

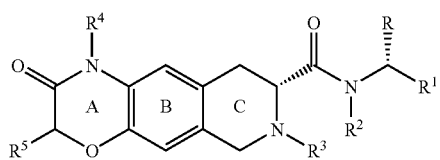

Formula (I-B)

wherein the variables are as defined above, or a pharmaceutically acceptable salt thereof.

In another embodiment of the present invention, the compound of Formula (I) of the first exemplary embodiment is represented by Formula (I-C):

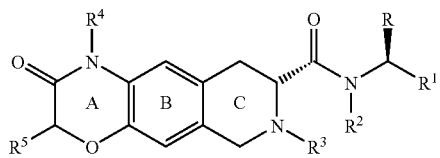

Formula (I-C)

wherein the variables are as defined above, or a pharmaceutically acceptable salt thereof.

In another embodiment of the present invention, the compound of Formula (I) of the first exemplary embodiment is represented by Formula (I-D):

Formula (I-D)

wherein the variables are as defined above, or a pharmaceutically acceptable salt thereof.

In another embodiment of the present invention, the compound of Formula (I) of the first exemplary embodiment is represented by Formula (I-E):

Formula (I-E)

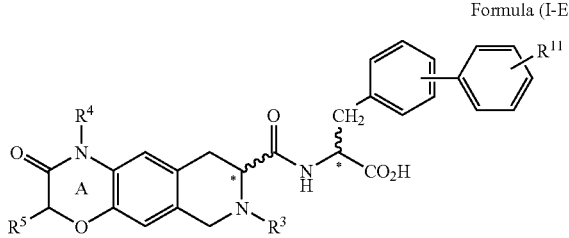

wherein * indicates the presence of a chiral center which may be in the R- or S-configuration and wherein the variables are as defined above, or a pharmaceutically acceptable salt thereof.

In another embodiment, the present invention provides a compound of Formula (II):

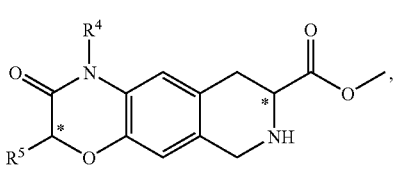

(II)

wherein
$R^4$ is selected from $R^a$; and
$R^5$ is $-G^3-L^2-Q^2-L^3-G^4$, wherein
   $L^2$ and $L^3$ are independently selected from the group consisting of: a direct bond, $-CH_2-$, $-O-$, $-N(R^{26})-$, $-C(O)-$, $-CON(R^{26})-$, $-N(R^{26})C(O)-$, $-N(R^{26})CON(R^{27})-$, $-N(R^{26})C(O)O-$, $-OC(O)N(R^{26})-$, $-N(R^{26})SO_2-$, $-SO_2N(R^{26})-$, $-C(O)-O-$, $-O-C(O)-$, $-S-$, $-S(O)-$, $-S(O)_2-$, and $-N(R^{26})SO_2N(R^{27})-$, wherein
      $R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$, or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
   $Q^2$ is selected from the group consisting of: a direct bond, $C_{1-10}$ alkylene, $C_{2-10}$ alkenylene, and $C_{2-10}$ alkynylene,
   $G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
      $G^3$ is optionally substituted 1-4 times with substituents independently selected from $R^8$, wherein $R^8$ is selected from $R^b$,
   $G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
      $G^4$ is optionally substituted 1-4 times with substituents independently selected from $R^9$, wherein $R^9$ is selected from $R^b$,
wherein $R^a$ is selected from the group consisting of:
   a) —hydrogen,
   b) $-S(O)_mR^d$,
   c) $-S(O)_2OR^d$,
   d) $-S(O)_mNR^dR^e$,
   e) $-C(O)R^d$,
   f) $-CO_2R^d$,
   g) $-C(O)NR^dR^e$,
   h) —haloalkyl,
   i) —cycloalkyl,
   j) —heterocyclyl,
   k) $-C_{1-10}$ alkyl,
   l) $-C_{2-10}$ alkenyl,
   m) $-C_{2-10}$ alkynyl,
   n) —aryl,
   o) —heteroaryl,
   p) $-C_{1-10}$ alkylene-aryl, q) —$C_{2-10}$ alkynylene-aryl,
r) —$C_{1-10}$ alkylene-heteroaryl,
s) —$C_{2-10}$ alkynylene-heteroaryl, and
t) —$C(R^fR^g)_n$-aryl,
wherein alkyl, alkenyl, alkynyl, aryl, heterocyclyl, heteroaryl, and cycloalkyl groups are optionally substituted 1-4 times with a group independently selected from $R^c$;

$R^b$ is selected from the group consisting of:
a) —cycloalkyl,
b) —cyano,
c) —$OR^d$,
d) —$NO_2$,
e) —halogen,
f) —$S(O)_mR^d$,
g) —$SR^d$,
h) —$S(O)_2OR^d$,
i) —$S(O)_mNR^dR^e$,
j) —$NR^dR^e$,
k) —$O(CR^fR^g)_nNR^dR^e$,
l) —$C(O)R^d$,
m) —$CO_2R^d$,
n) —$CO_2(CR^fR^g)_nCONR^dR^e$,
o) —$OC(O)R^d$,
p) —$C(O)NR^dR^e$,
q) —$NR^dC(O)R^e$,
r) —$OC(O)NR^dR^e$,
s) —$NR^dC(O)OR^e$,
t) —$NR^dC(O)NR^dR^e$,
u) —$CF_3$,
v) —$OCF_3$,
w) —haloalkyl,
x) —haloalkoxy,
y) —$C_{1-10}$ alkyl,
z) —$C_{2-10}$ alkenyl,
aa) —$C_{2-10}$ alkynyl,
ab) —$C_{1-10}$ alkylene-aryl,
ac) —$C_{1-10}$ alkylene-heteroaryl, and
ad) —heteroaryl,
wherein alkyl, alkenyl, alkynyl, aryl, heteroaryl, and cycloalkyl groups are optionally substituted 1-4 times with a group independently selected from $R^c$;

$R^c$ is selected from the group consisting of:
a) —halogen,
b) —amino,
c) —carboxy,
d) —cyano,
e) —$C_{1-4}$ alkyl,
f) —O—$C_{1-4}$ alkyl,
g) —O—$CF_3$,
h) —cycloalkyl,
i) —O-cycloalkyl,
j) —aryl,
k) —$C_{1-4}$ alkylene-aryl,
l) —hydroxy,
m) —$CF_3$,
n) —haloalkyl,
o) —haloalkoxy,
p) —O-aryl,
q) —heteroaryl,
r) —heteroarylene-$C_{1-10}$ alkyl,
s) —heterocyclyl,
t) —$CO_2$—$C_{1-10}$ alkyl,
u) —$CO_2$—$C_{1-10}$ alkyl-aryl,
v) —fused arylcycloalkyl,
w) —alkynylene-heteroaryl,
x) —alkylene-aryl, y) —alkynylene-aryl,
z) —nitro,
aa) —N(H)—C(O)—$C_{1-6}$-alkyl, and
bb) —S—$C_{1-6}$-alkyl, $R^d$ and $R^e$ are independently selected from the group consisting of: hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$, $R^f$ and $R^g$ are independently selected from the group consisting of: hydrogen, $C_{1-10}$ alkyl, cycloalkyl, —$C_{1-10}$ alkylene-cycloalkyl, —carboxy, and aryl, wherein alkyl, cycloalkyl, and aryl groups are optionally substituted with one to four substituents independently selected from $R^e$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$;

m is an integer from 1 to 2;
n is an integer from 1 to 10; and
p is an integer from 0 to 2;

or a pharmaceutically acceptable salt thereof.

In another embodiment, the present invention provides a compound of Formula (III):

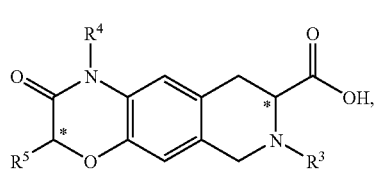

(III)

wherein
$R^3$ is selected from $R^a$;
$R^4$ is selected from $R^a$; and
$R^5$ is -$G^3$-$L^2$-$Q^2$-$L^3$-$G^4$, wherein
$L^2$ and $L^3$ are independently selected from the group consisting of: a direct bond, —$CH_2$—, —O—, —$N(R^{26})$—, —$C(O)$—, —$CON(R^{26})$—, —$N(R^{26})C(O)$—, —$N(R^{26})CON(R^{27})$—, —$N(R^{26})C(O)O$—, —$OC(O)N(R^{26})$—, —$N(R^{26})SO_2$—, —$SO_2N(R^{26})$—, —$C(O)$—O—, —O—$C(O)$—, —S—, —$S(O)$—, —$S(O)_2$—, and —$N(R^{26})SO_2N(R^{27})$—, wherein
$R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$, or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
$Q^2$ is selected from the group consisting of: a direct bond, $C_{1-10}$ alkylene, $C_{2-10}$ alkenylene, and $C_{2-10}$ alkynylene,
$G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
  $G^3$ is optionally substituted 1-4 times with substituents independently selected from $R^8$, wherein $R^8$ is selected from $R^b$,
$G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
  $G^4$ is optionally substituted 1-4 times with substituents independently selected from $R^9$, wherein $R^9$ is selected from $R^b$, wherein $R^a$ is selected from the group consisting of:
a) —hydrogen,
b) —S(O)$_m$R$^d$,
c) —S(O)$_2$OR$^d$,
d) —S(O)$_m$NR$^d$R$^e$,
e) —C(O)R$^d$,
f) —CO$_2$R$^d$,
g) —C(O)NR$^d$R$^e$,
h) —haloalkyl,
i) —cycloalkyl,
j) —heterocyclyl,
k) —C$_{1-10}$ alkyl,
l) —C$_{2-10}$ alkenyl,
m) —C$_{2-10}$ alkynyl,
n) —aryl,
o) —heteroaryl,
p) —C$_{1-10}$ alkylene-aryl,
q) —C$_{2-10}$ alkynylene-aryl,
r) —C$_{1-10}$ alkylene-heteroaryl,
s) —C$_{2-10}$ alkynylene-heteroaryl,
t) —C(R$^f$R$^g$)$_n$-aryl,
  wherein alkyl, alkenyl, alkynyl, aryl, heterocyclyl, heteroaryl, and cycloalkyl groups are optionally substituted 1-4 times with a group independently selected from R$^c$;
$R^b$ is selected from the group consisting of:
a) —cycloalkyl,
b) —cyano,
c) —OR$^d$,
d) —NO$_2$,
e) —halogen,
f) —S(O)$_m$R$^d$,
g) —SR$^d$,
h) —S(O)$_2$OR$^d$,
i) —S(O)$_m$NR$^d$R$^e$,
j) —NR$^d$R$^e$,
k) —O(CR$^f$R$^g$)$_n$NR$^d$R$^e$,
l) —C(O)R$^d$,
m) —CO$_2$R$^d$,
n) —CO$_2$(CR$^f$R$^g$)$_n$CONR$^d$R$^e$,
o) —OC(O)R$^d$,
p) —C(O)NR$^d$R$^e$,
q) —NR$^d$C(O)R$^e$,
r) —OC(O)NR$^d$R$^e$,
s) —NR$^d$C(O)OR$^e$,
t) —NR$^d$C(O)NR$^d$R$^e$,
u) —CF$_3$,
v) —OCF$_3$,
w) —haloalkyl,
x) —haloalkoxy,
y) —C$_{1-10}$ alkyl,
z) —C$_{2-10}$ alkenyl,
aa) —C$_{2-10}$ alkynyl,
ab) —C$_{1-10}$ alkylene-aryl,
ac) —C$_{1-10}$ alkylene-heteroaryl, and
ad) —heteroaryl,
  wherein alkyl, alkenyl, alkynyl, aryl, heteroaryl, and cycloalkyl groups are optionally substituted 1-4 times with a group independently selected from R$^c$;
$R^c$ is selected from the group consisting of:
a) —halogen,
b) —amino,
c) —carboxy,
d) —cyano,
e) —C$_{1-4}$ alkyl,
f) —O—C$_{1-4}$ alkyl,
g) —O—CF$_3$,
h) —cycloalkyl,
i) —O-cycloalkyl,
j) —aryl,
k) —C$_{1-4}$ alkylene-aryl,
l) —hydroxy,
m) —CF$_3$,
n) —haloalkyl,
o) —haloalkoxy,
p) —O-aryl,
q) —heteroaryl,
r) —heteroarylene-C$_{1-10}$ alkyl,
s) —heterocyclyl,
t) —CO$_2$—C$_{1-10}$ alkyl,
u) —CO$_2$—C$_{1-10}$ alkyl-aryl,
v) —fused arylcycloalkyl,
w) —alkynylene-heteroaryl,
x) —alkylene-aryl,
y) —alkynylene-aryl,
z) —nitro,
aa) —N(H)—C(O)—C$_{1-6}$-alkyl, and
bb) —S—C$_{1-6}$-alkyl, $R^d$ and $R^e$ are independently selected from the group consisting of: hydrogen, C$_{1-10}$ alkyl, C$_{2-10}$ alkenyl, C$_{2-10}$ alkynyl, cycloalkyl, —C$_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from R$^c$; or R$^d$ and R$^e$ together with the atoms to which they are attached form a heterocyclic ring of 5 to 7 members containing 0-2 additional heteroatoms independently selected from oxygen, sulfur and nitrogen and optionally substituted with 1-3 times with R$^c$, $R^f$ and $R^g$ are independently selected from the group consisting of: hydrogen, C$_{1-10}$ alkyl, cycloalkyl, —C$_{1-10}$ alkylene-cycloalkyl, —carboxy, and aryl, wherein alkyl, cycloalkyl, and aryl groups are optionally substituted with one to four substituents independently selected from R$^c$; or R$^f$ and R$^g$ together with the carbon to which they are attached form a ring of 5 to 7 members containing 0-2 heteroatoms independently selected from oxygen, sulfur and nitrogen optionally substituted with 1-3 times with R$^c$;

m is an integer from 1 to 2;

n is an integer from 1 to 10; and p is an integer from 0 to 2;

or a pharmaceutically acceptable salt thereof.

In another embodiment, the present invention provides a compound of Formula (IV):

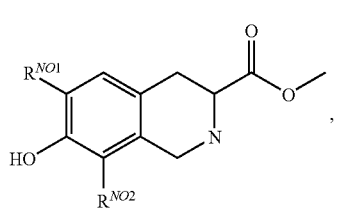

wherein $R^{NO1}$ and $R^{NO2}$ are independently selected from $NO_2$ and hydrogen, provided that one of $R^{NO1}$ and $R^{NO2}$ is hydrogen and the other is $NO_2$;

or a pharmaceutically acceptable salt thereof.

Pharmaceutically-acceptable salts of the compounds of the present invention, where a basic or acidic group is present in the structure, are also included within the scope of the invention. The term "pharmaceutically acceptable salts" refers to salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like.

Other salts which are not pharmaceutically acceptable may be useful in the preparation of compounds of the invention and these form a further aspect of the invention.

Thus, in a further embodiment, there is provided a pharmaceutical composition comprising a compound of the present invention, or a pharmaceutically acceptable salt thereof, and a pharmaceutically acceptable carrier, excipient, diluent, or mixture thereof.

Compounds set forth in the examples below demonstrated utility as modulators of GLP-1R. Within the context of the present invention, a modulator of GLP-1R may be an agonist, antagonist, partial agonist, partial antagonist, inverse agonist or inverse antagonist. In one embodiment, compounds of the invention are agonists of GLP-1R. In another embodiment, compounds of the invention are antagonists of GLP-1R.

Within the context of the present invention, a GLP-1R agonist is understood to refer to any compound which fully or partially activates the human GLP-1 receptor. Within the context of the present invention, a partial GLP-1R agonist is understood to refer to any compound which increases the activity of the human GLP-1 receptor but which compared to GLP-1 itself, is not able to effect a full response ($E_{max}$<100% relative to GLP-1). Within the context of the present invention, a GLP-1 antagonist is understood to refer to any compound which decreases the activity of the human GLP-1 receptor seen after stimulation with GLP-1. Within the context of the present invention, GLP-1 is understood to refer to either or both of the two known native forms GLP-1 (7-36) and GLP-1 (7-37).

In general, embodiments of the present invention useful for pharmaceutical applications may have EC50's as determined by the method for determining the ability to stimulate cAMP formation in a cell line expressing the cloned GLP-1R, such as the one described below, of less than 100 µM. Embodiments of the present invention useful for pharmaceutical applications may have EC50's of less than 10 µM. For particular medical indications, EC50's lower than 0.01 µM may be useful. Thus, in another embodiment, compounds of the present invention may have EC50's in a range of about 0.001 µM to about 10 µM. In another embodiment, compounds of the present invention may have EC50's of about 0.01 µM to about 3 µM. As stated above, agonist activity may be determined by the assay described in the Examples below.

Embodiments of the invention described herein are additionally directed to pharmaceutical compositions and use thereof in methods for modulating GLP-1R, which methods comprise administering to a subject in need of modulation of GLP-1R a compound of Formula (I), defined above.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like.

Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax or the like.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a nontoxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Depending on the stability of the compound, oral fluids may be administered by admixing two separate oral fluids, one, for example, which may contain concentrated compound in a stable solution (for example, at a stable pH), and a second, for example, which may contain diluent, flavoring, buffers and the like. The second oral fluid may not be stable under the same stability conditions for which the first oral fluid is stable.

Any solvent which is pharmaceutically acceptable and which is able to dissolve a compound of the present invention may be used. The solution may also contain one or more additional components such as a co-solubilizing agent, which may be the same as a solvent, a tonicity adjustment agent, a stabilizing agent, a preservative, or mixtures thereof. Suitable solvents and co-solubilizing agents may include, but are not limited to, water; sterile water for injection (SWFI); physiological saline; alcohols, such as ethanol, benzyl alcohol and the like; glycols and polyalcohols, such as propyleneglycol, glycerin and the like; esters of polyalcohols, such as diacetine, triacetine and the like; polyglycols and polyethers, such as polyethyleneglycol 400, propyleneglycol methylethers and the like; dioxolanes, such as isopropylideneglycerin and the like; dimethylisosorbide; pyrrolidone derivatives, such as 2-pyrrolidone, N-methyl-2-pyrrolidone, polyvinylpyrrolidone, as a co-solubilizing agent and the like; polyoxyethylenated fatty alcohols; esters of polyoxyethylenated fatty acids; polysorbates, such as Tween™, polyoxyethylene derivatives of polypropyleneglycols, such as Pluronics™. Suitable tonicity adjustment agents may include, but are not limited to, pharmaceutically acceptable inorganic chlorides, such as sodium chloride; dextrose; lactose; mannitol; sorbitol, and the like. Preservatives suitable for physiological administration may be, for instance, esters of parahydroxybenzoic acid, for example methyl, ethyl, propyl and butyl esters, or mixtures thereof, chlorocresol, and the like. Suitable stabilizing agents include, but are not limited to, monosaccharides such as galactose and fructose, disaccharides such as lactose, polysaccharides such as dextran, cyclic oligosaccharides such as alpha-, beta-, and gamma-cyclodextrin, aliphatic polyols such as mannitol, sorbitol, and thioglycerol, cyclic polyols such as inositol and organic solvents such as ethyl alcohol and glycerol. The above mentioned solvents and co-solubilizing agents, tonicity adjustment agents, stabilizing agents and preservatives can be used alone or as a mixture of two or more of them in a solution formulation.

For example, a pharmaceutical solution formulation may comprise a compound the present invention, SWFI, and an agent selected from the group consisting of sodium chloride solution, namely physiological saline, dextrose, mannitol, or sorbitol, wherein the agent is present in an effective amount. The pH of such a formulation may also be adjusted to improve the storage stability using a pharmaceutically acceptable acid or base.

The compounds of the present invention may be supplied as a two-component system including a first bottle of concentrated compound solution (from about 20 mg/g to about 60 mg/g, typically about 40 mg/g) and a second bottle of sterile diluent at pH 12.

The concentrated compound solution (the first bottle) may be reconstituted with the entire contents of the diluent solution (the second bottle) to give a solution, at, for example, 10 mg/ml and having pH 10.5-11.5.

In one embodiment, a pharmaceutical formulation may include components as described in the table below.

| Concentrated Compound Solution | Diluent for Concentrated Compound Solution |
| --- | --- |
| Compound of the present invention Polyethylene glycol 400, USP/NF Polysorbate 80 (Tween 80). USP/NF | Povidone, USP/NF Dibasic sodium phosphate•7H2O, USP/NF Sucralose, USP/NF Banana flavor D&C yellow #10 Purified water, USP/NF Sodium hydroxide to adjust pH |

In this embodiment, the concentrated compound solution may be reconstituted as described by first warming the concentrated compound solution and the diluent solution to room temperature by placing them at room temperature for 2 to 3 hours. Then, using a syringe, the entire contents of the diluent bottle (typically about 7.5 mL) may be transferred into the concentrated compound solution bottle. After complete addition, the bottle may be swirled and gently shaken to mix the contents while avoiding foam formation. The reconstituted solution (typically about 10 mg/ml) may be stored at room temperature (15°-30° C., 59°-86° F.) and should be used within about six hours of its reconstitution. The required volume of reconstituted solution from various bottles may be transferred into a dispensing cup prior to administration.

Suitable packaging for the pharmaceutical solution formulations may be all approved containers intended for parenteral use, such as plastic and glass containers, ready-to-use syringes and the like. In an embodiment, the container is a sealed glass container, such as a vial or an ampoule. A hermetically sealed glass vial is one example of a typical sealed glass container. According to an embodiment of the present invention, there is provided, in a sealed glass container, a sterile, injectable solution comprising a compound of the present invention in a physiologically acceptable solvent, and which has an appropriate pH for stability. Acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide and the pH of the combined formulation administered is between pH 5.0 and 7.0. One or more additional components such as co-solubilizing agents, tonicity adjustment agents, stabilizing agents and preservatives, for instance of the kind previously specified, may be added to the solution prior to passing the solution through the sterilizing filter.

The compounds may also be coupled with soluble polymers as targetable drug carriers. Such polymers can include polyvinylpyrrolidone (PVP), pyran copolymer, polyhydroxypropylmethacrylamidephenol, polyhydroxyethyl aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Further, the compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example. Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds can be prepared according to the following reaction Schemes (in which variables are as defined before or are defined) using readily available starting materials, and reagents. In these reactions, it is also possible to make use of variants which are themselves known to those of ordinary skill in this art, but are not mentioned in greater detail.

Scheme I below describes a method for making key intermediates useful in the synthesis of compounds of the present invention. Inasmuch, the present invention is also directed to certain methods and intermediate compounds, such as compounds XVIII and XX described below.

Scheme 1

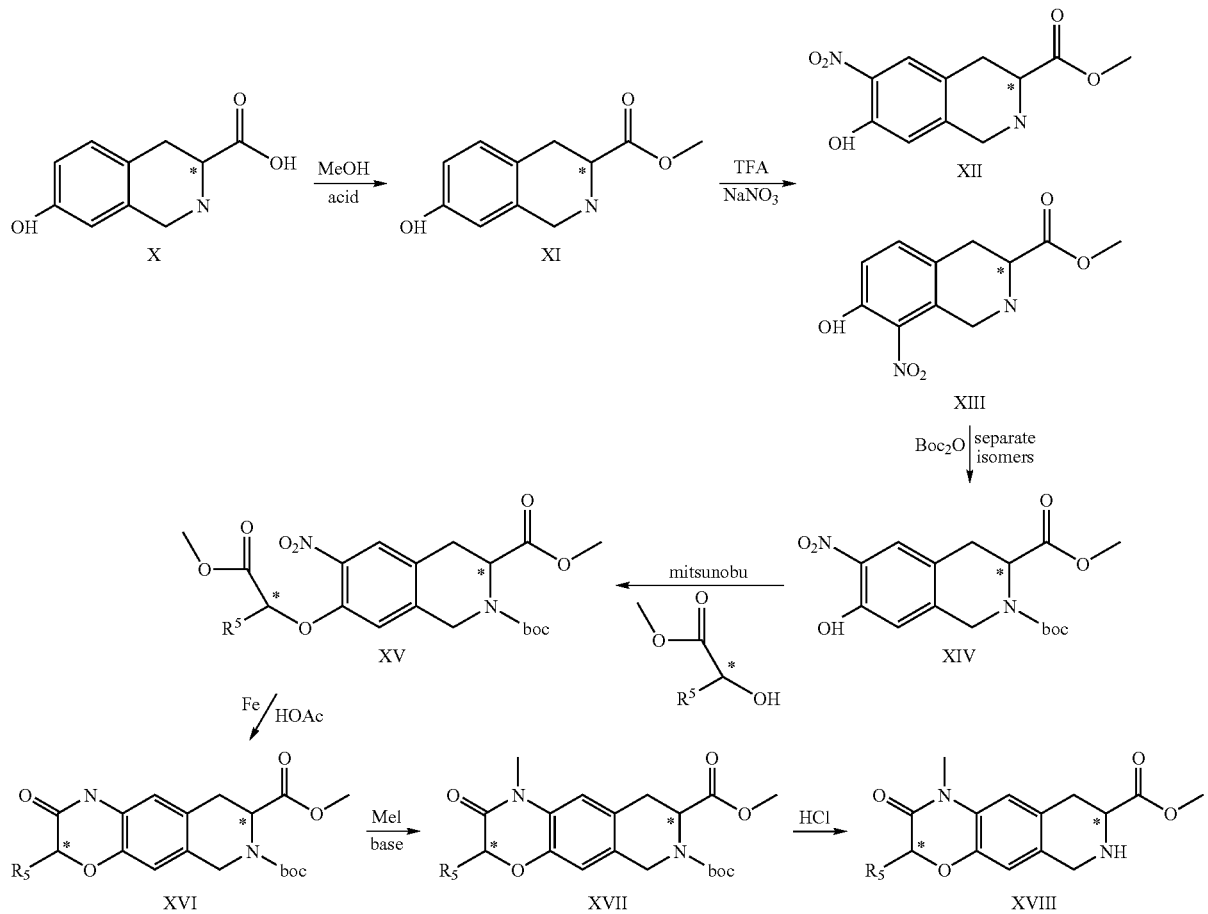

In the above Scheme 1 (as well as the below Scheme 2), * represents the presence of a stereocenter. Each stereocenter may independently be in the R-configuration, in the S-configuration or be a mixture of R- and S-isomers.

The acid X may be treated with, for example, MeOH in an acidic environment, such as in the presence of HCl, to give the methyl ester XI. Treatment of the methyl ester XI with trifluoroacetic acid (TFA) and $NaNO_3$ gives the nitro methyl ester compound XII and XIII as a mixture of isomers. The amino group is protected by methods known in the art, for example, with $Boc_2O$, and the isomers are separated to give the nitro-boc-methyl ester XIV. This compound may be treated with 1-hydroxy-1-$R^5$-acetic acid methyl ester under Mitsunobu conditions to give the coupled product XV. Ring closure of the coupled product XV in the presence of Fe and an organic acid, such as acetic acid (HOAc) gives the tricyclic compound XVI, which may be contacted with methyl iodide (MeI) in the presence of base, such as $K_2CO_3$, to give the methylated tricyclic compound XVII. Finally, deprotection of the amine, for example, treatment of the boc-protected amine with HCl, gives intermediate compound A, compound XVIII. In one embodiment of the present invention, compound XVIII has the following stereospecific structure:

XVIII

The group $R^5$ in the above Scheme 1 may be as defined as herewithin. In one embodiment of the present invention, $R^5$ is a mono- or di-substituted benzyloxy-phenylene group. In another embodiment of the present invention, $R^5$ is a dichloro-benzyloxy-phenylene group. In still another embodiment $R^5$ is dichloro-pyridinylmethoxy-phenylene group.

Scheme 2 below, shows the steps to take the intermediate compound A, compound XVIII from above, to intermediate compound B, compound XX shown below.

Scheme 2

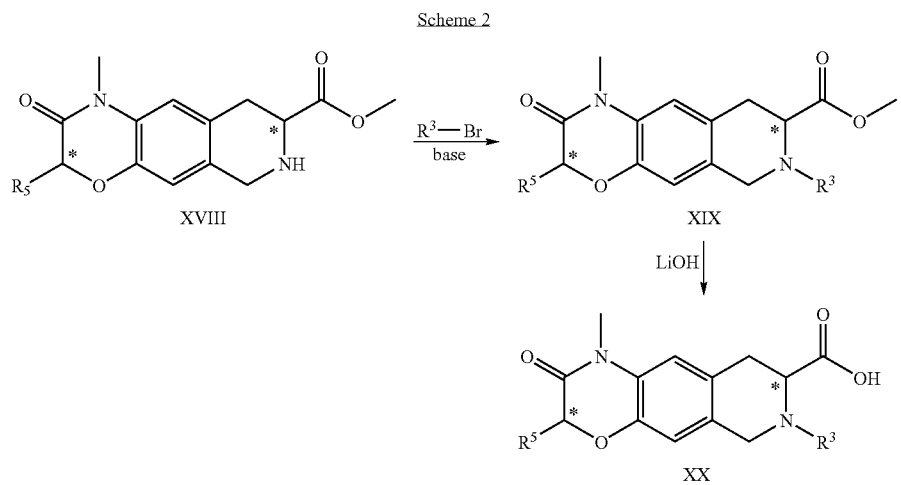

In the above Scheme 2, intermediate compound A, compound XVIII may be treated with $R^3$—Br in the presence of a base, such as $NaHCO_3$ to give the $R^3$-substituted tricyclic compound XIX. This $R^3$-substituted tricyclic compound XIX may then be treated with base, such as LiOH, to hydrolyze the methyl ester to give the acid as intermediate compound B, compound XX.

In the above Scheme 2, $R^3$ may be as defined herewithin. In one embodiment of the present invention, $R^3$ is 1-phenylpropane. In another embodiment of the present invention, $R^3$ may be a substituted carbonyl group. In still another embodiment of the present invention, $R^3$ may be a substituted sulfoxide group. In yet another embodiment of the present invention, $R^3$ may contain an aryl or heteryl group attached to the ring nitrogen through an alkylene linker.

The acid compound XX, intermediate compound B, may be coupled with an amine of the formula

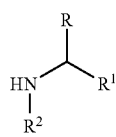

wherein R, $R^1$ and $R^2$ are as defined herewithin, by treatment with o-benzotriazol-1-yl-tetramethyluronium hexafluorophosphate (HBTU) to give a compound of the present invention having the above described Formula (I).

The above Schemes are further described with reference to the specific examples and procedures described in the below-identified Examples section.

Methods of Medical Treatment

In another aspect, the present invention provides a method of activating GLP-1R comprising the step of administering to a subject in need thereof a therapeutically effective amount of a compound of the present invention. The invention further provides a pharmaceutical composition comprising a pharmaceutically acceptable carrier and a therapeutically effective amount of a compound of the present invention sufficient to activate GLP-1R. A GLP-1R activating amount can be an amount that stimulates cAMP formation in a cell line expressing cloned GLP-1R, or increase insulin release from isolated human islet cells, or increase insulin release in a subject.

In a further aspect, the present invention may provide a method comprising administering to a subject a compound of Formula (I) or a pharmaceutically acceptable salt thereof. In one embodiment, the present invention comprises a method for the activation of GLP-1R comprising administering to a subject a compound of Formula (I). In another embodiment, the present invention provides a method of treatment comprising administering to a subject in need thereof a compound of Formula (I). In alternate embodiments, the disease, condition, disorder or indication treated using methods of the present invention comprise 1 disorders wherein activation of the GLP-1 receptor is beneficial.
2. metabolic disorders, wherein activation of the GLP-1 receptor is beneficial.
3. glucose intolerance,
4. hyperglycaemia,
5. dyslipidemia,
6. Type 1 diabetes,
7. Type 2 diabetes,
8. hypertriglyceridemia,
9. syndrome X,
10. insulin resistance,
11. IGT,
12. obesity,
13. diabetes as a consequence of obesity,
14. diabetic dyslipidemia,
15. hyperlipidemia,
16. cardiovascular diseases,
17. hypertension, and
18. complications resulting from or associated with diabetes including but not limited to neuropathy, retinopathy, nephropathy, impaired wound healing, and the like.

In another embodiment, the present invention provides a method for the inhibition of intestinal motility comprising administering a compound of the present invention or a pharmaceutical composition comprising a compound of the present invention.

In another embodiment, the present invention provides a method for lowering blood glucose in a human comprising administering a compound of the present invention or a pharmaceutical composition comprising a compound of the present invention.

In another embodiment, the present invention provides a method for delaying or preventing the progression from IGT to Type 2 diabetes comprising administering a compound of the present invention or a pharmaceutical composition comprising a compound of the present invention.

In another embodiment, the present invention provides a method for delaying or preventing the progression from non-insulin requiring Type 2 diabetes to insulin requiring Type 2 diabetes comprising administering a compound of the present invention or a pharmaceutical composition comprising a compound of the present invention.

In another embodiment, the present invention provides a method for delaying or preventing Type 1 diabetes comprising administering a compound of the present invention or a pharmaceutical composition comprising a compound of the present invention.

In another embodiment, the present invention provides a method for appetite regulation or treatment of an energy expenditure disorder such as eating disorders eg bulimia, and other conditions where a weight reduction is required comprising administering a compound of the present invention or a pharmaceutical composition comprising a compound of the present invention.

In an embodiment, a therapeutically effective amount may be administered.

In another embodiment, at least one compound of Formula (I) is used, either alone or in combination with one or more known therapeutic agents. In a further embodiment, the present invention provides method of prevention and/or treatment of a GLP-1R mediated human disease, treatment comprising a) alleviation of one or more symptoms resulting from that disorder, to b) an outright cure for that particular disorder; and prevention comprising a) prevention of the onset of the disorder, the method comprising administering to a human in need thereof a therapeutically effective amount of a compound of Formula (I) or a pharmaceutically acceptable salt thereof.

Factors which may influence what constitutes a therapeutically effective amount include, but are not limited to, the size and weight of the subject, the biodegradability of the therapeutic agent, the activity of the therapeutic agent, as well as its bioavailability. Accordingly, in the context of the therapeutic method of the invention, this method also is comprised of a method for treating a subject prophylactically, or prior to the onset of diagnosis such disease(s) or disease state(s).

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s).

The following is a non-exhaustive listing of classes of additional therapeutic agents which may be utilized in combination with the compounds of the present invention: antidiabetics, antiobesity agents, antihypertensive agents, antihypertensive agents, antiatherosclerotic agent, a lipid lowering agent, and agents for the treatment and/or prevention of complications resulting from or associated with diabetes including but not limited to neuropathy, retinopathy, nephropathy, impaired wound healing, and the like.

In addition, the compounds of the present invention may also be combined with one or more of the following therapeutic agents; infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Antidiabetic

Examples of suitable anti-diabetic agents for use in combination with the compounds of the present invention include
1. biguanides (e.g., metformin or phenformin),
2. glucosidase inhibitors (e.g, acarbose or miglitol),
3. insulins (including insulin secretagogues or insulin sensitizers),
4. meglitinides (e.g., repaglinide, and nateglinide),
5. sulfonylureas (e.g., glimepiride, glyburide, gliclazide, chlorpropamide and glipizide),
6. biguanide/glyburide combinations (e.g., Glucovance®),
7. thiazolidinediones (e.g., troglitazone, rosiglitazone and pioglitazone),
8. PPAR-alpha agonists,
9. PPAR-gamma agonists,
10. PPAR alpha/gamma dual agonists,
11. glycogen phosphorylase inhibitors,
12. inhibitors of fatty acid binding protein (aP2),
13. DPP-IV inhibitors, and
14. SGLT2 inhibitors.

Examples of other suitable glucagon-like peptide-1 compounds that may be used in combination with the compounds of the present invention include GLP-1 (1-36) amide, GLP-1 (7-36) amide, GLP-1 (7-37).

Hypolipidemic/Lipid Lowering Agents

Examples of suitable hypolipidemic/lipid lowering agents that may be used in combination with the compounds of the present invention include one or more
1. MTP inhibitors,
2. HMG CoA reductase inhibitors,
3. squalene synthetase inhibitors,
4. fibric acid derivatives,
5. lipoxygenase inhibitors,
6. cholesterol absorption inhibitors,
7. ileal $Na^+$/bile acid cotransporter inhibitors,
8. upregulators of LDL receptor activity,
9. bile acid sequestrants,
10. cholesterol ester transfer protein inhibitors and/or
11. nicotinic acid and derivatives thereof.

The HMG CoA reductase inhibitors which may be employed in combination with one or more compounds of the present invention include
mevastatin and related compounds,
lovastatin (mevinolin) and related compounds,
pravastatin and related compounds,
simvastatin and related compounds,
atorvastatin, fluvastatin, cerivastatin, and atavastatin Examples of fibric acid derivatives which may be employed in combination with one or more compounds of the present invention include fenofibrate, gemfibrozil, clofibrate, bezafibrate, ciprofibrate, clinofibrate, probucol and the like.

Antihypertensive Agents

Examples of suitable anti-hypertensive agents for use in combination with the compounds of the present invention include
1. beta adrenergic blockers (e.g., alprenolol, atenolol, timolol, pindolol propranolol and metoprolol),
2. calcium channel blockers (L-type and T-type; e.g. nicardipine, isradipine, nimodipine, diltiazem, felodipine, verapamil, nifedipine, amlodipine and mybefradil)
3. diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone),
4. renin inhibitors,
5. ACE inhibitors (e.g., captopril, zofenopril, fosinopril, enalapril, ceranopril, cilazopril, delapril, pentopril, quinapril, ramipril, lisinopril, benazepril)
6. AT-1 receptor antagonists (e.g., losartan, irbesartan, valsartan),
7. ET receptor antagonists (e.g., sitaxsentan and atrsentan),
8. Dual ET/AII antagonist,
9. neutral endopeptidase (NEP) inhibitors,
10. vasopepsidase inhibitors (dual NEP-ACE inhibitors) (e.g., omapatrilat and gemopatrilat), and
11. nitrates.

Antiobesity Agents

Examples of anti-obesity agents that may be used in combination with the compounds of the present invention include
1. a NPY receptor antagonist,
2. a MCH antagonist,
3. a GHSR antagonist,
4. a CRH antagonist,
5. a beta 3 adrenergic agonist,
6. a lipase inhibitor (orlistat),
7. a serotonin (and dopamine) reuptake inhibitor (sibutramine, topiramate or axokine),
8. a thyroid receptor beta drug and/or
9. an anorectic agent (dexamphetamine, amphetamine, phentermine, phenylpropanolamine or mazindol).

Antipsychotic Agents

Examples of anti-psychotic agents which may be optionally employed in combination with compounds of the present invention include clozapine, haloperidol, olanzapine and aripiprazole.

It should be understood that any suitable combination of the compounds according to the invention with one or more of the above-mentioned compounds and optionally one or more further pharmacologically active substances are considered to be within the scope of the present invention.

Pharmaceutical Formulations and Dosage

In another aspect, the present invention comprises a pharmaceutical composition comprising a compound of Formula (I) and a pharmaceutically acceptable carrier, excipient, diluent, or a mixture thereof.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Generally speaking, a compound of Formula (I) may be administered at a dosage level of from about 0.003 to 500 mg/kg of the body weight of the subject being treated. In an embodiment, a compound of Formula (I) may be administered at a dosage range between about 0.003 and 200 mg/kg of body weight per day. In an embodiment, a compound of Formula (I) may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms may generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

EXAMPLES

General Procedure A. Preparation of amides using HBTU: To a stirring solution of a mixture of a carboxylic acid (1.0 eq) HBTU (1.1 eq) and DIEA (2.0 eq) in DMF at room temperature is added an amino acid methyl ester (1.0 eq), and the mixture is stirred 4-16 h. After completion of the reaction, sufficient amount of water is added and the mixture is extracted with ethyl acetate. The combined organic layer is washed with 1 N HCl, saturated $NaHCO_3$ and brine, and then dried over sodium sulfate. The solvent is removed under reduced pressure to afford the amide, which may be purified by column chromatography on silica gel to afford the desired amide.

General Procedure B. Methyl ester hydrolysis: To a solution of ester in THF, methanol (4:1 to 1:4), 2 N lithium hydroxide solution (2-10 eq) is added, and the resulting reaction mixture is stirred at 0° C. or room temperature for 10-120 minutes (if started at 0° C.) and then warmed to room temperature and stirred until reaction complete. After completion of the reaction, 1N HCl is used to neutralize the base, extracted with ethyl acetate or DCM, the organic layer was washed with brine, dried over sodium sulfate, and the solvent is removed under reduced pressure to afford the product in pure form.

General Procedure C. Removal of tert-butyl carbamate: To a stirred solution of the carbamate in DCM is added 4 N HCl in dioxane (excess). The reaction is stirred at room temperature until reaction was complete. Solvents are removed under reduced pressure. The residue is triturated with ethyl ether and the precipitated solid is filtered and dried under vacuum to give desired amine as hydrochloric acid salt.

General Procedure D. Reductive amination. To a solution of a secondary amine (1.0 eq) in dichloroethane or dichloromethane is added an aldehyde (1.0-3 eq), acetic acid (0.25 eq) and sodium triacetoxyborohydride or sodium cyanoborohydride (2-5 eq) and the mixture is stirred overnight. After completion of the reaction, DCM is added and the organic layer is washed with 10% $Na_2CO_3$ solution and brine, and then dried over sodium sulfate. The solvent is removed under reduced pressure to afford the desired amine, which may be purified by flash chromatography.

General Procedure E. Preparation of sulfonamides: To a solution of an amine (1.0 eq) in DCM is added a sulfonyl chloride (1-3 eq), pyridine (1-5 eq) or triethylamine (1-5 eq) and DMAP (cat. amount if required) and the mixture is stirred for 1-16 h. After completion of the reaction, ethyl acetate is added and the organic layer is washed with 1N HCl, saturated sodium bicarbonate solution and brine, and then dried over sodium sulfate. The solvent is removed under reduced pressure to afford the sulfonamide, which may be purified by flash chromatography. Alternatively, after completion of the reaction, the reaction mixture may be directly purified by flash chromatography.

General Procedure F. Preparation of amides: To a solution of an amine (1.0 eq) in DCM is added an acid chloride (1-3 eq), and pyridine (1-5 eq) or triethylamine (1-5 eq) and the mixture is stirred for 1-16 h. After completion of the reaction, ethyl acetate is added and the organic layer is washed with 1N HCl, saturated sodium bicarbonate solution and brine, and then dried over sodium sulfate. The solvent is removed under reduced pressure to afford the amide, which may be purified by flash chromatography. Alternatively, after completion of the reaction, the reaction mixture may be directly purified by flash chromatography.

General Procedure G. Preparation of alkyl chloroformates: To a solution of an alcohol (1.0 eq) in DCM is slowly added phosgene (5-6 eq, 20% solution in toluene) at −5° C. stirred for 2-4 h. After completion of the reaction, the solvents and excess phosgene are removed under reduced pressure to afford the alkyl chloroformate, which may be subjected to carbamate formation (General procedure H) without further purification.

General Procedure H. Preparation of carbamates: To a solution of an amine (1.0 eq) in DCM is added a chloroformate (1-3 eq), and triethylamine (1-5 eq) and the mixture is stirred for 1-16 h. After completion of the reaction, ethyl acetate is added and the organic layer is washed with 1N HCl, saturated sodium bicarbonate solution and brine, and then dried over sodium sulfate. The solvent is removed in vacuo to afford the carbamate, which may be purified by flash chromatography. Alternatively, after completion of the reaction, the reaction mixture may be directly purified by flash chromatography.

General Procedure I. Preparation of ureas: To a solution of an amine (1.0 eq) in DCM is added a carbamoyl chloride (1-5 eq), and triethylamine (1-5 eq) and the mixture is stirred for 1-16 h. After completion of the reaction, ethyl acetate is added and the organic layer is washed with 1N HCl, saturated sodium bicarbonate solution and brine, and then dried over sodium sulfate. The solvent is removed under reduced pressure to afford the urea, which may be purified by flash chromatography. Alternatively, after completion of the reaction, the reaction mixture may be directly purified by flash chromatography.

General Procedure J. Preparation of ureas: To a stirred solution of an amine (1.0 eq) in THF or DCM is added DIEA (0-2 eq) followed by alkyl/aryl isocyanate (2 eq). The resulting solution is stirred at r.t. for 2 h. The reaction mixture is poured into saturated $NaHCO_3$ solution and extracted with ethyl acetate. The combined organic layer is washed with brine and dried over $Na_2SO_4$, and concentrated under reduced pressure, and then may be purified by silica gel flash column chromatography to give the desired urea.

General Procedure K. Alkylation of secondary amines: To a solution of a secondary amine (1.0 eq) in DMF is added an alkyl halide (1-10 eq), and potassium carbonate or sodium bicarbonate (1-10 eq) and the mixture is stirred at room temperature for 2-72 h. After completion of the reaction, ethyl acetate and water are added. The organic layer is washed with water, and then dried over sodium sulfate. The solvent is removed under reduced pressure to afford the desired tertiary amine, which may be purified by flash chromatography.

General Procedure L. Ether formation under Mitsunobu reaction conditions: To a solution of a phenol (1 eq), an alcohol (1-4 eq) and polymer supported triphenylphosphine (1-4 eq) in anhydrous DCM and/or THF is added DIAD (1-4 eq) at rt to −5° C. and the reaction mixture is slowly allowed to warm up to r.t. and stirred for 1-24 h. After completion of the reaction the polymer supported triphenylphosphine is removed from reaction mixture and concentrated under reduced pressure to afford desired product after flash chromatography on silica gel.

General Procedure M. N-Alkylation of anilides using Mitsunobu reaction conditions: To a solution of an anilide (1.0 eq) and alcohol (1-5 eq) in DCM or THF is added polymer supported triphenylphosphine or triphenylphosphine (1-5 eq). The mixture is cooled to (−20° C.-0° C.) and DIAD (1-5 eq) is added. The mixture is stirred at −20° C.-0° C. for 10 min-1 h and then at room temperature for 1-24 h. After completion of the reaction, the reaction mixture is filtered and the organics concentrated under reduced pressure. The resulting material may be purified by flash chromatography to give desired product.

General Procedure N. Acid catalyzed methyl ester hydrolysis: To a solution of ester (1 mmol) in dioxane (30 mL), 6 N hydrochloric acid (20 mL) is added, and the resulting reaction mixture is stirred at 70° C. for 100 h. After completion, the reaction mixture is concentrated, neutralized with sodium bicarbonate, extracted with ethyl acetate. The organic layer is washed with brine, dried over sodium sulfate, and the solvent is removed under reduced pressure to afford the product.

General Procedure O. Preparation of amides using EDCI coupling. To a solution of acid (1 eq) in dichloromethane at room temperature is added HOBt (1-2 eq) followed by EDCI (1-2 eq), amine (0.9-2 eq) and NMM (2-4 eq). The reaction mixture is stirred for 1 h then the sample is taken and analyzed by LC-MS. After complete conversion, the reaction mixture is diluted with DCM. The mixture is washed with water, with 1 N aqueous solution of HCl, with saturated aqueous solution of $NaHCO_3$ then with brine. The DCM solution is dried over anhydrous $Na_2SO_4$ and concentrated by evaporation. The residue may be purified by column chromatography. Alternatively, the crude mixture was concentrated and purified by flash chromatography.

General Procedure P. Acetamide Deprotection. To a solution of acetamine (1.0 eq) in methanol is added 4N HCl in dioxane (10.0 eq.). The mixture is heated at 62° C. for 2-4 h. The mixture is concentrated and the residue is dissolved in DCM and the organic layer is washed with 10% $Na_2CO_3$ solution and brine, and dried over sodium sulfate. The solvent is removed under reduced pressure to afford the desired amine, which may be purified by flash chromatography (9:1 to 7:3 hexanes/EtOAc).

General procedure Q: Alkyl bromide preparation Alcohol (1 eq) and triphenylphosphine polystyrene or triphenylphosphine (1-2 eq) are taken in anhydrous dichloromethane and cooled to 0° C., carbon tetrabromide (1-2 eq) and stirred for 1 h. The reaction is allowed to warm to room temperature and stirred for 2 h. Resin is filtered and washed with dichloromethane, filtrate is concentrated and dried in vacuum gave corresponding bromide.

Synthesis of Intermediates

6-Amino-7-hydroxy-3,4-dihydro-1-isoquinoline-2,3-dicarboxylic acid 2-tert-butyl ester 3-methyl ester

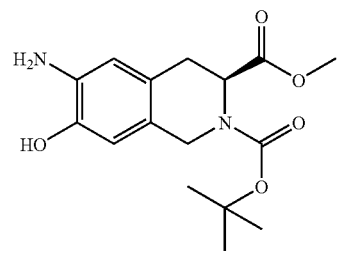

Step 1. Esterification

To a suspension of (S)-7-hydroxy-1,2,3,4-tetrahydro-isoquinoline-3-carboxylic acid dehydrate (109 mmol) in methanol (150 mL) was added hydrochloric acid (27 mL of 4M solution in dioxane.) at r.t and the reaction mixture was refluxed for 4 h. The mixture was concentrated, resuspended in 150 mL of MeOH and hydrochloric acid (27 mL of 4M solution in dioxane.) added. The mixture refluxed for 4 h and was concentrated under reduced pressure. The residue was triturated with ether, filtered and washed with ether to give (S)-7-hydroxy-1,2,3,4-tetrahydro-isoquinoline-3-carboxylic acid methyl ester hydrochloride salt (25.1 g). $^1$H NMR (400 MHz, DMSO d6): 10.1 (m, 2H), 9.62 (s, 1H), 7.03 (d, 1H), 6.7 (m, 1H), 6.26 (d, 1H), 4.48 (m, 1H), 4.21 (s, 2H), 3.77 (s, 3H), 3.17-2.96 (m, 2H).

Step 2. Nitration

To a solution of (S)-7-hydroxy-1,2,3,4-tetrahydro-isoquinoline-3-carboxylic acid methyl ester hydrochloride (102 mmol) in TFA (300 mL) was slowly added sodium nitrite (102 mmol) at 0° C. The mixture stirred at 0° C. for 3 h. After completion, excess TFA was removed in vacuo. The residue was taken up in DCM (200 mL) and neutralized with triethylamine (300 mL). The mixture was concentrated, dissolved in DCM (200 mL) and cooled to 0° C. Triethylamine (306 mmol) and di-tert-butyl dicarbonate (204 mmol) was added. After carbamate formation was complete, the reaction mixture was treated with hydrazine hydrate (30 mL 33% solution in water) to cleave the carbonate. The reaction mixture was stirred at r.t. for 30 min. The mixture was poured onto 1 N HCl and ethyl acetate. The organic layer was washed with saturated sodium bicarbonate and brine, dried over sodium sulfate and concentrated under reduced pressure to give both nitrated regioisomers (6- and 8-Nitro substituted analogs). The residue was purified with silica gel chromatography using hexanes:ethyl acetate (from 95:5 to 9:1) as an eluent to provide (S)-7-hydroxy-6-nitro-3,4-dihydro-1H-isoquinoline-2,3-dicarboxylic acid 2-tert-butyl ester 3-methyl ester (9.8 g). $^1$H NMR (400 MHz, CDCl3): 10.45 (d, 1H), 7.9 (s, 1H), 6.95 (d, 1H), 5.19-4.83 (m, 1H), 4.79-4.49 (m, 2H), 3.64 (d, 3H), 3.30-3.14 9 m, 2H), 1.50 (d, 9H).

Step 3. (S)-6-Amino-7-hydroxy-3,4-dihydro-1H-isoquinoline-2,3-dicarboxylic acid 2-tert-butyl ester 3-methyl ester To a stirred solution of nitro derivative (3.42 g, 10.0 mmol) in methanol (50 mL) was added Pd—C (342 mg, 10% on activated carbon) and the resultant reaction mixture was subjected to hydrogenation (balloon pressure). The reaction mixture was stirred under hydrogen balloon at r.t. for 16 h. The catalyst was filter off through a pad of celite and the celite pad was washed with ethyl acetate-methanol mixture (1:1, 25 mL). The combined filtrate was concentrated under reduced pressure. The resulting residue, (S)-6-amino-7-hydroxy-3,4-dihydro-1H-isoquinoline-2,3-dicarboxylic acid 2-tert-butyl ester 3-methyl ester was used in the next step without further purification.

Preparation of Substituted Mandelic Acid Esters

To a solution of hydroxy-(4-hydroxy-phenyl)-acetic acid monohydrate (10 g) in DMF (50 mL) was added $K_2CO_3$ (29.7 g), followed by 3,4-dichlorobenzyl bromide (16.1 mL). The mixture was stirred at room temperature for 3 h. The mixture was poured into water (250 mL) and extracted with EtOAc. The organic layer was washed with water 1N HCl, brine, dried over $Na_2SO_4$, and concentrated. The resulting solid was triturated with diethyl ether and filtered to provide [4-(3,4-dichloro-benzyloxy)-phenyl]-hydroxy-acetic acid 3,4-dichloro-benzyl ester as a white solid (9.4 g). $^1$H NMR (400 MHz, DMSO d6): 7.69 (d, 1H), 7.63 (d, 1H), 7.55 (d, 1H), 7.41 (m, 1H), 7.37 (d, 1H), 7.31 (m, 2H), 7.20 (m, 1H), 6.97 (m, 2H), 6.06 (d, 1H), 5.16 (d, 1H), 5.1 (m, 4H).

Similar procedure was used to prepare the following mandelic acid derivatives: [4-(5,6-Dichloro-pyridin-3-yl-methoxy)-phenyl]-hydroxy-acetic acid methyl ester [hydroxy-(4-hydroxy-phenyl)-acetic acid methyl ester was used in place of hydroxy-(4-hydroxy-phenyl)-acetic acid monohydrate)], [4-(2,5-dichloro-benzyloxy)-phenyl]-hydroxy-acetic acid 2,5-dichloro-benzyl ester, [4-(2,6-dichloro-benzyloxy)-phenyl]-hydroxy-acetic acid 2,6-dichloro-benzyl ester, [4-(3-chloro-benzyloxy)-phenyl]-hydroxy-acetic acid 3-chloro-benzyl ester and [4-(4-chloro-benzyloxy)-phenyl]-hydroxy-acetic acid 4-chloro-benzyl ester.

2-Chloro-2-[4-(3,4-dichloro-benzyloxy)-phenyl]-acetyl chloride

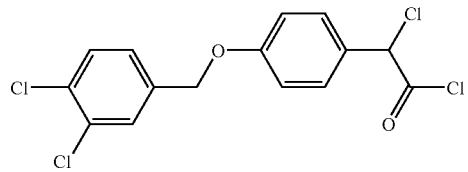

Step 1. Ester hydrolysis: 2-[4-(3,4-Dichloro-benzyloxy)-phenyl]-2-hydroxy-acetic acid 3,4-dichloro-benzyl ester (9.4 g), was dissolved in 120 mL of THF-methanol (4:1) and 2N lithium hydroxide solution (39 mL) added. The resulting reaction mixture was stirred at room temperature 16 h. The mixture was poured onto 1N HCl and EtOAc and the organic layer was washed with brine, dried over sodium sulfate, and concentrated. The residual oil was taken up in minimal DCM and hexanes added to give a solid. The solid was filtered and washed with hexanes to afford the desired product [4-(3,4-dichloro-benzyloxy)-phenyl]-hydroxy-acetic acid in pure form (6.1 g). $^1$H NMR (400 MHz, DMSO d6): 7.69 (d, 1H), 7.63 (d, 1H), 7.41 (m, 1H), 7.31 (m, 2H), 6.96 (m, 2H), 5.10 (s, 2H), 4.94 (s, 1H).

Step 2. Acid chloride preparation: To [4-(3,4-dichloro-benzyloxy)-phenyl]-hydroxy-acetic acid (2.13 g) was added neat $SOCl_2$ (20 mL) and the solution was refluxed at 70° C. for 3 hours and then slowly cooled to room temperature. The excess thionyl chloride was removed under reduced pressure. The residue was dissolved in DCM (3×50 mL) and concentrated under reduced pressure and dried under vacuum to give the product, 2-chloro-2-[4-(3,4-dichloro-benzyloxy)-phenyl]-acetyl chloride (2.4 g) which was used without further purification.

(7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester

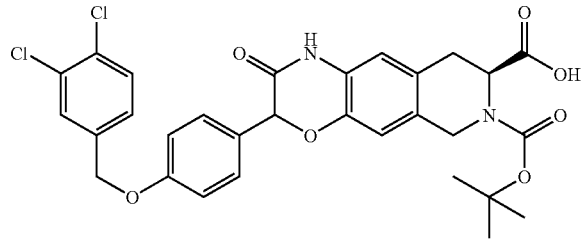

A solution of (S)-7-hydroxy-6-nitro-3,4-dihydro-1H-isoquinoline-2,3-dicarboxylic acid 2-tert-butyl ester 3-methyl ester (3.0 g, 8.5 mmol), resin-bound triphenylphosphine (17 mmol), [4-(3,4-dichloro-benzyloxy)-phenyl]-hydroxy-acetic acid 3,4-dichloro-benzyl ester (13.0 mmol) in DCM-THF (1-1, 80 mL) was cooled to 0° C. To this solution was added DIAD (13.0 mmol) and the mixture was agitated for 10 min at 0° C. and the mixture was slowly allowed to warm up to r.t. and agitated for 16 h. The reaction mixture was filtered, concentrated and the residue passed over a plug of silica-gel hexanes-ethyl acetate (9:1). The resulting residue was dissolved in glacial acetic acid (65 mL) and iron powder (170 mmol) added. The resulting mixture was heated at 100° C. for 1 h. The mixture was poured onto water and EtOAc. The organic layer was washed with water, brine, saturated sodium bicarbonate solution and dried over sodium sulfate. The solution was concentrated under reduced pressure to give the desired product. This crude product was purified by silica gel column chromatography using hexanes-ethyl acetate (7:3) to afford (7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester (1.6 g). LC-MS (m/z) 614.

(7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester (1.6 g) was dissolved in THF-methanol (4:1, 20 mL), 2 N lithium hydroxide solution (2.5 mL) was added, and the resulting reaction mixture was stirred at 0° C. for 3 h when an additional equiv of LiOH (2N) was added. The resulting mixture stirred at 0° C. for 3 h. The reaction mixture was neutralized with 1N HCl and extracted with ethyl acetate. The organic layer was washed with brine, dried over sodium sulfate, and the solvent was removed under reduced pressure to afford 3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester (1.5 g). LC-MS (m/z) 601.

Similar procedures were used to prepare the following derivatives. (7S)-3-[4-(5,6-dichloro-pyridin-3-ylmethoxy)-phenyl]-2-oxo-1,2,3,5,7,8-hexahydro-4-oxa-1,6-diaza-anthracene-6,7-dicarboxylic acid 6-tert-butyl ester 7-methyl ester, (7S)-3-[4-(2,6-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester, (7S)-3-[4-(2,5-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester, (7S)-3-[4-(3-chloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester and (7S)-3-[4-(4-chloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester.

Preparation of (3S,7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester and (3R,7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester

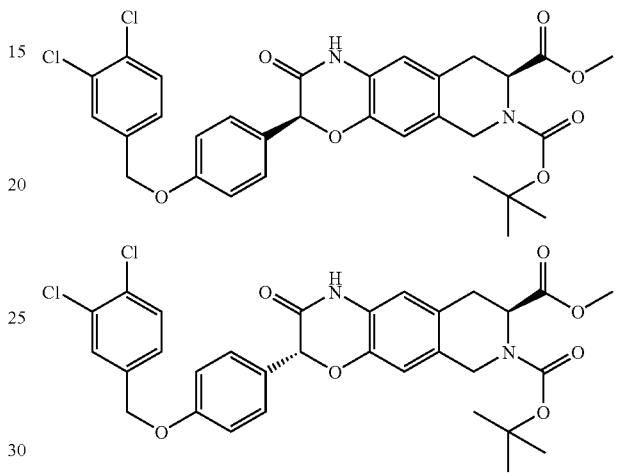

Step 1: Ether formation by Mitsunobu reaction: A solution of (S)-7-hydroxy-6-nitro-3,4-dihydro-1H-isoquinoline-2,3-dicarboxylic acid 2-tert-butyl ester 3-methyl ester (1 mmol), triphenylphosphine (1.2 mmol) and (R)-[4-(3,4-dichloro-benzyloxy)-phenyl]-hydroxy-acetic acid methyl ester (1.1 mmol) in DCM was cooled to −5° C. To this solution was added DIAD (1.3 mmol) and the mixture was stirred for 45 min at −5° C. and the mixture was slowly allowed to warm up to r.t. and stirred for 1 h. After completion of the reaction, the mixture was concentrated and the residue was purified by silica-gel column chromatography using hexanes-ethyl acetate (9:1) to afford the desired ether.

Step 2: Cyclization reaction: To solution of above ether (~1 mmol) in glacial acetic acid (5 mL) was added iron powder (5 mmol). The mixture was heated at 80° C. for 30 min. The TLC indicated the complete conversion of starting material. After cooling, the solution was diluted with EtOAc (30 mL) and filtered through a pad of celite to remove the insoluble solids. The organic layer was washed with water (2×50 mL), saturated sodium carbonate solution (1×30 mL), brine (1×30 mL), dried over sodium sulfate. The solution was concentrated under reduced pressure to give the desired product as brown oil. This crude product was purified by silica gel column chromatography using hexanes-ethyl acetate (6:4) to afford (3S,7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester (70%). $^1$H NMR (400 MHz, CDCl$_3$): 9.45 (d, 1H), 7.50 (s, 1H), 7.43 (d, 1H), 7.34 (d, 2H), 7.22 (d, 1H), 6.92 (d, 2H), 6.93 (d, 1H), 5.59 (s, 2H), 5.12 (m, 1H), 4.98 (s, 2H), 4.62 (t, 1H), 4.37 (t, 1H), 4.13 (t, 1H), 3.60 (s, 3H), 3.05 (m, 1H), and 1.46 (d, 9H). LC-MS (m/z) 614.

Similarly (3R,7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester was synthesized from (S) mandelic acid derivative. ¹H NMR (400 MHz, CDCl₃): 9.45 (d, 1H), 7.50 (s, 1H), 7.43 (d, 1H), 7.34 (d, 2H), 7.22 (d, 1H), 6.92 (d, 2H), 6.93 (d, 1H), 5.63 (s, 2H), 5.12 (m, 1H), 4.98 (s, 2H), 4.62 (t, 1H), 4.37 (t, 1H), 4.13 (t, 1H), 3.60 (s, 3H), 3.05 (m, 1H), and 1.46 (d, 9H). LC-MS (m/z) 614.

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester, (3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester, (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester, and (3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester

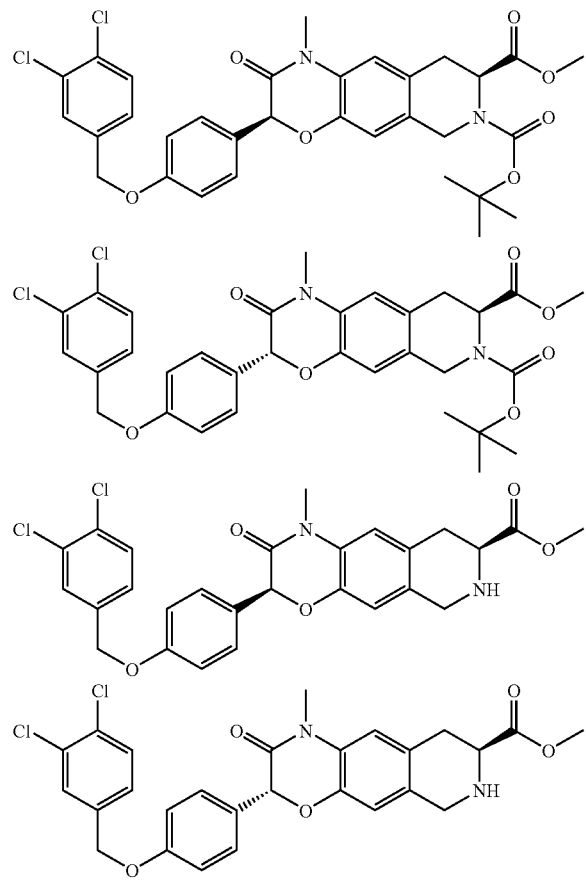

(S)-2-tert-Butoxycarbonylamino-3-(4-hydroxy-3-nitrophenyl)-propionic acid methyl ester (16.8 mmol) and (R)-[4-(3,4-dichloro-benzyloxy)-phenyl]-hydroxy-acetic acid methyl ester (20.1 mmol) were dissolved in 80 mL of DCM, resin-bound triphenylphosphine (33.6 mmol) added and the mixture cooled to −20° C. To this solution was added DIAD (25.2 mmol) and the mixture was agitated for 30 min at −20° C. The mixture was slowly allowed to warm to r.t. and agitated for 1.5 h. The reaction mixture was filtered and concentrated. The resulting residue was dissolved in glacial acetic acid (60 mL) and heated to 100° C. Iron powder (336 mmol) was added and the resulting mixture heated at 100° C. for 1 h. The mixture was poured onto water and EtOAc. The mixture was brought to ~pH 7 with sodium carbonate. The organic layer was dried over sodium sulfate and concentrated. The residue was treated with diethyl ether and the resulting solid filtered and washed with diethyl ether to provide (S)-2-tert-Butoxycarbonylamino-3-{(S)-2-[4-(3,4-dichloro-benzyloxy)-phenyl]-3-oxo-3,4-dihydro-2H-benzo[1,4]oxazin-6-yl}-propionic acid methyl ester (5.7 g). LC-MS (m/z) 502 (M-Boc).

(S)-2-tert-Butoxycarbonylamino-3-{(S)-2-[4-(3,4-dichloro-benzyloxy)-phenyl]-3-oxo-3,4-dihydro-2H-benzo[1,4]oxazin-6-yl}-propionic acid methyl ester (9.5 mmol) was dissolved in 60 mL THF-DCM (1:1) and methanol (14.2 mmol) and resin-bound triphenylphosphine (14.2 mmol) was added. The mixture was cooled to 0° C. and DIAD (14.2 mmol) added. The mixture was agitated for 10 min at 0° C. and the mixture was slowly allowed to warm up to r.t. and agitated for 16 h. The reaction mixture was filtered, concentrated and the residue purified over silica-gel hexanes-ethyl acetate (8-2) to afford (S)-2-tert-Butoxycarbonylamino-3-{(S)-2-[4-(3,4-dichloro-benzyloxy)-phenyl]-4-methyl-3-oxo-3,4-dihydro-2H-benzo[1,4]oxazin-6-yl}-propionic acid methyl ester. (4.9 g). ¹H NMR (400 MHz, CDCl3): 7.51 (d, 1H), 7.44 (d, 1H), 7.31 (m, 2H), 7.25 (m, 1H), 6.96-6.88 (m, 3H), 6.74 (m, 2H), 5.63 (s, 1H), 5.03 (m, 1H), 4.98 (s, 2 h), 4.58 (m, 1 h), 3.70 (s, 3H), 3.41 (s, 3H), 3.05 (m, 2H), 1.28 (s, 9H).

(S)-2-tert-Butoxycarbonylamino-3-{(S)-2-[4-(3,4-dichloro-benzyloxy)-phenyl]-4-methyl-3-oxo-3,4-dihydro-2H-benzo[1,4]oxazin-6-yl}-propionic acid methyl ester (4.9 g) was deprotected according to general procedure C to provide (S)-2-amino-3-{(S)-2-[4-(3,4-dichloro-benzyloxy)-phenyl]-4-methyl-3-oxo-3,4-dihydro-2H-benzo[1,4]oxazin-6-yl}-propionic acid methyl ester hydrochloride (4.2 g). LC-MS (m/z) 516.

(S)-2-Amino-3-{(S)-2-[4-(3,4-dichloro-benzyloxy)-phenyl]-4-methyl-3-oxo-3,4-dihydro-2H-benzo[1,4]oxazin-6-yl}-propionic acid methyl ester hydrochloride (7.25 mmol) was suspended in 120 mL of dichloroethane and paraformaldehyde (9.4 mmol) and TFA (20 mL) added. The resulting mixture heated at 70° C. for 5 h. The mixture was concentrated and dissolved in DCM. Triethylamine (21.8 mmol) and di-tert-butyl dicarbonate (10.9 mmol) were added and the mixture stirred at room temperature for 3 h. The mixture was concentrated and purified over silica gel (hexanes-EtOAc) to provide (3S,7S)-3-[4-(3,4-dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester (4.2 g). NMR (400 MHz, CDCl3): 7.51 (d, 1H), 7.44 (d, 1H), 7.30 (m, 2H), 7.23 (m, 1H), 6.90 (m, 2H), 6.82-6.71 (m, 2H), 5.62 (s, 1H), 5.16-4.78 (m, 1H), 4.98 (s, 2H), 4.68-4.34 (m, 2H), 3.61 (s, 3H), 3.23 (s, 3H), 3.22-3.11 (m, 2H), 1.48 (d, 9H).

(3S,7S)-3-[4-(3,4-dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester (4.2 g) was deprotected following general procedure C. The hydrochloride salt was treated with 10% sodium carbonate and EtOAc. The aqueous layer was washed with EtOAc and the organic layers combined. The organic layers were dried over sodium sulfate and concentrated to provide (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester (3.4 g). LC-MS (m/z) 528. NMR (400 MHz, CDCl3): 7.51 (d, 1H), 7.44 (d, 1H), 7.29 (m, 2H), 7.23 (m, 1H), 7.68 (m, 2H), 6.69 (s, 1H), 6.68 (s, 1H), 5.64 (s, 1H), 4.97 (s, 2H), 4.03 (m, 2H), 3.79 (s, 3H), 3.73 (m, 1H), 3.40 (s, 3H), 3.09-2.90 (m, 2H).

Similarly ((3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester [NMR (400 MHz, CDCl3): 7.48 (d, 1H), 7.43 (d, 1H), 7.28 (m, 2H), 7.21 (m, 1H), 6.88 (m, 2H), 6.80-6.69 (m, 2H), 5.64 (s, 1H), 5.18-4.83 (m, 1H), 4.96 (s, 2H), 4.65-4.36 (m, 2H), 3.64 (m, 3H), 3.40 (m, 3H), 3.23-3.03 (m, 2H), 1.48 (d, 9H)] and (3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester [NMR (400 MHz, CDCl3): 7.49 (d, 1H), 7.43 (d, 1H), 7.29 (m, 2H), 7.21 (m, 1H), 6.87 (m, 2H), 6.68 (s, 1H), 6.67 (s, 1H), 5.62 (s, 1H), 4.96 (s, 2H), 4.03 (m, 2H), 3.78 (s, 3H), 3.68 (m, 1H), 3.39 (s, 3H), 2.94 (m, 2H) were synthesized from (S) mandelic acid derivative.

(3S,7S)-3-[4-(3,4-dichloro-benzyloxy)-phenyl]-1-methyl-2-oxo-6-(1S-1-phenyl-propyl)-2,3,5,6,7,8-hexahydro-1H-4-oxa-1,6-diaza-anthracene-7-carboxylic acid and (3S,7S)-3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid 3.1-2.81 (m, 2H), 2.3 (m, 1H), 1.8 (m, 1H), 0.53 (t, 3H); and (3S,7S)-3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid methyl ester LC-MS (m/z): 646.

Hydrolysis of (3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid methyl ester using general procedure N provided (3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid. LC-MS (m/z): 632.

Similar procedures can be adopted to furnish (3S,7S)-3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid.

(3R,7S)-3-[4-(3,4-dichloro-benzyloxy)-phenyl]-1-methyl-2-oxo-6-(1S-1-phenyl-propyl)-2,3,5,6,7,8-hexahydro-1H-4-oxa-1,6-diaza-anthracene-7-carboxylic acid and (3R,7S)-3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid

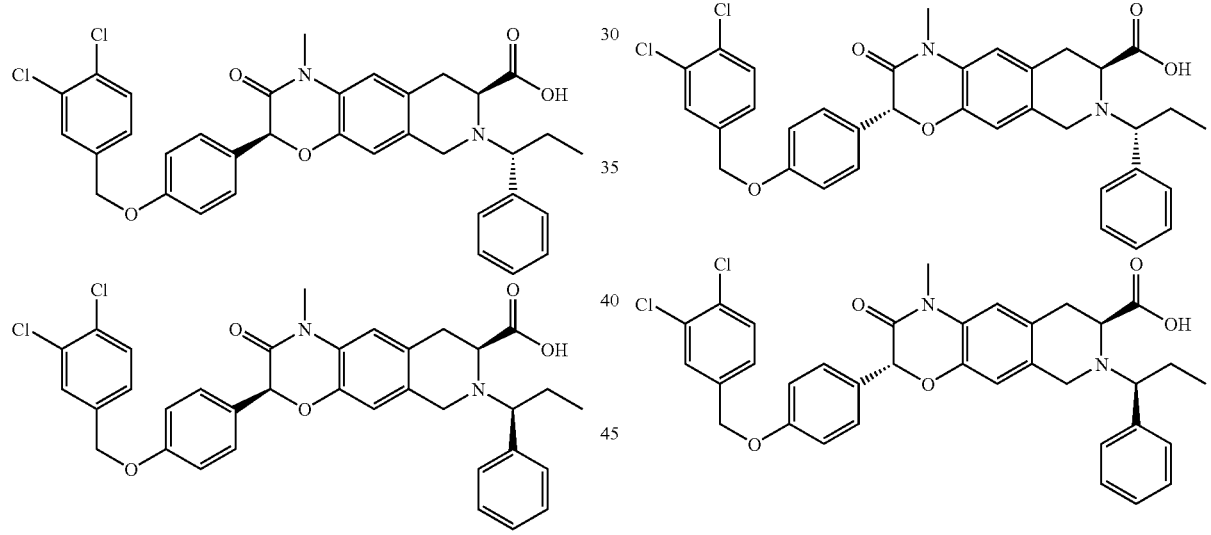

(1-Bromo-propyl)-benzene was prepared from 1-phenyl-propan-1-ol following general procedure Q and used to prepare the title compound. (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester (6.0 g, 11.3 mmol) was reacted with 1-bromo-1-phenylpropane (60 mmol) and NaHCO₃ (60 mmol) as described in general procedure K to obtain a 60:40 mixture of methyl esters of title acids. These compounds were separated by column chromatography on silica gel using hexanes-ethyl acetate. (3:1) to furnish (3S,7S)-3-[4-(3,4-dichloro-benzyloxy)-phenyl]-1-methyl-2-oxo-6-(1S-1-phenyl-propyl)-2,3,5,6,7,8-hexahydro-1H-4-oxa-1,6-diaza-anthracene-7-carboxylic acid methyl ester (2 g) ¹H NMR (400 MHz, CDCl₃): 7.51 (d, 1H), 7.45 (d, 1H), 7.35-7.24 (m, 8H), 6.88 (m, 2H), 6.72 (s, 1H), 6.62 (s, 1H), 5.59 (s, 1H), 4.9 (s, 2H), 4.13 (m, 2H), 3.87 (m, 1H), 3.62 (m, 1H), 3.54 (s, 3H), 3.38 (s, 3H), (1-Bromo-propyl)-benzene was prepared from 1-phenyl-propan-1-ol following general procedure Q and used to prepare the title compound. (3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid methyl ester (6.2 g, 12 mmol) was reacted with 1-bromo-1-phenylpropane (60 mmol) and NaHCO₃ (60 mmol) as described in general procedure K to obtain a 60:40 mixture of methyl esters of title acids. These compounds were separated by column chromatography on silica gel using hexanes-ethyl acetate. (3:1) to furnish (3R,7S)-3-[4-(3,4-dichloro-benzyloxy)-phenyl]-1-methyl-2-oxo-6-(1S-1-phenyl-propyl)-2,3,5,6,7,8-hexahydro-1H-4-oxa-1,6-diaza-anthracene-7-carboxylic acid methyl ester (23 g) ¹H NMR (400 MHz, CDCl₃): 7.51 (d, 1H), 7.45 (d, 1H), 7.35-7.24 (m, 8H), 6.88 (m, 2H), 6.72 (s, 1H), 6.62 (s, 1H), 5.64 (s, 1H), 4.98 (s, 2H), 4.13 (m, 2H), 3.80 (m, 1H), 3.63 (m, 1H), 3.56 (s, 3H), 3.38 (s, 3H), 3.1-2.85 (m, 2H), 2.15 (m, 1H), 1.65 (m, 1H), 0.65 (t, 3H); and (3S,7S)-

3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid methyl ester LC-MS (m/z): 646.

Hydrolysis of (3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid methyl ester using general procedure N provided (3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid. LC-MS (m/z): 632.

Similar procedure can be adopted to furnish (3R,7S)-3-[4-(3,4-dichloro-benzyloxy)-phenyl]-1-methyl-2-oxo-6-(1R-1-phenyl-propyl)-2,3,5,6,7,8-hexahydro-1H-4-oxa-1,6-diaza-anthracene-7-carboxylic acid.

(S)-2-Amino-3-(4'-cyano-biphenyl-4-yl)-propionic acid methyl ester-hydrochloride

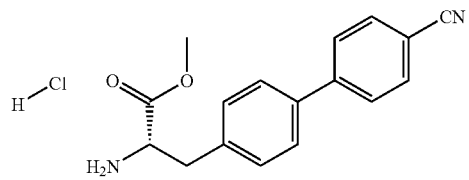

crude product. The residue was purified by column chromatography (hexanes-EtOAc) to provide (S)-2-tert-Butoxycarbonylamino-3-(4'-cyano-biphenyl-4-yl)-propionic acid methyl ester (18.2 g). LC-MS (m/z) 382.

Step 3. Removal of t-butyl carbamate: (S)-2-tert-Butoxycarbonylamino-3-(4'-cyano-biphenyl-4-yl)-propionic acid methyl ester (18.1 g) was deprotected following general procedure C to provide (S)-2-amino-3-(4'-cyano-biphenyl-4-yl)-propionic acid methyl ester-hydrochloride (16.2 g). $^1$H NMR (400 MHz, DMSO d6): 8.71 (bs, 3H), 7.90 (m, 4H), 7.73 (d, 2H), 7.37 (d, 2H), 4.31 (t, 1H), 3.54 (s, 3H), 3.16 (m, 2H).

Similar procedures were used to prepare the following biphenyl alanine derivatives: (S)-2-amino-3-(4'-chloro-biphenyl-4-yl)-propionic acid methyl ester; hydrochloride, (S)-2-amino-3-(4'-methoxy-biphenyl-4-yl)-propionic acid methyl ester; hydrochloride, (S)-2-amino-3-(4-pyridin-4-yl-phenyl)-propionic acid methyl ester; bis-hydrochloride. (S)-2-amino-3-(4'-methyl-biphenyl-4-yl)-propionic acid methyl ester; hydrochloride, (S)-2-amino-3-(4'-fluoro-biphenyl-4-yl)-propionic acid methyl ester; hydrochloride, and (R)-2-amino-3-(4'-cyano-biphenyl-4-yl)-propionic acid methyl ester hydrochloride.

(S)-3-(4'-Cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester; hydrochloride ("Intermediate A")

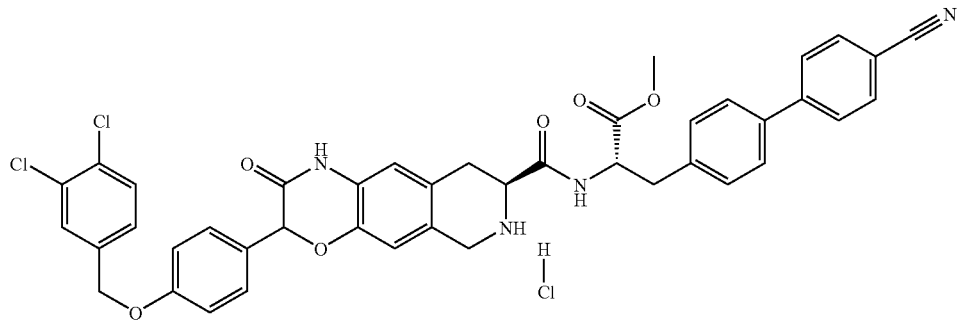

Step 1. Esterification: To a solution of (S)-3-(4-Bromo-phenyl)-2-tert-butoxycarbonylamino-propionic acid (72.6 mmol) in DMF (50 mL) was added DIEA (145 mmol) and methyl iodide (363 mmol). The reaction mixture stirred at rt for 2.5 h and was poured onto EtOAc and water. The organic layer was washed with 1 N HCl and 10% sodium carbonate, dried over sodium sulfate and concentrated. (S)-3-(4-Bromo-phenyl)-2-tert-butoxycarbonylamino-propionic acid methyl ester (25.1 g) was used without further purification. LC-MS (m/z) 359.

Step 2. Suzuki coupling: To a solution of (S)-3-(4-Bromo-phenyl)-2-tert-butoxycarbonylamino-propionic acid methyl ester (70.1 mmol) in toluene (250 mL) was added 4-cyanobenzeneboronic acid (105 mmol), Pd(PPh$_3$)$_4$ (3.5 mmol), and 1N Na$_2$CO$_3$ solution (105 mL). The mixture was heated at reflux for 7 h. After completion of the reaction, the aqueous layer was drained. The organic was washed with 10% Na$_2$CO$_3$ and 1 N HCl. The organic was dried over sodium sulfate and concentrated under reduced pressure to afford the (S)-7-hydroxy-6-nitro-3,4-dihydro-1H-isoquinoline-2,3-dicarboxylic acid 2-tert-butyl ester 3-methyl ester (5.1 mmol) was hydrolyzed and coupled with (S)-2-amino-3-(4'-cyano-biphenyl-4-yl)-propionic acid methyl ester (5.85 mmol) according to general procedures B and A to provide (S)-3-[(S)-2-(4'-cyano-biphenyl-4-yl)-1-methoxycarbonyl-ethylcarbamoyl]-7-hydroxy-6-nitro-3,4-dihydro-1H-isoquinoline-2-carboxylic acid tert-butyl ester (2.4 g). (S)-3-[(S)-2-(4'-cyano-biphenyl-4-yl)-1-methoxycarbonyl-ethylcarbamoyl]-7-hydroxy-6-nitro-3,4-dihydro-1H-isoquinoline-2-carboxylic acid tert-butyl ester (1.1 g) was dissolved in MeOH, Pd/C was added and the mixture stirred under balloon pressure of hydrogen for 1 h. Mixture was filtered through celite, washed with MeOH and EtOAc and concentrated to provide (S)-6-amino-3-[(S)-2-(4'-cyano-biphenyl-4-yl)-1-methoxycarbonyl-ethylcarbamoyl]-7-hydroxy-3,4-dihydro-1H-isoquinoline-2-carboxylic acid tert-butyl ester (1.06 g) which was used without further purification.

(S)-6-amino-3-[(S)-2-(4'-cyano-biphenyl-4-yl)-1-methoxycarbonyl-ethylcarbamoyl]-7-hydroxy-3,4-dihydro-1H-isoquinoline-2-carboxylic acid tert-butyl ester (1.75 mmol) was dissolved in 5 mL EtOAc, 10 mL water and 15 g sodium bicarbonate added. 2-Chloro-2-[4-(3,4-dichloro-benzyloxy)-phenyl]-acetyl chloride (1.93 mmol) in 5 mL EtOAc was added to the mixture. The resulting mixture stirred at r.t. for 1.5 h. The organic layer was washed with brine, dried over sodium sulfate and concentrated. The resulting residue was dissolved in 5 mL DMF and potassium carbonate (8.75 mmol) added. The reaction stirred at r.t. for 3 h and was poured onto ethyl acetate and water. The organic was dried and concentrated. The residue was purified over silica gel (-hexanes-ethyl acetate) to provide (S)-7-[(S)-2-(4'-Cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tert-butyl ester (931 mg). LC-MS (m/z) 862.

(S)-3-(4'-Cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester hydrochloride (740 mg) was prepared from (S)-7-[(S)-2-(4'-Cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tert-butyl ester (900 mg) following general procedure C. LC-MS (m/z) 762.

Alternate Procedure to Prepare Intermediate A

Step 1: Amide Coupling:

To a solution of 3-[4-(3,4-dichloro-benzyloxy)-phenyl]-2-oxo-1,2,3,5,7,8-hexahydro-4-oxa-1,6-diaza-anthracene-6,7 (S)-dicarboxylic acid 6-tert-butyl ester (2.5 mmol) in DMF was added (S)-2-amino-3-(4'-cyano-biphenyl-4-yl)-propionic acid methyl ester hydrochloride (2.8 mmol), HBTU (2.8 mmol), and DIEA (5.0 mmol) and the mixture was stirred for 3 h. After completion of the reaction, sufficient amount of 1 N HCl was added and the mixture was extracted with ethyl acetate. The organic layer was washed with 10% sodium carbonate and dried over sodium sulfate. The solvent was removed under reduced pressure to afford the amide, which was purified with silica gel chromatography using DCM-ethyl acetate and DCM-acetone to afford the desired product, (S)-7-[(S)-2-(4'-cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tert-butyl ester (807 mg). LC-MS (m/z) 862.

Step 2. Boc-Deprotection:

To a stirred solution of this above carbamate (800 mg) in DCM (5 mL) was added 4 N HCl in dioxane (15 mL). The reaction was stirred at room temperature for 2.5 h. Solvents were removed under reduced pressure to provide (S)-3-(4'-Cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester hydrochloride (0.758 g) as hydrochloric acid salt. This product was then used as such for further manipulations. LC-MS (m/z) 762.

Similar procedures may be used to prepare the following intermediates: (S)-3-(4'-Cyano-biphenyl-4-yl)-2-({(S)-3-[4-(5,6-dichloro-pyridin-3-ylmethoxy)-phenyl]-2-oxo-2,3,5,6,7,8-hexahydro-1H-4-oxa-1,6-diaza-anthracene-7-carbonyl}-amino)-propionic acid methyl ester; hydrochloride, (S)-3-(4'-cyano-biphenyl-4-yl)-2-({(S)-3-[4-(2,5-dichloro-benzyloxy)-phenyl]-2-oxo-2,3,5,6,7,8-hexahydro-1H-4-oxa-1,6-diaza-anthracene-7-carbonyl}-amino)-propionic acid methyl ester; hydrochloride, (S)-3-(4'-cyano-biphenyl-4-yl)-2-({(S)-3-[4-(2,6-dichloro-benzyloxy)-phenyl]-2-oxo-2,3,5,6,7,8-hexahydro-1H-4-oxa-1,6-diaza-anthracene-7-carbonyl}-amino)-propionic acid methyl ester; hydrochloride, (S)-2-({(S)-3-[4-(3-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester; hydrochloride, and (S)-2-({(S)-3-[4-(4-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester; hydrochloride.

Preparation of (S)-3-(4'-Cyano-biphenyl-4-yl)-2-({(S)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid methyl ester hydrochloride ("Intermediate B")

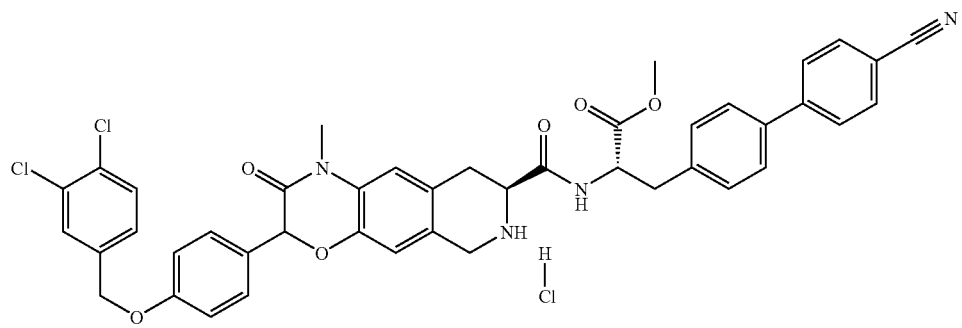

(7S)-3-[4-(3,4-dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester (3.0 g, 4.9 mmol) and methanol (9.8 mmol) were dissolved in 60 mL DCM. Resin-bound triphenylphosphine (9.8 mmol) was added and the mixture cooled to 0° C. To this solution was added DIAD (9.8 mmol) and the mixture was agitated for 10 min at 0° C. and the mixture was slowly allowed to warm up to r.t. and agitated for 4 h. The reaction mixture was filtered, concentrated and the residue purified over silica-gel hexanes-ethyl acetate (7-3) to afford. (S)-3-[4-(3,4-dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester (3.0 g). LC-MS (m/z) 628.

(S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester (3.0 g) was dissolved in THF-methanol (4:1, 10 mL), 2 N lithium hydroxide solution (4.8 mL) was added, and the resulting reaction mixture was stirred at 0° C. for 5 h. The reaction mixture was neutralized with 1N HCl and extracted with ethyl acetate. The organic layer was washed with brine, dried over sodium sulfate, and the solvent was removed under reduced pressure to afford (S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester (2.9 g). LC-MS (m/z) 614. The Boc group of (S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester may be removed to provide the compound Intermediate C ("Intermediate C").

(S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester (2.9 g) was coupled to (S)-2-amino-3-(4'-cyano-biphenyl-4-yl)-propionic acid methyl ester hydrochloride (1.5 g) following general procedure A to provide (S)-7-[(S)-2-(4'-Cyano-biphenyl-4-yl)-1-methoxycarbonyl-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid tert-butyl ester (3.0 g). LC-MS (m/z) 878.

Intermediate B (2.2 g) was prepared from (S)-7-[(S)-2-(4'-cyano-biphenyl-4-yl)-1-methoxycarbonyl-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid tert-butyl ester (3.0 g) following general procedure C. LC-MS (m/z) 776.

(S)-2-Benzyloxycarbonylamino-3-(4-hydroxy-phenyl)-2-methyl-propionic acid methyl ester To a solution of (S)-2-amino-3-(4-hydroxy-phenyl)-2-methyl-propionic acid (976 mg, 5 mmol) in methanol (50 mL) was added 4N. HCl in dioxane (1.88 mL, 7.5 mmol) and the mixture was refluxed for 4 h. After the completion of the esterification, the methanol was evaporated and the residue was used as such for the next step.

To a suspension of (S)-2-amino-3-(4-hydroxy-phenyl)-2-methyl-propionic acid methyl ester hydrochloride in ethyl acetate (25 mL) was added 1N NaHCO₃ solution (12.5 ml.) and the mixture was stirred rapidly at ambient temperature for the addition of neat benzyl chloroformate (0.859 g, 1.01 eq., 5.05 mmol). Following addition, the reaction mixture was stirred for an additional hour; TLC and LC-MS analysis showed the reaction to be complete. The mixture was partitioned and the organic phase was separated and dried over Na₂SO₄ and concentrated. The crude product was used directly in the subsequent reaction without purification.

(S)-2-Benzyloxycarbonylamino-2-methyl-3-(4-trifluoro-methanesulfonyloxy-phenyl)-propionic acid methyl ester To a 0° solution of the crude (S)-2-benzyloxycarbonylamino-3-(4-hydroxy-phenyl)-2-methyl-propionic acid methyl ester (440 mg, 1.28 mmol) in dry DCM (13 mL) was added dry pyridine (155 µL) followed by triflic anhydride (259 µL). The reaction mixture was stirred at 0° C. for an additional hour at which point starting material was no longer visible by TLC or LC-MS. The mixture was quenched with of saturated NaHCO₃ solution. The mixture was partitioned and the aqueous phase discarded. The crude product in DCM was washed with water (30 mL), dried over Na₂SO₄ and concentrated to furnish a brown oil. The crude triflate was used as is without further purification.

(S)-2-Benzyloxycarbonylamino-3-(4'-cyano-biphenyl-4-yl)-2-methyl-propionic acid methyl ester

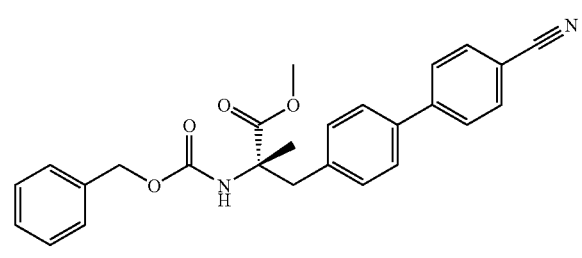

In a three necked flask, equipped with reflux condenser, was taken the crude triflate (609 mg, 1.28 mmol), 4-cyanophenyl boronic acid (226 mg, 1.54 mmol), Na₂CO₃ (350 mg, 2.82 mmol) water (1.41 mL) and totune (5 mL). The mixture was stirred and degassed with a stream of nitrogen for 45 minutes before adding Pd (PPh₃)₄ (0.01 eq. 30 mg). The solution was degassing for an additional 20 minutes. The mixture was heated, under nitrogen, to 85° C. for 6 h. The reaction continued until the triflate was no longer detected by TLC (50% EtOAc/hexanes, PMA char) or by LC-MS. The reaction mixture was cooled to ambient temperature and partitioned. The crude product in toluene concentrated and purified by flash chromatography (7:3 hexane-EtOAc) to get a solid (488 mg). LC-MS (m/z): 429. ¹H NMR (400 MHz, CDCl₃): 7.72 (m, 2H), 7.64 (m, 2H), 7.39 (m, 7H), 7.06 (d, 2H), 5.52 (bs, 1H) 5.2 (d, 1H), 5.1 (d, 1H), 3.78 (s, 3H), 3.52 (m, 2H), 3.23 (d, 2H), 1.68 (s, 3H).

(S)-2-Amino-3-(4'-cyano-biphenyl-4-yl)-2-methyl-propionic acid methyl ester

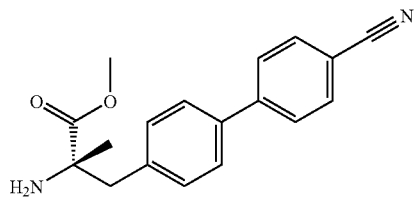

The purified cbz-protected amino acid ester (475 mg, 1.11 mmol) was dissolved in cyclohexene (fw=82.15, ρ=0.811, 0.23 mL, 2.23 mmol) and ethanol (10 mL). To this solution was added Pd/C (48 mg) and the mixture was degassed for 30 minutes. The mixture was heated at reflux (74-75° C.) for 4-6 hours, at which point starting material was no longer detected. The reaction mixture was cooled and filtered through celite and washed with ethyl acetate. The organic layer was concentrated and the residue was purified by flash column chromatography (gradient elution with 5-50% ethyl acetate in hexanes) afforded the purified product as a white solid. ¹H NMR (400 MHz, CDCl₃): 7.72 (m, 2H), 7.66 (m, 2H), 7.52 (m, 2H), 7.28 (m, 2H), 3.73 (s, 3H), 3.18 (d, 1H), 2.86 (d, 1H), 1.7 (bs, 2H), 1.42 (s, 3H).

(3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester and (3R,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester

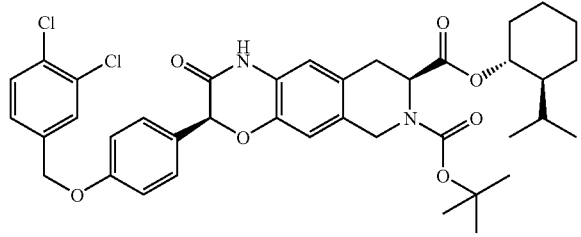

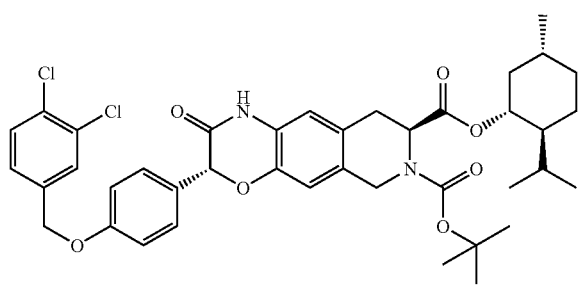

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester (6.9 g, 11.5 mmol) was suspended in 30 mL DCM and 1R-2S-5R (−)-menthol (23.0 mmol), EDC (23.0 mmol) and DMAP (cat.) added. The mixture stirred at r.t. for 16 h and the mixture diluted with DCM. The organic layer was washed with 1 N HCl, dried over sodium sulfate and concentrated. The residue was purified over silica with hexanes-EtOAc gradient (25% EtOAc to 30%) to provide (3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.0 g) LC-MS (m/z) 738; $^1$H NMR (400 MHz, CDCl$_3$): 8.87 (m, 1H), 7.5 (m, 1H), 7.42 (d, 1H), 7.35 (m, 2H), 7.24 (m, 1H), 6.9 (m, 2H), 6.75 (m, 1H), 6.6 (s, 1H), 5.56 (m, 1H), 4.8-5.1 (m, 1H), 5.0 (m, 2H), 4.3-4.6 (m, 3H), 3.1 (m, 2H), 1.78 (m, 1H), 1.6 (m, 3H), 1.5 (d, 9H), 1.28 (m, 2H), 0.7-1.0 (m, 9H), 0.4 (m, 3H). and (3R,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester. (3.1 g) LC-MS (m/z) 738; $^1$H NMR (400 MHz, CDCl$_3$): 8.50 (m, 1H), 7.5 (d, 1H), 7.43 (d, 1H), 7.37 (m, 2H), 7.21 (m, 1H), 6.9 (m, 2H), 6.76 (m, 1H), 6.58 (s, 1H), 5.62 (m, 1H), 4.8-5.1 (m, 1H), 5.0 (s, 2H), 4.6-4.35 (m, 3H), 3.05 (m, 2H), 1.8 (m, 1H), 1.6 (m, 3H), 1.5 (d, 9H), 1.26 (m, 2H), 0.7-1.0 (m, 9H), 0.4 (m, 3H).

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester

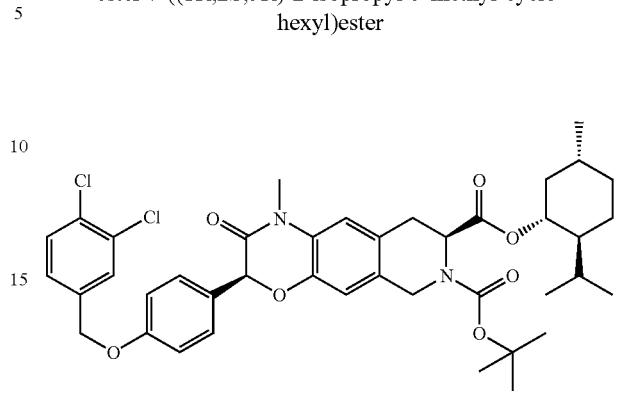

(3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.0 g) was N-methylated according to general procedure M to provide (3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.7 g) LC-MS (m/z) 752.

(3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester

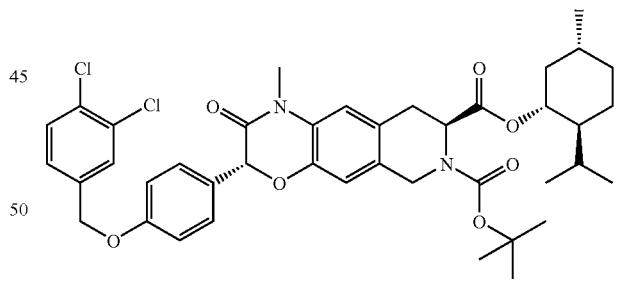

(3R,7S)-3-[4-(3,4-Dichloro-benzyloxy)-phenyl]-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester (3.0 g) was N-methylated according to general procedure M to provide (3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.7 g) LC-MS (m/z) 752.

(3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride

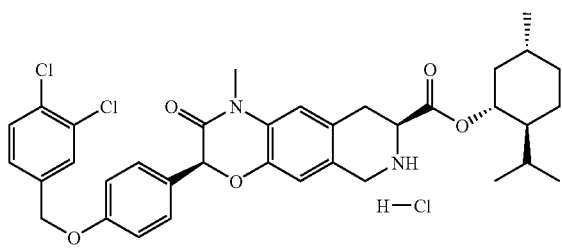

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.7 g) was deprotected using general procedure C to provide (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride (3.1 g, LC/MS: m/z 652).

(3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride

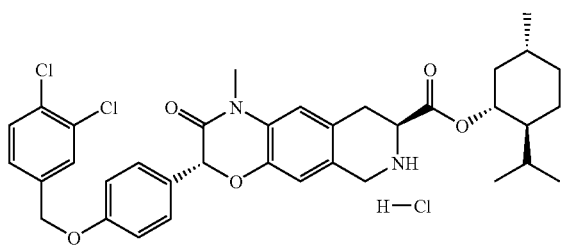

(3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.9 g) was deprotected using general procedure C to provide (3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride (3.2 g, LC/MS: m/z 652).

(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester and (3S,7S)-3-[4-(3,4-Dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester

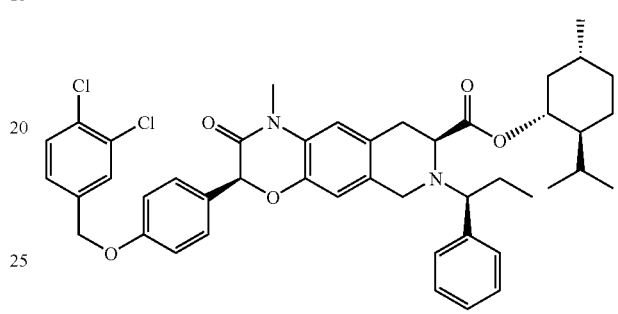

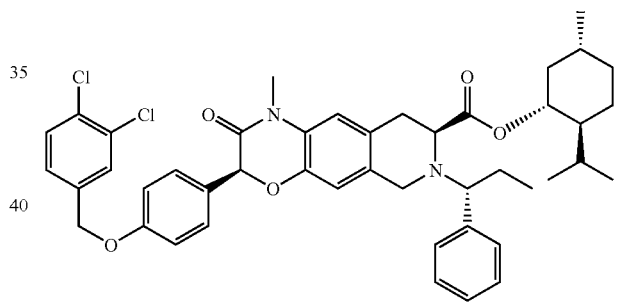

(3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (2.6 g, 4 mmol) in DMF was treated with (1-bromo-propyl)-benzene (15 mmol) and NaHCO$_3$ (16 mmol). The mixture was stirred at 40° C. for 48 h. The mixture was poured into water, extracted with EtOAc, washed with water, brine, dried and concentrated. The residue was purified over silica (EtOAc-hexanes-DCM-TEA, 0.5/5/4.5/0.02) to provide (3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (401 mg), $^1$H NMR (400 MHz, d$_6$ acetone): 7.7 (d, 1H), 7.6 (d, 1H), 7.46 (d, 1H), 7.33 (m, 7H), 6.98 (m, 2H), 6.87 (s, 1H), 6.77 (s, 1H), 5.65 (s, 1H), 5.13 (s, 2H), 4.55 (m, 1H), 4.20 (s, 2H), 3.9 (m, 1H), 3.55 (m, 1H), 3.38 (s, 3H), 2.95 (m, 2H), 1.6 (m, 6H), 1.15 (m, 1H), 0.95 (m, 1H) 0.9 (m, 2H), 0.8 (m, 4H), 0.7 (d, 3H), 0.65 (m, 6H) and (3S,7S)-3-[4-(3,4-Dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (230 mg).

61

(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester and (3R,7S)-3-[4-(3,4-Dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester

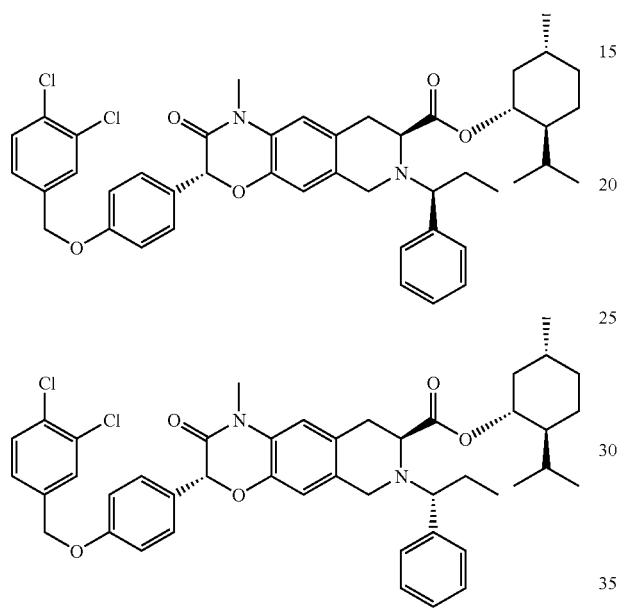

(3R,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (2.6 g, 4 mmol) in DMF was treated with (1-bromo-propyl)-benzene (15 mmol) and NaHCO$_3$ (16 mmol). The mixture was stirred at 40° C. for 48 h. The mixture was poured into water, extracted with EtOAc, washed with water, brine, dried and concentrated. The residue was purified by flash chromatography (Hexane-EtOAc 4:1) to furnish (3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester $^1$H NMR (400 MHz, d$_6$ acetone): 7.68 (s, 1H), 7.58 (d, 1H), 7.45 (d, 1H), 7.33 (m, 7H), 6.98 (m, 2H), 6.85 (s, 1H), 6.76 (s, 1H), 5.67 (s, 1H), 5.12 (s, 2H), 4.57 (m, 1H), 4.21 (m, 2H), 3.85 (m, 1H), 3.56 (m, 1H), 3.37 (s, 3H), 2.95 (m, 2H), 2.9 (3H), 2.2 (m, 1H), 1.6 (m, 6H), 1.15 (m, 1H), 1.0 (m, 2H), 0.83 (m, 4H), 0.78 (d, 3H), 0.64 (m, 6H) and (3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid 1R,2S,5R)-2-isopropyl-5-methyl-cyclohexyl ester ($^1$H NMR (400 MHz, d$_6$ acetone): 7.67 (d, 1H), 7.59 (d, 1H), 7.46 (d, 1H), 7.33-7.35 (m, 7H), 6.91 (m, 2H), 6.88 (s, 1H), 6.54 (s, 1H), 5.62 (s, 1H), 5.09 (s, 2H), 4.61 (m, 1H), 4.28 (s, 2H), 3.86-3.74 (m, 3H), 3.55 (d, 1H), 3.38 (s, 3H), 3.21-3.0 (m, 3H), 1.6 (m, 6H), 1.4-1.1 (m, 2H), 0.95 (m, 1H) 0.9 (m, 2H), 0.8 (m, 4H), 0.79 (d, 3H), 0.62 (m, 6H).

62

(3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid and (3S,7S)-3-(4-Hydroxy-phenyl)-1-methyl-2-oxo-6-((R)-1-phenyl-propyl)-2,3,5,6,7,8-hexahydro-1H-4-oxa-1,6-diaza-anthracene-7-carboxylic acid

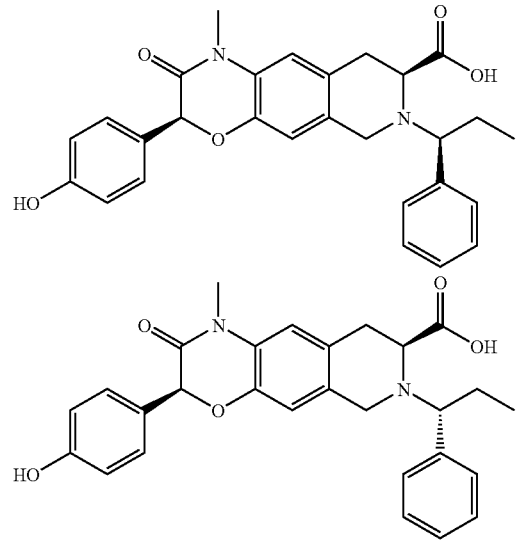

(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (300 mg) was dissolved in 10 mL of dry DCM and cooled to 0° C. Boron trichloride (3 mL, 1M solution in hexanes) was added and the mixture stirred at 0° C. for 3 hours. The mixture was concentrated and treated with water/saturated sodium bicarbonate until pH 7. The aqueous mixture was extracted three times with ethyl acetate-THF (9-1) and organic layer combined. The combined organic layer were dried over sodium sulfate and concentrated to provide (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (183 mg, LC/MS: m/z 474).

(3S,7S)-3-[4-(3,4-Dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (230 mg) was dissolved in 10 mL of dry DCM and cooled to 0° C. Boron trichloride (3 mL, 1M solution in hexanes) was added and the mixture stirred at 0° C. for 3 hours. Mixture was concentrated and treated with water/saturated sodium bicarbonate until pH 7. Aqueous mixture was extracted three times with ethyl acetate-THF (9-1) and organic layer combined. The combined organic layer were dried over sodium sulfate and concentrated to provide (3S,7S)-3-(4-Hydroxy-phenyl)-1-methyl-2-oxo-6-((R)-1-phenyl-propyl)-2,3,5,6,7,8-hexahydro-1H-4-oxa-1,6-diaza-anthracene-7-carboxylic acid (153 mg, LC/MS: m/z 474).

(3R,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid and (3R,7S)-3-(4-Hydroxy-phenyl)-1-methyl-2-oxo-6-((R)-1-phenyl-propyl)-2,3,5,6,7,8-hexahydro-1H-4-oxa-1,6-diaza-anthracene-7-carboxylic acid

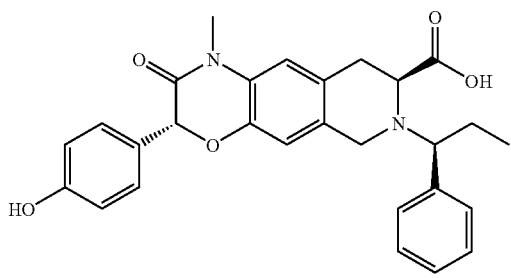

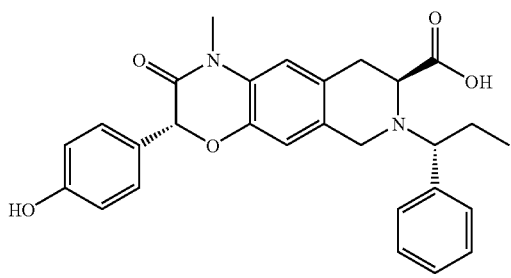

To a solution of (3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (0.2 mmol) in DCM (3 mL) was added 1N $BCl_3$ solution in hexane (0.5 mL) at 0° C. and the mixture was stirred for 3 h. The mixture was evaporated to dryness and the residue was quenched with water. The mixture was basified using sodium bicarbonate solution to pH 7. The residue was extracted with EtOAc and 10% THF. The organic layer was washed and dried to get (3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid as a yellow solid (122 mg). This solid was used as is for the next step.

(3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester was converted to (3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (118 mg) using similar procedure as described above and was used as is for the next step.

(S)-3-(4'-Cyano-biphenyl-4-yl)-2-{[(3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester

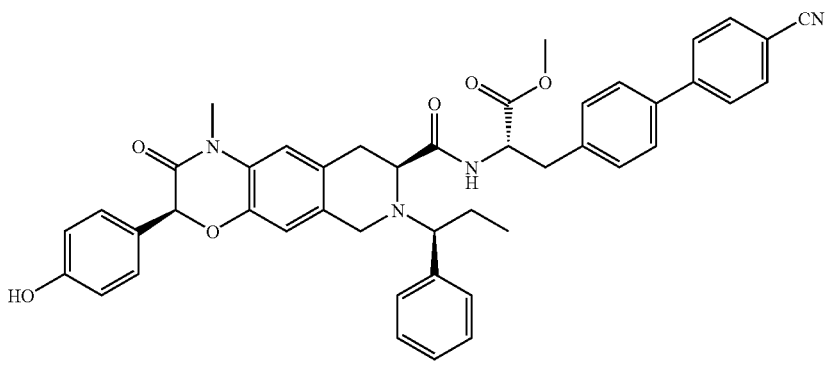

(S)-3-(4'-Cyano-biphenyl-4-yl)-2-{[(3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (190 mg) was prepared from (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (183 mg) and (S)-2-amino-3-(4'-cyano-biphenyl-4-yl)-propionic acid methyl ester hydrochloride following general procedure A. LC-MS (m/z) 736.

(S)-3-(4'-Cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester

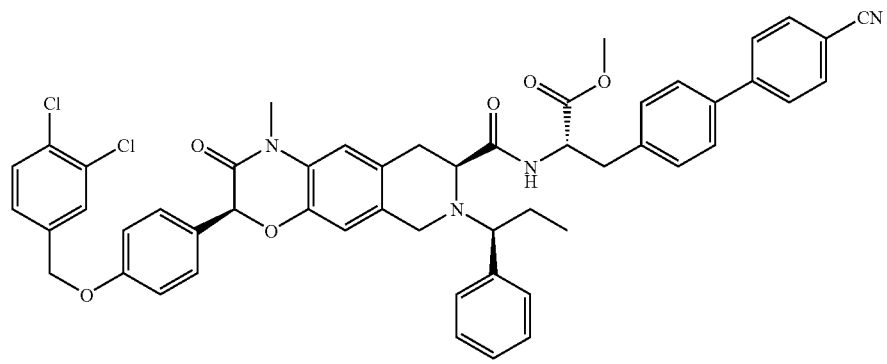

(S)-3-(4'-Cyano-biphenyl-4-yl)-2-{[(3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (0.259 mmol) was dissolved in 2 mL of DMF and 3,4-dichlorobenzyl bromide (1.30 mmol) and potassium carbonate (1.30 mmol) were added. The mixture was stirred at room temperature for 6 hours and was poured onto ethyl acetate and saturated sodium bicarbonate. The organic layer was dried over sodium sulfate and concentrated. The residue was purified over silica (hexanes-ethyl acetate-MeOH, 7-3-0.1) to provide (S)-3-(4'-Cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (96 mg, LC/MS: m/z 895). $^1$H NMR (400 MHz, $d_6$ acetone): 7.89-7.77 (m, 5H), 7.56 (m, 2H), 7.49 (m, 2H), 7.34 (m, 1H), 7.30-7.18 (m, 7H), 6.97 (s, 1H), 6.84 (m, 2H), 6.78 (m, 2H), 6.71 (s, 1H), 5.65 (s, 1H), 4.88 (m, 2H), 4.73 (m, 1H), 3.71 (s, 3H), 3.68 (m, 1H), 3.53 (d, 1H), 3.47 (m, 1H), 3.41 (s, 3H), 3.34 (d, 1H), 3.10 (m, 1H), 3.02 (m, 1H), 2.83-2.71 (m, 2H), 1.90-1.66 (m, 2H), 0.54 (t, 3H).

(S)-3-(4'-Cyano-biphenyl-4-yl)-2-{[(3S,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester

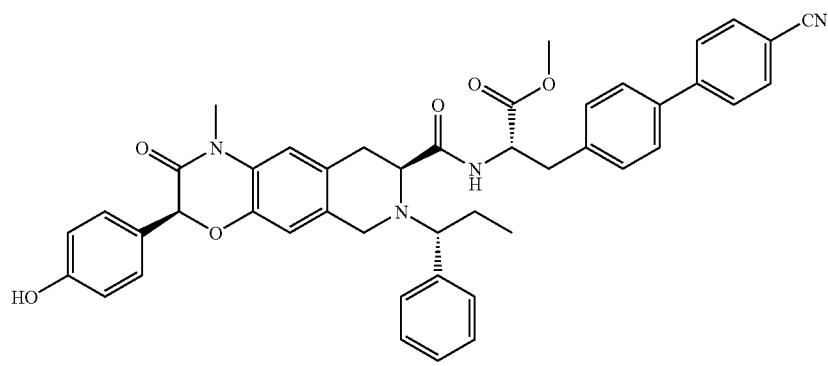

(S)-3-(4'-Cyano-biphenyl-4-yl)-2-{[(3S,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (130 mg) was prepared from (3S,7S)-3-(4-Hydroxy-phenyl)-1-methyl-2-oxo-6-((R)-1-phenyl-propyl)-2,3,5,6,7,8-hexahydro-1H-4-oxa-1,6-diaza-anthracene-7-carboxylic acid (153 mg) and (S)-2-amino-3-(4'-cyano-biphenyl-4-yl)-propionic acid methyl ester hydrochloride following general procedure A. LC-MS (m/z) 736.

(S)-3-(4'-Cyano-biphenyl-4-yl)-2-{[(3S,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester

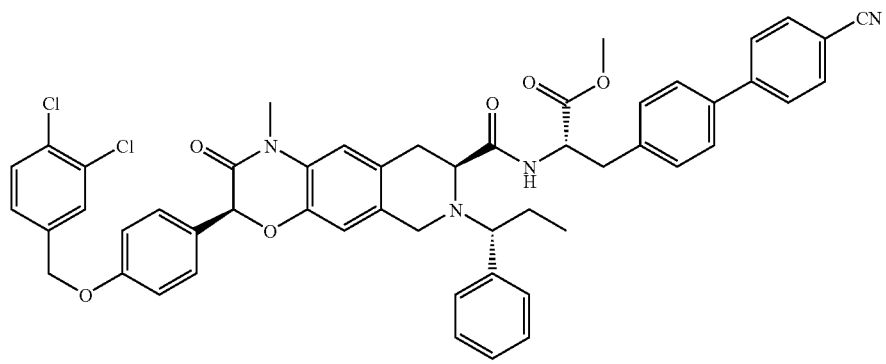

(S)-3-(4'-Cyano-biphenyl-4-yl)-2-{[(3S,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (0.177 mmol) was dissolved in 2 mL of DMF and 3,4-dichlorobenzyl bromide (0.885 mmol) and potassium carbonate (0.885 mmol) were added. The mixture was stirred at room temperature for 6 hours and was poured onto ethyl acetate and saturated sodium bicarbonate. The organic layer was dried over sodium sulfate and concentrated. The residue was purified over silica (hexanes-ethyl acetate-MeOH, 7-3-0.1) to provide (S)-3-(4'-Cyano-biphenyl-4-yl)-2-{[(3S,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester. $^1$H NMR (400 MHz, d$_6$ acetone): 7.77-7.86 (m, 5H), 7.60 (d, 1H), 7.54 (m, 3H), 7.37 (dd, 1H), 7.32-7.18 (m, 7H), 6.97 (d, 1H), 6.92 (s, 1H), 6.82 (m, 3H), 6.78 (m, 2H), 6.71 (s, 1H), 5.65 (s, 1H), 4.95 (m, 2H), 4.66 (m, 1H), 3.76 (m, 2H), 3.70 (s, 3H), 3.58 (m, 2H), 3.40 (s, 3H), 3.06 (m, 2H), 3.02 (m, 2H), 2.83-2.72 (m, 2H), 1.96-1.7 (m, 2H), 0.54 (t, 3H).

(S)-3-(4'-cyano-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester

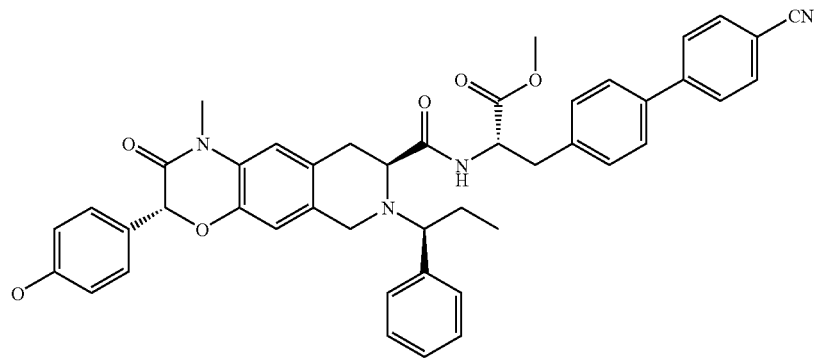

(S)-3-(4'-Cyano-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (84 mg) was prepared from (3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (100 mg) and (S)-2-amino-3-(4'-cyano-biphenyl-4-yl)-propionic acid methyl ester hydrochloride following general procedure A. A similar procedure was used to prepare the following compounds: (S)-3-(4'-chloro-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester, (S)-3-(4'-fluoro-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester, and (S)-2-{[(3R,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester.

(S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester

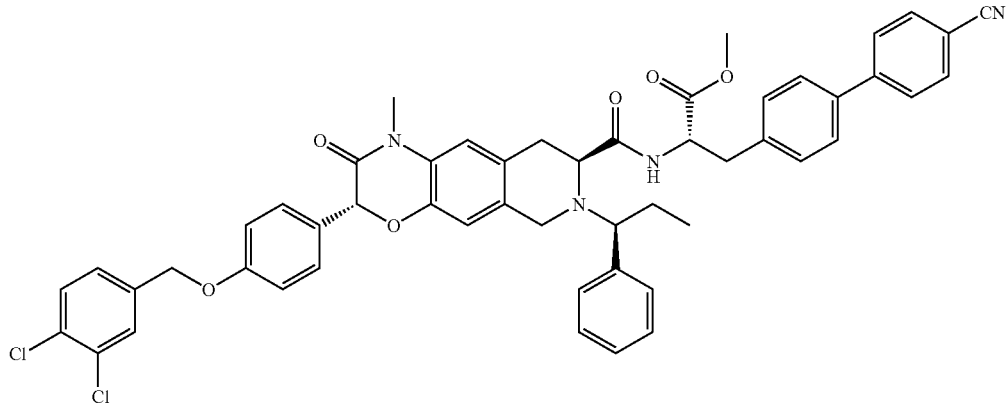

(S)-3-(4'-Cyano-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (15 mg) was dissolved in 1 mL of DMF and 3,4-dichlorobenzyl bromide (46 mg) and potassium carbonate (26 mg) were added. The mixture was stirred at room temperature for 6 hours and was poured onto ethyl acetate and saturated sodium bicarbonate. The organic layer was dried over sodium sulfate and concentrated. The residue was purified over silica (hexanes-ethyl acetate-MeOH, 6-4-0.1) to provide (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (18 mg, LC/MS: m/z 894). $^1$H NMR (400 MHz, $d_6$ acetone): 7.92-7.81 (m, 5H), 7.66 (s, 1H), 7.57 (m, 3H), 7.43 (m, 1H), 7.32-7.21 (m, 7H), 7.01-6.94 (m, 5H), 6.66 (s, 1H), 5.60 (s, 1H), 5.1 (s, 2H), 4.78 (m, 1H), 3.74 (s, 3H), 3.66 (m, 1H), 3.56 (d, 1H), 3.46 (m, 1H), 3.35 (s, 3H), 3.34 (d, 1H), 3.02-2.98 (m, 2H), 2.27 (m, 2H), 1.90-1.66 (m, 2H), 0.60 (t, 3H).

(S)-3-(4'-cyano-biphenyl-4-yl)-2-{[(3R,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester

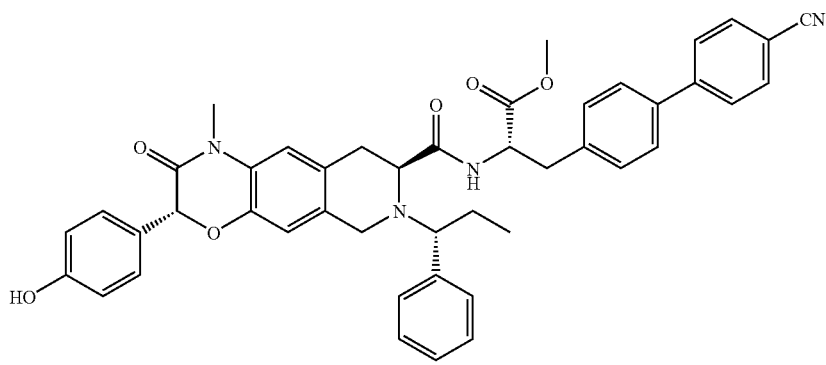

(S)-3-(4'-cyano-biphenyl-4-yl)-2-{[(3R,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (68 mg) was prepared from (3R,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carboxylic acid (100 mg) and (S)-2-amino-3-(4'-cyano-biphenyl-4-yl)-propionic acid methyl ester hydrochloride following general procedure A.

(S)-3-(4'-cyano-biphenyl-4-yl)-2-{[(3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester

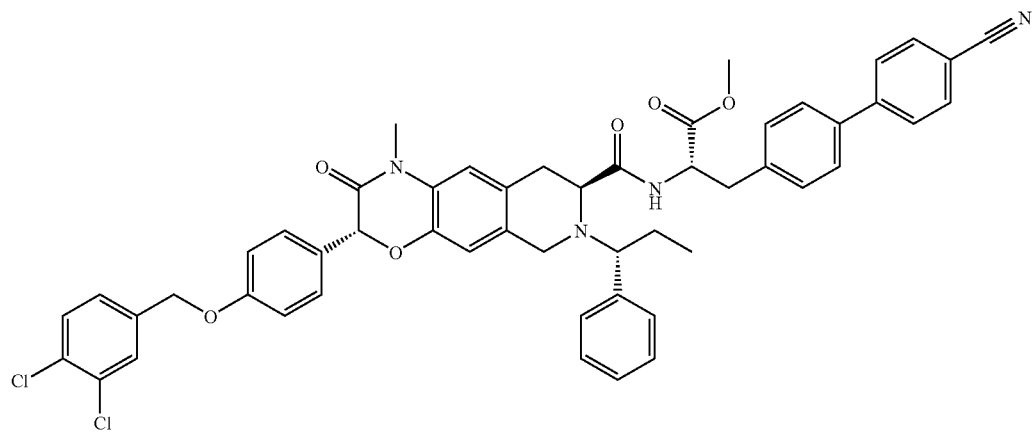

(S)-3-(4'-cyano-biphenyl-4-yl)-2-{[(3R,7S)-3-(4-hydroxy-phenyl)-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (52 mg) was dissolved in 1 mL of DMF To this solution was added 3,4-dichlorobenzyl bromide (33 mg) and potassium carbonate. The mixture was stirred at room temperature for 6 hours and was poured onto ethyl acetate and saturated sodium bicarbonate. The organic layer was dried over sodium sulfate and concentrated. The residue was purified over silica (hexanes-ethyl acetate-MeOH, 6-4-0.1) to provide (S)-3-(4'-cyano-biphenyl-4-yl)-2-{[(3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (16 mg). LC/MS: m/z 894). $^1$H NMR (400 MHz, $d_6$ acetone): 7.92-7.81 (m, 5H), 7.66 (s, 1H), 7.57 (m, 3H), 7.43 (m, 1H), 7.32-7.21 (m, 7H), 7.01-6.94 (m, 5H), 6.66 (s, 1H), 5.60 (s, 1H), 5.1 (s, 2H), 4.78 (m, 1H), 3.74 (s, 3H), 3.66 (m, 1H), 3.56 (d, 1H), 3.46 (m, 1H), 3.35 (s, 3H), 3.34 (d, 1H), 3.02-2.98 (m, 2H), 2.27 (m, 2H), 1.90-1.66 (m, 2H), 0.60 (t, 3H).

(S)-7-[(S)-2-(4'-Cyano-biphenyl-4-yl)-1-methoxy-carbonyl-ethylcarbamoyl]-3-(4-hydroxy-phenyl)-2-oxo-1,2,3,5,7,8-hexahydro-4-oxa-1,6-diaza-anthracene-6-carboxylic acid tert-butyl ester

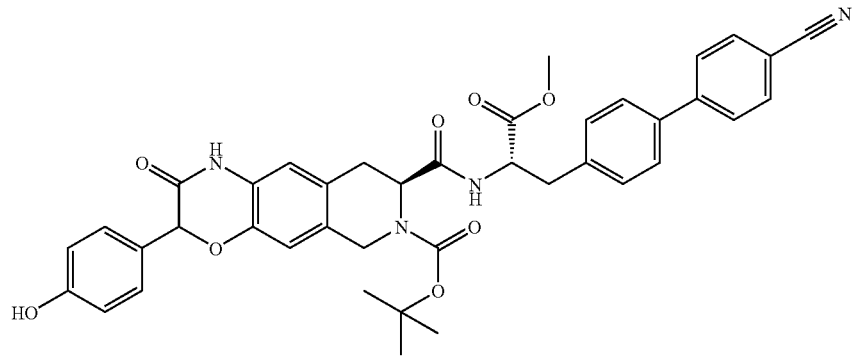

To a solution of (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester (1 mmol) in methanol was added Pd/C (0.2 mmol). The mixture was hydrogenated using balloon for 2-4 h. The mixture was passed through a pad of celite and the filtrate was evaporated to furnish (S)-3-(4-Hydroxy-phenyl)-2-oxo-1,2,3,5,7,8-hexahydro-4-oxa-1,6-diaza-anthracene-6,7-dicarboxylic acid 6-tert-butyl ester. This ester was converted to (S)-7-[(S)-2-(4'-Cyano-biphenyl-4-yl)-1-methoxycarbonyl-ethylcarbamoyl]-3-(4-hydroxy-phenyl)-2-oxo-1,2,3,5,7,8-hexahydro-4-oxa-1,6-diaza-anthracene-6-carboxylic acid tert-butyl ester using the general procedure A. LC-MS (m/z): 704.

The compounds specifically exemplified below were named based on their chemical structure using Autonom 2000 (Version 4.1, SP1, Elsevier MDL) plug-in for ISIS Draw and MDL Crossfire Commander AutoNom.

Example 1

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 4-hydroxy-cyclohexyl ester

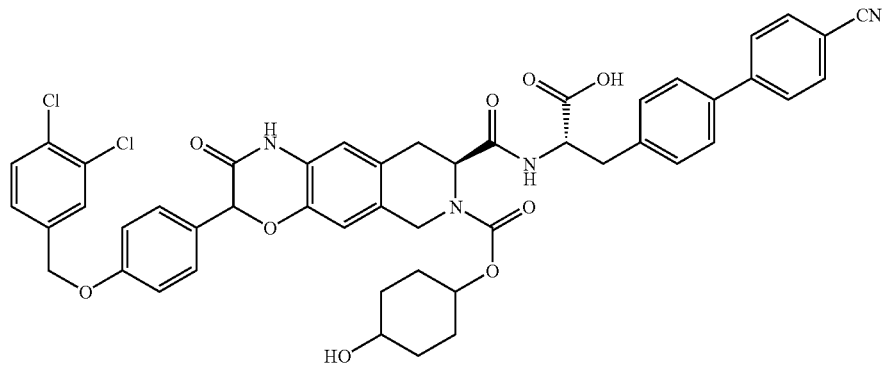

Title compound (66 mg) was prepared from Intermediate A (76 mg, 0.1 mmol) following general procedures H and B. LC-MS (m/z): 890.

Example 2

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 3-hydroxy-cyclopentyl ester

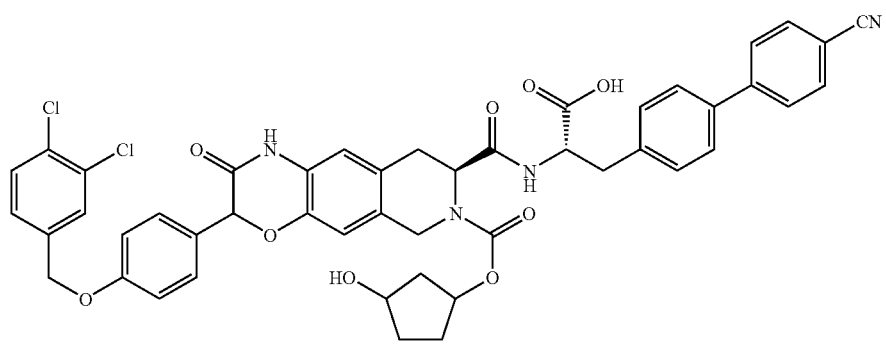

Title compound (61 mg) was prepared from Intermediate A (76 mg, 0.1 mmol) following general procedures H and B. LC-MS (m/z): 876.

Example 3

(S)-3-(4'-Cyano-biphenyl-4-yl)-2-{[(S)-3-[4-(3,4-dichloro-benzyloxy)-phenyl]-2-oxo-6-(pyridine-4-carbonyl)-2,3,5,6,7,8-hexahydro-1H-4-oxa-1,6-diaza-anthracene-7-carbonyl]-amino}-propionic acid

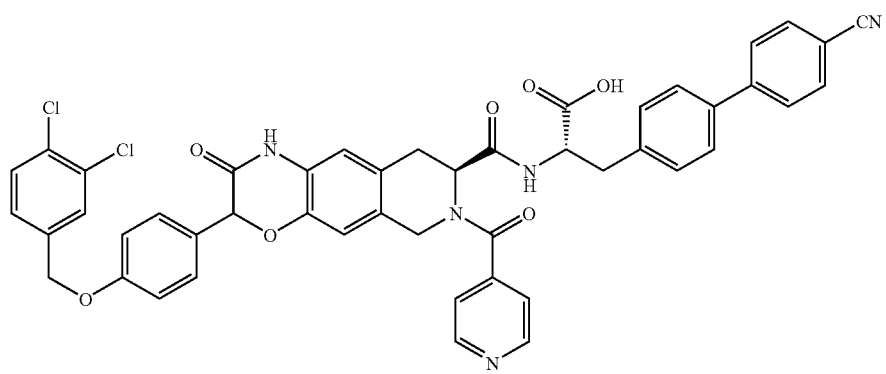

Title compound (73 mg) was prepared from Intermediate A (76 mg, 0.1 mmol) following general procedures F and B. LC-MS (m/z): 853.

Example 4

(S)-3-(4'-Cyano-biphenyl-4-yl)-2-{[(S)-3-[4-(3,4-dichloro-benzyloxy)-phenyl]-2-oxo-6-(pyridine-3-carbonyl)-2,3,5,6,7,8-hexahydro-1H-4-oxa-1,6-diaza-anthracene-7-carbonyl]-amino}-propionic acid

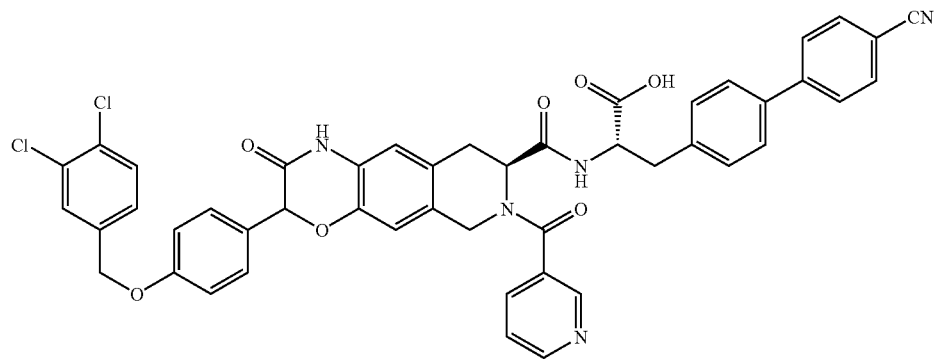

Title compound (69 mg) was prepared from Intermediate A (76 mg, 0.1 mmol) following general procedures F and B. LC-MS (m/z): 852.

Example 5

(S)-3-(4'-Cyano-biphenyl-4-yl)-2-{[(S)-3-[4-(3,4-dichloro-benzyloxy)-phenyl]-2-oxo-6-((S)-tetrahydro-furan-2-carbonyl)-2,3,5,6,7,8-hexahydro-1H-4-oxa-1,6-diaza-anthracene-7-carbonyl]-amino}-propionic acid

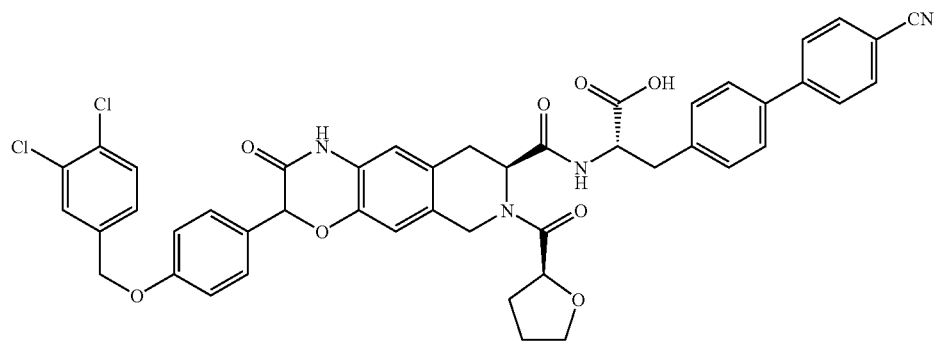

Title compound (57 mg) was prepared from Intermediate A (76 mg, 0.1 mmol) following general procedures F and B. LC-MS (m/z): 845.

Example 6

(S)-3-(4'-Cyano-biphenyl-4-yl)-2-{[(S)-3-[4-(3,4-dichloro-benzyloxy)-phenyl]-2-oxo-6-((R)-tetrahydro-furan-2-carbonyl)-2,3,5,6,7,8-hexahydro-1H-4-oxa-1,6-diaza-anthracene-7-carbonyl]-amino}-propionic acid

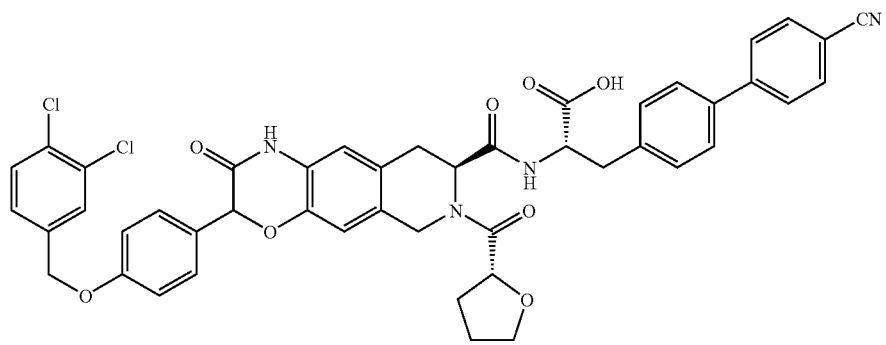

Title compound (62 mg) was prepared from Intermediate A (76 mg, 0.1 mmol) following general procedures F and B. LC-MS (m/z): 845.

Example 7

(S)-3-(4'-Cyano-biphenyl-4-yl)-2-{[(S)-3-[4-(3,4-dichloro-benzyloxy)-phenyl]-2-oxo-6-(3-phenyl-prop-2-ynyl)-2,3,5,6,7,8-hexahydro-1H-4-oxa-1,6-diaza-anthracene-7-carbonyl]-amino}-propionic acid

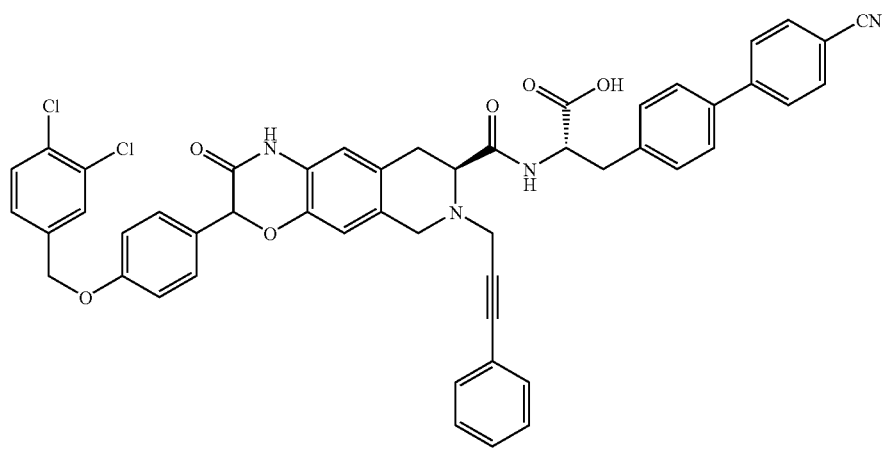

Title compound (44 mg) was prepared from Intermediate A (76 mg, 0.1 mmol) following general procedures K and B. LC-MS (m/z): 862.

Example 8

(S)-7-[(S)-1-Carboxy-2-(4'-cyano-biphenyl-4-yl)-
ethylcarbamoyl]-3-[4-(3,4-dichloro-benzyloxy)-phe-
nyl]-2-oxo-1,2,3,5,7,8-hexahydro-4-oxa-1,6-diaza-
anthracene-6-carboxylic acid isopropyl ester

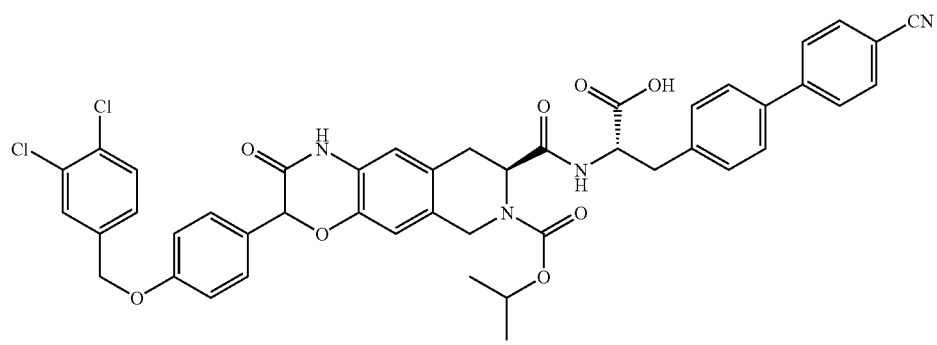

(S)-7-Hydroxy-6-nitro-3,4-dihydro-1H-isoquinoline-2,3-dicarboxylic acid 2-isopropyl ester 3-methyl ester To a solution of (S)-7-hydroxy-1,2,3,4-tetrahydro-isoquinoline-3-carboxylic acid methyl ester hydrochloride (3.0 g 12.3 mmol) in TFA (40 mL) was slowly added sodium nitrate (12.3 mmol) at 0° C., then stirred and slowly warmed to room temperature. After completion excess TFA was removed. The residue was taken up in DCM (100 mL), neutralized with triethylamine (10 mL) and passed over a silica plug with ammonia-MeOH/DCM as the eluent. The mixture was concentrated, redissolved in DCM and triethylamine (36.9 mmol) and isopropyl chloroformate (29.6 mmol) was added. After carbamate formation was complete, the reaction mixture was treated with hydrazine hydrate (5 mL 33% solution in water) to cleave the carbonate. The reaction mixture was stirred at r.t. overnight. The mixture was concentrated and dissolved in ethyl acetate. The organic was washed with 1 N HCl and saturated sodium bicarbonate. The organic layer was dried over sodium sulfate and concentrated under reduced pressure to give both nitrated regioisomers (6- and 8-Nitro substituted analogs). The regioisomers (S)-7-hydroxy-6-nitro-3,4-dihydro-1H-isoquinoline-2,3-dicarboxylic acid 2-isopropyl ester 3-methyl ester and (S)-7-hydroxy-8-nitro-3,4-dihydro-1H-isoquinoline-2,3-dicarboxylic acid 2 isopropyl ester 3-methyl ester were separated with silica gel chromatography using hexanes:ethyl acetate (from 90:10 to 70:30) as an eluent. LC/MS: m/z 339. $^1$H NMR (400 MHz, d$_6$ DMSO): 10.8 (d, 1H), 7.8 (s, 1H), 7.0 (d, 1H), 4.7-5.0 (m, 1H), 4.5-4.7 (m, 1H), 4.4 (m, 1H), 3.5 (d, 3H), 3.1 (m, 2H), 1.2 (m, 6H).

(S)-3-[(S)-2-(4'-Cyano-biphenyl-4-yl)-1-methoxycarbonyl-ethylcarbamoyl]-7-hydroxy-6-nitro-3,4-dihydro-1H-isoquinoline-2-carboxylic acid isopropyl ester. (S)-7-Hydroxy-6-nitro-3,4-dihydro-1H-isoquinoline-2,3-dicarboxylic acid 2-isopropyl ester 3-methyl ester (2.4 mmol) was hydrolyzed according to general procedure B to provide the acid (0.704 g). (S)-7-Hydroxy-6-nitro-3,4-dihydro-1H-isoquinoline-2,3-dicarboxylic acid 2-isopropyl ester (2.16 mmol) was coupled with (S)-2-amino-3-(4'-cyano-biphenyl-4-yl)-propionic acid methyl ester-hydrochloride (2.38 mmol) according to general procedure A to provide the amide (1.01 g) LC/MS: m/z 588.

(S)-7-[(S)-2-(4'-Cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isopropyl ester. (S)-3-[(S)-2-(4'-Cyano-biphenyl-4-yl)-1-methoxycarbonyl-ethylcarbamoyl]-7-hydroxy-6-nitro-3,4-dihydro-1H-isoquinoline-2-carboxylic acid isopropyl ester was reduced and alkylated/cyclized following a similar procedure described in the synthesis of Intermediate A to provide (S)-7-[(S)-2-(4'-Cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isopropyl ester (0.037 mg) LC/MS: m/z 848, 850.

(S)-7-[(S)-2-(4'-Cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isopropyl ester (35 mg) was hydrolyzed according to general procedure B to provide Title compound (28 mg) LC/MS: m/z 834.

Example 9

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isobutyl ester

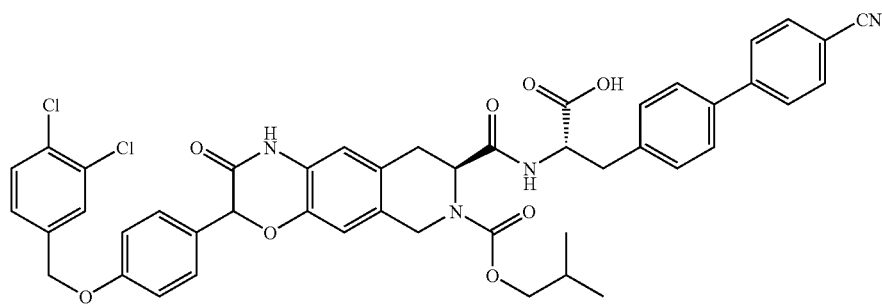

Title compound (37 mg) was prepared from (S)-3-(4'-cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester; hydrochloride (100 mg) following general procedures H and B. LC-MS (m/z): 850.

Example 10

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 2,2-dimethyl-propyl ester

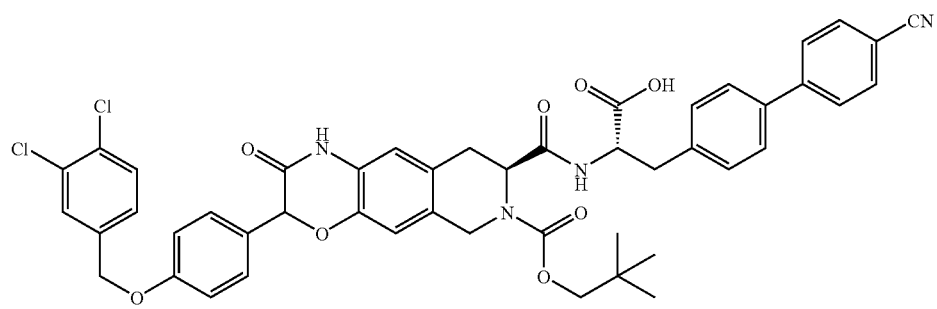

Title compound (34 mg) was prepared from Intermediate A (100 mg) following general procedures H and B. LC-MS (m/z): 862.

Example 11

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tetrahydro-pyran-4-yl ester

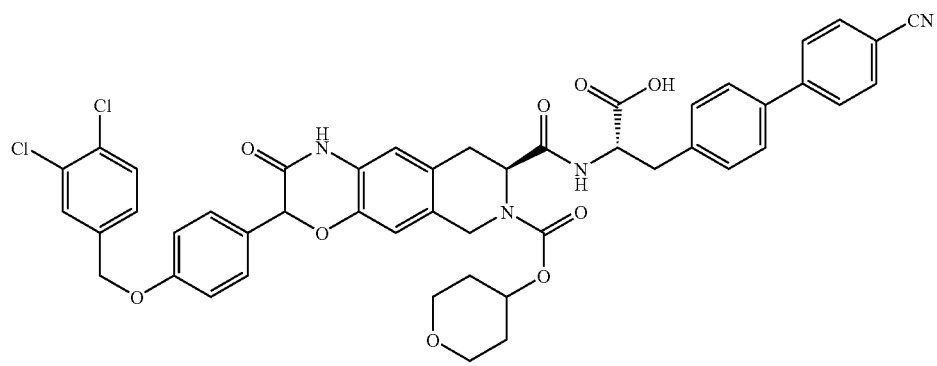

Title compound (42 mg) was prepared from Intermediate A (100 mg, 0.13 mmol) following general procedures H and B. LC-MS (m/z): 877.

Example 12

(S)-3-(4'-Cyano-biphenyl-4-yl)-2-({(S)-6-cyclobutanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

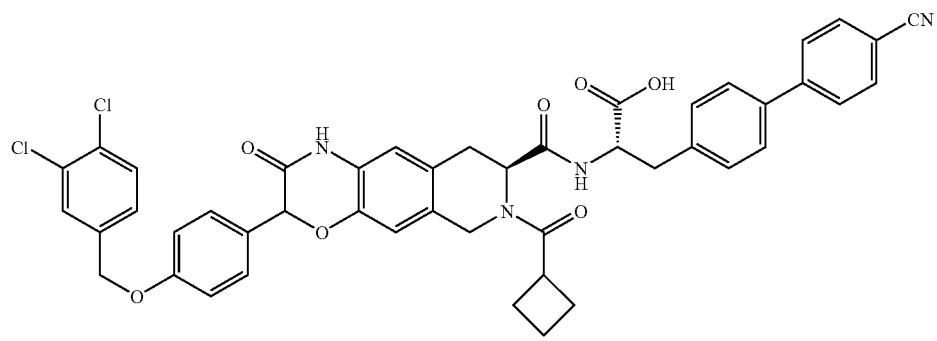

Title compound (46 mg) was prepared from Intermediate A (100 mg, 0.13 mmol) following general procedures F and B. LC-MS (m/z): 832.

Example 13

(S)-3-(4'-Cyano-biphenyl-4-yl)-2-({(S)-3-[4-(3,4-dichloro-benzyloxy)-phenyl]-6-isobutyryl-2-oxo-2,3,5,6,7,8-hexahydro-1H-4-oxa-1,6-diaza-anthracene-7-carbonyl}-amino)-propionic acid

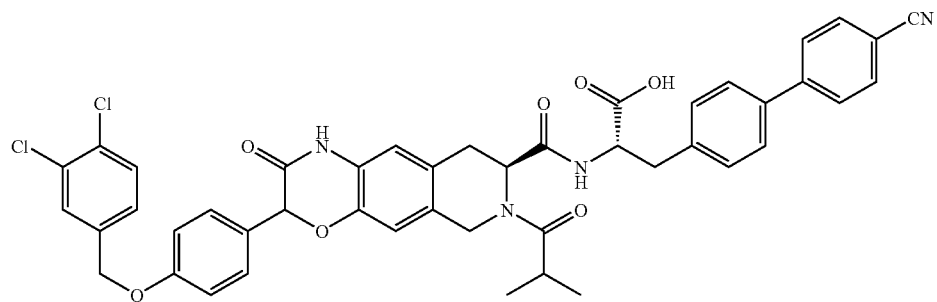

Title compound was prepared from Intermediate A (40 mg) following general procedures F and B. LC-MS (m/z): 819.

Example 14

(S)-2-({(S)-6-Benzenesulfonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

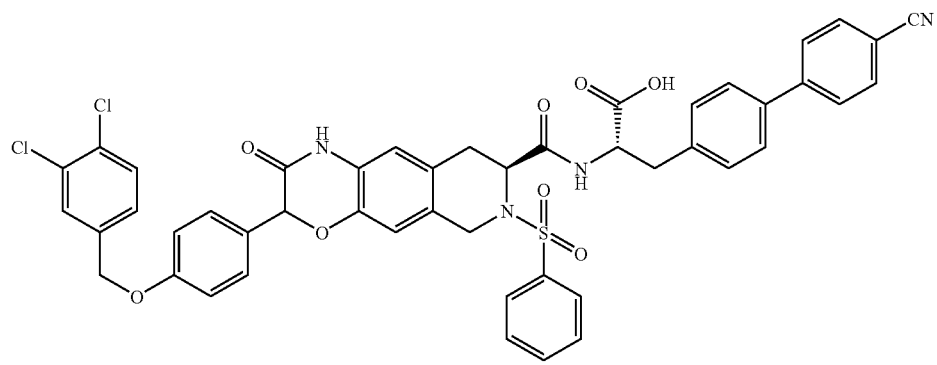

Title compound was prepared from Intermediate A (30 mg) following general procedures E and B. LC-MS (m/z): 888.

Example 15

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

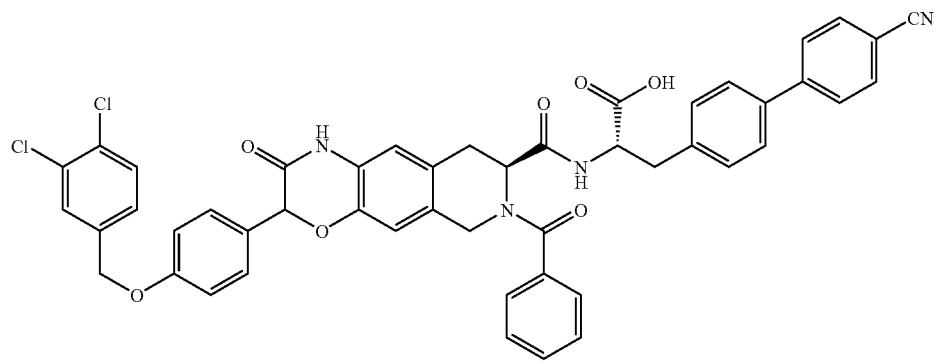

Title compound was prepared from Intermediate A (30 mg) following general procedures F and B. LC-MS (m/z): 852.

Example 16

(S)-3-(4'-Cyano-biphenyl-4-yl)-2-({(S)-6-cyclopentanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

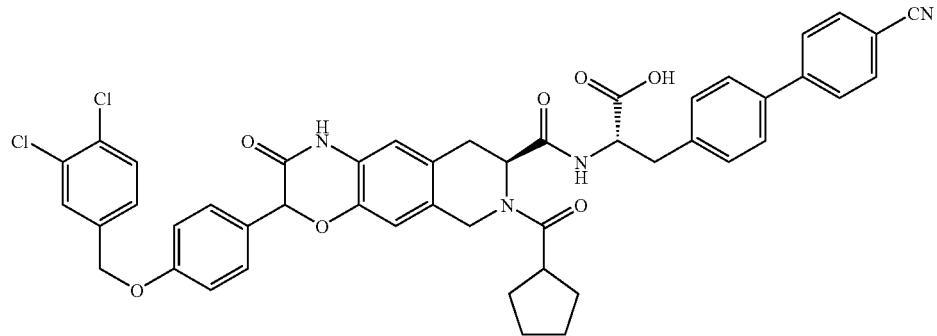

Title compound was prepared from Intermediate A (30 mg) following general procedures F and B. LC-MS (m/z): 845.

Example 17

(S)-3-(4'-Cyano-biphenyl-4-yl)-2-{[(S)-3-[4-(3,4-dichloro-benzyloxy)-phenyl]-2-oxo-6-(piperidine-1-carbonyl)-2,3,5,6,7,8-hexahydro-1H-4-oxa-1,6-diaza-anthracene-7-carbonyl]-amino}-propionic acid

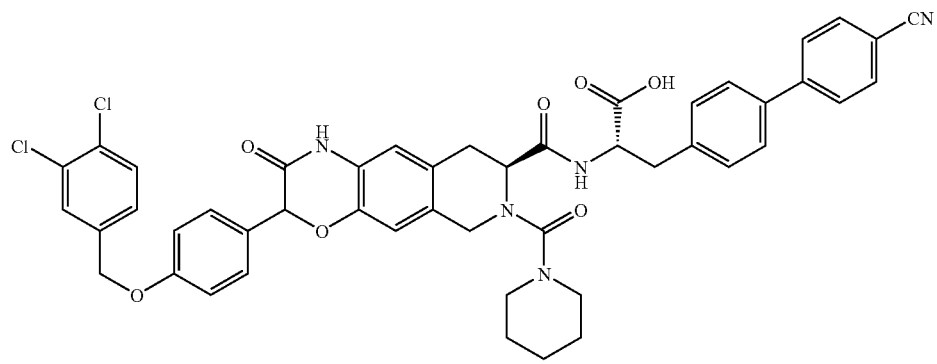

Title compound was prepared from Intermediate A (30 mg) following general procedures I and B. LC-MS (m/z): 859.

Example 18

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid cyclopropylmethyl ester

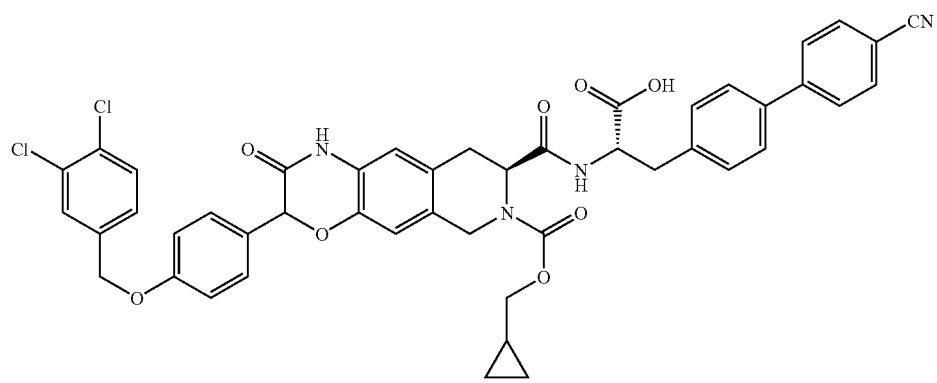

Title compound was prepared from Intermediate A (40 mg) following general procedures H and B. LC-MS (m/z): 845.

Example 19

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid (R)-(tetrahydro-furan-3-yl)ester

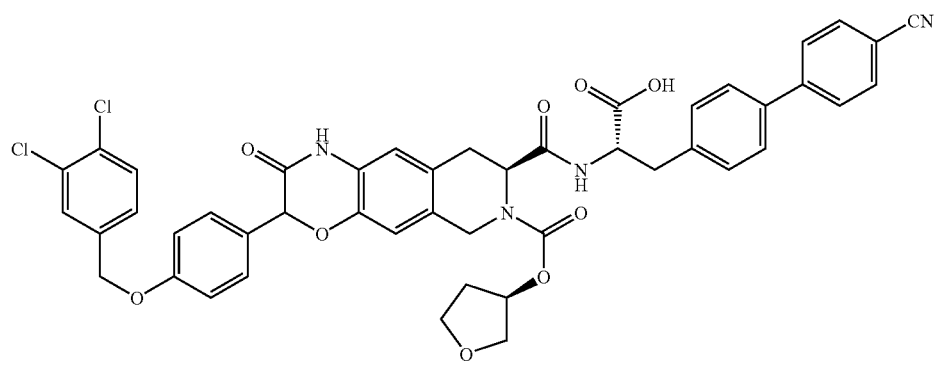

Title compound was prepared from Intermediate A (40 mg) following general procedures H and B. LC-MS (m/z): 862.

Example 20

(S)-3-(4'-Cyano-biphenyl-4-yl)-2-{[(S)-3-[4-(3,4-dichloro-benzyloxy)-phenyl]-6-(furan-2-carbonyl)-2-oxo-2,3,5,6,7,8-hexahydro-1H-4-oxa-1,6-diaza-anthracene-7-carbonyl]-amino}-propionic acid

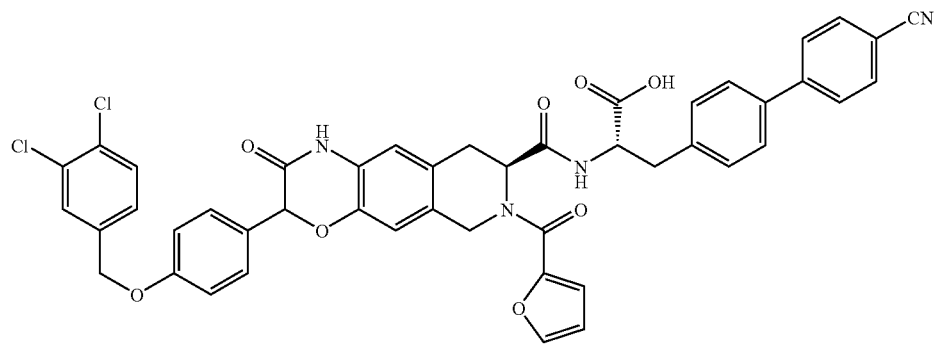

Title compound was prepared from Intermediate A (25 mg) following general procedures F and B. LC-MS (m/z): 842.

Example 21

(S)-3-(4'-Cyano-biphenyl-4-yl)-2-{[(S)-3-[4-(3,4-dichloro-benzyloxy)-phenyl]-6-(3-methyl-benzoyl)-2-oxo-2,3,5,6,7,8-hexahydro-1H-4-oxa-1,6-diaza-anthracene-7-carbonyl]-amino}-propionic acid

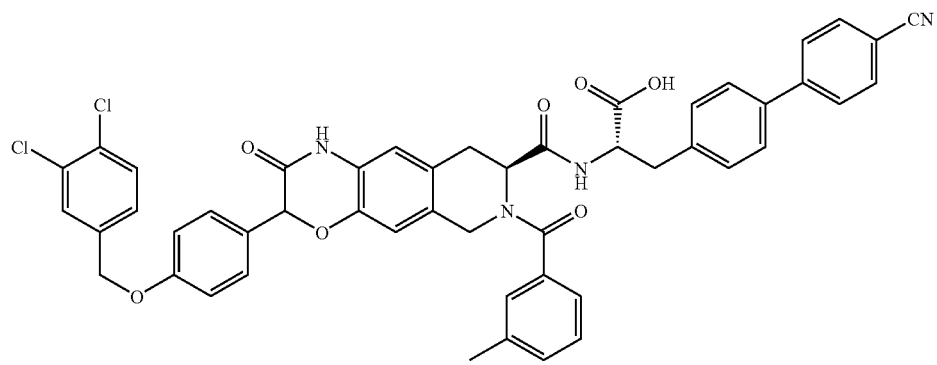

Title compound was prepared from Intermediate A (25 mg) following general procedures F and B. LC-MS (m/z): 865.

Example 22

(S)-3-(4'-Cyano-biphenyl-4-yl)-2-{[(S)-3-[4-(3,4-dichloro-benzyloxy)-phenyl]-6-(4-fluoro-benzoyl)-2-oxo-2,3,5,6,7,8-hexahydro-1H-4-oxa-1,6-diaza-anthracene-7-carbonyl]-amino}-propionic acid

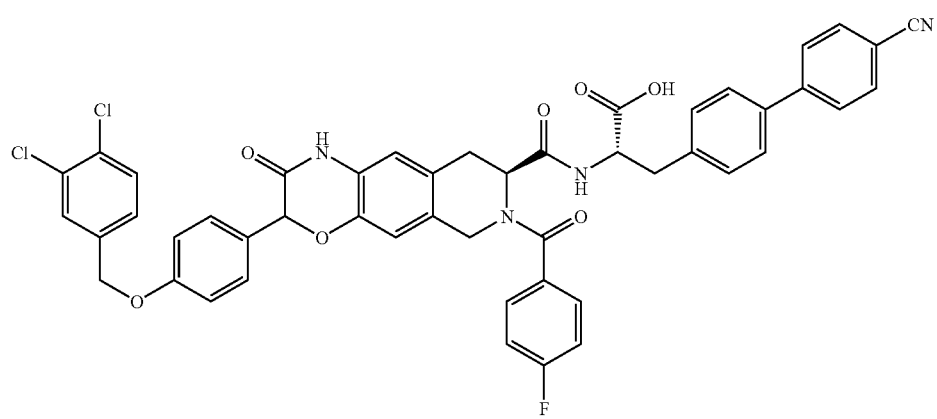

Title compound was prepared from Intermediate A (25 mg) following general procedures F and B. LC-MS (m/z): 870.

Example 23

(S)-3-(4'-Cyano-biphenyl-4-yl)-2-{[(S)-3-[4-(3,4-dichloro-benzyloxy)-phenyl]-6-(4-methoxy-benzoyl)-2-oxo-2,3,5,6,7,8-hexahydro-1H-4-oxa-1,6-diaza-anthracene-7-carbonyl]-amino}-propionic acid

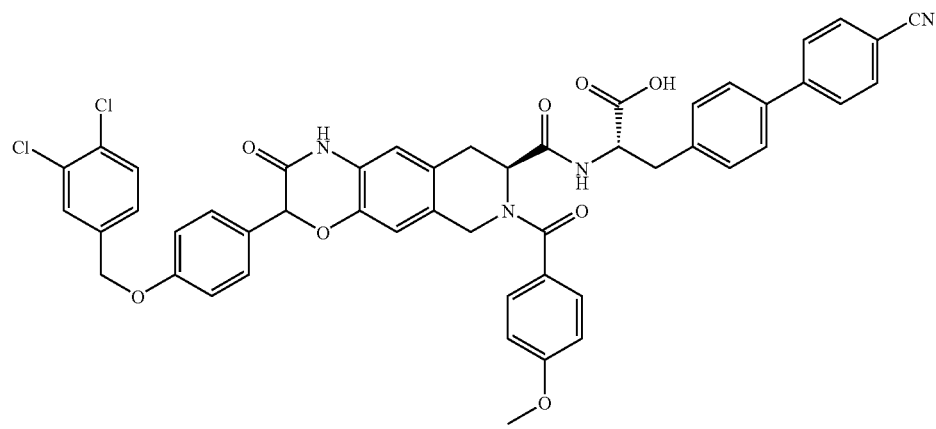

Title compound was prepared from Intermediate A (25 mg) following general procedures F and B. LC-MS (m/z): 882.

Example 24

(S)-3-(4'-Cyano-biphenyl-4-yl)-2-{[(S)-3-[4-(3,4-dichloro-benzyloxy)-phenyl]-2-oxo-6-(3-trifluoromethyl-benzoyl)-2,3,5,6,7,8-hexahydro-1H-4-oxa-1,6-diaza-anthracene-7-carbonyl]-amino}-propionic acid

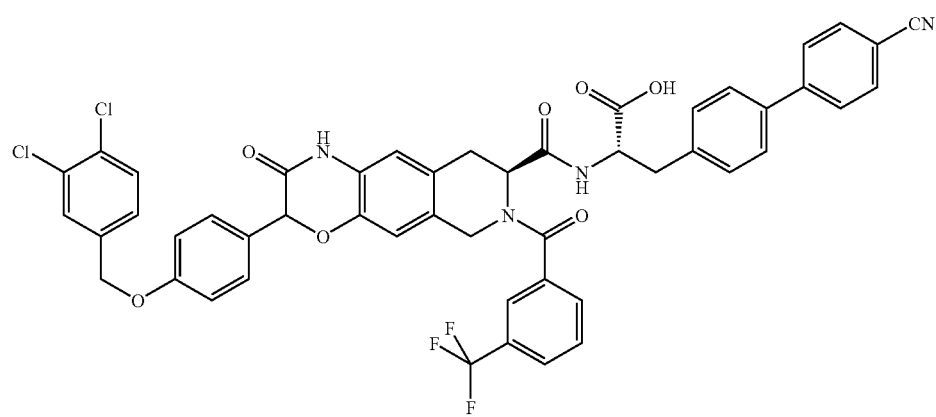

Title compound was prepared from Intermediate A (25 mg) following general procedures F and B. LC-MS (m/z): 922.

Example 25

(S)-3-(4'-Cyano-biphenyl-4-yl)-2-({(S)-6-cyclohexanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

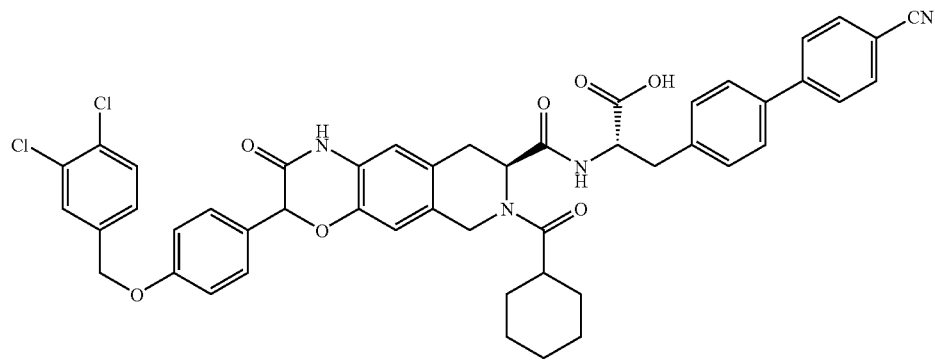

Title compound (31 mg) was prepared from Intermediate A (50 mg) following general procedures F and B. LC-MS (m/z): 860.

Example 26

(S)-3-(4'-Cyano-biphenyl-4-yl)-2-{[(S)-3-[4-(3,4-dichloro-benzyloxy)-phenyl]-6-(naphthalene-1-carbonyl)-2-oxo-2,3,5,6,7,8-hexahydro-1H-4-oxa-1,6-diaza-anthracene-7-carbonyl]-amino}-propionic acid

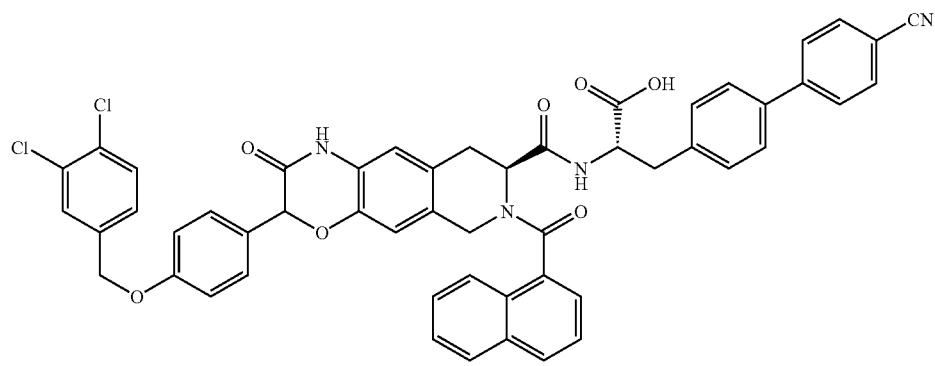

Title compound (28 mg) was prepared from Intermediate A (50 mg) following general procedures F and B. LC-MS (m/z): 902.

Example 27

(S)-3-(4'-Cyano-biphenyl-4-yl)-2-{[(S)-3-[4-(3,4-dichloro-benzyloxy)-phenyl]-6-(naphthalene-2-carbonyl)-2-oxo-2,3,5,6,7,8-hexahydro-1H-4-oxa-1,6-diaza-anthracene-7-carbonyl]-amino}-propionic acid

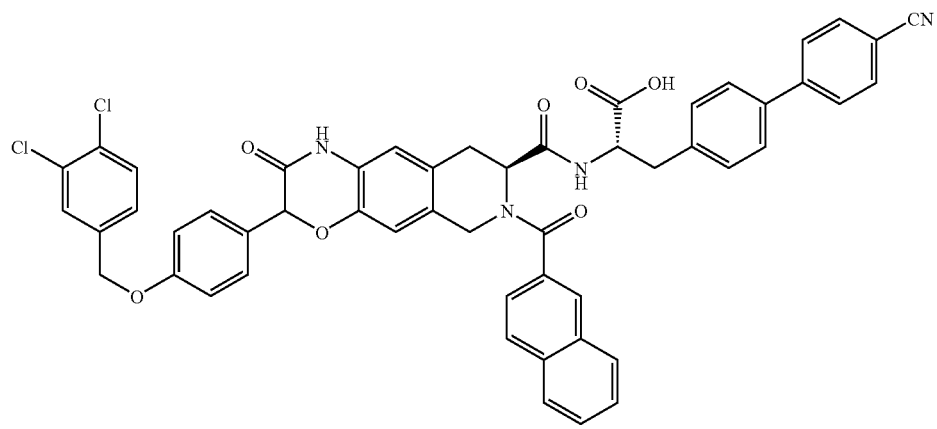

Title compound (28 mg) was prepared from Intermediate A (50 mg) following general procedures F and B. LC-MS (m/z): 904.

Example 28

(S)-3-(4'-Cyano-biphenyl-4-yl)-2-{[(S)-3-[4-(3,4-dichloro-benzyloxy)-phenyl]-2-oxo-6-(thiophene-2-carbonyl)-2,3,5,6,7,8-hexahydro-1H-4-oxa-1,6-diaza-anthracene-7-carbonyl]-amino}-propionic acid

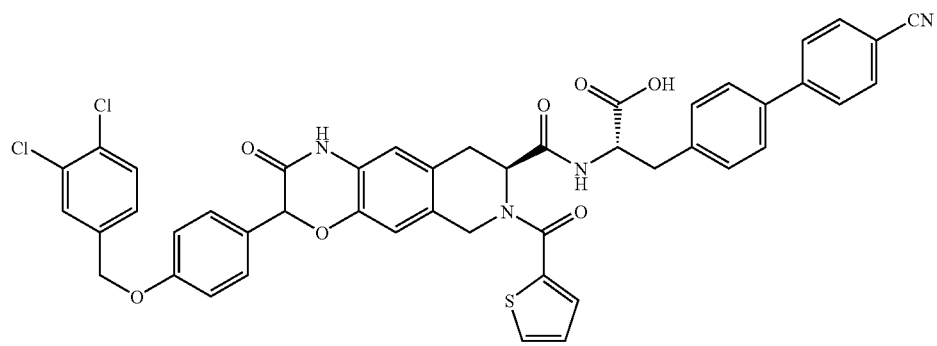

Title compound (25 mg) was prepared from Intermediate A (30 mg) following general procedures F and B. LC-MS (m/z): 858.

Example 29

(S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tert-butyl ester

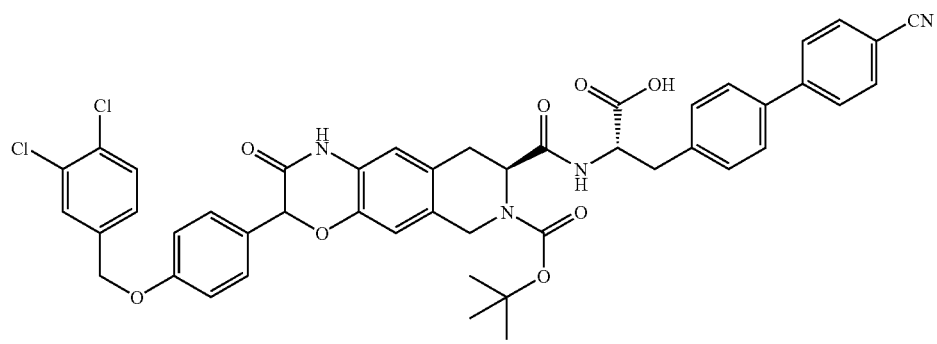

Title compound was prepared from (S)-7-[(S)-2-(4'-cyano-biphenyl-4-yl)-1-methoxycarbonyl-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tert-butyl ester (20 mg) following general procedure B. LC-MS (m/z): 850.

Example 30

(S)-3-(4'-Cyano-biphenyl-4-yl)-2-({(S)-6-(2-cyclopentyl-acetyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

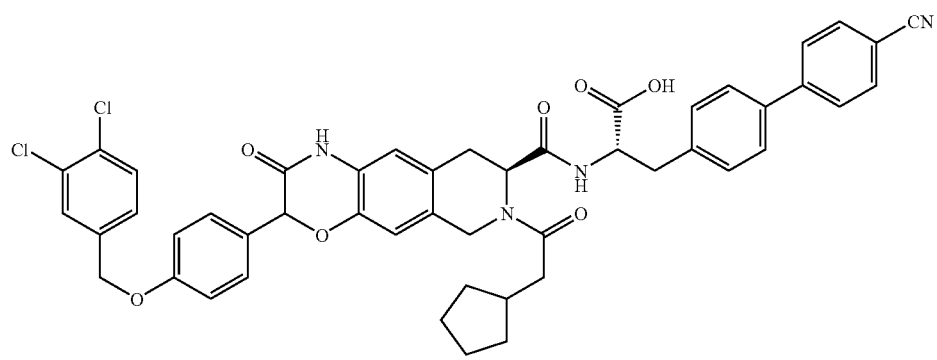

Title compound (20 mg) was prepared from Intermediate A (40 mg) following general procedures F and B. LC-MS (m/z): 860.

Example 31

(S)-3-(4'-Cyano-biphenyl-4-yl)-2-{[(S)-3-[4-(3,4-dichloro-benzyloxy)-phenyl]-6-(5-methyl-isoxazole-3-carbonyl)-2-oxo-2,3,5,6,7,8-hexahydro-1H-4-oxa-1,6-diaza-anthracene-7-carbonyl]-amino}-propionic acid

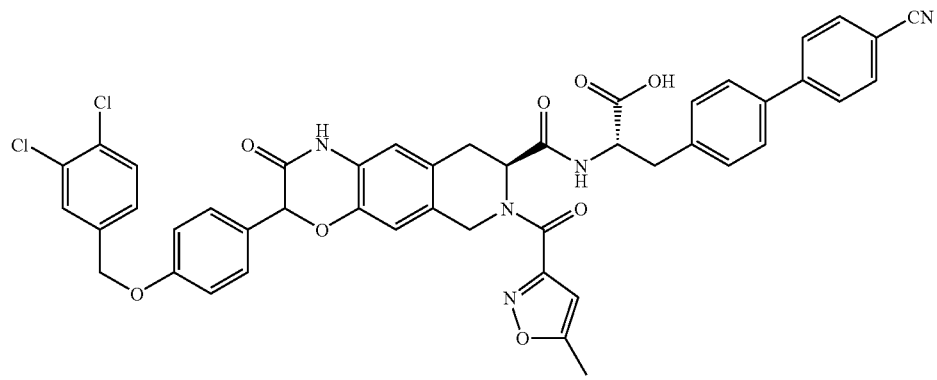

Title compound (20 mg) was prepared from Intermediate A (40 mg) following general procedures F and B. LC-MS (m/z): 858.

Example 32

(S)-3-(4'-Cyano-biphenyl-4-yl)-2-{[(S)-3-[4-(3,4-dichloro-benzyloxy)-phenyl]-2-oxo-6-(thiophene-2-sulfonyl)-2,3,5,6,7,8-hexahydro-1H-4-oxa-1,6-diaza-anthracene-7-carbonyl]-amino}-propionic acid

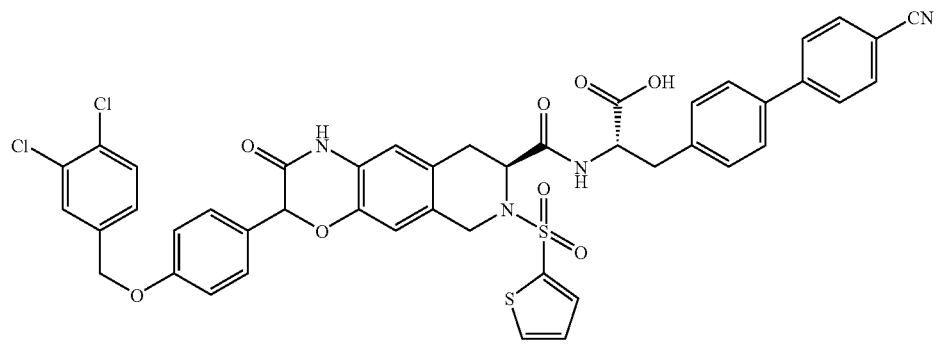

Title compound (20 mg) was prepared from Intermediate A (40 mg) following general procedures E and B. LC-MS (m/z): 896.

Example 33

(S)-3-(4'-Cyano-biphenyl-4-yl)-2-({(S)-3-[4-(3,4-dichloro-benzyloxy)-phenyl]-6-dimethylcarbamoyl-2-oxo-2,3,5,6,7,8-hexahydro-1H-4-oxa-1,6-diaza-anthracene-7-carbonyl}-amino)-propionic acid

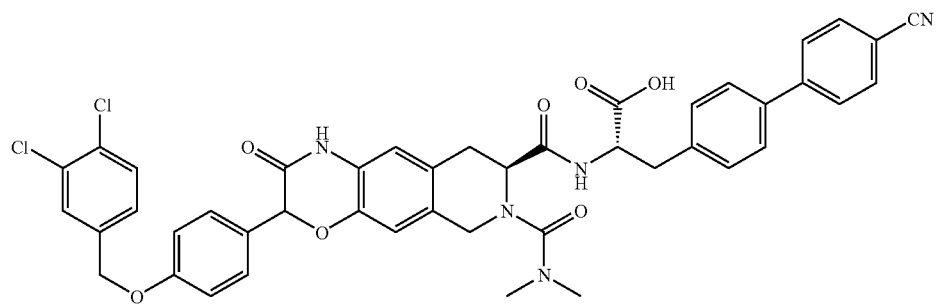

Title compound (20 mg) was prepared from (S)-3-(4'-cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester; hydrochloride (40 mg) following general procedures I and B. LC-MS (m/z): 819.

Example 34

(S)-2-({(S)-6-Benzyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

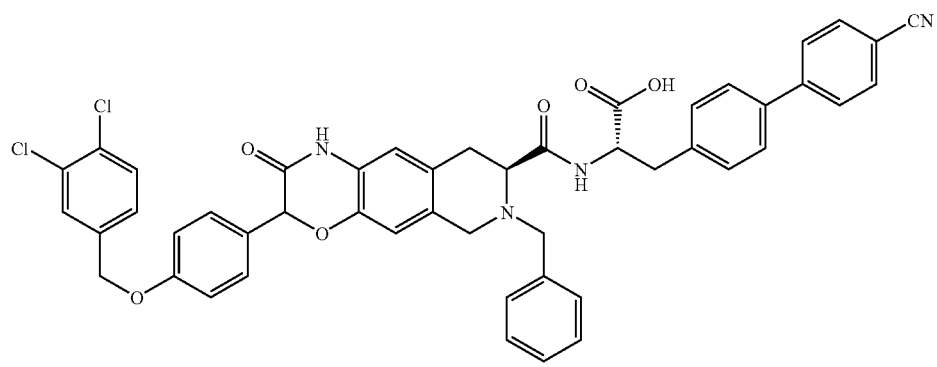

Title compound was prepared from Intermediate A (40 mg) following general procedures D and B. LC-MS (m/z): 838.

Example 35

(S)-3-(4'-Cyano-biphenyl-4-yl)-2-({(S)-3-[4-(3,4-dichloro-benzyloxy)-phenyl]-2-oxo-6-phenethyl-2,3,5,6,7,8-hexahydro-1H-4-oxa-1,6-diaza-anthracene-7-carbonyl}-amino)-propionic acid

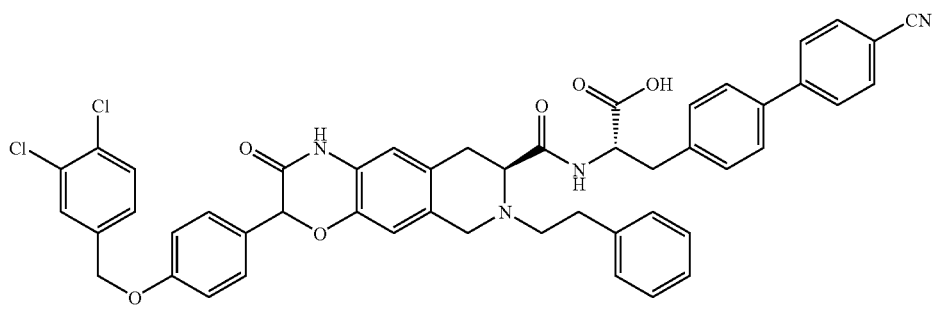

Title compound was prepared from Intermediate A (40 mg) following general procedures D and B. LC-MS (m/z): 852.

Example 36

(S)-3-(4'-Cyano-biphenyl-4-yl)-2-{[(S)-3-[4-(3,4-dichloro-benzyloxy)-phenyl]-2-oxo-6-(2,4,6-trifluoro-benzoyl)-2,3,5,6,7,8-hexahydro-1H-4-oxa-1,6-diaza-anthracene-7-carbonyl]-amino}-propionic acid

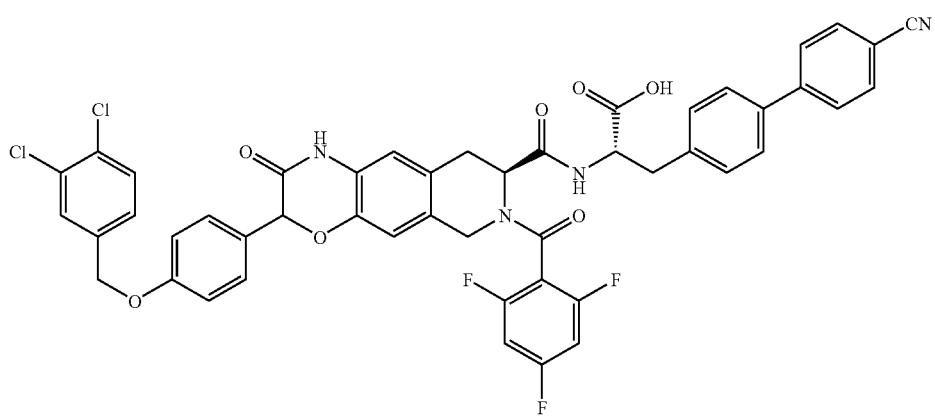

Title compound was prepared from Intermediate A (20 mg) following general procedures F and B. LC-MS (m/z): 908.

Example 37

(S)-3-(4'-Cyano-biphenyl-4-yl)-2-{[(S)-3-[4-(3,4-dichloro-benzyloxy)-phenyl]-2-oxo-6-(toluene-2-sulfonyl)-2,3,5,6,7,8-hexahydro-1H-4-oxa-1,6-diaza-anthracene-7-carbonyl]-amino}-propionic acid

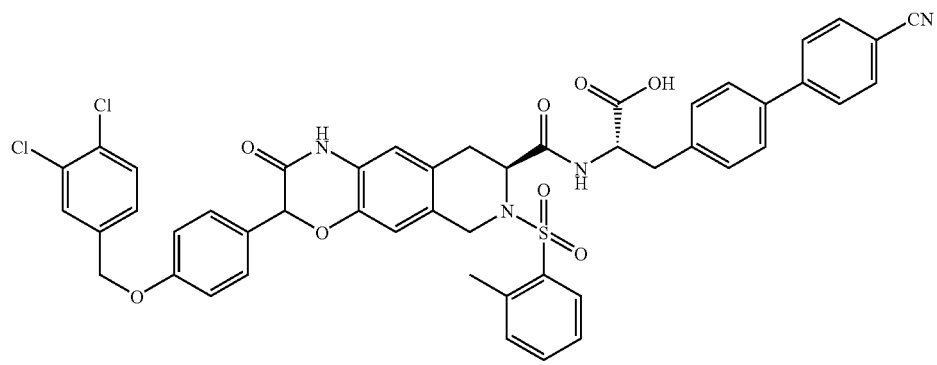

Title compound was prepared from Intermediate A (20 mg) following general procedures E and B. LC-MS (m/z): 903.

Example 38

(S)-3-(4'-Cyano-biphenyl-4-yl)-2-{[(S)-3-[4-(3,4-dichloro-benzyloxy)-phenyl]-6-(2-methyl-benzyl)-2-oxo-2,3,5,6,7,8-hexahydro-1H-4-oxa-1,6-diaza-anthracene-7-carbonyl]-amino}-propionic acid

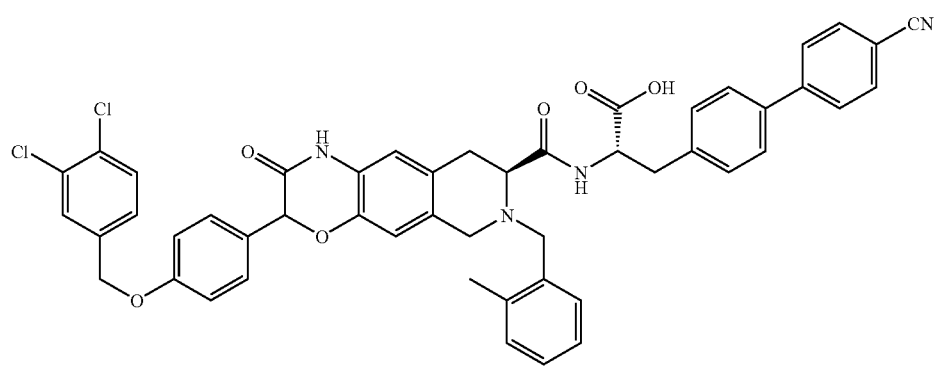

Title compound was prepared from Intermediate A (20 mg) following general procedures D and B. LC-MS (m/z): 852.

Example 39

(S)-3-(4'-Cyano-biphenyl-4-yl)-2-({(S)-3-[4-(3,4-dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-propionic acid

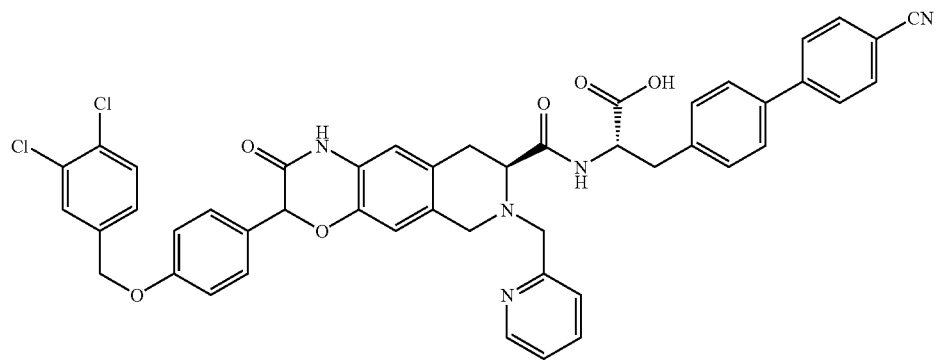

Title compound was prepared from Intermediate A (20 mg) following general procedures D and B. LC-MS (m/z): 839.

Example 40

(S)-3-(4'-Cyano-biphenyl-4-yl)-2-({(S)-3-[4-(3,4-dichloro-benzyloxy)-phenyl]-2-oxo-6-thiophen-2-ylmethyl-2,3,5,6,7,8-hexahydro-1H-4-oxa-1,6-diaza-anthracene-7-carbonyl}-amino)-propionic acid

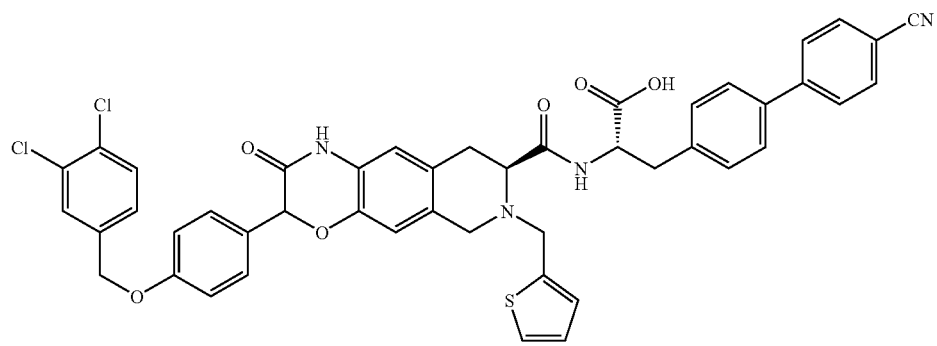

Title compound was prepared from Intermediate A (20 mg) following general procedures D and B. LC-MS (m/z): 844.

Example 41

(S)-3-(4'-Cyano-biphenyl-4-yl)-2-{[(S)-3-[4-(3,4-dichloro-benzyloxy)-phenyl]-6-(2-fluoro-benzyl)-2-oxo-2,3,5,6,7,8-hexahydro-1H-4-oxa-1,6-diaza-anthracene-7-carbonyl]-amino}-propionic acid

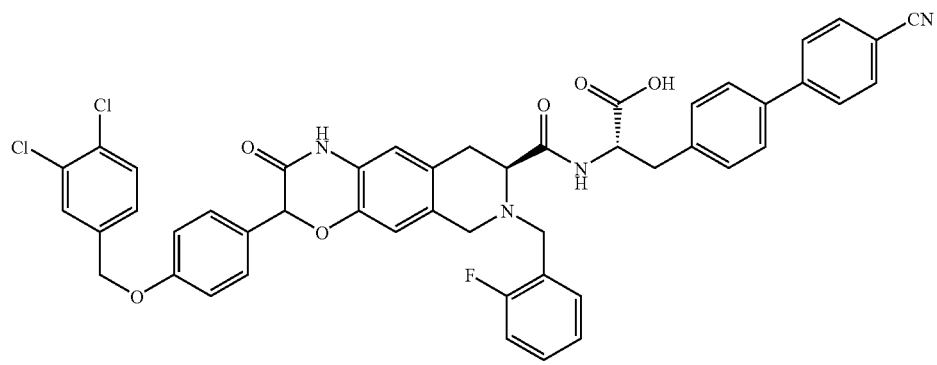

Title compound (7 mg) was prepared from Intermediate A (40 mg) following general procedures D and B. LC-MS (m/z): 856.

Example 42

(S)-2-({(S)-6-(2-Chloro-benzyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

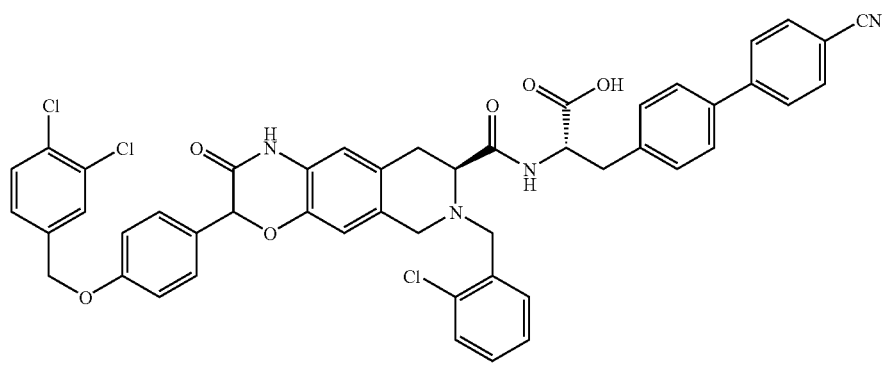

Title compound (7 mg) was prepared from Intermediate A (40 mg) following general procedures D and B. LC-MS (m/z): 873.

Example 43

(S)-3-(4'-Cyano-biphenyl-4-yl)-2-{[(S)-3-[4-(3,4-dichloro-benzyloxy)-phenyl]-6-(2-methoxy-benzyl)-2-oxo-2,3,5,6,7,8-hexahydro-1H-4-oxa-1,6-diaza-anthracene-7-carbonyl]-amino}-propionic acid

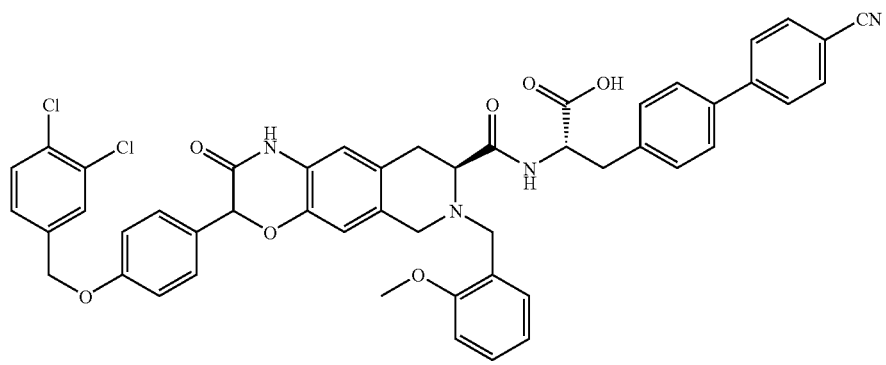

Title compound (11 mg) was prepared from Intermediate A (40 mg) following general procedures D and B. LC-MS (m/z): 868.

Example 44

(S)-3-(4'-Cyano-biphenyl-4-yl)-2-{[(S)-3-[4-(3,4-dichloro-benzyloxy)-phenyl]-6-(6-methyl-pyridin-2-ylmethyl)-2-oxo-2,3,5,6,7,8-hexahydro-1H-4-oxa-1,6-diaza-anthracene-7-carbonyl]-amino}-propionic acid

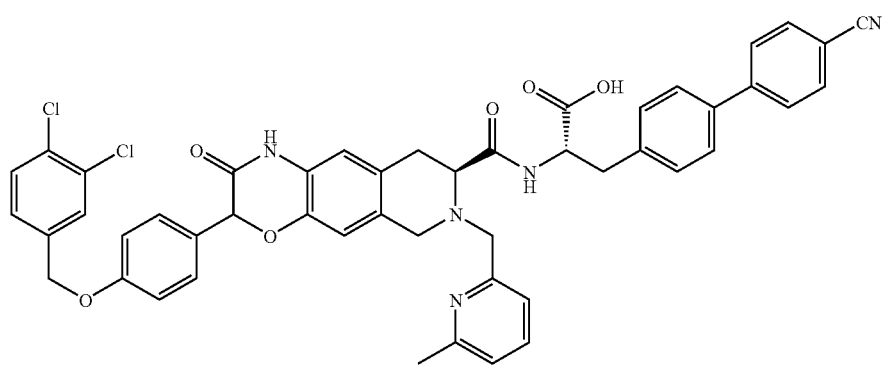

Title compound was prepared from Intermediate A (39.9 mg) following general procedures D and B. LC-MS (m/z): 853.

Example 45

(S)-2-({(S)-6-(6-Bromo-pyridin-2-ylmethyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

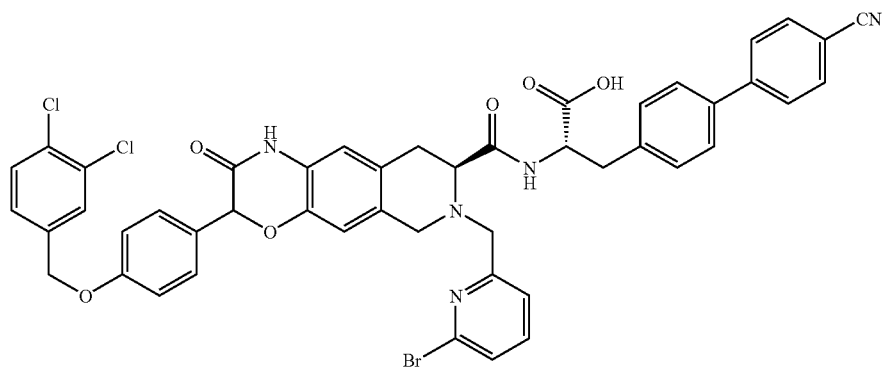

Title compound was prepared from Intermediate A (39.9 mg) following general procedures D and B. LC-MS (m/z): 921.

Example 46

(S)-3-(4'-Cyano-biphenyl-4-yl)-2-({(S)-6-(5-cyano-6-methylsulfanyl-pyridin-2-ylmethyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

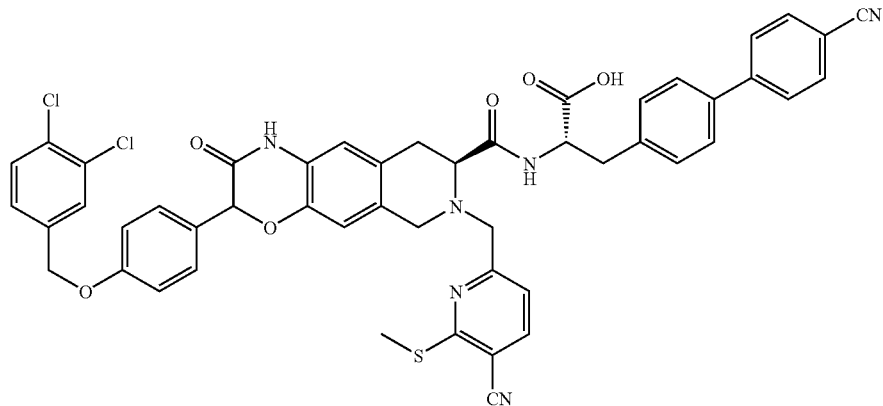

Title compound was prepared from Intermediate A (39.9 mg) following general procedures D and B. LC-MS (m/z): 909.

Example 47

(S)-3-(4'-Cyano-biphenyl-4-yl)-2-{[(S)-3-[4-(3,4-dichloro-benzyloxy)-phenyl]-6-(1H-imidazol-2-ylmethyl)-2-oxo-2,3,5,6,7,8-hexahydro-1H-4-oxa-1,6-diaza-anthracene-7-carbonyl]-amino}-propionic acid

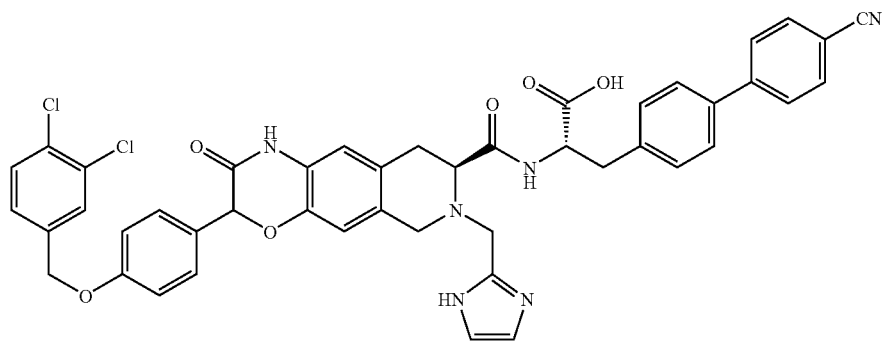

Title compound was prepared from Intermediate A (39.9 mg) following general procedures D and B. LC-MS (m/z): 828.

Example 48

(S)-3-(4'-Cyano-biphenyl-4-yl)-2-{[(S)-3-[4-(3,4-dichloro-benzyloxy)-phenyl]-6-(1-methyl-1H-imidazol-2-ylmethyl)-2-oxo-2,3,5,6,7,8-hexahydro-1H-4-oxa-1,6-diaza-anthracene-7-carbonyl]-amino}-propionic acid

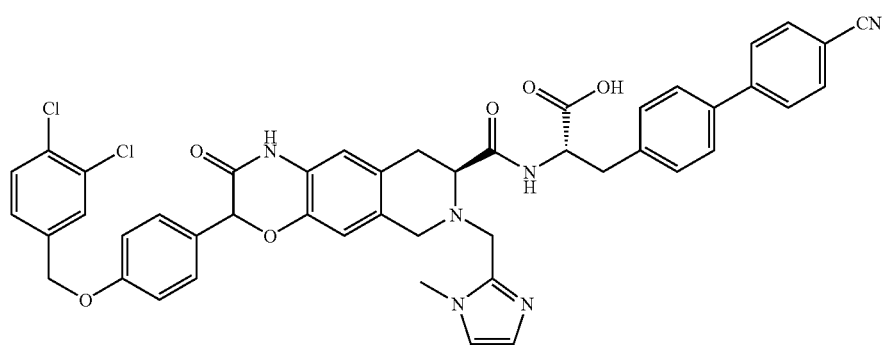

Title compound was prepared from Intermediate A (20 mg) following general procedures D and B. LC-MS (m/z): 842.

Example 49

(S)-3-(4'-Cyano-biphenyl-4-yl)-2-({(S)-3-[4-(3,4-dichloro-benzyloxy)-phenyl]-2-oxo-6-thiazol-2-ylmethyl-2,3,5,6,7,8-hexahydro-1H-4-oxa-1,6-diaza-anthracene-7-carbonyl}-amino)-propionic acid

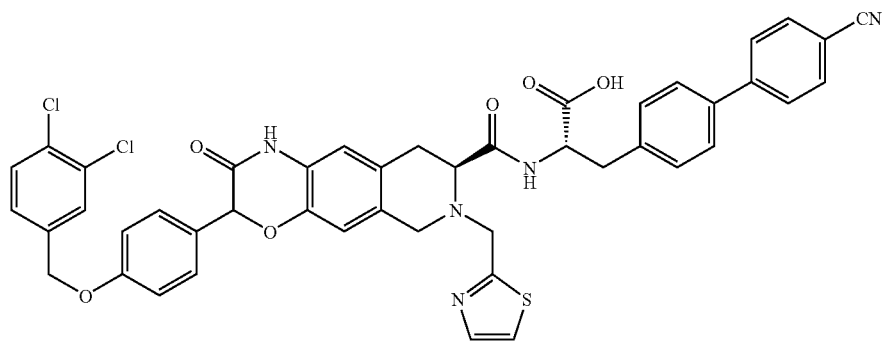

Title compound was prepared from Intermediate A (25 mg) following general procedures D and B. LC-MS (m/z): 846.

Example 50

(S)-3-(4'-Cyano-biphenyl-4-yl)-2-{[(S)-3-[4-(3,4-dichloro-benzyloxy)-phenyl]-2-oxo-6-(pyridine-2-carbonyl)-2,3,5,6,7,8-hexahydro-1H-4-oxa-1,6-diaza-anthracene-7-carbonyl]-amino}-propionic acid

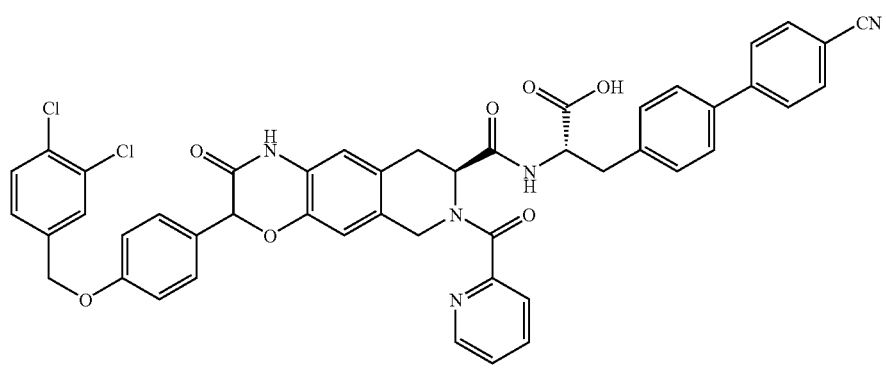

Title compound was prepared from Intermediate A (20 mg) following general procedures F and B. LC-MS (m/z): 853.

Example 51

(S)-3-(4'-Cyano-biphenyl-4-yl)-2-{[(S)-3-[4-(3,4-dichloro-benzyloxy)-phenyl]-6-(2-nitro-benzene-sulfonyl)-2-oxo-2,3,5,6,7,8-hexahydro-1H-4-oxa-1,6-diaza-anthracene-7-carbonyl]-amino}-propionic acid

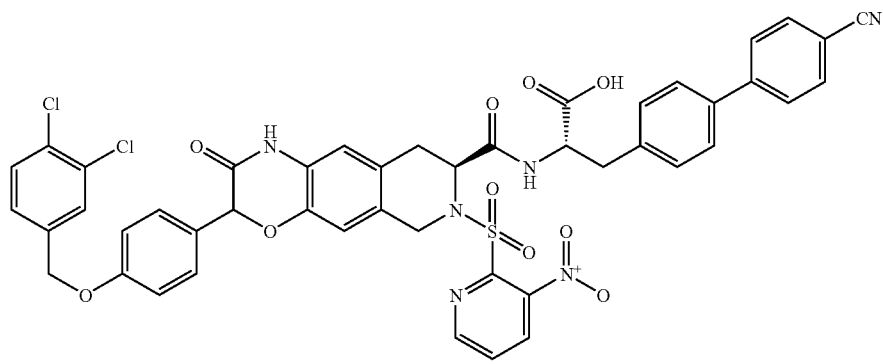

Title compound was prepared from Intermediate A (30 mg) following general procedures E and B. LC-MS (m/z): 932.

Example 52

(S)-3-(4'-Cyano-biphenyl-4-yl)-2-{[(S)-3-[4-(3,4-dichloro-benzyloxy)-phenyl]-6-(3-nitro-benzene-sulfonyl)-2-oxo-2,3,5,6,7,8-hexahydro-1H-4-oxa-1,6-diaza-anthracene-7-carbonyl]-amino}-propionic acid

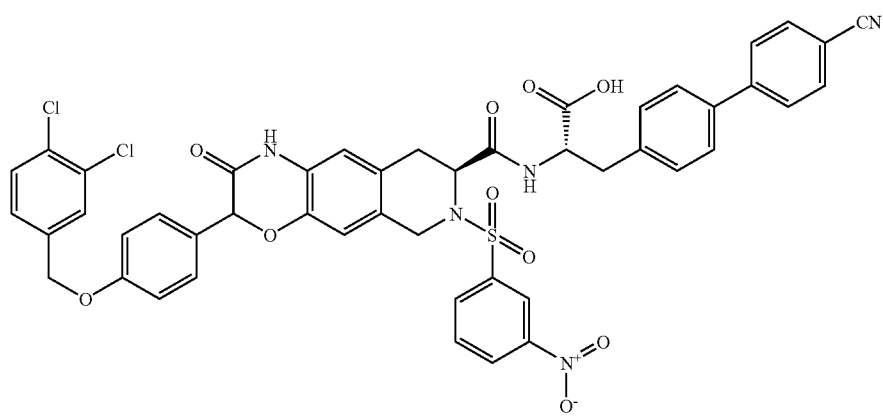

Title compound was prepared from Intermediate A (30 mg) following general procedures E and B. LC-MS (m/z): 933.

Example 53

(S)-2-({(S)-6-(2-Cyano-benzyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

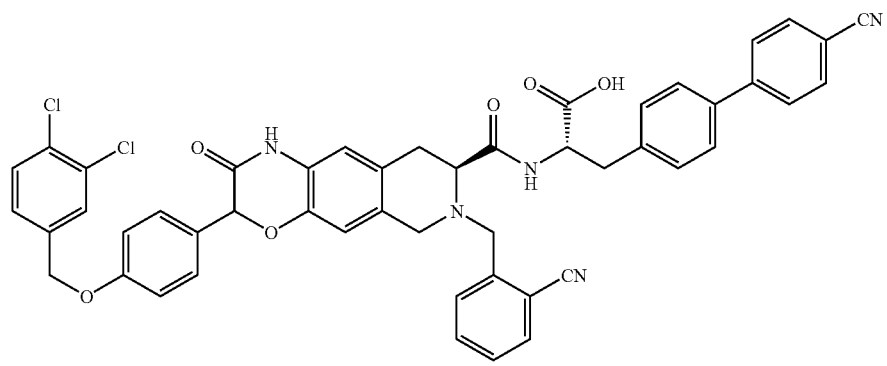

Title compound was prepared from Intermediate A (20 mg) following general procedures D and B. LC-MS (m/z): 863.

Example 54

(S)-3-(4'-Cyano-biphenyl-4-yl)-2-({(S)-6-cyclopropylmethyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid

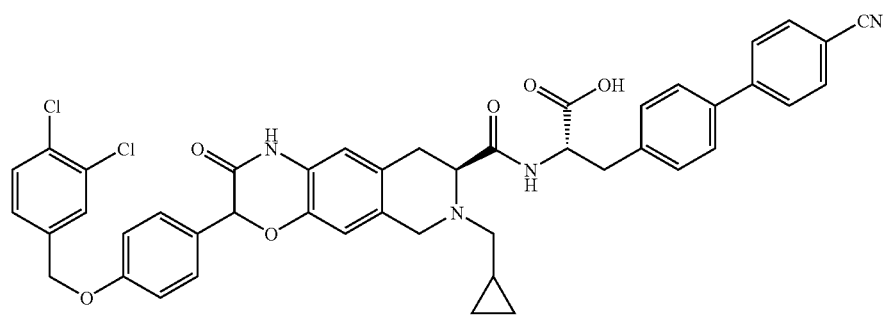

Title compound was prepared from Intermediate A (25 mg) following general procedures D and B. LC-MS (m/z): 802.

Example 55

(S)-3-(4'-Cyano-biphenyl-4-yl)-2-{[(S)-3-[4-(3,4-dichloro-benzyloxy)-phenyl]-2-oxo-6-(3-pyrimidin-2-yl-prop-2-ynyl)-2,3,5,6,7,8-hexahydro-1H-4-oxa-1,6-diaza-anthracene-7-carbonyl]-amino}-propionic acid

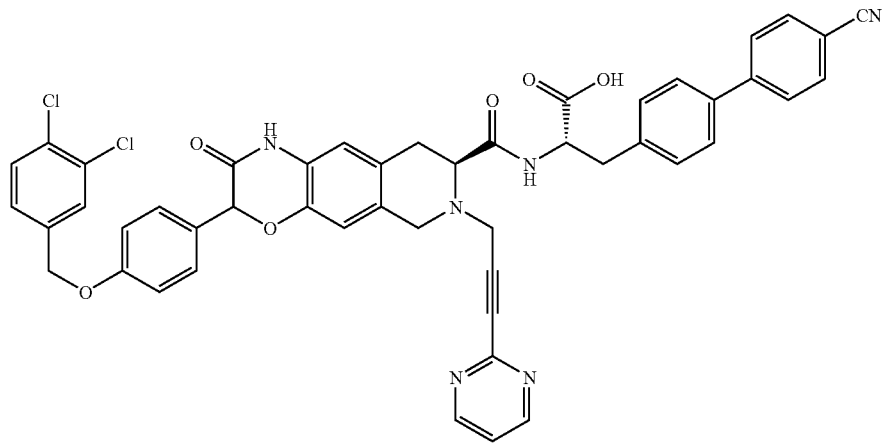

2-(3-Bromo-prop-1-ynyl)-pyrimidine was prepared from 3-Pyrimidin-2-yl-prop-2-yn-1-ol following general procedure Q and used to prepare the title compound. Title compound (24 mg) was prepared from Intermediate A (38 mg, 0.05 mmol) following general procedures K and B. LC-MS (m/z): 866.

Example 56

(S)-3-(4'-Cyano-biphenyl-4-yl)-2-{[(S)-3-[4-(3,4-dichloro-benzyloxy)-phenyl]-2-oxo-6-(3-thiophen-3-yl-prop-2-ynyl)-2,3,5,6,7,8-hexahydro-1H-4-oxa-1,6-diaza-anthracene-7-carbonyl]-amino}-propionic acid

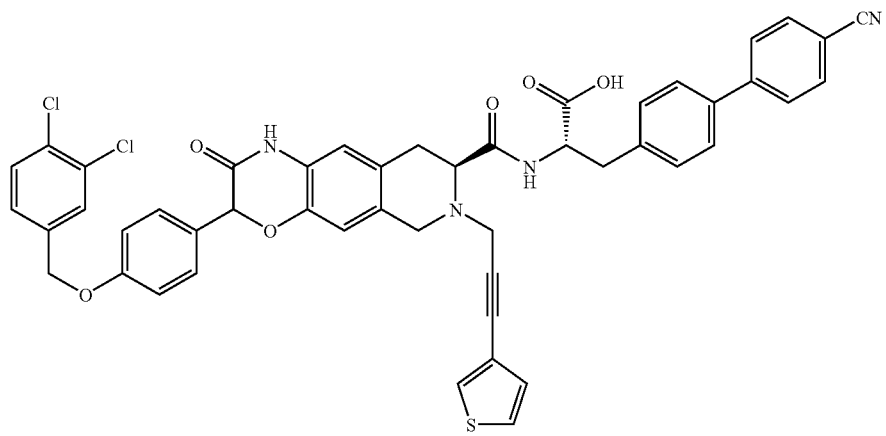

Title compound was prepared from Intermediate A (200 mg) following general procedures D and B. LC-MS (m/z): 869.

Example 57

(S)-2-({(S)-6-Benzoyl-3-[4-(2,6-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

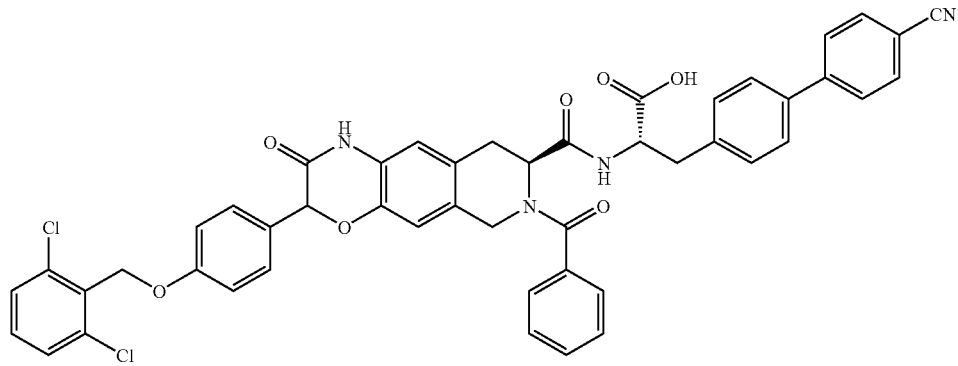

Title compound (16 mg) was prepared from (S)-7-[(S)-2-(4'-Cyano-biphenyl-4-yl)-1-methoxycarbonyl-ethylcarbamoyl]-3-[4-(2,6-dichloro-benzyloxy)-phenyl]-2-oxo-1,2,3,5,7,8-hexahydro-4-oxa-1,6-diaza-anthracene-6-carboxylic acid tert-butyl ester (50 mg, 0.05 mmol) following the Procedure C, F and B. LC-MS (m/z): 853.

Example 58

(S)-2-({(S)-6-Benzoyl-3-[4-(2,5-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

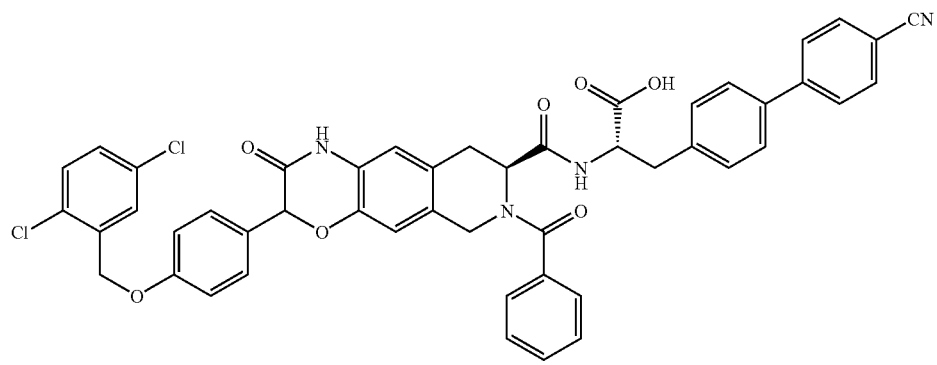

Title compound (20 mg) was prepared from (S)-7-[(S)-2-(4'-Cyano-biphenyl-4-yl)-1-methoxycarbonyl-ethylcarbamoyl]-3-[4-(2,5-dichloro-benzyloxy)-phenyl]-2-oxo-1,2,3,5,7,8-hexahydro-4-oxa-1,6-diaza-anthracene-6-carboxylic acid tert-butyl ester (40 mg, 0.05 mmol) following the general procedure C and F and B. LC-MS (m/z): 853.

Example 59

(S)-2-({(S)-6-Benzoyl-3-[4-(3-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

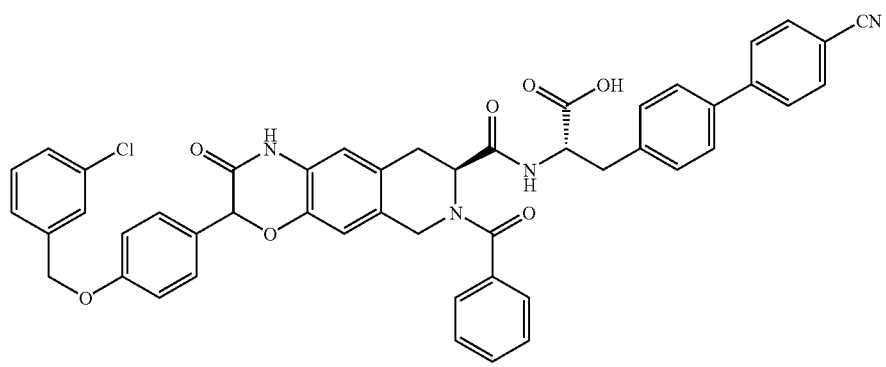

Title compound (17 mg) was prepared from (S)-3-[4-(3-chloro-benzyloxy)-phenyl]-7-[(S)-2-(4'-cyano-biphenyl-4-yl)-1-methoxycarbonyl-ethylcarbamoyl]-2-oxo-1,2,3,5,7,8-hexahydro-4-oxa-1,6-diaza-anthracene-6-carboxylic acid tert-butyl ester (40 mg, 0.05 mmol) following the general procedure C, F and B. LC-MS (m/z): 822.

Example 60

(S)-2-({(S)-6-Benzoyl-3-[4-(4-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

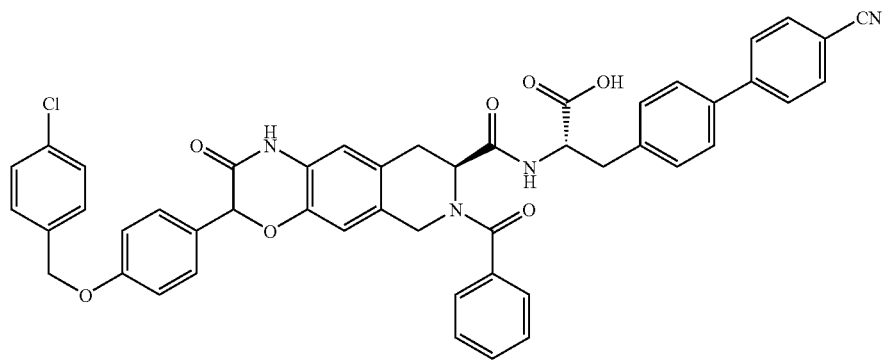

Title compound (16 mg) was prepared from (S)-3-[4-(4-chloro-benzyloxy)-phenyl]-7-[(S)-2-(4'-cyano-biphenyl-4-yl)-1-methoxycarbonyl-ethylcarbamoyl]-2-oxo-1,2,3,5,7,8-hexahydro-4-oxa-1,6-diaza-anthracene-6-carboxylic acid tert-butyl ester (40 mg, 0.05 mmol) following the general procedure C, F and B. LC-MS (m/z): 823.

Example 61

(S)-2-({(S)-6-Benzoyl-3-[4-(4-chloro-3-trifluorom-ethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

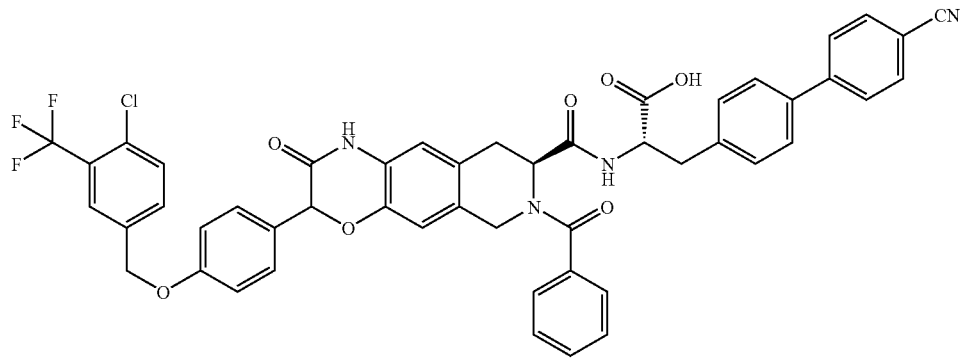

(S)-7-[(S)-2-(4'-Cyano-biphenyl-4-yl)-1-methoxycarbonyl-ethylcarbamoyl]-3-(4-hydroxy-phenyl)-2-oxo-1,2,3,5,7,8-hexahydro-4-oxa-1,6-diaza-anthracene-6-carboxylic acid tert-butyl ester was converted to (S)-2-({(S)-3-[4-(4-chloro-3-trifluoromethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester hydrochloride following general procedure L. and C. Title compound was prepared from (S)-2-({(S)-3-[4-(4-chloro-3-trifluoromethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester hydrochloride (0.05 mmol) following the general procedure F and B. LC-MS (m/z): 886.

Example 62

(S)-2-({(S)-6-Benzoyl-3-[4-(4-methoxy-3-trifluoromethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

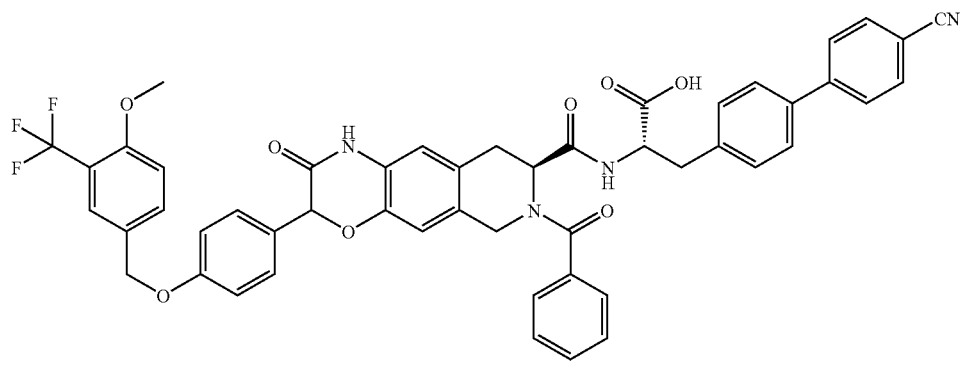

(S)-7-[(S)-2-(4'-Cyano-biphenyl-4-yl)-1-methoxycarbonyl-ethylcarbamoyl]-3-(4-hydroxy-phenyl)-2-oxo-1,2,3,5,7,8-hexahydro-4-oxa-1,6-diaza-anthracene-6-carboxylic acid tert-butyl ester was converted to (S)-3-(4'-cyano-biphenyl-4-yl)-2-({(S)-3-[4-(4-methoxy-3-trifluoromethyl-benzyloxy)-phenyl]-2-oxo-2,3,5,6,7,8-hexahydro-1H-4-oxa-1,6-diaza-anthracene-7-carbonyl}-amino)-propionic acid methyl ester hydrochloride following the general procedure L and C. Title compound (9 mg) was prepared from (S)-3-(4'-cyano-biphenyl-4-yl)-2-({(S)-3-[4-(4-methoxy-3-trifluoromethyl-benzyloxy)-phenyl]-2-oxo-2,3,5,6,7,8-hexahydro-1H-4-oxa-1,6-diaza-anthracene-7-carbonyl}-amino)-propionic acid methyl ester hydrochloride following general procedures F and B. LC-MS (m/z): 882.

Example 63

(S)-7-[(S)-1-Carboxy-2-(4'-cyano-biphenyl-4-yl)-ethylcarbamoyl]-3-[4-(5,6-dichloro-pyridin-3-yl-methoxy)-phenyl]-2-oxo-1,2,3,5,7,8-hexahydro-4-oxa-1,6-diaza-anthracene-6-carboxylic acid tert-butyl ester

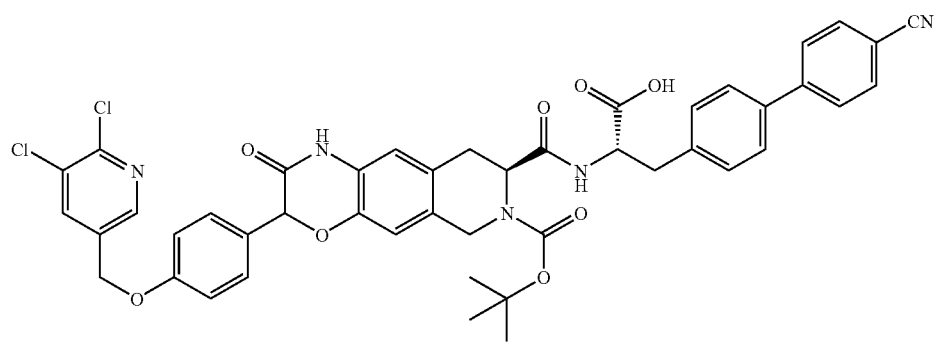

Title compound (6 mg) was prepared from (S)-7-[(S)-2-(4'-Cyano-biphenyl-4-yl)-1-methoxycarbonyl-ethylcarbamoyl]-3-[4-(5,6-dichloro-pyridin-3-ylmethoxy)-phenyl]-2-oxo-1,2,3,5,7,8-hexahydro-4-oxa-1,6-diaza-anthracene-6-carboxylic acid tert-butyl ester (10 mg) following the general procedure B. LC-MS (m/z): 851.

Example 64

(S)-2-({(S)-6-Benzoyl-3-[4-(5,6-dichloro-pyridin-3-ylmethoxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

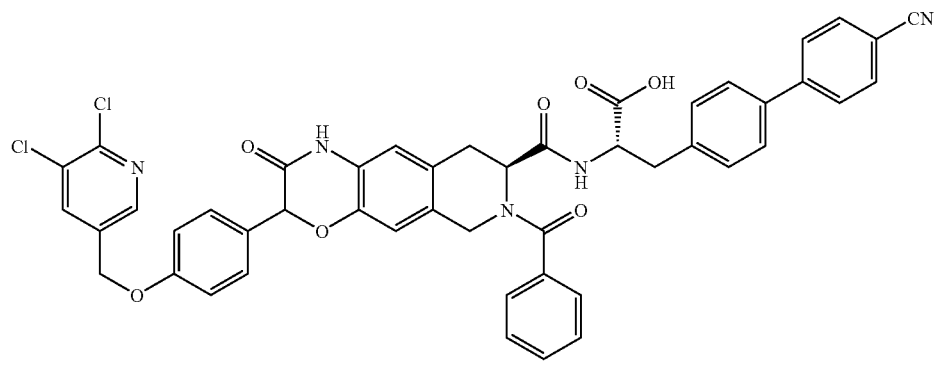

Title compound (12 mg) was prepared from (S)-7-[(S)-2-(4'-cyano-biphenyl-4-yl)-1-methoxycarbonyl-ethylcarbamoyl]-3-[4-(5,6-dichloro-pyridin-2-ylmethoxy)-phenyl]-2-oxo-1,2,3,5,7,8-hexahydro-4-oxa-1,6-diaza-anthracene-6-carboxylic acid tert-butyl ester (30 mg) following the general procedure C, F and B. LC-MS (m/z): 855.

Example 65

(S)-2-({(S)-6-Benzyl-3-[4-(5,6-dichloro-pyridin-3-ylmethoxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid

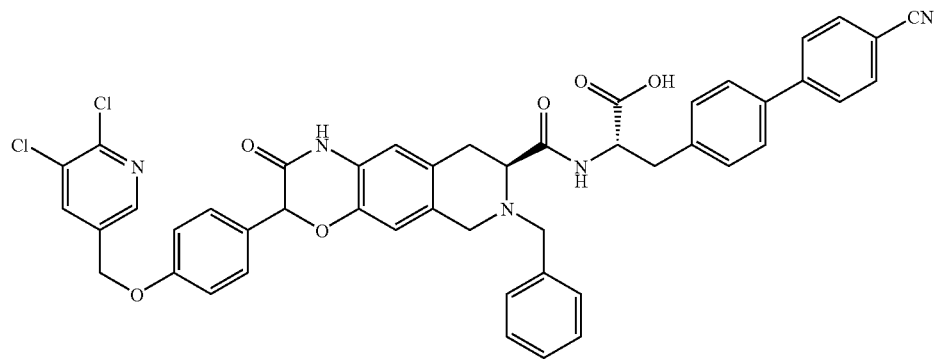

Title compound (7 mg) was prepared from (S)-7-[(S)-2-(4'-cyano-biphenyl-4-yl)-1-methoxycarbonyl-ethylcarbamoyl]-3-[4-(5,6-dichloro-pyridin-2-ylmethoxy)-phenyl]-2-oxo-1,2,3,5,7,8-hexahydro-4-oxa-1,6-diaza-anthracene-6-carboxylic acid tert-butyl ester (15 mg) following general procedures C, D and B. LC-MS (m/z): 839.

Example 66

(S)-3-(4'-Cyano-biphenyl-4-yl)-2-{[(S)-3-[4-(5,6-dichloro-pyridin-3-ylmethoxy)-phenyl]-2-oxo-6-(thiophene-2-carbonyl)-2,3,5,6,7,8-hexahydro-1H-4-oxa-1,6-diaza-anthracene-7-carbonyl]-amino}-propionic acid

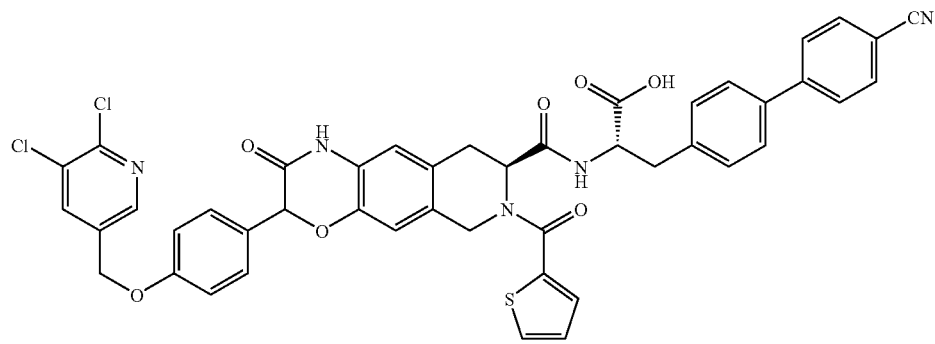

Title compound (16 mg) was prepared from (S)-7-[(S)-2-(4'-cyano-biphenyl-4-yl)-1-methoxycarbonyl-ethylcarbamoyl]-3-[4-(5,6-dichloro-pyridin-2-ylmethoxy)-phenyl]-2-oxo-1,2,3,5,7,8-hexahydro-4-oxa-1,6-diaza-anthracene-6-carboxylic acid tert-butyl ester (42 mg, 0.05 mmol) following general procedures C, F and B. LC-MS (m/z): 859.

Example 67

(S)-2-({(S)-3-[4-(3-Chloro-benzyloxy)-phenyl]-2-oxo-6-thiazol-2-ylmethyl-2,3,5,6,7,8-hexahydro-1H-4-oxa-1,6-diaza-anthracene-7-carbonyl}-amino)-3-(4'-cyano-biphenyl-4-yl)-propionic acid

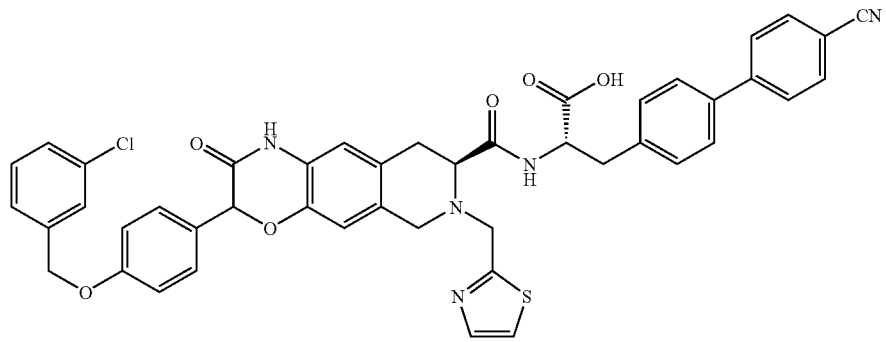

Title compound (16 mg) was prepared from (S)-3-[4-(3-chloro-benzyloxy)-phenyl]-7-[(S)-2-(4'-cyano-biphenyl-4-yl)-1-methoxycarbonyl-ethylcarbamoyl]-2-oxo-1,2,3,5,7,8-hexahydro-4-oxa-1,6-diaza-anthracene-6-carboxylic acid tert-butyl ester (40 mg, 0.05 mmol) following general procedures C, D and B. LC-MS (m/z): 811.

Example 68

(S)-7-[(S)-1-Carboxy-2-(4'-cyano-biphenyl-4-yl)-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid isopropyl ester

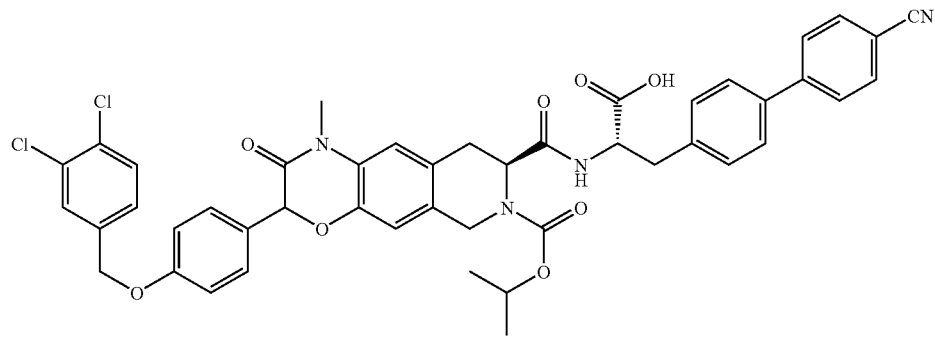

(S)-7-Hydroxy-6-nitro-3,4-dihydro-1H-isoquinoline-2,3-dicarboxylic acid 2-isopropyl ester 3-methyl ester (2.0 g, LC-MS (m/z) 340) was prepared from (S)-7-Hydroxy-6-nitro-1,2,3,4-tetrahydro-isoquinoline-3-carboxylic acid methyl ester (2.0 g) following general procedure H.

(S)-7-Hydroxy-6-nitro-3,4-dihydro-1H-isoquinoline-2,3-dicarboxylic acid 2-isopropyl ester 3-methyl ester (2.0 g) was dissolved in MeOH and 200 mg Pd/C added. The flask was evacuated and placed under balloon pressure of hydrogen. The reaction stirred at r.t. for 1.5 h and was filtered over a plug of celite. The celite plug was washed with EtOAc and DCM. The filtrates were combined and evaporated to provide (S)-6-amino-7-hydroxy-3,4-dihydro-1H-isoquinoline-2,3-dicarboxylic acid 2-isopropyl ester 3-methyl ester (1.8 g). LC-MS (m/z) 310.

(S)-6-amino-7-hydroxy-3,4-dihydro-1H-isoquinoline-2,3-dicarboxylic acid 2-isopropyl ester 3-methyl ester (1.8 g) was dissolved in 10 mL EtOAc, 20 mL water and 5.0 g sodium bicarbonate added. 2-Chloro-2-[4-(3,4-dichloro-benzyloxy)-phenyl]-acetyl chloride in 10 mL of EtOAc was added and the mixture stirred at rt for 1.5 h. The organic layer was washed with brine, dried and evaporated. The residue was dissolved in 15 mL DMF and potassium carbonate (4.1 g) added. The mixture stirred at r.t. for 3 h and was poured onto water and EtOAc. The organic was washed with 1N HCl, dried and evaporated. The residue was purified over silica (hexanes-EtOAc-2M ammonia in MeOH) to provide (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester 7-methyl ester (2.0 g). LC-MS (m/z) 600.

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester 7-methyl ester (2.0 g) was hydrolyzed following general procedure B to provide (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester (1.7 g). LC-MS (m/z) 586.

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester (0.342 mmol) was dissolved in DMF (2 mL) and potassium carbonate (1.71 mmol) and methyl iodide (3.42 mmol) added. Mixture stirred at room temperature for 30 minutes and heat at 40° C. for 4 hours. Mixture was poured on ethyl acetate and water. Organic layer was washed with 1 N HCl, dried, and concentrated to provide (S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-isopropyl ester 7-methyl ester (204 mg, LC/MS: m/z 616).

(S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-isopropyl ester 7-methyl ester (204 mg) was hydrolyzed and coupled to 2-amino-3-(4'-cyano-biphenyl-4-yl)-propionic acid methyl ester-hydrochloride according to general procedures A and B to provide (S)-7-[(S)-2-(4'-Cyano-biphenyl-4-yl)-1-methoxycarbonyl-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid isopropyl ester (161 mg, LC/MS: m/z 862).

Title compound (96 mg) was prepared from (S)-7-[(S)-2-(4'-Cyano-biphenyl-4-yl)-1-methoxycarbonyl-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid isopropyl ester (140 mg) according to general procedure B. LC/MS: m/z 848.

Example 69

(S)-3-(4'-Cyano-biphenyl-4-yl)-2-{[(S)-3-[4-(3,4-dichloro-benzyloxy)-phenyl]-1-methyl-2-oxo-6-(3-phenyl-prop-2-ynyl)-2,3,5,6,7,8-hexahydro-1H-4-oxa-1,6-diaza-anthracene-7-carbonyl]-amino}-propionic acid

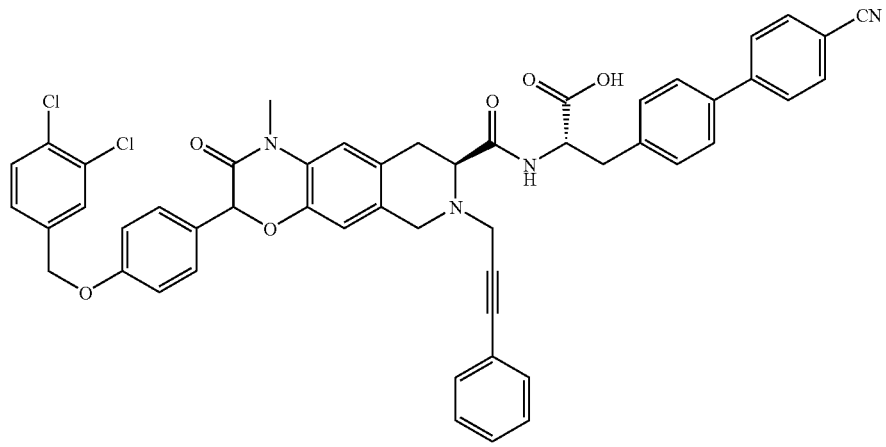

(3-Bromo-prop-1-ynyl)-benzene was prepared from 3-phenyl-prop-2-yn-1-ol following general procedure Q and used to prepare the title compound. Title compound (140 mg) was prepared from Intermediate B (150 mg) and 3-bromo-prop-1-ynyl benzene following general procedures K and B. LC-MS (m/z): 876.

Example 70

(S)-3-(4'-Cyano-biphenyl-4-yl)-2-{[(S)-3-[4-(3,4-dichloro-benzyloxy)-phenyl]-1-methyl-2-oxo-6-(1-phenyl-propyl)-2,3,5,6,7,8-hexahydro-1H-4-oxa-1,6-diaza-anthracene-7-carbonyl]-amino}-propionic acid

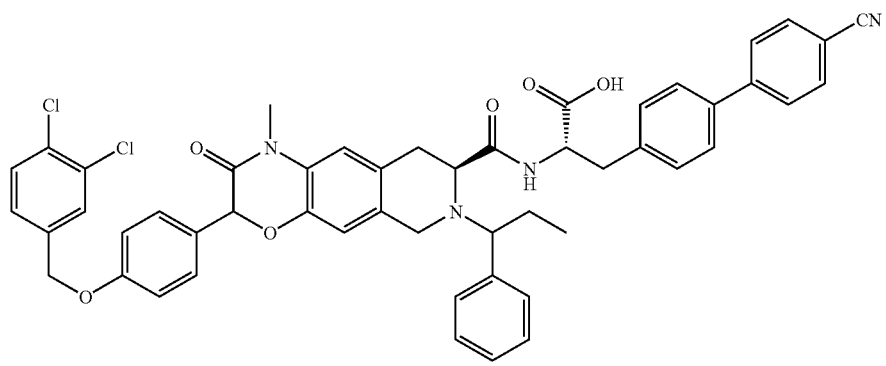

Title compound (42 mg) was prepared from Intermediate B (242 mg), following general procedures D (sodium cyanoborohydride was used in place of sodium triacetoxy borohydride) and B. LC-MS (m/z): 882.

Example 71

(S)-3-(4'-Cyano-biphenyl-4-yl)-2-{[(S)-3-[4-(3,4-dichloro-benzyloxy)-phenyl]-6-(2-ethyl-benzyl)-1-methyl-2-oxo-2,3,5,6,7,8-hexahydro-1H-4-oxa-1,6-diaza-anthracene-7-carbonyl]-amino}-propionic acid

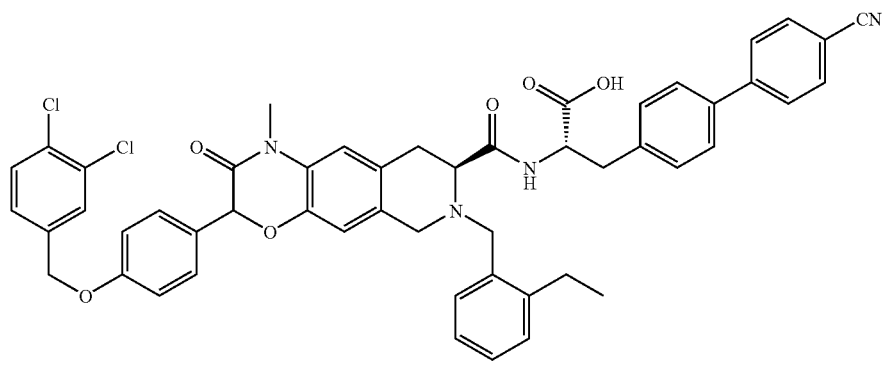

Title compound (33 mg) was prepared from Intermediate B (38 mg, 0.05 mmol) following general procedures D and B. LC-MS (m/z): 880.

Example 72

(S)-3-(4'-Cyano-biphenyl-4-yl)-2-{[(S)-3-[4-(3,4-dichloro-benzyloxy)-phenyl]-6-(2-isopropyl-benzyl)-1-methyl-2-oxo-2,3,5,6,7,8-hexahydro-1H-4-oxa-1,6-diaza-anthracene-7-carbonyl]-amino}-propionic acid

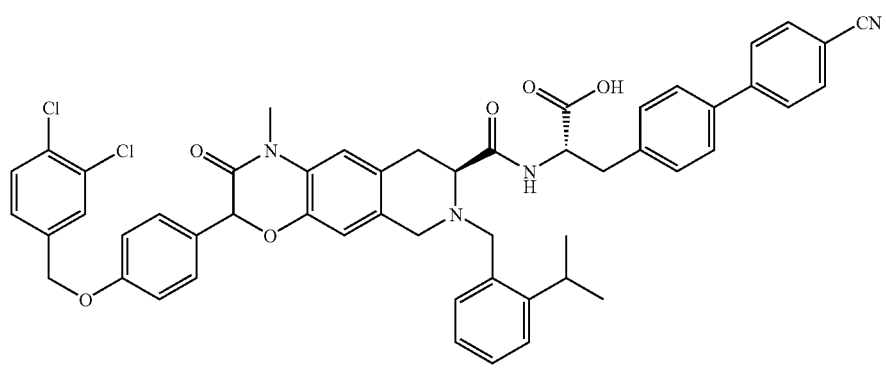

Title compound (28 mg) was prepared from Intermediate B (38 mg, 0.05 mmol) following general procedures D and B. LC-MS (m/z): 894.

Example 73

(S)-3-(4'-Cyano-biphenyl-4-yl)-2-({(S)-3-[4-(3,4-dichloro-benzyloxy)-phenyl]-6-indan-2-yl-1-methyl-2-oxo-2,3,5,6,7,8-hexahydro-1H-4-oxa-1,6-diaza-anthracene-7-carbonyl}-amino)-propionic acid

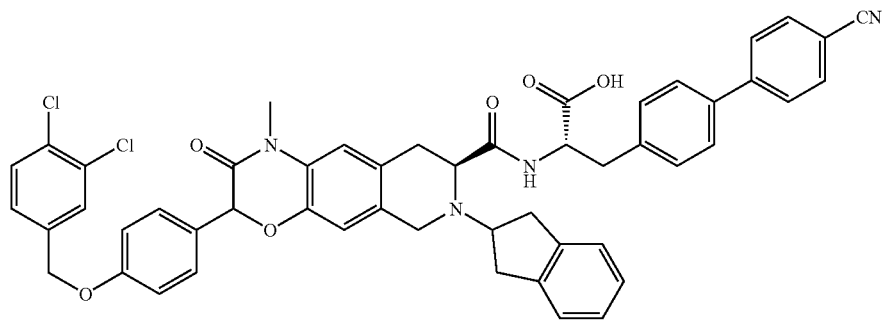

The indanyl intermediate, (S)-3-[4-(3,4-Dichloro-benzyloxy)-phenyl]-6-indan-2-yl-1-methyl-2-oxo-2,3,5,6,7,8-hexahydro-1H-4-oxa-1,6-diaza-anthracene-7-carboxylic acid, (158 mg) was prepared from Intermediate C (175 mg, 0.3 mmol) and 2-indanone (0.6 mmol) following the general procedures D and B. This indanyl intermediate was used without further purification.

Title compound (32 mg) was prepared from the indanyl intermediate (63 mg, 0.1 mmol) and (S)-2-amino-3-(4'-cyano-biphenyl-4-yl)-propionic acid methyl ester hydrochloride (36 mg, 0.12 mmol) following general procedures A and B. LC-MS (m/z): 879.

Example 74

(S)-3-(4'-Cyano-biphenyl-4-yl)-2-({(S)-6-cyclopentyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid

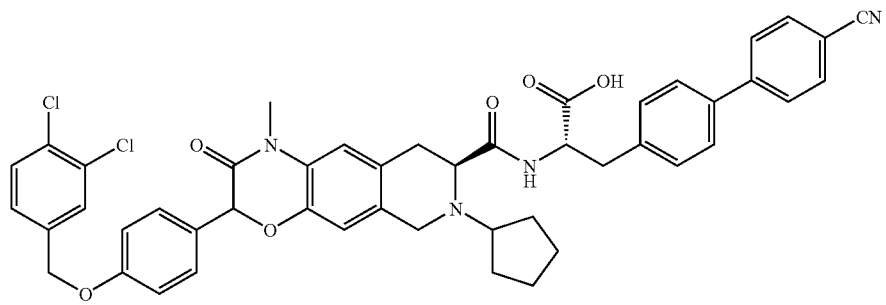

The cyclopentyl intermediate, (S)-6-Cyclopentyl-3-[4-(3,4-dichloro-benzyloxy)-phenyl]-1-methyl-2-oxo-2,3,5,6,7,8-hexahydro-1H-4-oxa-1,6-diaza-anthracene-7-carboxylic acid, (95 mg) was prepared from Intermediate C (130 mg, 0.25 mmol) and cyclopentanone (0.5 mmol) following the general procedures D and B. This cyclopentyl intermediate was used without further purification.

Title compound (13 mg) was prepared from the cyclopentyl intermediate (15 mg, 0.025 mmol) and (S)-2-amino-3-(4'-cyano-biphenyl-4-yl)-propionic acid methyl ester hydrochloride (8 mg, 0.025 mmol) following general procedures A and B. LC-MS (m/z): 830.

Example 75

(S)-3-(4'-Cyano-biphenyl-4-yl)-2-({(S)-6-cyclohexyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid

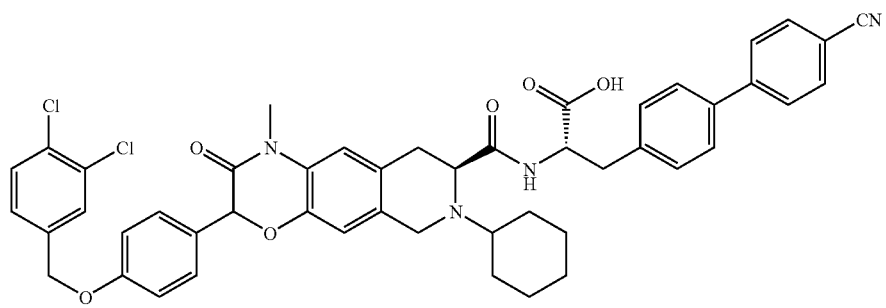

Title compound (24 mg) was prepared from Intermediate B (38 mg, 0.05 mmol) following general procedures D and B. LC-MS (m/z): 844.

Example 76

(S)-3-(4'-Cyano-biphenyl-4-yl)-2-({(S)-6-cyclobutyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid

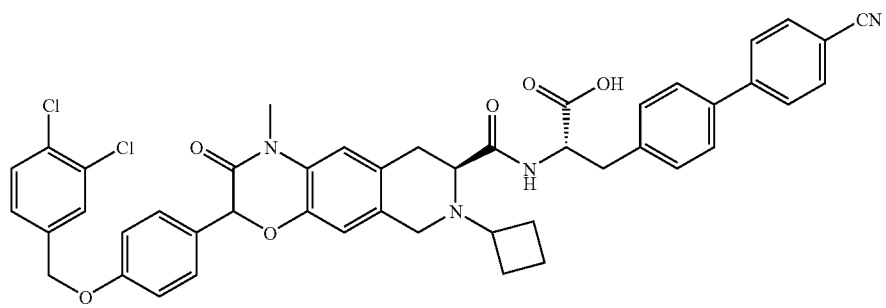

Title compound (22 mg) was prepared from Intermediate B (38 mg, 0.05 mmol) following general procedures D and B. LC-MS (m/z): 816.

Example 77

(S)-3-(4'-Cyano-biphenyl-4-yl)-2-{[(S)-3-[4-(3,4-dichloro-benzyloxy)-phenyl]-1-methyl-2-oxo-6-(1-phenyl-cyclopentylmethyl)-2,3,5,6,7,8-hexahydro-1H-4-oxa-1,6-diaza-anthracene-7-carbonyl]-amino}-propionic acid

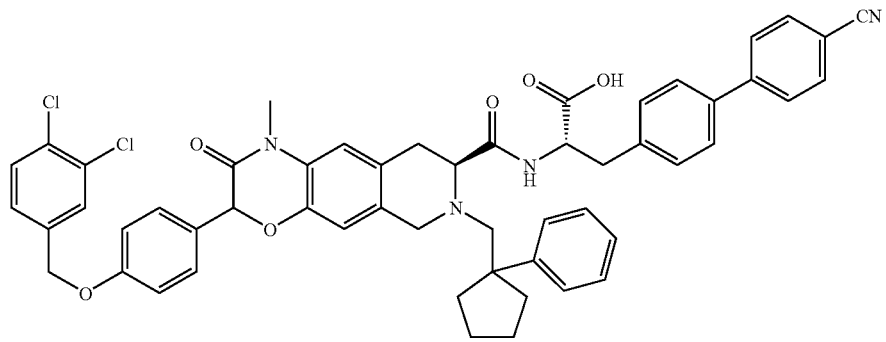

To a solution of (1-Phenyl-cyclopentyl)-methanol (1.0 g, 5.7 mmol) in DCM (20 mL) was added Dess-Martin Periodine (6.8 mmol, 1.2 eq) and sodium bicarbonate (6.8 mmol, 1.2 eq) at 0° C. The reaction mixture stirred at this temperature for 2 h and allowed to warm up slowly to room temperature. After completion of the reaction, the mixture was poured into water (50 mL) and extracted with DCM (50 mL). The organic mixture was then dried over sodium sulfate and concentrated under reduced pressure to give 1-Phenyl-cyclopentanecarbaldehyde (812 mg) which was immediately used to synthesize title compound (14 mg) from Intermediate B (20 mg, 0.025 mmol) following general procedures D and B. LC-MS (m/z): 923.

Example 78

(S)-3-(4'-Cyano-biphenyl-4-yl)-2-({(S)-3-[4-(3,4-dichloro-benzyloxy)-phenyl]-6-ethyl-1-methyl-2-oxo-2,3,5,6,7,8-hexahydro-1H-4-oxa-1,6-diaza-anthracene-7-carbonyl}-amino)-propionic acid

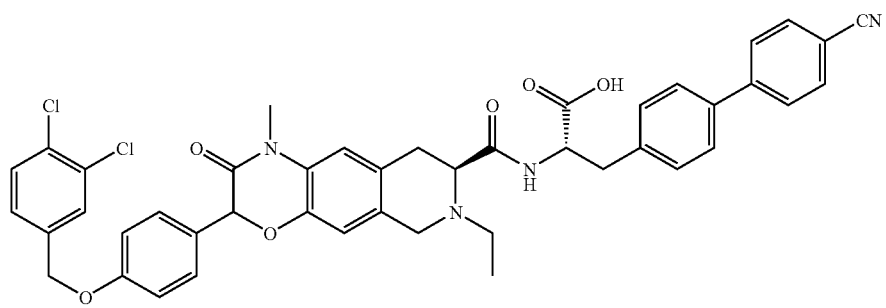

Title compound (18 mg) was prepared from Intermediate B (38 mg, 0.05 mmol) following general procedures D and B. LC-MS (m/z): 792.

Example 79

(S)-2-({(S)-6-(Carboxy-phenyl-methyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid

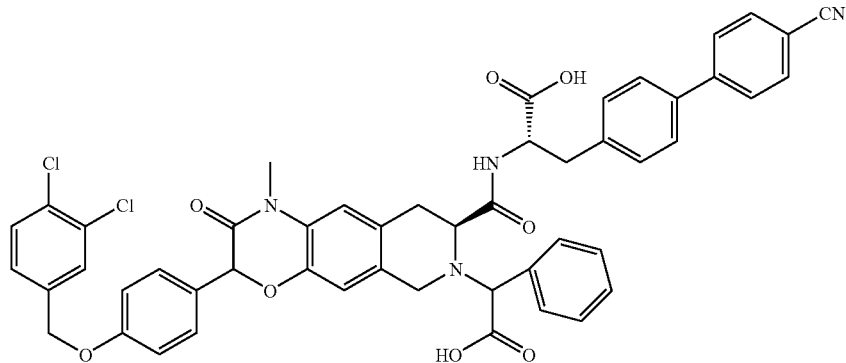

Title compound (32 mg) was prepared from Intermediate B (38 mg, 0.05 mmol) following general procedures K and B. LC-MS (m/z): 895.

Example 80

(S)-3-(4'-Cyano-biphenyl-4-yl)-2-{[(S)-3-[4-(3,4-dichloro-benzyloxy)-phenyl]-1-methyl-2-oxo-6-(1-phenyl-ethyl)-2,3,5,6,7,8-hexahydro-1H-4-oxa-1,6-diaza-anthracene-7-carbonyl]-amino}-propionic acid

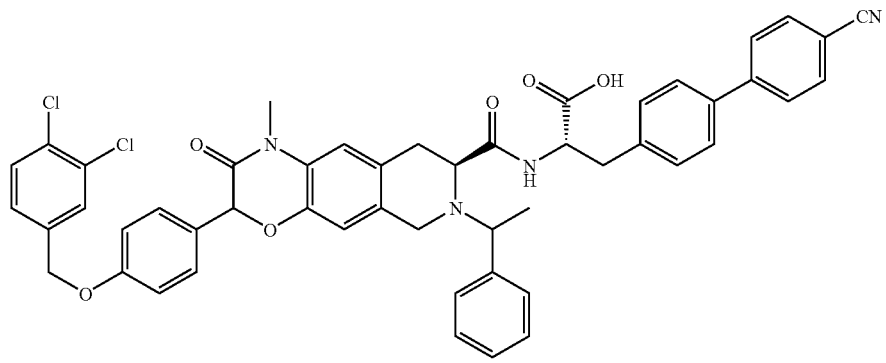

The 1-phen-ethyl intermediate, (S)-3-[4-(3,4-dichloro-benzyloxy)-phenyl]-1-methyl-2-oxo-6-(1-phenyl-ethyl)-2,3,5,6,7,8-hexahydro-1H-4-oxa-1,6-diaza-anthracene-7-carboxylic acid, (44 mg) was prepared from Intermediate C (53 mg, 0.1 mmol) and (1-bromo-ethyl)-benzene (38 mg, 0.2 mmol) following the general procedures K and B. This 1-phen-ethyl intermediate was used without further purification.

Title compound (27 mg) was prepared from the 1-phen-ethyl intermediate (31 mg, 0.05 mmol) and (S)-2-amino-3-(4'-cyano-biphenyl-4-yl)-propionic acid methyl ester hydrochloride (16 mg, 0.05 mmol) following general procedures A and B. LC-MS (m/z): 865.

Example 81

(S)-2-({(S)-6-(2-Acetylamino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid (more polar diastereomer)

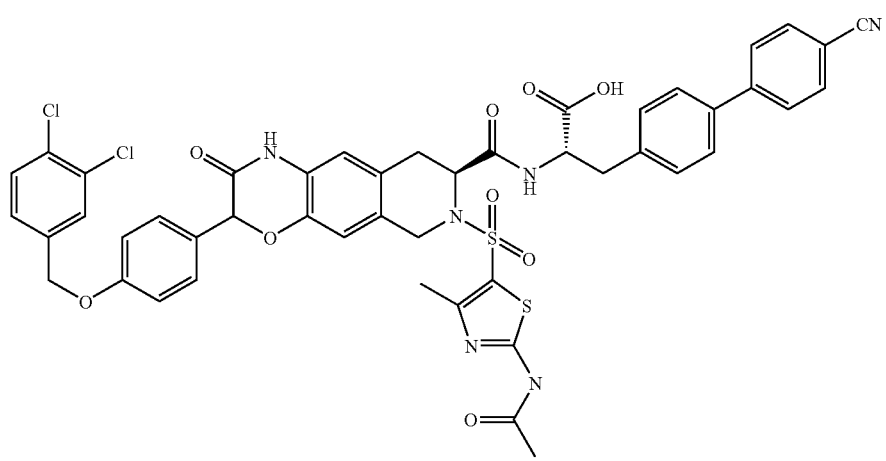

(S)-3-(4'-Cyano-biphenyl-4-yl)-2-({(S)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid methyl ester (760 mg) was reacted with 2-acetylamino-4-methyl-thiazole-5-sulfonyl chloride (381 mg) following general procedure E to furnish (S)-2-({(S)-6-(2-acetylamino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (800 mg) as a mixture of diastereomers. The diastereomers were separated by flash chromatography over silica (DCM:EtOAc 9:1-6:4). The more polar diasteromer (LC-MS m/z 982, 12 mg) was hydrolyzed using the general procedure B to furnish title compound (8 mg, more polar diastereomer). LC-MS (m/z): 967.

Example 82

(S)-7-((S)-2-Biphenyl-4-yl-1-carboxy-ethylcarbamoyl)-3-[4-(3,4-dichloro-benzyloxy)-phenyl]-2-oxo-1,2,3,5,7,8-hexahydro-4-oxa-1,6-diaza-anthracene-6-carboxylic acid isopropyl ester

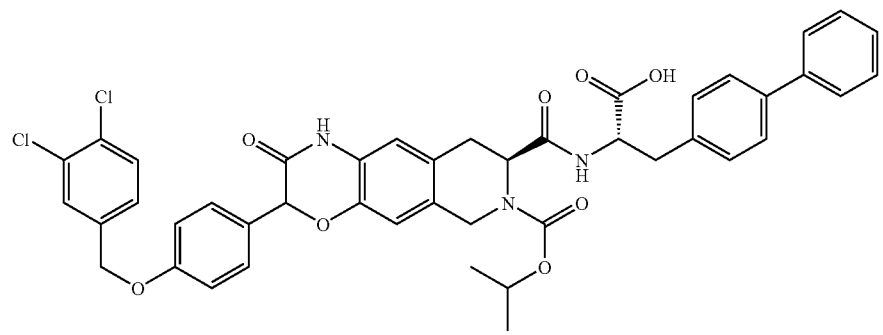

(S)-7-Hydroxy-6-nitro-3,4-dihydro-1H-isoquinoline-2,3-dicarboxylic acid 2-isopropyl ester 3-methyl ester (2.0 g, LC-MS (m/z) 340) was prepared from (S)-7-Hydroxy-6-nitro-1,2,3,4-tetrahydro-isoquinoline-3-carboxylic acid methyl ester (2.0 g) following general procedure H.

(S)-7-Hydroxy-6-nitro-3,4-dihydro-1H-isoquinoline-2,3-dicarboxylic acid 2-isopropyl ester 3-methyl ester (2.0 g) was dissolved in MeOH and 200 mg Pd/C added. The flask was evacuated and placed under balloon pressure of hydrogen. The reaction stirred at rt for 1.5 h and was filtered over a plug of celite. The celite plug was washed with EtOAc and DCM. The filtrates were combined and evaporated to provide (S)-6-amino-7-hydroxy-3,4-dihydro-1H-isoquinoline-2,3-dicarboxylic acid 2-isopropyl ester 3-methyl ester (1.8 g). LC-MS (m/z) 310.

(S)-6-amino-7-hydroxy-3,4-dihydro-1H-isoquinoline-2,3-dicarboxylic acid 2-isopropyl ester 3-methyl ester (1.8 g) was dissolved in 10 mL EtOAc, 20 mL water and 5.0 g sodium bicarbonate added. 2-Chloro-2-[4-(3,4-dichloro-benzyloxy)-phenyl]-acetyl chloride in 10 mL of EtOAc was added and the mixture stirred at rt for 1.5 h. The organic layer was washed with brine, dried and evaporated. The residue was dissolved in 15 mL DMF and potassium carbonate (4.1 g) added. The mixture stirred at rt for 3 h and was poured onto water and EtOAc. The organic was washed with 1N HCl, dried and evaporated. The residue was purified over silica (hexanes-EtOAc-2M ammonia in MeOH) to provide (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester 7-methyl ester (2.0 g). LC-MS (m/z) 600.

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester 7-methyl ester (2.0 g) was hydrolyzed following general procedure B to provide (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester (1.7 g). LC-MS (m/z) 586.

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-isopropyl ester (120 mg) was coupled with (S)-2-amino-3-biphenyl-4-yl-propionic acid methyl ester hydrochloride according to general procedure A to provide (S)-7-((S)-2-biphenyl-4-yl-1-methoxycarbonyl-ethylcarbamoyl)-3-[4-(3,4-dichloro-benzyloxy)-phenyl]-2-oxo-1,2,3,5,7,8-hexahydro-4-oxa-1,6-diaza-anthracene-6-carboxylic acid isopropyl ester (151 mg, LC/MS: m/z 825).

Title compound (71 mg) was prepared from (S)-7-((S)-2-biphenyl-4-yl-1-methoxycarbonyl-ethylcarbamoyl)-3-[4-(3,4-dichloro-benzyloxy)-phenyl]-2-oxo-1,2,3,5,7,8-hexahydro-4-oxa-1,6-diaza-anthracene-6-carboxylic acid isopropyl ester (101 mg) according to general procedure B. LC/MS: m/z 809.

Example 83

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4-pyridin-4-yl-phenyl)-propionic acid

Example 83

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4-pyridin-4-yl-phenyl)-propionic acid (S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid ("Intermediate D") (1.4 g, LC/MS: m/z 604) was prepared from (S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid methyl ester (1.6 g) according to general procedure B.

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4-pyridin-4-yl-phenyl)-propionic acid methyl ester (61 m g, LC/MS: m/z 842) was prepared from Intermediate D (100 mg) and (S)-2-amino-3-(4-pyridin-4-yl-phenyl)-propionic acid methyl ester bis hydrochloride according to general procedure A.

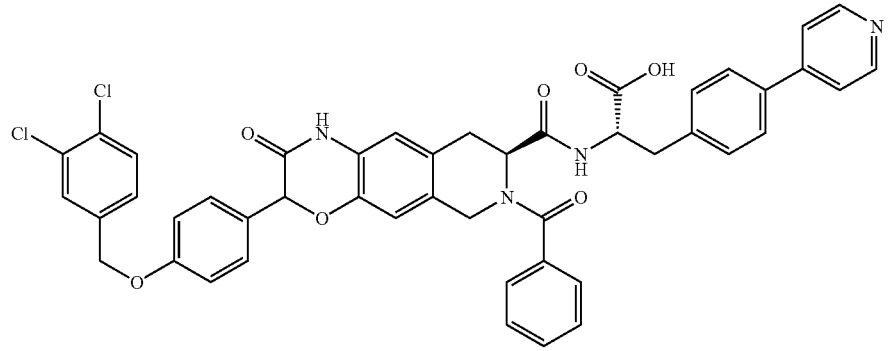

(S)-3-[4-(3,4-Dichloro-benzyloxy)-phenyl]-2-oxo-2,3,5,6,7,8-hexahydro-1H-4-oxa-1,6-diaza-anthracene-7-carboxylic acid methyl ester hydrochloride (1.8 g, LC/MS: m/z 514) was prepared from (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-methyl ester (2.2 g) according to general procedure C.

(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid methyl ester (1.6 g, LC/MS: m/z 618) was prepared from (S)-3-[4-(3,4-Dichloro-benzyloxy)-phenyl]-2-oxo-2,3,5,6,7,8-hexahydro-1H-4-oxa-1,6-diaza-anthracene-7-carboxylic acid methyl ester hydrochloride (1.8 g) according to general procedure F except no work-up was done. The mixture was evaporated and placed directly onto silica.

Title compound (41 m g) was prepared from (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4-pyridin-4-yl-phenyl)-propionic acid methyl ester (50 mg) according to general procedure B. LC/MS: m/z 828.

Example 84

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-chloro-biphenyl-4-yl)-propionic acid

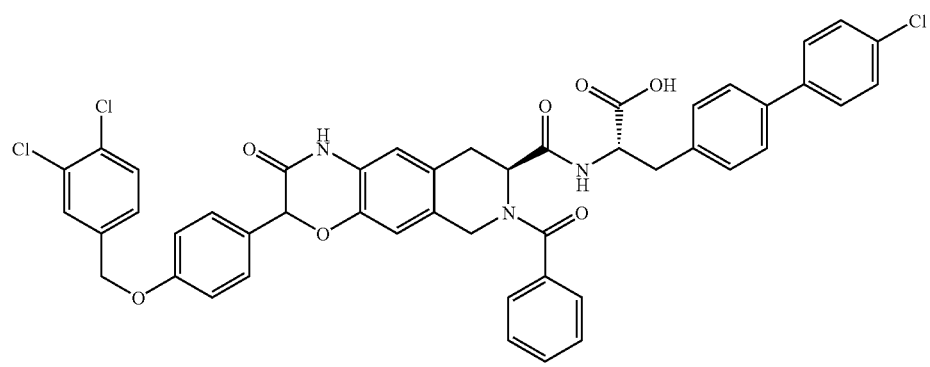

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-chloro-biphenyl-4-yl)-propionic acid methyl ester (71 m g, LC/MS: m/z 878) was prepared from Intermediate D (100 mg) and (S)-2-amino-3-(4'-chloro-biphenyl-4-yl)-propionic acid methyl ester hydrochloride according to general procedure A.

Title compound (50 m g) was prepared from (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-chloro-biphenyl-4-yl)-propionic acid methyl ester (61 mg) according to general procedure B. LC/MS: m/z 862.

Example 85

(S)-2-({(S)-3-[4-(3,4-Dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-3-(4'-methyl-biphenyl-4-yl)-propionic acid and (S)-2-Amino-3-(4'-methyl-biphenyl-4-yl)-propionic acid methyl ester hydrochloride according to general procedures A and C.

(S)-2-({(S)-3-[4-(3,4-Dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-3-(4'-methyl-biphenyl-4-yl)-propionic acid methyl ester (16 mg, LC/MS: m/z 842) was prepared from (S)-2-({(S)-3-[4-(3,4-Dichloro-benzyloxy)-phenyl]-2-oxo-2,3,5,6,7,8-hexahydro-1H-4-oxa-1,6-diaza-anthracene-7-carbonyl}-amino)-3-(4'-methyl-biphenyl-4-yl)-propionic acid methyl ester hydrochloride (54 mg) according to general procedure D.

Title compound (9 mg) was prepared from Title compound methyl ester (16 mg) according to general procedure B. LC/MS: m/z 828.

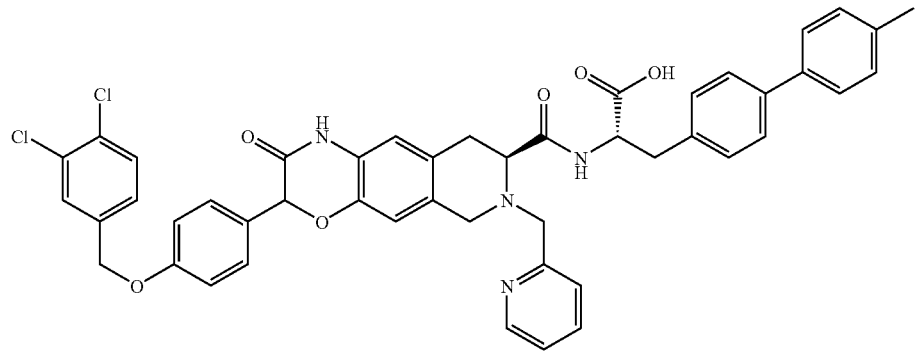

(S)-2-({(S)-3-[4-(3,4-Dichloro-benzyloxy)-phenyl]-2-oxo-2,3,5,6,7,8-hexahydro-1H-4-oxa-1,6-diaza-anthracene-7-carbonyl}-amino)-3-(4'-methyl-biphenyl-4-yl)-propionic acid methyl ester hydrochloride (74 mg, LC/MS: m/z 751) was prepared from (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester (150 mg)

Example 86

(S)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid

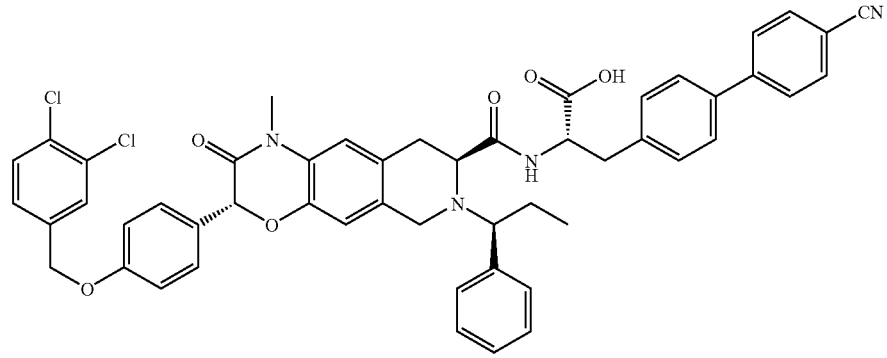

Title compound (28 mg) was prepared from (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (46 mg) using general procedures B. LC-MS (m/z): 881.

Example 87

(S)-3-(4'-Cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid

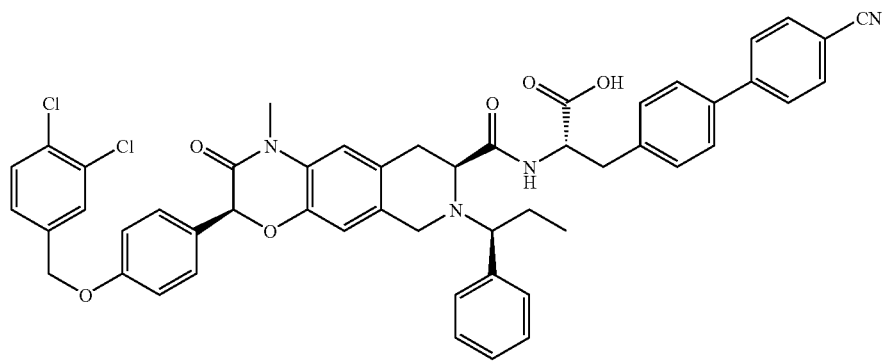

Title compound (28 mg) was prepared from (S)-3-(4'-cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (32 mg) r using general procedures B. LC-MS (m/z): 881.

Example 88

(S)-3-(4'-Cyano-biphenyl-4-yl)-2-{[(3S,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid

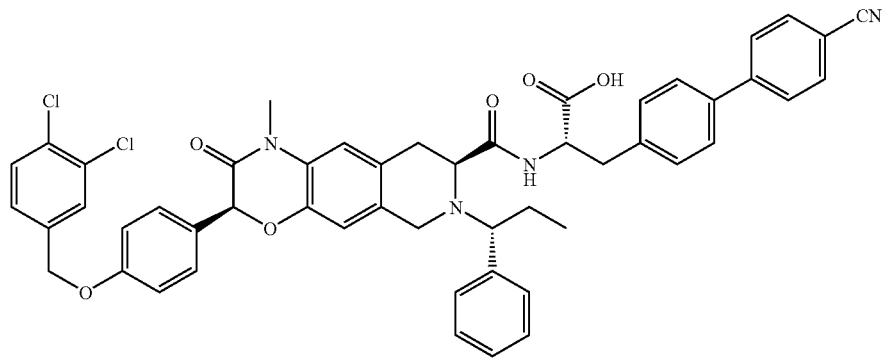

Title compound (22 mg) was prepared from (S)-3-(4'-Cyano-biphenyl-4-yl)-2-{[(3S,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (25 mg) using general procedures B. LC-MS (m/z): 879.

Example 89

(S)-3-(4'-Cyano-biphenyl-4-yl)-2-{[(3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid

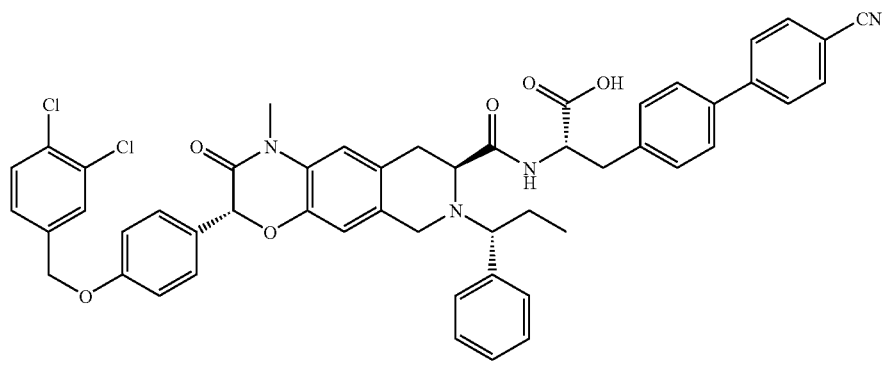

Title compound (54 mg) was prepared from (S)-3-(4'-cyano-biphenyl-4-yl)-2-{[(3R,7S)-3-[4-(3,4-dichloro-benzyloxy)-phenyl]-1-methyl-2-oxo-6-((R)-1-phenyl-propyl)-2,3,5,6,7,8-hexahydro-1H-4-oxa-1,6-diaza-anthracene-7-carbonyl]-amino}-propionic acid methyl ester (60 mg) using general procedure B. LC-MS (m/z): 879.

Example 90

(S)-3-(4'-Chloro-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid

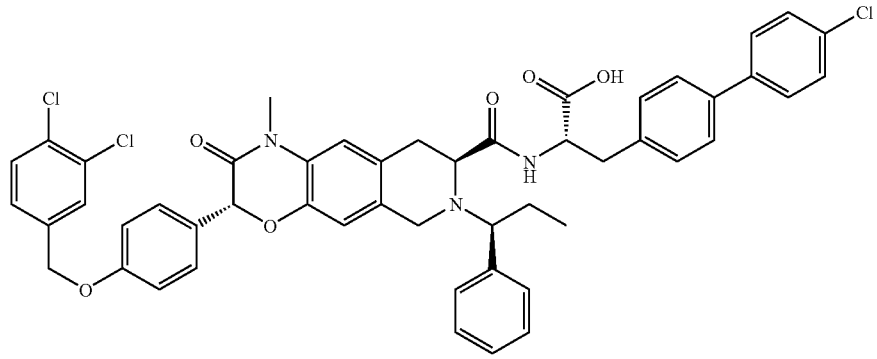

(S)-3-(4'-chloro, —biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (74 mg) was converted to (S)-3-(4'-chloro-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (60 mg) using general procedure K. This ester upon hydrolysis furnished title compound (52 mg) using general procedures B. LC-MS (m/z): 888.

Example 91

(S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid

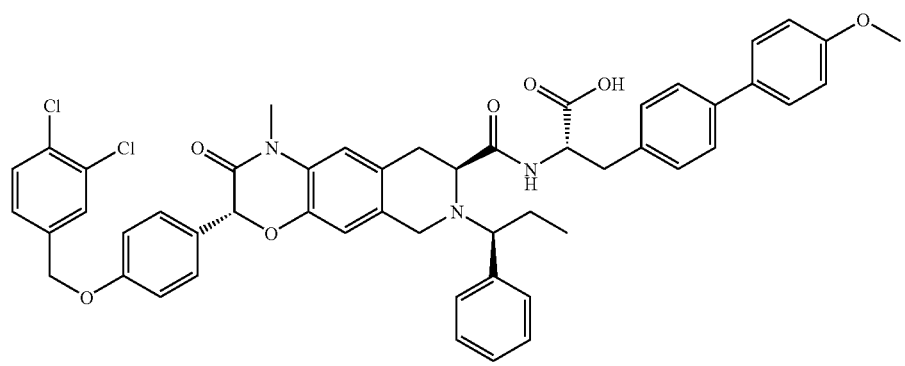

(S)-2-{[(3R,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester was converted to (S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester (64 mg) using general procedure K. This ester upon hydrolysis furnished title compound (58 mg) LCMS (m/z): 884.

Example 92

(S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid

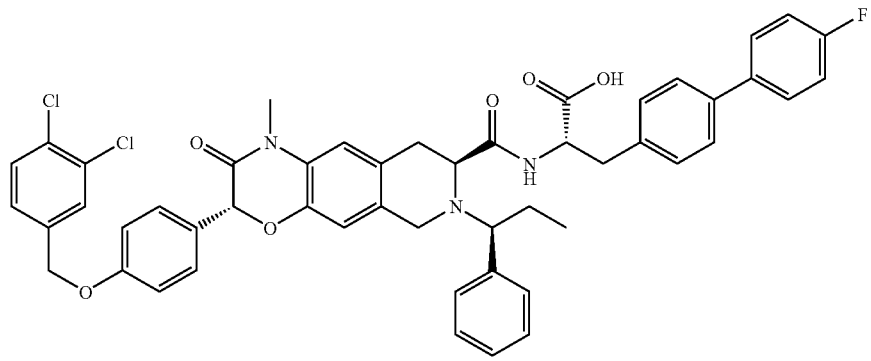

(S)-3-(4'-Fluoro-biphenyl-4-yl)-2-{[(3R,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester was converted to (S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid methyl ester (70 mg) using general procedure K. This ester upon hydrolysis furnished title compound (64 mg) LCMS (m/z): 872.

Example 93

(S)-3-(4'-Chloro-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid (S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester (8.0 g, 13.3 mmol) was suspended in 30 mL DCM and 1R-2S-5R (−)-menthol (26.6 mmol), EDC (26.6 mmol) and DMAP (cat.) added. The mixture was stirred at rt for 6 h and the mixture was diluted with DCM. The organic layer was washed with water and brine, dried over sodium sulfate and concentrated. The residue purified over silica with hexanes-EtOAc gradient (0% EtOAc to 30%) to provide (3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (2.4 g, $^1$H NMR (400 MHz, CDCl$_3$): 8.2 (m, 1H), 7.5 (m, 1H), 7.42 (d, 1H), 7.35 (m, 2H), 7.25 (m, 1H), 6.9 (m, 2H), 6.7 (m, 1H), 6.6 (s, 1H), 5.55 (m, 1H), 4.8-5.1 (m, 1H), 5.0 (s, 2H), 4.3-4.6 (m, 3H), 3.1 (m, 2H), 1.8 (m, 1H), 1.6 (m, 3H), 1.5 (d, 9H), 1.3 (m, 2H), 0.7-1.0 (m, 9H), 0.4 (m, 3H).

(3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester was N-methylated (3.9 g) according to general procedure M to provide (3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (4.9 g, not isolated as pure material).

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.9 g) was deprotected using general procedure C to provide (3S,7S)-3-

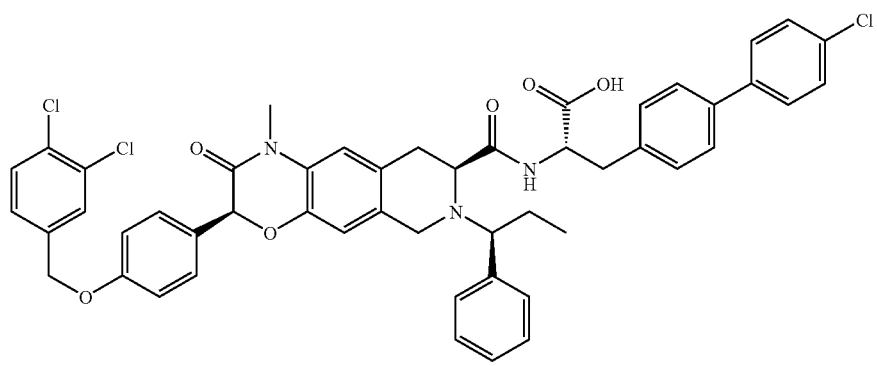

[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride (3.5 g, LC/MS: m/z 652).

(3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester (3.5 g, 5.37 mmol) was dissolved in 10 mL DMF and sodium bicarbonate (21.5 mmol) and (1-Bromo-propyl)-benzene (10.7 mmol) added. The mixture was stirred at 50° C. for 20 h and room temperature for 48 hours. The mixture was poured onto diethyl ether and 10% sodium carbonate. The aqueous layer was extracted with ether and organic layers combined. The organic layer was dried over sodium sulfate and concentrated. The residue was purified over silica (EtOAc-hexanes-DCM-TEA, 0.5/5/4.5/0.02) to provide (3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (803 mg, $^1$H NMR (400 MHz, $d_6$ acetone): 7.7 (d, 1H), 7.6 (d, 1H), 7.46 (d, 1H), 7.33 (m, 7H), 6.98 (m, 2H), 6.87 (s, 1H), 6.77 (s, 1H), 5.65 (s, 1H), 5.13 (s, 2H), 4.55 (m, 1H), 4.20 (s, 2H), 3.9 (m, 1H), 3.55 (m, 1H), 3.38 (s, 3H), 2.95 (m, 2H), 1.6 (m, 6H), 1.15 (m, 1H), 0.95 (m, 1H) 0.9 (m, 2H), 0.8 (m, 4H), 0.7 (d, 3H), 0.65 (m, 6H).

(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (0.80 g) was dissolved in 20 mL of dry DCM and cooled to 0° C. Boron trichloride (8 mL, 1M solution in hexanes) was added and the mixture stirred at 0° C. for 3.5 hours. The mixture was concentrated and treated with water/saturated sodium bicarbonate until pH 7. The aqueous mixture was extracted three times with ethyl acetate-THF (9-1) and organic layers combined. The combined organic layers were dried over sodium sulfate and concentrated to provide (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (601 mg, LC/MS: m/z 474).

(S)-3-(4'-Chloro-biphenyl-4-yl)-2-{[(3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (68 mg, LC/MS: m/z 745) was prepared from (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (70 mg) and (S)-2-Amino-3-(4'-chloro-biphenyl-4-yl)-propionic acid methyl ester hydrochloride using general procedure A.

(S)-3-(4'-Chloro-biphenyl-4-yl)-2-{[(3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (68 mg, 0.091 mmol) was dissolved in 2 mL of DMF and 3,4-dichlorobenzyl bromide (0.46 mmol) and potassium carbonate (0.46 mmol) were added. The mixture was stirred at room temperature for 8 hours and was poured onto ethyl acetate and 10% sodium carbonate. The organic layer was washed with brine, dried over sodium sulfate and concentrated. The residue was purified over silica (hexanes-ethyl acetate-MeOH, 7-3-0.1) to provide (S)-3-(4'-Chloro-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (17 mg, LC/MS: m/z 903).

Title compound (8 mg) was prepared from (S)-3-(4'-Chloro-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (17 mg) according to general procedure B. LC/MS: m/z 889.

Example 94

(S)-2-{[(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid

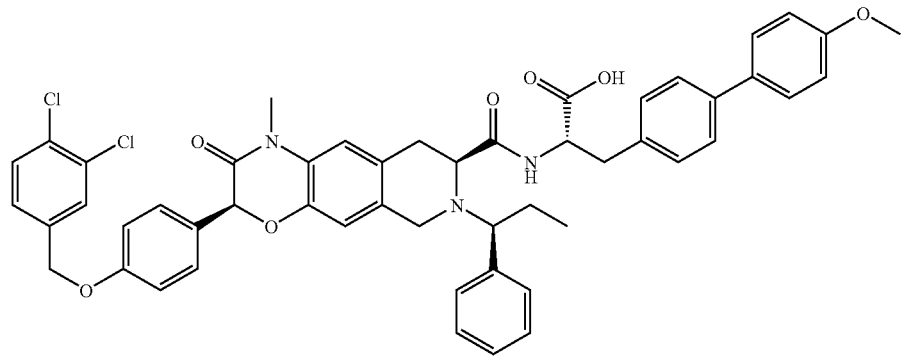

(S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester (8.0 g, 13.3 mmol) was suspended in 30 mL DCM and 1R-2S-5R (−)-menthol (26.6 mmol), EDC (26.6 mmol) and DMAP (cat.) added. The mixture was stirred at r.t. for 6 h and the mixture diluted with DCM. The organic layer was washed with water and brine, dried over sodium sulfate and concentrated. The residue purified over silica with hexanes-EtOAc gradient (0% EtOAc to 30%) to provide (3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (2.4 g, $^1$H NMR (400 MHz, CDCl$_3$): 8.2 (m, 1H), 7.5 (m, 1H), 7.42 (d, 1H), 7.35 (m, 2H), 7.25 (m, 1H), 6.9 (m, 2H), 6.7 (m, 1H), 6.6 (s, 1H), 5.55 (m, 1H), 4.8-5.1 (m, 1H), 5.0 (s, 2H), 4.3-4.6 (m, 3H), 3.1 (m, 2H), 1.8 (m, 1H), 1.6 (m, 3H), 1.5 (d, 9H), 1.3 (m, 2H), 0.7-1.0 (m, 9H), 0.4 (m, 3H).

(3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester was N-methylated (3.9 g) according to general procedure M to provide (3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (4.9 g, not isolated as pure material).

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.9 g) was deprotected using general procedure C to provide (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride (3.5 g, LC/MS: m/z 652).

(3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester (3.5 g, 5.37 mmol) was dissolved in 10 mL DMF and sodium bicarbonate (21.5 mmol) and (1-Bromo-propyl)-benzene (10.7 mmol) added. The mixture was stirred at 50° C. for 20 h and room temperature for 48 hours. The mixture was poured onto diethyl ether and 10% sodium carbonate. The aqueous layer was extracted with ether and organic layers combined. The organic layer was dried over sodium sulfate and concentrated. The residue was purified over silica (EtOAc-hexanes-DCM-TEA, 0.5/5/4.5/0.02) to provide (3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (803 mg, $^1$H NMR (400 MHz, $d_6$ acetone): 7.7 (d, 1H), 7.6 (d, 1H), 7.46 (d, 1H), 7.33 (m, 7H), 6.98 (m, 2H), 6.87 (s, 1H), 6.77 (s, 1H), 5.65 (s, 1H), 5.13 (s, 2H), 4.55 (m, 1H), 4.20 (s, 2H), 3.9 (m, 1H), 3.55 (m, 1H), 3.38 (s, 3H), 2.95 (m, 2H), 1.6 (m, 6H), 1.15 (m, 1H), 0.95 (m, 1H) 0.9 (m, 2H), 0.8 (m, 4H), 0.7 (d, 3H), 0.65 (m, 6H).

(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (0.80 g) was dissolved in 20 mL of dry DCM and cooled to 0° C. Boron trichloride (8 mL, 1M solution in hexanes) was added and the mixture stirred at 0° C. for 3.5 hours. The mixture was concentrated and treated with water/saturated sodium bicarbonate until pH 7. The aqueous mixture was extracted three times with ethyl acetate-THF (9-1) and organic layers combined. The combined organic layers were dried over sodium sulfate and concentrated to provide (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (601 mg, LC/MS: m/z 474).

(S)-2-{[(3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester (64 mg, LC/MS: m/z 741) was prepared from (3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (70 mg) and (S)-2-amino-3-(4'-methoxy-biphenyl-4-yl)-propionic acid methyl ester hydrochloride using general procedure A.

(S)-2-{[(3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester (64 mg, 0.087 mmol) was dissolved in 2 mL of DMF and 3,4-dichlorobenzyl bromide (0.43 mmol) and potassium carbonate (0.43 mmol) were added. The mixture was stirred at room temperature for 8 hours and was poured onto ethyl acetate and 10% sodium carbonate. The organic layer was washed with brine, dried over sodium sulfate and concentrated. The residue was purified over silica (hexanes-ethyl acetate-MeOH, 7-3-0.1) to provide (S)-2-{[(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester (24 mg, LC/MS: m/z 899).

Title compound (19 mg) was prepared from (S)-2-{[(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid methyl ester (21 mg) according to general procedure B. LC/MS: m/z 886.

Example 95

(S)-2-{[(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid

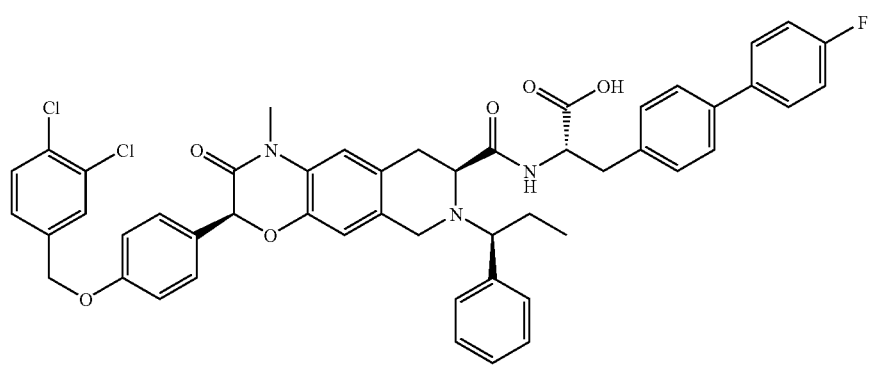

(S)-3-[4-(3,4-Dichloro-benzyloxy)-phenyl]-2-oxo-1,2,3, 5,7,8-hexahydro-4-oxa-1,6-diaza-anthracene-6,7-dicarboxylic acid 6-tert-butyl ester (8.0 g, 13.3 mmol) was suspended in 30 mL DCM and 1R-2S-5R (−)-menthol (26.6 mmol), EDC (26.6 mmol) and DMAP (cat.) added. The mixture was stirred at r.t. for 6 h and the mixture was diluted with DCM. The organic layer was washed with water and brine, dried over sodium sulfate and concentrated. The residue purified over silica with hexanes-EtOAc gradient (0% EtOAc to 30%) to provide (3S,7S)-3-[4-(3,4-Dichloro-benzyloxy)-phenyl]-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (2.4 g, $^1$H NMR (400 MHz, CDCl$_3$): 8.2 (m, 1H), 7.5 (m, 1H), 7.42 (d, 1H), 7.35 (m, 2H), 7.25 (m, 1H), 6.9 (m, 2H), 6.7 (m, 1H), 6.6 (s, 1H), 5.55 (m, 1H), 4.8-5.1 (m, 1H), 5.0 (s, 2H), 4.3-4.6 (m, 3H), 3.1 (m, 2H), 1.8 (m, 1H), 1.6 (m, 3H), 1.5 (d, 9H), 1.3 (m, 2H), 0.7-1.0 (m, 9H), 0.4 (m, 3H).

(3S,7S)-3-[4-(3,4-Dichloro-benzyloxy)-phenyl]-2-oxo-1, 2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester was N-methylated (3.9 g) according to general procedure M to provide (3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (4.9 g, not isolated as pure material).

(3S,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-((1R,2S,5R)-2-isopropyl-5-methyl-cyclohexyl)ester (3.9 g) was deprotected using general procedure C to provide (3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester hydrochloride (3.5 g, LC/MS: m/z 652).

(3S,7S)-3-[4-(3,4-Dichloro-benzyloxy)-phenyl]-1-methyl-2-oxo-2,3,5,6,7,8-hexahydro-1H-4-oxa-1,6-diaza-anthracene-7-carboxylic acid (1R,2S,5R)-2-isopropyl-5-methyl-cyclohexyl ester (3.5 g, 5.37 mmol) was dissolved in 10 mL DMF and sodium bicarbonate (21.5 mmol) and (1-bromo-propyl)-benzene (10.7 mmol) added. The mixture was stirred at 50° C. for 20 h and room temperature for 48 hours. The mixture was poured onto diethyl ether and 10% sodium carbonate. The aqueous layer was extracted with ether and organic layers combined. The organic layer was dried over sodium sulfate and concentrated. The residue was purified over silica (EtOAc-hexanes-DCM-TEA, 0.5/5/4.5/0.02) to provide (3S,7S)-3-[4-(3,4-Dichloro-benzyloxy)-phenyl]-1-methyl-2-oxo-6-((S)-1-phenyl-propyl)-2,3,5,6,7, 8-hexahydro-1H-4-oxa-1,6-diaza-anthracene-7-carboxylic acid (1R,2S,5R)-2-isopropyl-5-methyl-cyclohexyl ester (803 mg, $^1$H NMR (400 MHz, d$_6$ acetone): 7.7 (d, 1H), 7.6 (d, 1H), 7.46 (d, 1H), 7.33 (m, 7H), 6.98 (m, 1H), 6.87 (s, 1H), 6.77 (s, 1H), 5.65 (s, 1H), 5.13 (s, 2H), 4.55 (m, 1H), 4.20 (s, 2H), 3.9 (m, 1H), 3.55 (m, 1H), 3.38 (s, 3H), 2.95 (m, 2H), 1.6 (m, 6H), 1.15 (m, 1H), 0.95 (m, 1H) 0.9 (m, 2H), 0.8 (m, 4H), 0.7 (d, 3H), 0.65 (m, 6H).

(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (1R,2S,5R)-2-isopropyl-5-methyl-cyclohexyl ester (0.80 g) was dissolved in 20 mL of dry DCM and cooled to 0° C. Boron trichloride (8 mL, 1M solution in hexanes) was added and the mixture stirred at 0° C. for 3.5 hours. The mixture was concentrated and treated with water/saturated sodium bicarbonate until pH 7. The aqueous mixture was extracted three times with ethyl acetate-THF (9-1) and organic layers combined. The combined organic layers were dried over sodium sulfate and concentrated to provide (3S,7S)-3-(4-Hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (601 mg, LC/MS: m/z 474).

(S)-3-(4'-Fluoro-biphenyl-4-yl)-2-{[(3S,7S)-3-(4-hydroxy-phenyl)-1-methyl-2-oxo-6-((S)-1-phenyl-propyl)-2,3, 5,6,7,8-hexahydro-1H-4-oxa-1,6-diaza-anthracene-7-carbonyl]-amino}-propionic acid methyl ester (57 mg, LC/MS: m/z 729) was prepared from (3S,7S)-3-(4-hydroxy-phenyl)-1-methyl-2-oxo-6-((S)-1-phenyl-propyl)-2,3,5,6,7,8-hexahydro-1H-4-oxa-1,6-diaza-anthracene-7-carboxylic acid (70 mg) and (S)-2-amino-3-(4'-fluoro-biphenyl-4-yl)-propionic acid methyl ester hydrochloride using general procedure A.

(S)-3-(4'-Fluoro-biphenyl-4-yl)-2-{[(3S,7S)-3-(4-hydroxy-phenyl)-1-methyl-2-oxo-6-((S)-1-phenyl-propyl)-2,3, 5,6,7,8-hexahydro-1H-4-oxa-1,6-diaza-anthracene-7-carbonyl]-amino}-propionic acid methyl ester (27 mg, 0.078 mmol) was dissolved in 2 mL of DMF and 3,4-dichlorobenzyl bromide (0.39 mmol) and potassium carbonate (0.39 mmol) were added. The mixture was stirred at room temperature for 8 hours and was poured onto ethyl acetate and 10% sodium carbonate. The organic layer was washed with brine, dried over sodium sulfate and concentrated. The residue was purified over silica (hexanes-ethyl acetate-MeOH, 7-3-0.1) to provide (S)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid methyl ester (21 mg, LC/MS: m/z 889).

Title compound (20 mg) was prepared from (S)-2-{[(3S, 7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid methyl ester (24 mg) according to general procedure B. LC/MS: m/z 873.

Example 96

(S)-3-(4'-Cyano-biphenyl-4-yl)-2-{[(S)-3-[4-(3,4-dichloro-benzyloxy)-phenyl]-6-(3,5-dimethyl-isoxazole-4-sulfonyl)-1-methyl-2-oxo-2,3,5,6,7,8-hexahydro-1H-4-oxa-1,6-diaza-anthracene-7-carbonyl]-amino}-propionic acid

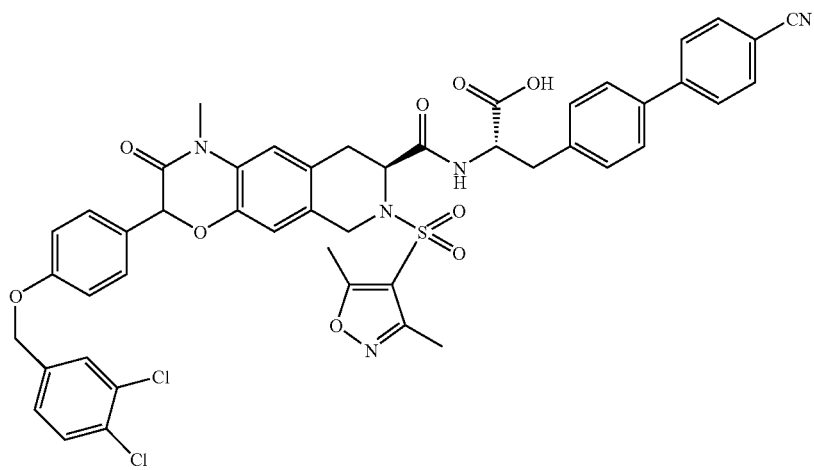

Title compound was prepared from Intermediate B following general procedures E and B. LC-MS (m/z): 921.

Example 97

(S)-3-(4'-Cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid

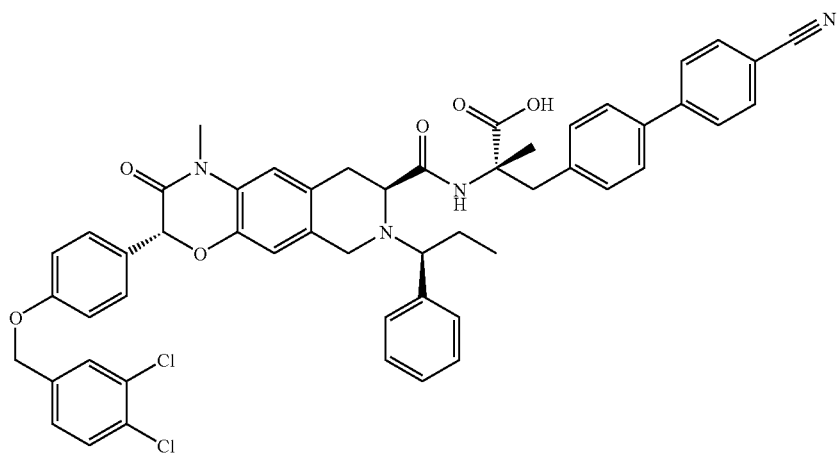

(S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid (31.6 mg) was coupled with (S)-2-amino-3-(4'-cyano-biphenyl-4-yl)-2-methyl-propionic acid methyl ester (14.7 mg) following general procedure O to provide (S)-3-(4'-Cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid methyl ester (LC-MS (m/z): 909). Title compound was prepared from (S)-3-(4'-Cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid methyl ester (25 mg) following general procedure B. LC-MS (m/z): 893.

Example 98

(R)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid

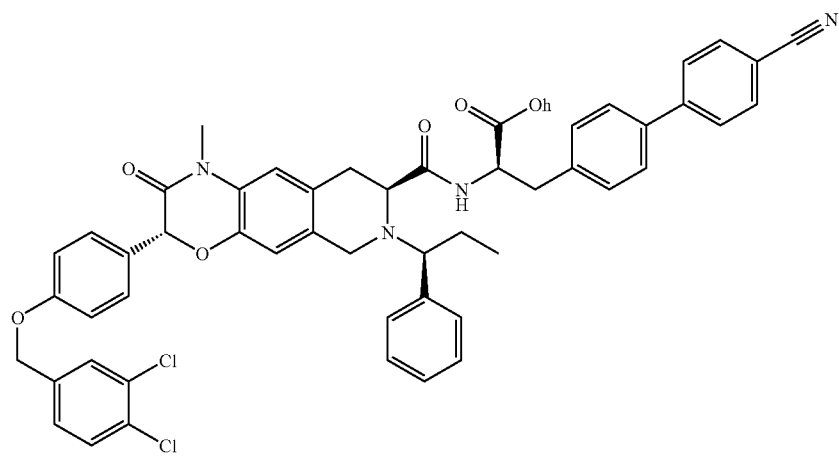

(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carboxylic acid was coupled to (R)-2-amino-3-(4'-cyano-biphenyl-4-yl)-propionic acid methyl ester following general procedure O to provide (R)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester. Title compound was prepared from (R)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid methyl ester (267 mg) following general procedure B. LC-MS (m/z): 880.

Example 99

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-[4-(pyridin-4-yloxy)-phenyl]-propionic acid

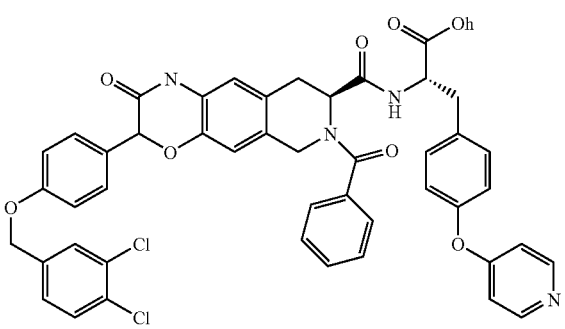

(S)-2-tert-Butoxycarbonylamino-3-(4-hydroxy-phenyl)-propionic acid (29.1 mmol) was dissolved in 20 mL of DMF and DIEA (58.2 mmol) and methyl iodide (146 mmol) added. The reaction mixture stirred at rt for 2 h and was poured onto EtOAc and 1 N HCl. The organic layer was washed with 1 N HCl and 10% sodium carbonate, dried over sodium sulfate and concentrated. (S)-2-tert-Butoxycarbonylamino-3-(4-hydroxy-phenyl)-propionic acid methyl ester (7.8 g) was used without further purification. LC-MS (m/z): 297.

(S)-2-tert-Butoxycarbonylamino-3-(4-hydroxy-phenyl)-propionic acid methyl ester (8.46 mmol), 4-pyridyl boronic acid (29.6 mmol), Cu(OAc)$_2$ (16.9 mmol), and molecular sieves were suspended in 25 mL of DCM. Triethylamine (59.2 mmol) was added and the mixture stirred at rt for 10 h. The mixture was diluted with ethyl acetate and washed with 10% sodium carbonate (6×). The organic layer was dried and concentrated under reduced pressure. The residue was puri fied over silica gel (hexanes-EtOAc) to provide (S)-2-tert-Butoxycarbonylamino-3-[4-(pyridin-4-yloxy)-phenyl]-propionic acid methyl ester (653 mg). LC-MS (m/z) 374.

(S)-2-Amino-3-[4-(pyridin-4-yloxy)-phenyl]-propionic acid methyl ester bis hydrochloride (543 mg) was prepared from (S)-2-tert-Butoxycarbonylamino-3-[4-(pyridin-4-yloxy)-phenyl]-propionic acid methyl ester (650 mg) following general procedure C. LC-MS (m/z) 274.

(S)-3-[4-(3,4-Dichloro-benzyloxy)-phenyl]-2-oxo-2,3,5,6,7,8-hexahydro-1H-4-oxa-1,6-diaza-anthracene-7-carboxylic acid methyl ester hydrochloride (1.8 g) was prepared from (S)-3-[4-(3,4-Dichloro-benzyloxy)-phenyl]-2-oxo-1,2,3,5,7,8-hexahydro-4-oxa-1,6-diaza-anthracene-6,7-dicar- Title compound (31 mg) was prepared from Title compound methyl ester (50 mg) following general procedure B. LC-MS (m/z) 844.

Example 100

(S)-2-({(S)-6-(2-Amino-4-methyl-thiazole-5-sulfonyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid (Less polar diastereomer)

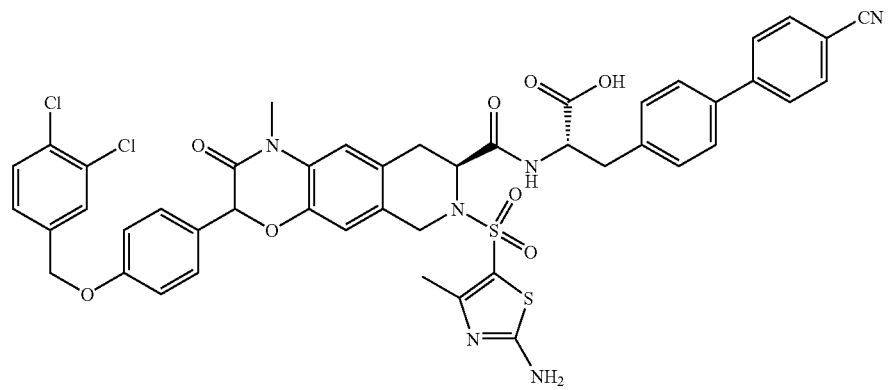

boxylic acid 6-tert-butyl ester 7-methyl ester (2.2 g) following general procedure C. LC-MS (m/z) 514.

(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid methyl ester (1.6 g) was prepared from (S)-3-[4-(3,4-Dichloro-benzyloxy)-phenyl]-2-oxo-2,3,5,6,7,8-hexahydro-1H-4-oxa-1,6-diaza-anthracene-7-carboxylic acid methyl ester hydrochloride (1.8 g) following general procedure F. LC-MS (m/z) 618.

(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid was prepared (1.4 g) from (S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carboxylic acid methyl ester (1.6 g) following general procedure B. LC-MS (m/z) 604.

(S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-[4-(pyridin-4-yloxy)-phenyl]-propionic acid methyl ester (57 mg) was prepared from (S)-6-Benzoyl-3-[4-(3,4-dichloro-benzyloxy)-phenyl]-2-oxo-2,3,5,6,7,8-hexahydro-1H-4-oxa-anthracene-7-carboxylic acid (100 mg) and (S)-2-Amino-3-[4-(pyridin-4-yloxy)-phenyl]-propionic acid methyl ester bis hydrochloride (63 mg) following general procedure A. LC-MS (m/z) 858.

(3R,7S)-3-[4-(3,4-Dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester 7-methyl ester was hydrolyzed as described in general procedure B to furnish (S)-3-[4-(3,4-dichloro-benzyloxy)-phenyl]-1-methyl-2-oxo-1,2,3,5,7,8-hexahydro-4-oxa-1,6-diaza-anthracene-6,7-dicarboxylic acid 6-tert-butyl ester as a mixture of diastereomers (1:1) at the morpholino center. This mixture of acids was converted to (S)-7-[(S)-2-(4'-cyano-biphenyl-4-yl)-1-methoxycarbonyl-ethylcarbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid tert-butyl ester using the general procedure O. This intermediate was further converted to (S)-2-({(S)-6-(2-acetylamino-4-methyl-thiazole-5-sulfonyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester as a mixture of diastereomeres following the general procedure C and E. This sulfonamide was deacylated using the general procedure P to furnish (S)-2-({(S)-6-(2-amino-4-methyl-thiazole-5-sulfonyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester as a mixture of diastereomeres. The diasteromers were separated by flash column chromatography (DCM: EtOAc, 9:1-7:3) The less polar diasteromer (LC-MS m/z 953, 16 mg) upon hydrolysis using the general procedure B furnished title compound (less polar diastereomer, 12 mg). LC-MS (m/z): 937.

Example 101

(S)-2-({(S)-6-(2-Amino-4-methyl-thiazole-5-sulfonyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid (more polar diastereomer)

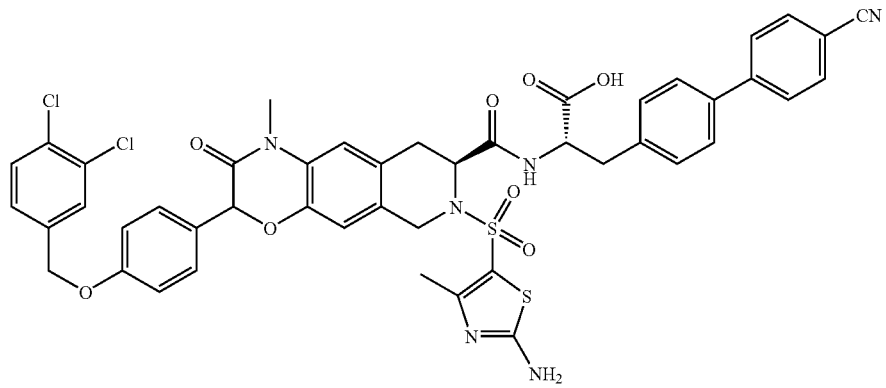

(S)-2-({(S)-6-(2-amino-4-methyl-thiazole-5-sulfonyl)-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (more polar diastereomer, LC-MS m/z 955, 10 mg) was hydrolyzed using the general procedure B furnished title compound (more polar diastereomer 8 mg). LC-MS (m/z) 937.

Example 102

(S)-2-({(S)-6-(2-Amino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid (more polar diastereomer)

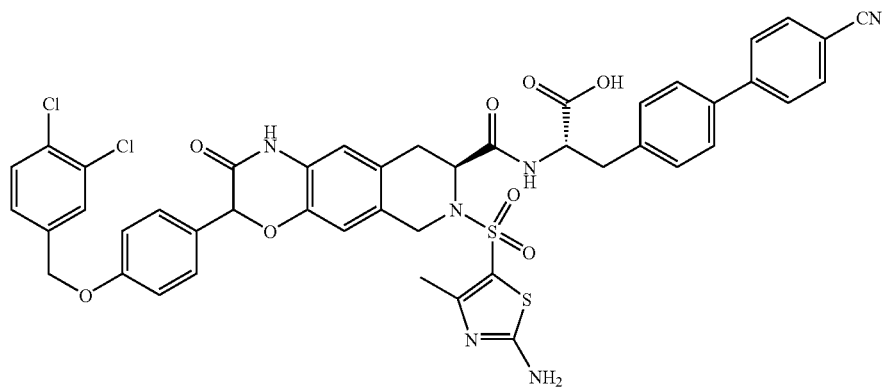

(S)-2-({(S)-6-(2-Acetylamino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (more polar diastereomer, 100 mg) was converted to (S)-2-({(S)-6-(2-amino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (LC-MS m/z 941) following the general procedure P. This ester on hydrolysis using general procedure B furnished title compound (more polar diastereomer, 70 mg). LC-MS (m/z): 923.

Example 103

(S)-2-({(S)-6-(2-Amino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid (less polar diastereomer)

(S)-2-({(S)-6-(2-acetylamino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (less polar diastereomer, 100 mg) was converted to (S)-2-({(S)-6-(2-amino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid methyl ester (LC-MS m/z 940) following the general procedure P. This ester on hydrolysis using general procedure B furnished title compound (less polar diastereomer, 72 mg). LC-MS (m/z): 923.

Example 104

Receptor Binding Assay

The affinity of compounds for GLP-1 receptor were studied in an [$^{125}$I]GLP-1 (aa 7-36) equilibrium radioligand binding assay. Membranes from HEK-293 or CHO cells expressing the human GLP-1 receptor were used in the GLP-1 receptor binding assay. Reactions were carried out in 96-well plates. Compound was diluted in 20% DMSO/water. The final assay concentration ranging from 0.1 nM to 100 uM in 2% final DMSO concentration was used. The final binding assay conditions were 25 mM Tris-HCL, pH 7.4 buffer containing 10 mM $MgCl_2$, 1 mM DTT, 0.1 mM EDTA, 0.1 mM EGTA, 0.1% BSA, 1-10 ug membrane, 20-200 pM [$^{125}$I] GLP-1 aa (7-36) (SA=2200 Ci/mmoL, (Perkin Elmer part no. NEX308), and compound in final DMSO concentration of 2% (final assay volume of 100 uL). Positive control wells (C+) lacked compound, and negative control wells (C−) lacked compound and contained cold excess GLP-1 (1 μM). Non-specific binding (NSB) was determined for each compound concentration by addition of cold excess GLP-1 (1 μM). The reaction was carried out at room temp for 120 min. Membrane containing bound an [$^{125}$I]GLP-1 (aa 7-36) ligand was isolated following filtration onto Unifilter-96 GF/C filter plates (PerkinElmer part no. 6005177) using a cell harvester instrument. Plates were washed 5 times with cold 25 mM Tris-HCL, pH 7.5 containing 0.05% bovine serum albumin (BSA). Following filtration, 50 uL of Microscint PS (Packard part no. 6013631) was added, plates were sealed with TopSeal-A adhesive seals (Packard part no. 6005185). $^{125}$I isotope bound to the Unifilter-96 GF/C plates was counted using a TopCount instrument (Packard).

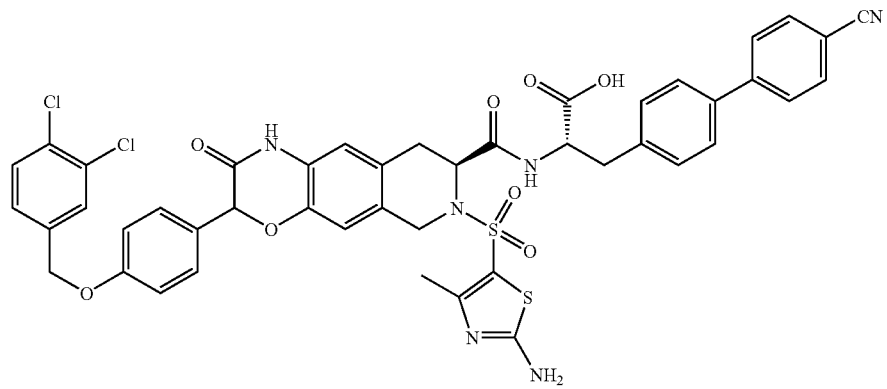

Receptor binding data typically ranged from about 40% to about 100% binding vs [$^{125}$I]GLP-1. For example, the compound of Example 15 exhibited 68% binding, the compound of Example 39 exhibited 60% binding, the compound of Example 88 exhibited 60% binding, the compound of example 89 exhibited 44% binding, and the compound of Example 95 exhibited 65% binding.

Data Analysis

Percent inhibition of [$^{125}$I]GLP-1 (aa 7-36) binding was calculated according to the equation $100 \times 1-\{(Sample_{cpm}-NSB_{cpm})/C+_{cpm}-C-_{cpm})\}$. Percent inhibition of [$^{125}$I]GLP-1 binding (Y) vs compound concentration (X) data were generated. The $IC_{50}$ values were calculated by fitting the data using parameters for a sigmoidal dose response, variable slope nonlinear regression (GraphPAD Prizm, San Diego, Calif.) according to the equation:

$$Y=Bottom+(Top-Bottom)/(1+10^{\wedge}((Log\, EC50-X)*HillSlope))$$

wherein, X is the logarithm of concentration and Y is the response, and Y starts at Bottom and goes to Top with a sigmoid shape. This is identical to the four parameter logistic equation.

Example 105

Functional Cell-Based Assay

The efficacy of GLP-1 receptor agonists was studied in a cAMP functional assay using either CHO or HEK-293 Cells expressing the cloned human GLP-1 receptor. GLP-1-expressing cells (10,000 cells per 0.1 mL) were plated in 96-well plates in Dulbecco's modified eagles media (DMEM) containing 10% fetal bovine serum and penicillin-streptomycin. Following overnight incubation of cells, media was removed, and compounds (at concentrations ranging from 0.0001 to 100 μM) were added to monolayer cells in Iscove's modified dulbecco's medium (IMDM), 100 μM RO 20-1724 PDE inhibitor, 0.1% BSA, 2% DMSO in a final volume of 100 μL, and incubated for 30 min at 37° C. 95% $O_2$, 5% $CO_2$ in a humidified incubator. cAMP was quantitated using a homogenous time-resolved fluorescence detection system (cAMP dynamic, CIS bio International). GLP-1 produced cAMP production dose response curves with $EC_{50}$ values ranging from 0.01 μM-100 μM, typically ranging from about 0.02 μM to about 10 μM. Receptor activation was expressed as percentage relative to maximal GLP-1-induced cAMP accumulation. Percent GLP-1 activation vs compound concentration dose response curves were generated by fitting the data using a sigmoidal dose response curve-fitting program (GraphPAD Prizm).

The Table below shows EC-50 and activation data for the above exemplary compounds of the present invention.

| Example # | EC-50 (nM) | % activation | Example # | EC-50 (nM) | % activation |
|---|---|---|---|---|---|
| 1 | 900 | 15 | 2 | 670 | 7.8 |
| 3 | na | na | 4 | 3800 | 20 |
| 5 | 30000 | 18 | 6 | 3600 | 7.0 |
| 7 | 474 | 35 | 8 | 134 | 64 |
| 9 | 500 | 54 | 10 | 418 | 51 |
| 11 | 606 | 71 | 12 | 427 | 61 |
| 13 | 1210 | 59 | 14 | 450 | 77 |
| 15 | 145 | 99.6 | 16 | 657 | 78 |
| 17 | 699 | 80 | 18 | 270 | 74.7 |
| 19 | 181 | 69.9 | 20 | 417 | 83.5 |
| 21 | 399 | 70.3 | 22 | 891 | 73.5 |
| 23 | 1280 | 65.5 | 24 | 1600 | 53.0 |
| 25 | 594 | 12.0 | 26 | 1097 | 14.0 |
| 27 | nd | Nd | 28 | 398 | 29.0 |
| 29 | 290 | 17 | 30 | na | na |
| 31 | 1000 | 13.0 | 32 | 700 | 8.3 |
| 33 | 1300 | 7.0 | 34 | 160 | 31.0 |
| 35 | 1200 | 16.0 | 36 | 660 | 13.0 |
| 37 | 490 | 32.0 | 38 | 710 | 32.0 |
| 39 | 130 | 56.0 | 40 | 1200 | 34.0 |
| 41 | 430 | 42.0 | 42 | 1000 | 56.0 |
| 43 | 500 | 34.0 | 44 | 1000 | 25.0 |
| 45 | 1000 | 18.0 | 46 | 1000 | 22.0 |
| 47 | 1200 | 29.0 | 48 | 895 | 64.0 |
| 49 | 557 | 57.0 | 50 | 1220 | 49.0 |
| 51 | 820 | 30.0 | 52 | 810 | 33.0 |
| 53 | 1040 | 52.5 | 54 | 1078 | 11.8 |
| 55 | 216 | 49.4 | 56 | 370 | 40.1 |
| 57 | 570 | 20.0 | 58 | 565 | 45.0 |
| 59 | 750 | 52.0 | 60 | 1630 | 62.0 |
| 61 | 850 | 29.0 | 62 | 1000 | 15.0 |
| 63 | 476 | 23.0 | 64 | 190 | 36.0 |
| 65 | 220 | 32.0 | 66 | 950 | 21.0 |
| 67 | 1150 | 55.0 | 68 | 1100 | 33.0 |
| 69 | 574 | 51.0 | 70 | 988 | 6.9 |
| 71 | 793 | 49 | 72 | na | na |
| 73 | na | na | 74 | 327 | 19.0 |
| 75 | 244 | 20 | 76 | 1135 | 8.12 |
| 77 | 1706 | 53 | 78 | nd | nd |
| 79 | nd | nd | 80 | 66.0 | 16 |
| 81 | 70.0 | 25 | 82 | nd | nd |
| 83 | 710 | 18 | 84 | 920 | 43 |
| 85 | 2000 | 55 | 86 | 59.3 | 58 |
| 87 | 64.5 | 82 | 88 | nd | nd |
| 89 | nd | nd | 90 | 1231 | 43 |
| 91 | 725 | 39 | 92 | 723 | 30 |
| 93 | 138 | 31 | 94 | 424 | 41 |
| 95 | 364 | 49 | 96 | 362 | 8.5 |
| 97 | 38.2 | 38 | 98 | 626 | 42 |
| 99 | 1000 | 28 | | | | na: Not active in the functional cell-based assay of Example 105.
nd: No data available for this compound in the functional cell-based assay of Example 105.

The specificity of GLP-1 agonists for GLP-1 receptor was confirmed by performing the assay with vector-control mock cells which lack the cloned human GLP-1 receptor. All compounds were devoid of cAMP accumulation in the mock-transfected cell lines.

We claim:
1. A compound of Formula (I):

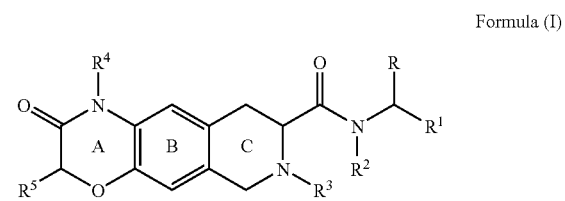

Formula (I)

wherein

R is —$(CH_2)_p$-$G^1$-$L^1$-$G^2$, wherein $L^1$ is selected from the group consisting of: a direct bond, —$CH_2$—, —O—, —N($R^{16}$)—, —C(O)—, —CON($R^{16}$)—, —N($R^{16}$)C(O)—, —N($R^{16}$)$SO_2$—, —$SO_2$N($R^{16}$)—, —C(O)—O—, —O—C(O)—, —S—, —S(O)—, —$S(O)_2$—, and —C≡C—, wherein $R^{16}$ is selected from the group consisting of: —hydrogen, —alkyl, —aryl, —alkylene-aryl;

$G^1$ is selected from the group consisting of: alkynylene, arylene, heteroarylene, fused arylcycloalkylene, fused cycloalkylarylene, fused cycloalkylheteroarylene, fused heterocyclylarylene, and fused heterocyclylheteroarylene, wherein $G^1$ is optionally substituted 1-4 times with substituents independently selected from $R^{10}$, wherein $R^{10}$ is $R^b$, $G^2$ is selected from the group consisting of: —aryl, —heteroaryl, —fused arylcycloalkyl, —fused cycloalkylaryl, —fused cycloalkylheteroaryl, —fused heterocyclylaryl, and —fused heterocyclylheteroaryl, wherein $G^2$ is optionally substituted 1-4 times with substituents independently selected from $R^{11}$, wherein
$R^{11}$ is $R^b$, $R^1$ is selected from the group consisting of: —$CO_2H$, —$CO_2R^{12}$, —$C(O)NH_2$, —$C(O)NHR^{12}$, —tetrazole, and acid isostere, wherein
$R^{12}$ is selected from the group consisting of: —$C_{1-10}$ alkyl, —cycloalkyl, and —aryl, wherein
$R^{12}$ is optionally substituted 1-4 times with a group independently selected from $R^c$;

$R^2$ is selected from the group consisting of: —hydrogen, —alkyl, —phenyl, —cycloalkyl, —alkylene-cycloalkyl, and —alkylene-phenyl, wherein alkyl, phenyl, and cycloalkyl groups are optionally substituted 1-4 times with a group independently selected from $R^c$;

$R^3$ is selected from $R^a$;

$R^4$ is selected from $R^a$; and $R^5$ is -$G^3$-$L^2$-$Q^2$-$L^3$-$G^4$, wherein
$L^2$ and $L^3$ are independently selected from the group consisting of: a direct bond, $CH_2$—, —O—, —N($R^{26}$)—, —C(O)—, —CON($R^{26}$)—, —N($R^{26}$)C(O)—, —N($R^{26}$)CON($R^{27}$)—, —N($R^{26}$)C(O)O—, —OC(O)N($R^{26}$)—, —N($R^{26}$)SO_2—, —SO_2N($R^{26}$)—, —C(O)—O—, —O—C(O)—, —S—, —S(O)—, —S(O)_2—, and —N($R^{26}$)SO_2N($R^{27}$)—, wherein
$R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$, or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;

$Q^2$ is selected from the group consisting of: a direct bond, $C_{1-10}$ alkylene, $C_{2-10}$ alkenylene, and $C_{2-10}$ alkynylene, $G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
$G^3$ is optionally substituted 1-4 times with substituents independently selected from $R^8$, wherein $R^8$ is selected from $R^b$, $G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
$G^4$ is optionally substituted 1-4 times with substituents independently selected from $R^9$, wherein $R^9$ is selected from $R^b$, Rings B and C are optionally substituted 1-4 times with substituents independently selected from the group consisting of $R^b$;

$R^a$ is selected from the group consisting of:
a) —hydrogen,
b) —$S(O)_mR^d$,
c) —$S(O)_2OR^d$,
d) —$S(O)_mNR^dR^e$,
e) —$C(O)R^d$,
f) —$CO_2R^d$,
g) —$C(O)NR^dR^e$,
h) —haloalkyl,
i) —cycloalkyl,
j) —heterocyclyl,
k) —$C_{1-10}$ alkyl,
l) —$C_{2-10}$ alkenyl,
m) —$C_{2-10}$ alkynyl,
n) —aryl,
o) —heteroaryl,
p) —$C_{1-10}$ alkylene-aryl,
q) —$C_{2-10}$ alkynylene-aryl,
r) —$C_{1-10}$ alkylene-heteroaryl,
s) —$C_{2-10}$ alkynylene-heteroaryl, and
t) —$C(R^fR^g)_n$-aryl,
wherein alkyl, alkenyl, alkynyl, aryl, heterocyclyl, heteroaryl, and cycloalkyl groups are optionally substituted 1-4 times with a group independently selected from $R^c$;

$R^b$ is selected from the group consisting of:
a) —cycloalkyl,
b) —cyano,
c) —$OR^d$,
d) —$NO_2$,
e) —halogen,
f) —$S(O)_mR^d$,
g) —$SR^d$,
h) —$S(O)_2OR^d$,
i) —$S(O)_mNR^dR^e$,
j) —$NR^dR^e$,
k) —$O(CR^fR^g)_nNR^dR^e$,
l) —$C(O)R^d$,
m) —$CO_2R^d$,
n) —$CO_2(CR^fR^g)_nCONR^dR^e$,
o) —$OC(O)R^d$,
p) —$C(O)NR^dR^e$,
q) —$NR^dC(O)R^e$,
r) —$OC(O)NR^dR^e$,
s) —$NR^dC(O)OR^e$,
t) —$NR^dC(O)NR^dR^e$,
u) —$CF_3$,
v) —$OCF_3$,
w) —haloalkyl,
x) —haloalkoxy,
y) —$C_{1-10}$ alkyl,
z) —$C_{2-10}$ alkenyl,
aa) —$C_{2-10}$ alkynyl,
ab) —$C_{1-10}$ alkylene-aryl,
ac) —$C_{1-10}$ alkylene-heteroaryl, and
ad) —heteroaryl,
wherein alkyl, alkenyl, alkynyl, aryl, heteroaryl, and cycloalkyl groups are optionally substituted 1-4 times with a group independently selected from $R^c$;

$R^c$ is selected from the group consisting of:
a) —halogen,
b) —amino,
c) —carboxy,
d) —cyano,
e) —$C_{1-4}$ alkyl,
f) —O—$C_{1-4}$ alkyl,
g) —O—$CF_3$,
h) —cycloalkyl,
i) —O-cycloalkyl,
j) —aryl,
k) —$C_{1-4}$ alkylene-aryl,
l) —hydroxy,
m) —$CF_3$,
n) —haloalkyl,
o) —haloalkoxy,
p) —O-aryl, q) —heteroaryl,
r) —heteroarylene-$C_{1-10}$ alkyl,
s) —heterocyclyl,
t) —$CO_2$—$C_{1-10}$ alkyl,
u) —$CO_2$—$C_{1-10}$ alkyl-aryl,
v) —fused arylcycloalkyl,
w) —alkynylene-heteroaryl,
x) —alkylene-aryl,
y) —alkynylene-aryl,
z) —nitro,
aa) —N(H)—C(O)—$C_{1-6}$-alkyl, and
bb) —S—$C_{1-6}$-alkyl;
$R^d$ and $R^e$ are independently selected from the group consisting of: hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$,
$R^f$ and $R^g$ are independently selected from the group consisting of: hydrogen, $C_{1-10}$ alkyl, cycloalkyl, —$C_{1-10}$ alkylene-cycloalkyl, —carboxy, and aryl, wherein alkyl, cycloalkyl, and aryl groups are optionally substituted with one to four substituents independently selected from $R^c$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$;
m is an integer from 1 to 2;
n is an integer from 1 to 10; and
p is an integer from 0 to 2;
or a pharmaceutically acceptable salt thereof.

2. The compound of claim 1, wherein $R^1$ is selected from the group consisting of $CO_2H$ and $CO_2R^{12}$.

3. The compound of claim 1, wherein $R^1$ is $CO_2H$.

4. The compound of claim 1, wherein $R^2$ is selected from the group consisting of: hydrogen and —$C_{1-10}$ alkyl.

5. The compound of claim 1, wherein $R^2$ is hydrogen.

6. The compound of claim 1, wherein p is 1.

7. The compound of claim 1, wherein $L^1$ is a direct bond.

8. The compound of claim 1, wherein:
p is 1;
$G^1$ is a substituted or unsubstituted phenyl;
$L^1$ is selected from the group consisting of a direct bond, —O—, and —N(H)C(O)—; and
$G^2$ is a phenyl group substituted 1-4 times with substituents independently selected from $R^{11}$, and $G^2$ is substituted with at least one substituent selected from the group consisting of:
a) —$C_{1-10}$ alkyl,
b) —haloalkyl,
c) —haloalkoxy,
d) —$CF_3$,
e) —$OCF_3$,
f) —halogen,
g) —O—$R^d$,
h) —cyano,
i) —C(O)$R^d$,
j) —N$R^d R^e$,
k) —cycloalkyl, and
l) —$CO_2R^d$, wherein alkyl and cycloalkyl groups are optionally substituted 1-4 times with a group independently selected from $R^c$.

9. The compound of claim 1, wherein:
p is 1;
$G^1$ is —C≡C—;
$L^1$ is a direct bond; and
$G^2$ is a substituted or unsubstituted phenyl group substituted 1-4 times with substituents independently selected from $R^{11}$, and $G^2$ is substituted with at least one substituent selected from the group consisting of:
a) —$C_{1-10}$ alkyl,
b) —haloalkyl,
c) —haloalkoxy,
d) —$CF_3$,
e) —$OCF_3$,
f) —halogen,
g) —O—$R^d$,
h) —cyano,
i) —C(O)$R^d$,
j) —N$R^d R^e$,
k) —cycloalkyl,
l) —$CO_2R^d$, wherein the alkyl and cycloalkyl groups are optionally substituted 1-4 times with a group independently selected from $R^c$.

10. The compound of claim 1, wherein:
p is 1;
$G^1$ is a substituted or unsubstituted phenyl;
$L^1$ is a direct bond; and
$G^2$ is selected from the group consisting of: indole, pyridine, pyrimidine, quinoline, isoxazole, wherein $G^2$ is optionally substituted or unsubstituted.

11. The compound of claim 1, wherein:
p is 1;
$G^1$ is an unsubstituted phenyl;
$L^1$ is a direct bond; and
$G^2$ is a phenyl, substituted with a cyano group.

12. The compound of claim 1, wherein $R^3$ is selected from the group consisting of:
a) —$C_{1-10}$ alkyl,
b) —phenyl,
c) —thiophenyl,
d) —furanyl,
e) —pyridyl,
f) —$C_{1-10}$ alkylene-pyridyl,
g) —$C_{1-10}$ alkylene-aminothiazolyl,
h) —$C_{1-10}$ alkylene-imidazolyl,
i) —$C_{1-10}$ alkylene-oxazolyl,
j) —$C_{1-10}$ alkylene-thiophenyl,
k) —$C_{2-10}$ alkynylene-phenyl,
l) —$C_{2-10}$ alkynylene-thiophenyl,
m) —$C_{2-10}$ alkynylene-pyridyl,
n) —$C_{2-10}$ alkynylene-pyrimidinyl,
o) —$SO_2$-phenyl,
p) —$CO_2$—$C_{1-10}$ alkyl,
q) —$CO_2$-cycloalkyl,
r) —$CO_2$-tetrahydrofuranyl,
s) —$CO_2$-tetrahydropyranyl,
t) —$CO_2$—$C_{1-10}$ alkylene-cycloalkyl,
u) —$CO_2$—$C_{2-10}$-alkynyl,
v) —$CO_2$—$CH_2$—C≡C-phenyl,
w) —C(O)—$C_{1-10}$ alkyl,
x) —C(O)-phenyl,
y) —C(O)-naphthyl,
z) —C(O)-cycloalkyl,
aa) —C(O)-furanyl, bb) —C(O)-thiophenyl,
cc) —C(O)-isoxazolyl,
dd) —C(O)—$C_{1-10}$ alkylene-cycloalkyl,
ee) —C(O)—NH—$C_{1-10}$ alkyl,
ff) —C(O)—NH-phenyl, and
gg) —C(O)—N(cycloalkyl)-$C_{1-10}$ phenyl,
wherein the alkyl, alkynyl, cycloalkyl, tetrahydrofuranyl, tetrahydropyranyl, phenyl, naphthyl, thiophenyl, furanyl, pyridyl, pyrimidinyl, thiazolyl, imidazolyl, oxazolyl, and isoxazolyl groups are optionally substituted 1-4 times with a group independently selected from $R^c$.

13. The compound of claim 1, wherein $R^3$ is —$C_{1-10}$ alkyl substituted with a phenyl group.

14. The compound of claim 1, wherein $R^3$ is selected from the group consisting of —(R)-1-(phenyl)-propyl, and —(S)-1-(phenyl)-propyl.

15. The compound of claim 1, wherein $R^4$ is selected from the group consisting of: hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heteroaryl, and heterocyclyl, wherein the alkyl, alkenyl, alkynyl, cycloalkyl, aryl, heteroaryl, heterocyclyl groups are optionally substituted with one to four substituents independently selected from $R^c$.

16. The compound of claim 1, wherein $R^4$ is selected from the group consisting of —hydrogen, —$C_{1-6}$ alkyl, and —C(O)—$C_{1-6}$ alkyl.

17. The compound of claim 1, wherein $R^5$ is -$G^3$-$L^2$-$Q^2$-$L^3$-$G^4$, wherein
  $L^2$ is selected from the group consisting of: —$CH_2$—, —O—, —N($R^{26}$)—, and —C(O)—,
    wherein $R^{26}$ is selected from the group consisting of: hydrogen, —alkyl, —aryl, and —alkylene-aryl;
  $L^3$ is a direct bond;
  $Q^2$ is a $C_{1-10}$ alkylene group;
  $G^3$ is a phenylene group,
    wherein $G^3$ is optionally substituted 1-4 times with substituents independently selected from $R^8$, wherein $R^8$ is selected from $R^b$; and
  $G^4$ is selected from the group consisting of: cycloalkyl, phenyl, pyridinyl, benzothiophenyl, and benzothiazolyl, wherein $G^4$ is optionally substituted 1-4 times with substituents independently selected from $R^9$, wherein $R^9$ is selected from $R^b$.

18. The compound of claim 1, wherein $R^5$ is -$G^3$-$L^2$-$Q^2$-$L^3$-$G^4$, wherein
  $L^2$ is —O—;
  $L^3$ is a direct bond;
  $Q^2$ is a $C_{1-10}$ alkylene group;
  $G^3$ is a phenylene group, and
  $G^4$ is a phenyl group, wherein $G^4$ is substituted 1-4 times with substituents independently selected from $R^9$, wherein $R^9$ is selected from $R^b$, and wherein $G^4$ is substituted with at least one substituent selected from the group consisting of:
  a) —$C_{1-6}$ alkyl,
  b) —haloalkyl,
  c) —halogen,
  d) —alkoxy,
  e) —haloalkoxy,
  f) —$CF_3$, and
  g) —O—$CF_3$.

19. The compound of claim 1, having the formula (I-E)

or a pharmaceutically acceptable salt thereof.

20. A compound selected from the group consisting of a compound of Formula (II) and a compound of Formula (III)

(II)

(III)

wherein * represents the presence of a stereocenter;

$R^3$ is selected from $R^a$;
$R^4$ is selected from $R^a$; and
$R^5$ is $G^3$-$L^2$-$Q^2$-$L^3$-$G^4$, wherein
  $L^2$ and $L^3$ are independently selected from the group consisting of: a direct bond, —$CH_2$—, —O—, —N($R^{26}$)—, —C(O)—, —CON($R^{26}$)—, —N($R^{26}$)C(O)—, —N($R^{26}$)CON($R^{27}$)—, —N($R^{26}$)C(O)O—, —OC(O)N($R^{26}$)—, —N($R^{26}$)$SO_2$—, —$SO_2$N($R^{26}$)—, —C(O)—O—, —O—C(O)—, —S—, —S(O)—, —S(O)$_2$—, and —N($R^{26}$)$SO_2$N($R^{27}$)—, wherein
  $R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$, or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
  $Q^2$ is selected from the group consisting of: a direct bond, $C_{1-10}$ alkylene, $C_{2-10}$ alkenylene, and $C_{2-10}$ alkynylene,
  $G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
    $G^3$ is optionally substituted 1-4 times with substituents independently selected from $R^8$, wherein $R^8$ is selected from $R^b$;
  $G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
  $G^4$ is optionally substituted 1-4 times with substituents independently selected from $R^9$, wherein $R^9$ is selected from $R^b$,
wherein $R^a$ is selected from the group consisting of:
  a) —hydrogen,
  b) —S(O)$_m$R$^d$,
  c) —S(O)$_2$OR$^d$,
  d) —S(O)$_m$NR$^d$R$^e$,
  e) —C(O)R$^d$,
  f) —CO$_2$R$^d$,
  g) —C(O)NR$^d$R$^e$,
  h) —haloalkyl,
  i) —cycloalkyl,
  j) —heterocyclyl,
  k) —C$_{1-10}$ alkyl,
  l) —C$_{2-10}$ alkenyl,
  m) —C$_{2-10}$ alkynyl,
  n) —aryl,
  o) —heteroaryl,
  p) —C$_{1-10}$ alkylene-aryl,
  q) —C$_{2-10}$ alkynylene-aryl,
  r) —C$_{1-10}$ alkylene-heteroaryl,
  s) —C$_{2-10}$ alkynylene-heteroaryl, and
  t) —C(R$^f$R$^g$)$_n$-aryl,
    wherein alkyl, alkenyl, alkynyl, aryl, heterocyclyl, heteroaryl, and cycloalkyl groups are optionally substituted 1-4 times with a group independently selected from R$^c$;
$R^b$ is selected from the group consisting of:
  a) —cycloalkyl,
  b) —cyano,
  c) —OR$^d$,
  d) —NO$_2$,
  e) —halogen,
  f) —S(O)$_m$R$^d$,
  g) —SR$^d$,
  h) —S(O)$_2$OR$^d$,
  i) —S(O)$_m$NR$^d$R$^e$,
  j) —NR$^d$R$^e$,
  k) —O(CR$^f$R$^g$)$_n$NR$^d$R$^e$,
  l) —C(O)R$^d$,
  m) —CO$_2$R$^d$,
  n) —CO$_2$(CR$^f$R$^g$)$_n$CONR$^d$R$^e$,
  o) —OC(O)R$^d$,
  p) —C(O)NR$^d$R$^e$,
  q) —NR$^d$C(O)R$^e$,
  r) —OC(O)NR$^d$R$^e$,
  s) —NR$^d$C(O)OR$^e$,
  t) —NR$^d$C(O)NR$^d$R$^e$,
  u) —CF$_3$,
  v) —OCF$_3$,
  w) —haloalkyl,
  x) —haloalkoxy,
  y) —C$_{1-10}$ alkyl,
  z) —C$_{2-10}$ alkenyl,
  aa) —C$_{2-10}$ alkynyl,
  ab) —C$_{1-10}$ alkylene-aryl,
  ac) —C$_{1-10}$ alkylene-heteroaryl, and
  ad) —heteroaryl,
    wherein alkyl, alkenyl, alkynyl, aryl, heteroaryl, and cycloalkyl groups are optionally substituted 1-4 times with a group independently selected from R$^c$;

$R^c$ is selected from the group consisting of:
  a) —halogen,
  b) —amino,
  c) —carboxy,
  d) —cyano,
  e) —C$_{1-4}$ alkyl,
  f) —O—C$_{1-4}$ alkyl,
  g) —O—CF$_3$,
  h) —cycloalkyl,
  i) —O-cycloalkyl,
  j) —aryl,
  k) —C$_{1-4}$ alkylene-aryl,
  l) —hydroxy,
  m) —CF$_3$,
  n) —haloalkyl,
  o) —haloalkoxy,
  p) —O-aryl,
  q) —heteroaryl,
  r) —heteroarylene-C$_{1-10}$ alkyl,
  s) —heterocyclyl,
  t) —CO$_2$—C$_{1-10}$ alkyl,
  u) —CO$_2$—C$_{1-10}$ alkyl-aryl,
  v) —fused arylcycloalkyl,
  w) —alkynylene-heteroaryl,
  x) —alkylene-aryl,
  y) —alkynylene-aryl,
  z) —nitro,
  aa) —N(H)—C(O)—C$_{1-6}$-alkyl, and
  bb) —S—C$_{1-6}$-alkyl;
$R^d$ and $R^e$ are independently selected from the group consisting of: hydrogen, C$_{1-10}$ alkyl, C$_{2-10}$ alkenyl, C$_{2-10}$ alkynyl, cycloalkyl, —C$_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from R$^c$; or R$^d$ and R$^e$ together with the atoms to which they are attached form a heterocyclic ring of 5 to 7 members containing 0-2 additional heteroatoms independently selected from oxygen, sulfur and nitrogen and optionally substituted with 1-3 times with R$^c$,
$R^f$ and $R^g$ are independently selected from the group consisting of: hydrogen, C$_{1-10}$ alkyl, cycloalkyl, —C$_{1-10}$ alkylene-cycloalkyl, —carboxy, and aryl, wherein alkyl, cycloalkyl, and aryl groups are optionally substituted with one to four substituents independently selected from R$^c$; or R$^f$ and R$^g$ together with the carbon to which they are attached form a ring of 5 to 7 members containing 0-2 heteroatoms independently selected from oxygen, sulfur and nitrogen optionally substituted with 1-3 times with R$^c$;
m is an integer from 1 to 2;
n is an integer from 1 to 10; and
p is an integer from 0 to 2;
or a pharmaceutically acceptable salt thereof.

21. The compound of claim 20, wherein $R^4$ is selected from the group consisting of —hydrogen, —C$_{1-6}$ alkyl, and —C(O)—C$_{1-6}$ alkyl.

22. The compound of claim 20, wherein $R^5$ is -G$^3$-L$^2$-Q$^2$-L$^3$-G$^4$, wherein
  $L^2$ is —O—,
  $L^3$ is a direct bond;
  $Q^2$ is a C$_{1-10}$ alkylene group;
  $G^3$ is a phenylene group, and
  $G^4$ is a phenyl group, wherein $G^4$ is substituted 1-4 times with substituents independently selected from $R^9$, wherein $R^9$ is selected from $R^b$, and wherein $G^4$ is substituted with at least one substituent selected from the group consisting of:
a) —$C_{1-6}$ alkyl,
b) —haloalkyl,
c) —halogen,
d) —alkoxy,
e) —haloalkoxy,
f) —$CF_3$, and
g) —O—$CF_3$.

23. The compound of claim 20, wherein $R^3$ is selected from the group consisting of:
a) —$C_{1-10}$ alkyl,
b) —phenyl,
c) —thiophenyl,
d) —furanyl,
e) —pyridyl,
f) —$C_{1-10}$ alkylene-pyridyl,
g) —$C_{1-10}$ alkylene-aminothiazolyl,
h) —$C_{1-10}$ alkylene-imidazolyl,
i) —$C_{1-10}$ alkylene-oxazolyl,
j) —$C_{1-10}$ alkylene-thiophenyl,
k) —$C_{2-10}$ alkynylene-phenyl,
l) —$C_{2-10}$ alkynylene-thiophenyl,
m) —$C_{2-10}$ alkynylene-pyridyl,
n) —$C_{2-10}$ alkynylene-pyrimidinyl,
o) —$SO_2$-phenyl,
p) —$CO_2$—$C_{1-10}$ alkyl,
q) —$CO_2$-cycloalkyl,
r) —$CO_2$-tetrahydrofuranyl,
s) —$CO_2$-tetrahydropyranyl,
t) —$CO_2$—$C_{1-10}$ alkylene-cycloalkyl,
u) —$CO_2$—$C_{2-10}$-alkynyl,
v) —$CO_2$—$CH_2$—C≡C-phenyl,
w) —C(O)—$C_{1-10}$ alkyl,
x) —C(O)-phenyl,
y) —C(O)-naphthyl,
z) —C(O)-cycloalkyl,
aa) —C(O)-furanyl,
bb) —C(O)-thiophenyl,
cc) —C(O)-isoxazolyl,
dd) —C(O)—$C_{1-10}$ alkylene-cycloalkyl,
ee) —C(O)—NH—$C_{1-10}$ alkyl,
ff) —C(O)—NH-phenyl, and
hh) —C(O)—N(cycloalkyl)-$C_{1-10}$ phenyl,
wherein the alkyl, alkynyl, cycloalkyl, tetrahydrofuranyl, tetrahydropyranyl, phenyl, naphthyl, thiophenyl, furanyl, pyridyl, pyrimidinyl, thiazolyl, imidazolyl, oxazolyl, and isoxazolyl groups are optionally substituted 1-4 times with a group independently selected from $R^c$.

24. A pharmaceutical composition comprising:
a compound of Formula (I):

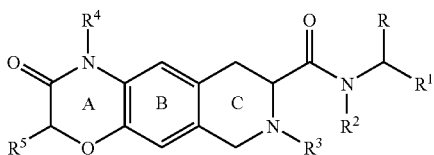

Formula (I)

or a pharmaceutically acceptable salt thereof, wherein
R is $(CH_2)_p$-$G^1$-$L^1$-$G^2$, wherein
$L^1$ is selected from the group consisting of: a direct bond, —$CH_2$—, —O—, —N($R^{16}$)—, —C(O)—, —CON($R^{16}$)—, —N($R^{16}$)C(O)—, —N($R^{16}$)$SO_2$—, —$SO_2$N($R^{16}$)—, —C(O)—O—, —O—C(O)—, —S—, —S(O)—, —S(O)$_2$—, and wherein
$R^{16}$ is selected from the group consisting of: —hydrogen, —alkyl, —aryl, —alkylene-aryl;
$G^1$ is selected from the group consisting of: alkynylene, arylene, heteroarylene, fused arylcycloalkylene, fused cycloalkylarylene, fused cycloalkylheteroarylene, fused heterocyclylarylene, and fused heterocyclylheteroarylene, wherein $G^1$ is optionally substituted 1-4 times with substituents independently selected from $R^{10}$, wherein
$R^{10}$ is $R^b$,
$G^2$ is selected from the group consisting of: —aryl, —heteroaryl, —fused arylcycloalkyl, —fused cycloalkylaryl, —fused cycloalkylheteroaryl, —fused heterocyclylaryl, and —fused heterocyclylheteroaryl, wherein $G^2$ is optionally substituted 1-4 times with substituents independently selected from $R^{11}$, wherein
$R^{11}$ is $R^b$,
$R^1$ is selected from the group consisting of: —$CO_2H$, —$CO_2R^{12}$, —C(O)$NH_2$, —C(O)$NHR^{12}$, —tetrazole, and acid isostere, wherein
$R^{12}$ is selected from the group consisting of: —$C_{1-10}$ alkyl, —cycloalkyl, and —aryl, wherein
$R^{12}$ is optionally substituted 1-4 times with a group independently selected from $R^c$;
$R^2$ is selected from the group consisting of: —hydrogen, —alkyl, —phenyl, —cycloalkyl, —alkylene-cycloalkyl, and —alkylene-phenyl, wherein alkyl, phenyl, and cycloalkyl groups are optionally substituted 1-4 times with a group independently selected from $R^c$;
$R^3$ is selected from $R^a$;
$R^4$ is selected from $R^a$; and
$R^5$ is $G^3$-$L^2$-$Q^2$-$L^3$-$G^4$, wherein
$L^2$ and $L^3$ are independently selected from the group consisting of: a direct bond, $CH_2$—, —O—, —N($R^{26}$)—, —C(O)—, —CON($R^{26}$)—, —N($R^{26}$)C(O)—, —N($R^{26}$)CON($R^{27}$)—, —N($R^{26}$)C(O)O—, —OC(O)N($R^{26}$)—, —N($R^{26}$)$SO_2$—, —$SO_2$N($R^{26}$)—, —C(O)—O—, —O—C(O)—, —S—, —S(O)—, —S(O)$_2$—, and —N($R^{26}$)$SO_2$N($R^{27}$)—, wherein
$R^{26}$ and $R^{27}$ are independently selected from the group consisting of: hydrogen, —alkyl, —aryl, and —alkylene-aryl, wherein $R^{26}$ and $R^{27}$ are optionally substituted 1-4 times with $R^c$, or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
$Q^2$ is selected from the group consisting of: a direct bond, $C_{1-10}$ alkylene, $C_{2-10}$ alkenylene, and $C_{2-10}$ alkynylene,
$G^3$ is selected from the group consisting of: —arylene, —cycloalkylene, —heterocyclylene, —heteroarylene, —fused arylcycloalkylene, —fused cycloalkylarylene, —fused cycloalkylheteroarylene, —fused heterocyclylarylene, and —fused heterocyclylheteroarylene, wherein
$G^3$ is optionally substituted 1-4 times with substituents independently selected from $R^8$, wherein $R^8$ is selected from $R^b$,
$G^4$ is selected from the group consisting of: —aryl, —cycloalkyl, —heterocyclyl, —heteroaryl, —fused arylcycloalkyl, —fused cycloalkylaryl, —fused cycloalkylheteroaryl, —fused heterocyclylaryl, and —fused heterocyclylheteroaryl, wherein
G$^4$ is optionally substituted 1-4 times with substituents independently selected from R$^9$, wherein R$^9$ is selected from R$^b$, Rings B and C are optionally substituted 1-4 times with substituents independently selected from the group consisting of R$^b$;

R$^a$ is selected from the group consisting of:
a) —hydrogen,
b) —S(O)$_m$R$^d$,
c) —S(O)$_2$OR$^d$,
d) —S(O)$_m$NR$^d$R$^e$,
e) —C(O)R$^d$,
f) —CO$_2$R$^d$,
g) —C(O)NR$^d$R$^e$,
h) —haloalkyl,
i) —cycloalkyl,
j) —heterocyclyl,
k) —C$_{1-10}$ alkyl,
l) —C$_{2-10}$ alkenyl,
m) —C$_{2-10}$ alkynyl,
n) —aryl,
o) —heteroaryl,
p) —C$_{1-10}$ alkylene-aryl,
q) —C$_{2-10}$ alkynylene-aryl,
r) —C$_{1-10}$ alkylene-heteroaryl,
s) —C$_{2-10}$ alkynylene-heteroaryl, and
t) —C(R$^f$R$^g$)$_n$-aryl,
   wherein alkyl, alkenyl, alkynyl, aryl, heterocyclyl, heteroaryl, and cycloalkyl groups are optionally substituted 1-4 times with a group independently selected from R$^c$;

R$^b$ is selected from the group consisting of:
a) —cycloalkyl,
b) —cyano,
c) —OR$^d$,
d) —NO$_2$,
e) —halogen,
f) —S(O)$_m$R$^d$,
g) —SR$^d$,
h) —S(O)$_2$OR$^d$,
i) —S(O)$_m$NR$^d$R$^e$,
j) —NR$^d$R$^e$,
k) —O(CR$^f$R$^g$)$_n$NR$^d$R$^e$,
l) —C(O)R$^d$,
m) —CO$_2$R$^d$,
n) —CO$_2$(CR$^f$R$^g$)$_n$CONR$^d$R$^e$,
o) —OC(O)R$^d$,
p) —C(O)NR$^d$R$^e$,
q) —NR$^d$C(O)R$^e$,
r) —OC(O)NR$^d$R$^e$,
s) —NR$^d$C(O)OR$^e$,
t) —NR$^d$C(O)NR$^d$R$^e$,
u) —CF$_3$,
v) —OCF$_3$,
w) —haloalkyl,
x) —haloalkoxy,
y) —C$_{1-10}$ alkyl,
z) —C$_{2-10}$ alkenyl,
aa) —C$_{2-10}$ alkynyl,
ab) —C$_{1-10}$ alkylene-aryl,
ac) —C$_{1-10}$ alkylene-heteroaryl, and
ad) —heteroaryl,
   wherein alkyl, alkenyl, alkynyl, aryl, heteroaryl, and cycloalkyl groups are optionally substituted 1-4 times with a group independently selected from R$^c$;

R$^c$ is selected from the group consisting of:
a) —halogen,
b) —amino,
c) —carboxy,
d) —cyano,
e) —C$_{1-4}$ alkyl,
f) —O—C$_{1-4}$ alkyl,
g) —O—CF$_3$,
h) —cycloalkyl,
i) —O-cycloalkyl,
j) —aryl,
k) —C$_{1-4}$ alkylene-aryl,
l) —hydroxy,
m) —CF$_3$,
n) —haloalkyl,
o) —haloalkoxy,
p) —O-aryl,
q) —heteroaryl,
r) —heteroarylene-C$_{1-10}$ alkyl,
s) —heterocyclyl,
t) —CO$_2$—C$_{1-10}$ alkyl,
u) —CO$_2$—C$_{1-10}$ alkyl-aryl,
v) —fused arylcycloalkyl,
w) —alkynylene-heteroaryl,
x) —alkylene-aryl,
y) —alkynylene-aryl,
z) —nitro,
aa) —N(H)—C(O)—C$_{1-6}$-alkyl, and
bb) —S—C$_{1-6}$-alkyl;

R$^d$ and R$^e$ are independently selected from the group consisting of: hydrogen, C$_{1-10}$ alkyl, C$_{2-10}$ alkenyl, C$_{2-10}$ alkynyl, cycloalkyl, —C$_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from R$^c$; or R$^d$ and R$^e$ together with the atoms to which they are attached form a heterocyclic ring of 5 to 7 members containing 0-2 additional heteroatoms independently selected from oxygen, sulfur and nitrogen and optionally substituted with 1-3 times with R$^c$, R$^f$ and R$^g$ are independently selected from the group consisting of: hydrogen, C$_{1-10}$ alkyl, cycloalkyl, —C$_{1-10}$alkylene-cycloalkyl, —carboxy, and aryl, wherein alkyl, cycloalkyl, and aryl groups are optionally substituted with one to four substituents independently selected from R$^c$; or R$^f$ and R$^g$ together with the carbon to which they are attached form a ring of 5 to 7 members containing 0-2 heteroatoms independently selected from oxygen, sulfur and nitrogen optionally substituted with 1-3 times with R$^c$;

m is an integer from 1 to 2;
n is an integer from 1 to 10;
p is an integer from 0 to 2; and
a pharmaceutically acceptable carrier or diluent.

25. (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid or a pharmaceutically acceptable salt thereof.

26. The compound of claim 25, wherein the compound is (S)-2-({(S)-6-benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid.

27. (S)-3-(4'-Cyano-biphenyl-4-yl)-2-({(S)-3-[4-(3,4-dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-propionic acid or a pharmaceutically acceptable salt thereof.

28. The compound of claim 27, wherein the compound is (S)-3-(4'-cyano-biphenyl-4-yl)-2-({(S)-3-[4-(3,4-dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-propionic acid.

29. (S)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid or a pharmaceutically acceptable salt thereof.

30. The compound of claim 29, wherein the compound is (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

31. (S)-3-(4'-Cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid or a pharmaceutically acceptable salt thereof.

32. The compound of claim 31, wherein the compound is (S)-3-(4'-cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

33. (S)-3-(4'-Cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid or a pharmaceutically acceptable salt thereof.

34. The compound of claim 33, wherein the compound is (S)-3-(4'-cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid.

35. A compound selected from the group consisting of:
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 4-hydroxy-cyclohexyl ester,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 3-hydroxy-cyclopentyl ester,
- (S)-3-(4'-Cyano-biphenyl-4-yl)-2-{[(S)-3-[4-(3,4-dichloro-benzyloxy)-phenyl]-2-oxo-6-(pyridine-3-carbonyl)-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-2-oxo-6-((S)-tetrahydro-furan-2-carbonyl)-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-2-oxo-6-((R)-tetrahydro-furan-2-carbonyl)-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-2-oxo-6-(3-phenyl-prop-2-ynyl)-2,3,5,6,7,8-hexahydro-1H-4-oxa-1,6-diaza-anthracene-7-carbonyl]-amino}-propionic acid,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isopropyl ester,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid isobutyl ester,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid 2,2-dimethyl-propyl ester,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tetrahydro-pyran-4-yl ester,
- (S)-3-(4'-Cyano-biphenyl-4-yl)-2-({(S)-6-cyclobutanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid,
- (S)-3-(4'-Cyano-biphenyl-4-yl)-2-({(S)-3-[4-(3,4-dichloro-benzyloxy)-phenyl]-6-isobutyryl-2-oxo-2,3,5,6,7,8-hexahydro-1H-4-oxa-1,6-diaza-anthracene-7-carbonyl}-amino)-propionic acid
- (S)-2-({(S)-6-Benzenesulfonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid,
- (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid,
- (S)-3-(4'-Cyano-biphenyl-4-yl)-2-({(S)-6-cyclopentanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid,
- (S)-3-(4'-Cyano-biphenyl-4-yl)-2-{[(S)-3-[4-(3,4-dichloro-benzyloxy)-phenyl]-2-oxo-6-(piperidine-1-carbonyl)-2,3,5,6,7,8-hexahydro-1H-4-oxa-1,6-diaza-anthracene-7-carbonyl]-amino}-propionic acid,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid cyclopropylmethyl ester,
- (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid (R)-(tetrahydro-furan-3-yl) ester,
- (S)-3-(4'-Cyano-biphenyl-4-yl)-2-{[(S)-3-[4-(3,4-dichloro-benzyloxy)-phenyl]-6-(furan-2-carbonyl)-2-oxo-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-6-(3-methyl-benzoyl)-2-oxo-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-6-(4-fluoro-benzoyl)-2-oxo-2,3,5,6,7,8-hexahydro-1H-4-oxa-1,6-diaza-anthracene-7-carbonyl]-amino}-propionic acid,
- (S)-3-(4'-Cyano-biphenyl-4-yl)-2-{[(S)-3-[4-(3,4-dichloro-benzyloxy)-phenyl]-6-(4-methoxy-benzoyl)-

2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-2-oxo-6-(3-trifluoromethyl-benzoyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-({(S)-6-cyclohexanecarbonyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-6-(naphthalene-1-carbonyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-2-oxo-6-(thiophene-2-carbonyl)-2,3,5,6,7,8-hexahydro-1H-4-oxa-1,6-diaza-anthracene-7-carbonyl]-amino}-propionic acid, (S)-7-[(S)-1-Carboxy-2-(4'-cyano-biphenyl-4-yl)-ethylcarbamoyl]-3-[4-(3,4-dichloro-benzyloxy)-phenyl]-2-oxo-1,2,3,5,7,8-hexahydro-4-oxa-1,6-diaza-anthracene-6-carboxylic acid tent-butyl ester, (S)-3-(4'-Cyano-biphenyl-4-yl)-2-{[(S)-3-[4-(3,4-dichloro-benzyloxy)-phenyl]-6-(5-methyl-isoxazole-3-carbonyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-2-oxo-6-(thiophene-2-sulfonyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-({(S)-3-[4-(3,4-dichloro-benzyloxy)-phenyl]-6-dimethylcarbamoyl-2-oxo-2,3,5,6,7,8-hexahydro-1H-4-oxa-1,6-diaza-anthracene-7-carbonyl}-amino)-propionic acid, (S)-2-({(S)-6-Benzyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2-oxo-6-phenethyl-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-2-oxo-6-(2,4,6-trifluoro-benzoyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-2-oxo-6-(toluene-2-sulfonyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(2-methyl-benzyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-({(S)-3-[4-(3,4-dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-propionic acid, (S)-3-(4'-Cyano-biphenyl-4-yl)-2-({(S)-3-[4-(3,4-dichloro-benzyloxy)-phenyl]-2-oxo-6-thiophen-2-ylmethyl-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-6-(2-fluoro-benzyl)-2-oxo-2,3,5,6,7,8-hexahydro-1H-4-oxa-1,6-diaza-anthracene-7-carbonyl]-amino}-propionic acid, (S)-2-({(S)-6-(2-Chloro-benzyl)-3-[4-(3,4-dichloro-benzyloxy)-phenyl]-2-oxo-2,3,5,6,7,8-hexahydro-1H-4-oxa-1,6-diaza-anthracene-7-carbonyl]-amino)-3-(4'-cyano-biphenyl-4-yl)-propionic acid, (S)-3-(4'-Cyano-biphenyl-4-yl)-2-{[(S)-3-[4-(3,4-dichloro-benzyloxy)-phenyl]-6-(2-methoxy-benzyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(6-methyl-pyridin-2-ylmethyl)-2-oxo-2,3,5,6,7,8-hexahydro-1H-4-oxa-1,6-diaza-anthracene-7-carbonyl]-amino}-propionic acid, (S)-2-({(S)-6-(6-Bromo-pyridin-2-ylmethyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-3-(4'-Cyano-biphenyl-4-yl)-2-({(S)-6-(5-cyano-6-methylsulfanyl-pyridin-2-ylmethyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-6-(1H-imidazol-2-ylmethyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(1-methyl-1H-imidazol-2-ylmethyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-({(S)-3-[4-(3,4-dichloro-benzyloxy)-phenyl]-2-oxo-6-thiazol-2-ylmethyl-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-2-oxo-6-(pyridine-2-carbonyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(2-nitro-benzenesulfonyl)-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(3-nitro-benzenesulfonyl)-2-oxo-2,3,5,6,7,8-hexahydro-1H-4-oxa-1,6-diaza-anthracene-7-carbonyl]-amino}-propionic acid, (S)-2-({(S)-6-(2-Cyano-benzyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-3-(4'-Cyano-biphenyl-4-yl)-2-({(S)-6-cyclopropylmethyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-2-oxo-6-(3-pyrimidin-2-yl-prop-2-ynyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-2-oxo-6-(3-thiophen-3-yl-prop-2-ynyl)-2,3,5,6,7,8-hexahydro-1H-4-oxa-1,6-diaza-anthracene-7-carbonyl]-amino}-propionic acid, (S)-2-({(S)-6-Benzoyl-3-[4-(2,6-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(2,5-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(3-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(4-chloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(4-chloro-3-trifluoromethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(4-methoxy-3-trifluoromethyl-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-7-[(S)-1-Carboxy-2-(4'-cyano-biphenyl-4-yl)-ethyl-carbamoyl]-3-[4-(5,6-dichloro-pyridin-3-ylmethoxy)-phenyl]-2-oxo-1,2,3,5,7,8-hexahydro-4-oxa-1,6-diaza-anthracene-6-carboxylic acid tent-butyl ester, (S)-2-({(S)-6-Benzoyl-3-[4-(5,6-dichloro-pyridin-3-ylmethoxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzyl-3-[4-(5,6-dichloro-pyridin-3-ylmethoxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-3-(4'-Cyano-biphenyl-4-yl)-2-{[(S)-3-[4-(5,6-dichloro-pyridin-3-ylmethoxy)-phenyl]-2-oxo-6-(thiophene-2-carbonyl)-2,3,5,6,7,8-hexahydro-1H-4-oxa-1,6-diaza-anthracene-7-carbonyl]-amino}-propionic acid, (S)-2-({(S)-3-[4-(3-Chloro-benzyloxy)-phenyl]-2-oxo-6-thiazol-2-ylmethyl-2,3,5,6,7,8-hexahydro-1H-4-oxa-1,6-diaza-anthracene-7-carbonyl}-amino)-3-(4'-cyano-biphenyl-4-yl)-propionic acid, (S)-7-[(S)-1-Carboxy-2-(4'-cyano-biphenyl-4-yl)-ethyl-carbamoyl]-3-[4-(3,4-dichloro-benzyloxy)-phenyl]-1-methyl-2-oxo-1,2,3,5,7,8-hexahydro-4-oxa-1,6-diaza-anthracene-6-carboxylic acid isopropyl ester, (S)-3-(4'-Cyano-biphenyl-4-yl)-2-{[(S)-3-[4-(3,4-dichloro-benzyloxy)-phenyl]-1-methyl-2-oxo-6-(3-phenyl-prop-2-ynyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-1-methyl-2-oxo-6-(1-phenyl-propyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-6-(2-ethyl-benzyl)-1-methyl-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-({(S)-6-cyclopentyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-({(S)-6-cyclohexyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-({(S)-6-cyclobutyl-3-[4-(3,4-dichloro-benzyloxy)-phenyl]-1-methyl-2-oxo-2,3,5,6,7,8-hexahydro-1H-4-oxa-1,6-diaza-anthracene-7-carbonyl}-amino)-propionic acid, (S)-3-(4'-Cyano-biphenyl-4-yl)-2-{[(S)-3-[4-(3,4-dichloro-benzyloxy)-phenyl]-1-methyl-2-oxo-6-(1-phenyl-cyclopentylmethyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-1-methyl-2-oxo-6-(1-phenyl-ethyl)-2,3,5,6,7,8-hexahydro-1H-4-oxa-1,6-diaza-anthracene-7-carbonyl]-amino}-propionic acid, (S)-2-({(S)-6-(2-Acetylamino-4-methyl-thiazole-5-sulfonyl)-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-cyano-biphenyl-4-yl)-propionic acid, (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4-pyridin-4-yl-phenyl)-propionic acid, (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-(4'-chloro-biphenyl-4-yl)-propionic acid, (S)-2-({(S)-3-[4-(3,4-Dichloro-benzyloxy)-phenyl]-2-oxo-6-pyridin-2-ylmethyl-2,3,5,6,7,8-hexahydro-1H-4-oxa-1,6-diaza-anthracene-7-carbonyl}-amino)-3-(4'-methyl-biphenyl-4-yl)-propionic acid, (S)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, (S)-3-(4'-Chloro-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, (S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid, (S)-2-{[(3R,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-fluoro-biphenyl-4-yl)-propionic acid, (S)-3-(4'-Chloro-biphenyl-4-yl)-2-{[(3S,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, (S)-2-{[(3S,7S)-3-[4-(3,4-Dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-3-(4'-methoxy-biphenyl-4-yl)-propionic acid, (S)-2-{[(3S,7S)-3-[4-(3,4-Dichloro-benzyloxy)-phenyl]-1-methyl-2-oxo-6-((S)-1-phenyl-propyl)-2,3,5,6,7,8- hexahydro-1H-4-oxa-1,6-diaza-anthracene-7-carbonyl]-amino}-3-(4'-fluoro-biphenyl-4-yl)-propionic acid, (S)-3-(4'-Cyano-biphenyl-4-yl)-2-{[(S)-3-[4-(3,4-dichloro-benzyloxy)-phenyl]-6-(3,5-dimethyl-isoxazole-4-sulfonyl)-1-methyl-2-oxo-2,3,5,6,7,8-hexahydro-1H-4-oxa-1,6-diaza-anthracene-7-carbonyl]-amino}-propionic acid, (S)-3-(4'-Cyano-biphenyl-4-yl)-2-{[(S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-2-methyl-propionic acid, (R)-3-(4'-Cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, and (S)-2-({(S)-6-Benzoyl-3-[4-(3,4-dichloro-benzyloxy)-phenyl]-2-oxo-2,3,5,6,7,8-hexahydro-1H-4-oxa-1,6-diaza-anthracene-7-carbonyl}-amino)-3-[4-(pyridin-4-yloxy)-phenyl]-propionic acid;

or a pharmaceutically acceptable salt thereof.

36. A pharmaceutical composition comprising a compound of claim 33 and a pharmaceutically acceptable carrier or diluent.

37. A pharmaceutical composition comprising a compound of claim 26 and a pharmaceutically acceptable carrier or diluent.

38. A pharmaceutical composition comprising a compound of claim 27 and a pharmaceutically acceptable carrier or diluent.

39. A pharmaceutical composition comprising a compound of claim 28 and a pharmaceutically acceptable carrier or diluent.

40. A pharmaceutical composition comprising a compound of claim 29 and a pharmaceutically acceptable carrier or diluent.

41. A pharmaceutical composition comprising a compound of claim 30 and a pharmaceutically acceptable carrier or diluent.

42. A pharmaceutical composition comprising a compound of claim 31 and a pharmaceutically acceptable carrier or diluent.

43. A pharmaceutical composition comprising a compound of claim 32 and a pharmaceutically acceptable carrier or diluent.

44. A pharmaceutical composition comprising a compound of claim 33 and a pharmaceutically acceptable carrier or diluent.

45. A pharmaceutical composition comprising a compound of claim 34 and a pharmaceutically acceptable carrier or diluent.

46. A pharmaceutical composition comprising a compound of claim 35 and a pharmaceutically acceptable carrier or diluent.

* * * * *

UNITED STATES PATENT AND TRADEMARK OFFICE
CERTIFICATE OF CORRECTION

PATENT NO.        : 7,727,983 B2                                           Page 1 of 1
APPLICATION NO.   : 12/399504
DATED             : June 1, 2010
INVENTOR(S)       : Adnan M. M. Mjalli et al.

It is certified that error appears in the above-identified patent and that said Letters Patent is hereby corrected as shown below:

In column 193, line 20, in claim 1, delete "$CH_2$—," and insert -- —$CH_2$—, --, therefor.

In column 195, line 40, in claim 2, delete "$CO_2H$ and $CO_2R^{12}$." and insert -- —$CO_2H$ and —$CO_2R^{12}$. --, therefor.

In column 195, line 41, in claim 3, delete, "$CO_2H$." and insert -- —$CO_2H$. --, therefor.

In column 196, line 6, in claim 9, delete, "G'" and insert -- $G^1$ --, therefor.

In column 198, line 36, in claim 20, delete "$G^3$'" and insert -- -$G^3$ --, therefor.

In column 202, line 3, in claim 24, after "and" insert -- —C≡C—, --.

In column 202, line 36, in claim 24, delete "$G^3$'" and insert -- -$G^3$ --, therefor.

In column 202, line 38, in claim 24, delete "$CH_2$—," and insert -- —$CH_2$—, --, therefor.

In column 211, line 25, in claim 36, delete "claim 33" and insert -- claim 25 --, therefor.

Signed and Sealed this

Seventeenth Day of August, 2010

David J. Kappos
*Director of the United States Patent and Trademark Office*